US009981928B2

(12) United States Patent
Alig et al.

(10) Patent No.: US 9,981,928 B2
(45) Date of Patent: May 29, 2018

(54) ARYL SULFIDE DERIVATIVES AND ARYL SULFOXIDE DERIVATIVES AS ACARICIDES AND INSECTICIDES

(71) Applicant: BAYER CROPSCIENCE AKTIENGESELLSCHAFT, Monheim am Rhein (DE)

(72) Inventors: Bernd Alig, Koenigswinter (DE); Silvia Cerezo-Galvez, Langenfeld (DE); Reiner Fischer, Monheim (DE); Adeline Koehler, Langenfeld (DE); Julia Johanna Hahn, Duesseldorf (DE); Angela Becker, Duesseldorf (DE); Kerstin Ilg, Cologne (DE); Arnd Voerste, Cologne (DE); Daniela Portz, Vettweiss (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 48 days.

(21) Appl. No.: 14/899,260

(22) PCT Filed: Jun. 16, 2014

(86) PCT No.: PCT/EP2014/062510

§ 371 (c)(1),
(2) Date: Dec. 17, 2015

(87) PCT Pub. No.: WO2014/202505

PCT Pub. Date: Dec. 24, 2014

(65) Prior Publication Data

US 2016/0130240 A1 May 12, 2016

(30) Foreign Application Priority Data

Jun. 20, 2013 (EP) .................................... 13172993

(51) Int. Cl.

| | |
|---|---|
| ***C07D 207/22*** | (2006.01) |
| ***C07D 207/404*** | (2006.01) |
| ***C07D 231/34*** | (2006.01) |
| ***C07D 233/32*** | (2006.01) |
| ***C07D 233/34*** | (2006.01) |
| ***C07D 233/74*** | (2006.01) |
| ***C07D 233/96*** | (2006.01) |
| ***C07D 249/12*** | (2006.01) |
| ***C07D 263/20*** | (2006.01) |
| ***C07D 263/44*** | (2006.01) |
| ***C07D 277/54*** | (2006.01) |
| ***A01N 43/36*** | (2006.01) |
| ***A01N 43/50*** | (2006.01) |
| ***A01N 43/56*** | (2006.01) |
| ***A01N 43/653*** | (2006.01) |
| ***A01N 43/76*** | (2006.01) |
| ***A01N 43/78*** | (2006.01) |

(52) U.S. Cl.

CPC ........... *C07D 277/54* (2013.01); *A01N 43/36* (2013.01); *A01N 43/50* (2013.01); *A01N 43/56* (2013.01); *A01N 43/653* (2013.01); *A01N 43/76* (2013.01); *A01N 43/78* (2013.01); *C07D 207/22* (2013.01); *C07D 207/404* (2013.01); *C07D 231/34* (2013.01); *C07D 233/32* (2013.01); *C07D 233/34* (2013.01); *C07D 233/74* (2013.01); *C07D 233/96* (2013.01); *C07D 249/12* (2013.01); *C07D 263/20* (2013.01); *C07D 263/44* (2013.01)

(58) Field of Classification Search

None

See application file for complete search history.

(56) References Cited

FOREIGN PATENT DOCUMENTS

| | | | | |
|---|---|---|---|---|
| EP | 1803712 A1 | | 7/2007 | |
| EP | 2202226 A1 | | 6/2010 | |
| JP | 2007284386 | | 1/2007 | |
| JP | 201142611 | | 3/2011 | |
| WO | 9726248 A1 | | 7/1997 | |
| WO | WO 2006/043635 | * | 4/2006 | ........... C07D 249/14 |
| WO | 2007131680 A1 | | 11/2007 | |
| WO | 2010100189 A1 | | 9/2010 | |

OTHER PUBLICATIONS

International Search Report from corresponding PCT/EP2014/062510, dated Jul. 17, 2014.

* cited by examiner

*Primary Examiner* — Alicia L Otton

(74) *Attorney, Agent, or Firm* — McBee Moore Woodward & Vanik IP, LLC

(57) ABSTRACT

The present invention relates to aryl sulfoxide derivatives, to the use thereof as acaricides and insecticides for controlling animal pests and to processes and intermediates for preparation thereof. The aryl sulfide and aryl sulfoxide derivatives have the general structure (I)

(I)

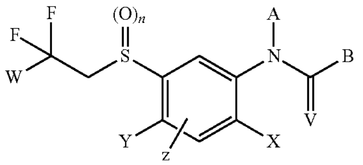

in which the respective radicals are as defined in the description.

20 Claims, No Drawings

ARYL SULFIDE DERIVATIVES AND ARYL SULFOXIDE DERIVATIVES AS ACARICIDES AND INSECTICIDES

CROSS REFERENCE TO RELATED APPLICATIONS

This application is a § 371 National Stage Application of PCT/EP2014/062521, filed 16 Jun. 2014, which claims priority to EP 13172990.7, filed 20 Jun. 2013.

BACKGROUND

Field of the Invention

The present invention relates to aryl sulfide, aryl sulfoxide and arylsulfone derivatives, to their use as acaricides and insecticides for controlling animal pests and to processes and intermediates for their preparation.

Description of Related Art

Various aryl sulfides and aryl sulfoxides and their insecticidal and acaricidal action are already known from WO 2007/131680 A, WO 2010/100189 A and JP 2011/42611.

The active compounds already known from the publications cited above have disadvantages on application, for example in that they may have only inadequate insecticidal and/or acaricidal activity, if any, against animal pests, especially at relatively low application rates.

SUMMARY

Accordingly, it is an object of the present invention to provide aryl sulfide, aryl sulfoxide and arylsulfone derivatives which can be employed as insecticides and/or acaricides with satisfactory insecticidal and/or acaricidal activity against animal pests, in particular at low application rates, with high selectivity and improved compatibility in crops of useful plants.

Novel Compounds of the Formula (I)

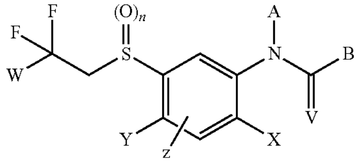

(I)

have now been found, in which

A and B together with the atoms to which they are attached represent an optionally substituted five-membered ring which may optionally be interrupted by a further carbonyl group, thiocarbonyl group, an optionally substituted imino group and/or by one or more heteroatoms;

W represents hydrogen or halogen;

V represents oxygen; sulfur, an optionally substituted nitrogen or salts of an optionally substituted nitrogen;

X, Y and Z each independently of one another represent hydrogen, halogen, hydroxyl, amino, cyano, nitro, OCN, SCN, $SF_5$; or represent trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulfinyl, haloalkylsulfinyl, alkoxyalkylsulfinyl, alkylsulfinylalkyl, alkylsulfonyl, haloalkylsulfonyl, alkoxyalkylsulfonyl, alkylsulfonylalkyl, alkylsulfonyloxy, alkylcarbonyl, haloalkylcarbonyl, carboxyl, alkylcarbonyloxy, alkoxycarbonyl, haloalkoxycarbonyl, aminocarbonyl, alkylaminocarbonyl, dialkylaminocarbonyl, alkenylaminocarbonyl, dialkenylaminocarbonyl, cycloalkylaminocarbonyl, alkylsulfonylamino, aminosulfonyl, alkylaminosulfonyl, dialkylaminosulfonyl, alkylsulfoximino, aminothiocarbonyl, alkylaminothiocarbonyl or dialkylaminothiocarbonyl, where all the aforementioned radicals may optionally be substituted; or represent phenylalkyl, phenoxy, phenylalkyloxy, phenoxyalkyl, phenylthio, phenylthioalkyl, phenylsulfinyl, phenylsulfonyl, hetarylalkyl, hetaryloxy, hetarylalkyloxy, hetarylthio, hetarylsulfinyl or hetarylsulfonyl, where all the aforementioned radicals may optionally be substituted; or represent cycloalkylalkyl, cycloalkyloxy, cycloalkylalkoxy, cycloalkylthio, cycloalkylalkylthio, cycloalkylsulfinyl, cycloalkylalkylsulfinyl, cycloalkylsulfonyl, cycloalkylalkylsulfonyl or cycloalkenyl, where all the aforementioned radicals may each optionally be substituted; or represent NR'R", where R' and R" each independently of one another represent hydrogen, cyano, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl; or R' and R" together with the nitrogen atom to which they are attached may form an optionally substituted, saturated or unsaturated five- to eight-membered ring optionally interrupted by one or more heteroatoms which are selected independently from the group consisting of O, S and N; or represent a 3- to 6-membered saturated, partly saturated or aromatic ring which may optionally contain one to three heteroatoms which are selected independently from the group consisting of O, S and N, and which may optionally be substituted;

or X and Z, or Y and Z, together with the carbon atoms to which they are attached, form a 5- or 6-membered ring which is optionally substituted and optionally interrupted by one or more heteroatoms which are selected independently from the group consisting of O, S, N and CO; and n represents the number 0, 1 or 2.

If appropriate, the compounds of the formula (I) may be present in various polymorphic forms or as a mixture of various polymorphic forms. Both the pure polymorphs and the polymorph mixtures form part of the subject-matter of the invention and can be used in accordance with the invention.

DETAILED DESCRIPTION OF A PREFERRED EMBODIMENT

The compounds of the formula (I) include any diastereomers or enantiomers.

A general definition of the compounds of the invention is provided by the formula (I).

In a preferred embodiment of the present invention, the compounds have a structure of the general formula (I) in which A and B together with the atoms to which they are attached represent a substructure selected from the group consisting of (I-A)

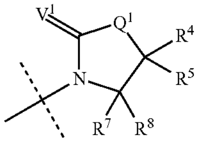

(I-B)

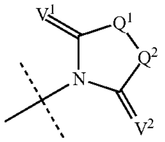

(I-C)

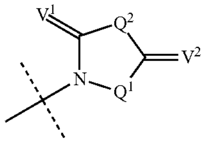

(I-D)

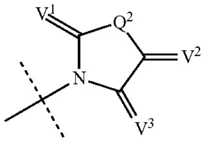

where $V^1$, $V^2$ and $V^3$ each independently of one another represent oxygen; sulfur, an optionally substituted nitrogen or salts of an optionally substituted nitrogen;

$Q^1$ and $Q^2$ each independently of one another represent oxygen, sulfur or an optionally substituted nitrogen; or represent an optionally substituted carbon atom; with the proviso, that $Q_1$ does not represent an alkylcarbonylamino radical;

$R^4$, $R^5$, $R^6$ and $R^7$ each independently of one another represent hydrogen, cyano, halogen or nitro; or represent alkyl, cycloalkylalkyl, haloalkyl, cyanoalkyl, hydroxyalkyl, alkoxyalkyl, aminoalkyl, alkoxycarbonylalkyl, alkylthioalkyl, haloalkylthioalkyl, alkoxyalkylthioalkyl, alkylsulfanylalkyl, alkylsulfinylalkyl, alkylsulfonylalkyl, haloalkylsulfanylalkyl, haloalkylsulfinylalkyl, haloalkylsulfonylalkyl, alkoxyalkylsulfanylalkyl, alkoxyalkylsulfinylalkyl, alkoxyalkylsulfonylalkyl, phenylalkyl, phenoxyalkyl, phenylsulfanylalkyl, phenylsulfinylalkyl, phenylsulfonylalkyl, hetarylalkyl, hetaryloxyalkyl or hetarylthioalkyl, where the aforementioned radicals may each be saturated or unsaturated and/or optionally substituted; or represent optionally substituted saturated or unsaturated cycloalkyl which may optionally be interrupted by one or more heteroatoms; or represent alkylcarbonyl, haloalkylcarbonyl, hydroxyalkylcarbonyl, alkoxyalkylcarbonyl, phenylcarbonyl, hetarylcarbonyl, alkoxycarbonyl, haloalkoxycarbonyl, aryloxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl(aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or represent carbonyl or carboxyl; or represent optionally substituted phenyl or optionally substituted hetaryl;

represent alkoxy, haloalkoxy, alkoxyalkoxy, aryloxy, arylalkyloxy, cycloalkyloxy, cycloalkylalkyloxy or carbonyloxy, where the aforementioned radicals may be saturated or unsaturated and/or optionally substituted, or represent hydroxyl; or represent alkylamino, dialkylamino, haloalkylamino, dihaloalkylamino, cycloalkylamino, dicycloalkylamino, cycloalkyl(alkyl)amino, arylamino, diarylamino, hetarylamino, dihetarylamino, alkyl(aryl)amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulfonylamino, or arylsulfonylamino, where the aforementioned radicals may each be saturated or unsaturated and/or optionally substituted, or represent amino; or represent alkylsulfanyl, alkylsulfinyl, alkylsulfonyl, haloalkylsulfanyl, haloalkylsulfinyl, haloalkylsulfonyl, cycloalkylsulfanyl, cycloalkylsulfinyl, cycloalkylsulfonyl, cycloalkylalkylsulfanyl, cycloalkylalkylsulfinyl, cycloalkylalkylsulfonyl, arylsulfanyl, arylsulfinyl, arylsulfonyl, arylalkylsulfanyl, arylalkylsulfinyl, arylalkylsulfonyl, aminosulfonyl, alkylaminosulfonyl, dialkylaminosulfonyl or arylaminosulfonyl, where the aforementioned radicals may each be saturated or unsaturated and/or optionally substituted, or represent sulfanyl; or $R^4$ and $R^5$ together with the atom to which they are attached may form an optionally substituted, saturated or unsaturated three- to eight-membered ring optionally interrupted by one or more heteroatoms which are selected independently from the group consisting of O, S and N; or $R^6$ and $R^7$ together with the atom to which they are attached may form an optionally substituted, saturated or unsaturated three- to eight-membered ring optionally interrupted by one or more heteroatoms which are selected independently from the group consisting of O, S and N;

W represents hydrogen or halogen;

X, Y and Z each and independently of one another have the meanings mentioned above; and n represents the number 0 or 1.

In this preferred embodiment of the present invention, the compounds have a structure of the general formula (I) in which A and B together with the atoms to which they are attached represent a substructure selected from the group consisting of (I-A) to (I-D), where $V^1$, $V^2$ and $V^3$ each independently of one another represent oxygen; sulfur, $NR^{11}$ or a salt of $NR^{11}$;

$Q^1$ represents oxygen, sulfur, $NR^1$ or $CR^2R$;

$Q^2$ represents $NR^{10}$ or $CR^8R^9$;

$R^1$ represents hydrogen, cyano or nitro; or represents alkyl, cycloalkylalkyl, haloalkyl, cyanoalkyl, hydroxyalkyl, alkoxyalkyl, aminoalkyl, alkoxycarbonylalkyl, alkylsulfanylalkyl, alkylsulfinylalkyl, alkylsulfonylalkyl, haloalkylsulfanylalkyl, haloalkylsulfinylalkyl, haloalkylsulfonylalkyl, alkoxyalkylsulfanylalkyl, alkoxyalkylsulfinylalkyl, alkoxyalkylsulfonylalkyl, phenylalkyl, phenoxyalkyl, phenylsulfanylalkyl, phenylsulfinylalkyl, phenylsulfonylalkyl, hetarylalkyl, hetaryloxyalkyl, hetarylthioalkyl, alkoxycarbonyl, aryloxycarbonyl, arylcarbamoyl, where the aforementioned radicals may each be saturated or unsaturated and/or optionally substituted; or represents optionally substituted saturated or unsaturated cycloalkyl which may optionally be interrupted by one or more heteroatoms; or represents haloalkylcarbonyl, hydroxyalkylcarbonyl, alkoxyalkylcarbonyl, phenylcarbonyl, hetarylcarbonyl, haloalkoxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl(aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or represents carbonyl or carboxyl; or represents optionally substituted phenyl or optionally substituted hetaryl; or represents alkoxy, haloalkoxy, cycloalkyloxy, aryloxy, arylalkyloxy or carbonyloxy, where the aforementioned radicals may optionally be substituted, or represents hydroxyl; or represents alkylamino, haloalkylamino, dihaloalkylamino, dialkylamino, cycloalkylamino, dicycloalkylamino, cycloalkyl(alkyl)amino, arylamino, diarylamino, hetarylamino, dihetarylamino, alkyl(aryl) amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulfonylamino, or arylsulfonylamino, where the aforementioned radicals may each be saturated or unsaturated and/or optionally substituted, or represents amino; or represents alkylsulfanyl, alkylsulfinyl, alkylsulfonyl, haloalkylsulfanyl, haloalkylsulfinyl, haloalkylsulfanyl, cycloalkylsulfanyl, cycloalkylsulfinyl, cycloalkylsulfonyl, cycloalkylalkylsulfanyl, cycloalkylalkylsulfinyl, cycloalkylalkylsulfonyl, arylsulfanyl, arylsulfinyl, arylsulfonyl, arylalkylsulfanyl, arylalkylsulfinyl, arylalkylsulfonyl, aminosulfonyl, alkylaminosulfonyl, dialkylaminosulfonyl or arylaminosulfonyl, where the aforementioned radicals may each be saturated or unsaturated and/or optionally substituted, or represents sulfanyl; and $R^{10}$ and $R^{11}$ each independently of one another represent hydrogen, cyano or nitro; or represent alkyl, cycloalkylalkyl, haloalkyl, cyanoalkyl, hydroxyalkyl, alkoxyalkyl, aminoalkyl, alkoxycarbonylalkyl, alkylsulfanylalkyl, alkylsulfinylalkyl, alkylsulfonylalkyl, haloalkylsulfanylalkyl, haloalkylsulfinylalkyl, haloalkylsulfonylalkyl, alkoxyalkylsulfanylalkyl, alkoxyalkylsulfinylalkyl, alkoxyalkylsulfonylalkyl, phenylalkyl, phenoxyalkyl, phenylsulfanylalkyl, phenylsulfinylalkyl, phenylsulfonylalkyl, hetarylalkyl, hetaryloxyalkyl, hetarylthioalkyl, alkoxycarbonyl, aryloxycarbonyl, arylcarbamoyl, where the aforementioned radicals may each be saturated or unsaturated and/or optionally substituted; or represent optionally substituted saturated or unsaturated cycloalkyl which may optionally be interrupted by one or more heteroatoms; or represent alkylcarbonyl, haloalkylcarbonyl, hydroxyalkylcarbonyl, alkoxyalkylcarbonyl, phenylcarbonyl, hetarylcarbonyl, haloalkoxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl(aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or represents carbonyl or carboxyl; or represent optionally substituted phenyl or optionally substituted hetaryl; or represent alkoxy, haloalkoxy, cycloalkyloxy, aryloxy, arylalkyloxy or carbonyloxy, where the aforementioned radicals may optionally be substituted, or represents hydroxyl; or represent alkylamino, haloalkylamino, dihaloalkylamino, dialkylamino, cycloalkylamino, dicycloalkylamino, cycloalkyl(alkyl)amino, arylamino, diarylamino, hetarylamino, dihetarylamino, alkyl(aryl)amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulfonylamino, or arylsulfonylamino, where the aforementioned radicals may each be saturated or unsaturated and/or optionally substituted, or represents amino; or represent alkylsulfanyl, alkylsulfinyl, alkylsulfonyl, haloalkylsulfanyl, haloalkylsulfinyl, haloalkylsulfanyl, cycloalkylsulfanyl, cycloalkylsulfinyl, cycloalkylsulfonyl, cycloalkylalkylsulfanyl, cycloalkylalkylsulfinyl, cycloalkylalkylsulfonyl, arylsulfanyl, arylsulfinyl, arylsulfonyl, arylalkylsulfanyl, arylalkylsulfinyl, arylalkylsulfonyl, aminosulfonyl, alkylaminosulfonyl, dialkylaminosulfonyl or arylaminosulfonyl, where the aforementioned radicals may each be saturated or unsaturated and/or optionally substituted, or represents sulfanyl; and $R^2$, $R^3$, $R^4$, $R^5$, $R^6$, $R^7$, $R^8$ and $R^9$ each independently of one another represent hydrogen, cyano, halogen or nitro; or represent alkyl, cycloalkylalkyl, haloalkyl, cyanoalkyl, hydroxyalkyl, alkoxyalkyl, aminoalkyl, alkoxycarbonylalkyl, alkylthioalkyl, haloalkylthioalkyl, alkoxyalkylthioalkyl, alkylsulfanylalkyl, alkylsulfinylalkyl, alkylsulfonylalkyl, haloalkylsulfanylalkyl, haloalkylsulfinylalkyl, haloalkylsulfonylalkyl, alkoxyalkylsulfanylalkyl, alkoxyalkylsulfinylalkyl, alkoxyalkylsulfonylalkyl, phenylalkyl, phenoxyalkyl, phenylsulfanylalkyl, phenylsulfinylalkyl, phenylsulfonylalkyl, hetarylalkyl, hetaryloxyalkyl or hetarylthioalkyl, where the aforementioned radicals may each be saturated or unsaturated and/or optionally substituted; or represent optionally substituted saturated or unsaturated cycloalkyl which may optionally be interrupted by one or more heteroatoms; or represent alkylcarbonyl, haloalkylcarbonyl, hydroxyalkylcarbonyl, alkoxyalkylcarbonyl, phenylcarbonyl, hetarylcarbonyl, alkoxycarbonyl, haloalkoxycarbonyl, aryloxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl (aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or represent carbonyl or carboxyl; or represent optionally substituted phenyl or optionally substituted hetaryl;

represent alkoxy, haloalkoxy, alkoxyalkoxy, aryloxy, arylalkyloxy, cycloalkyloxy, cycloalkylalkyloxy or carbonyloxy, where the aforementioned radicals may be saturated or unsaturated and/or optionally substituted, or represent hydroxyl; or represent alkylamino, dialkylamino, haloalkylamino, dihaloalkylamino, cycloalkylamino, dicycloalkylamino, cycloalkyl(alkyl)amino, arylamino, diarylamino, hetarylamino, dihetarylamino, alkyl(aryl) amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulfonylamino, or arylsulfonylamino, where the aforementioned radicals may each be saturated or unsaturated and/or optionally substituted, or represent amino; or represent alkylsulfanyl, alkylsulfinyl, alkylsulfonyl, haloalkylsulfanyl, haloalkylsulfinyl, haloalkylsulfonyl, cycloalkylsulfanyl, cycloalkylsulfinyl, cycloalkylsulfonyl, cycloalkylalkylsulfanyl, cycloalkylalkylsulfinyl, cycloalkylalkylsulfonyl, arylsulfanyl, arylsulfinyl, arylsulfonyl, arylalkylsulfanyl, arylalkylsulfinyl, arylalkylsulfonyl, aminosulfonyl, alkylaminosulfonyl, dialkylaminosulfonyl or arylaminosulfonyl, where the aforementioned radicals may each be saturated or unsaturated and/or optionally substituted, or represent sulfanyl; or $R^2$ and $R^3$ together with the atom to which they are attached may form an optionally substituted, saturated or unsaturated three- to eight-membered ring optionally interrupted by one or more heteroatoms which are selected independently from the group consisting of O, S and N; or $R^4$ and $R^5$ together with the atom to which they are attached may form an optionally substituted, saturated or unsaturated three- to eight-membered ring optionally interrupted by one or more heteroatoms which are selected independently from the group consisting of O, S and N; or $R^6$ and $R^7$ together with the atom to which they are attached may form an optionally substituted, saturated or unsaturated three- to eight-membered ring optionally interrupted by one or more heteroatoms which are selected independently from the group consisting of O, S and N; or $R^8$ and $R^9$ together with the atom to which they are attached may form an optionally substituted, saturated or unsaturated three- to eight-membered ring optionally interrupted by one or more heteroatoms which are selected independently from the group consisting of O, S and N;

W represents hydrogen or halogen;

X, Y and Z each and independently of one another have the meanings mentioned above; and n represents the number 0 or 1.

Compounds according to the invention which may be present in tautomeric forms are all embraced by the present invention.

In a particularly preferred embodiment of the present invention, the compounds have a structure of the general formula (I) in which A and B together with the atoms to which they are attached represent a substructure selected from the group consisting of (I-A) to (I-D), where $V^1$, $V^2$ and $V^3$ each independently of one another represent oxygen; sulfur, $NR^{11}$ or a salt of $NR^{11}$;

$Q^1$ represents oxygen, sulfur, $NR^1$ or $CR^2R^3$;

$Q^2$ represents $NR^{10}$ or $CR^8R^9$;

$R^1$ represents hydrogen, cyano or nitro; or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl, hetarylsulfanyl$(C_1-C_6)$alkyl, hetarylsulfinyl$(C_1-C_6)$alkyl, hetarylsulfonyl$(C_1-C_6)$alkyl, $(C_1-C_6)$alkoxycarbonyl, aryloxycarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated $(C_3-C_6)$cycloalkyl which may optionally be interrupted by one or more heteroatoms; or represents halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl($(C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$(C_1-C_6)$alkylamino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^{10}$ and $R^{11}$ each independently of one another represent hydrogen, cyano or nitro; or represent $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl, hetarylsulfanyl$(C_1-C_6)$alkyl, hetarylsulfinyl$(C_1-C_6)$alkyl, hetarylsulfonyl$(C_1-C_6)$alkyl, $(C_1-C_6)$alkoxycarbonyl, aryloxycarbonyl, $(C_1-C_6)$alkylcarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represent optionally substituted saturated or unsaturated $(C_3-C_6)$cycloalkyl which may optionally be interrupted by one or more heteroatoms; or represent halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl($(C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represent optionally substituted phenyl or optionally substituted hetaryl; or represent $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or represents hydroxyl; or represent $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$(C_1-C_6)$alkylamino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^2$, $R^3$, $R^4$, $R^5$, $R^6$, $R^7$, $R^8$ and $R^9$ each independently of one another represent hydrogen, cyano, halogen or nitro; or represent $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylthio$(C_1-C_6)$alkyl, halo$(C_1-C_6)$alkylthio$(C_1-C_6)$alkyl, $(C_1-C_6)$alkoxy$(C_1-C_6)$alkylthioalkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl or hetarylthio$(C_1-C_6)$alkyl, where the aforementioned radicals may each be saturated or unsaturated and/or optionally be substituted; or represent optionally substituted saturated or unsaturated $(C_3-C_6)$cycloalkyl which may optionally be interrupted by one or more heteroatoms; or represent $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalky laminocarbonyl, $(C_3-C_6)$cycloalkyl($(C_1-C_6)$alkyl) aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represent carbonyl or carboxyl; or represent optionally substituted phenyl or optionally substituted hetaryl;

represent $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or represent hydroxyl; or represent $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl($(C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^4$ and $R^5$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^6$ and $R^7$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N;

W represents hydrogen or halogen;

X, Y and Z each and independently of one another have the meanings mentioned above; and n represents the number 0 or 1.

In this preferred embodiment, it is particularly preferred that

X, Y and Z each independently of one another represent hydrogen, halogen, hydroxyl, amino, cyano, nitro, OCN, SCN, $SF_5$; or represent tri$(C_1-C_6)$alkylsilyl, $(C_1-C_6)$alkyl, halo$(C_1-C_6)$alkyl, cyano$(C_1-C_6)$alkyl, hydroxy$(C_1-C_6)$alkyl, $(C_1-C_6)$alkoxycarbonyl$(C_1-C_6)$alkyl, $(C_1-C_6)$alkoxy$(C_1-C_6)$alkyl, $(C_2-C_6)$alkenyl, halo$(C_2-C_6)$alkenyl, cyano$(C_2-C_6)$alkenyl, $(C_2-C_6)$alkynyl, halo$(C_2-C_6)$alkynyl, cyano$(C_2-C_6)$alkynyl, $(C_1-C_6)$alkoxy, halo$(C_1-C_6)$alkoxy, cyano$(C_1-C_6)$alkoxy, hydroxycarbonyl$(C_1-C_6)$alkoxy, $(C_1-C_6)$alkoxycarbonyl$(C_1-C_6)$alkoxy, $(C_1-C_6)$alkoxy$(C_1-C_6)$alkoxy, $(C_1-C_6)$alkylhydroxyimino, $(C_1-C_6)$alkoxyimino, $(C_1-C_6)$alkyl$(C_1-C_6)$alkoxyimino, halo$(C_1-C_6)$alkyl$(C_1-C_6)$alkoxyimino, $(C_1-C_6)$alkylthio, halo$(C_1-C_6)$alkylthio, $(C_1-C_6)$alkoxy$(C_1-C_6)$alkylthio, $(C_1-C_6)$alkylthio$(C_1-C_6)$alkyl, $(C_1-C_6)$alkylsulfinyl, halo$(C_1-C_6)$alkylsulfinyl, $(C_1-C_6)$alkoxy$(C_1-C_6)$alkylsulfinyl, $(C_1-C_6)$alkylsulfinyl$(C_1-C_6)$alkyl, $(C_1-C_6)$alkylsulfonyl, halo$(C_1-C_6)$alkylsulfonyl, $(C_1-C_6)$alkoxy$(C_1-C_6)$alkylsulfonyl, $(C_1-C_6)$alkylsulfonyl$(C_1-C_6)$alkyl, $(C_1-C_6)$alkylsulfonyloxy, $(C_1-C_6)$ alkylcarbonyl, halo($C_1$-$C_6$)alkylcarbonyl, carboxyl, ($C_1$-$C_6$)alkylcarbonyloxy, ($C_1$-$C_6$)alkoxycarbonyl, halo ($C_1$-$C_6$)alkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_6$)cycloalkylaminocarbonyl, ($C_1$-$C_6$) alkylsulfonylamino, aminosulfonyl, ($C_1$-$C_6$)alkylaminosulfonyl, di($C_1$-$C_6$)alkylaminosulfonyl, ($C_1$-$C_6$) alkylsulfoximino, aminothiocarbonyl, ($C_1$-$C_6$) alkylaminothiocarbonyl or di($C_1$-$C_6$) alkylaminothiocarbonyl, where all the aforementioned radicals may optionally be substituted by halogen; or represent phenyl($C_1$-$C_3$)alkyl, phenoxy, phenyl($C_1$-$C_3$) alkyloxy, phenoxy($C_1$-$C_3$)alkyl, phenylthio, phenylthio ($C_1$-$C_3$)alkyl, phenylsulfinyl, phenylsulfonyl, hetaryl ($C_1$-$C_3$)alkyl, hetaryloxy, hetaryl($C_1$-$C_3$)alkyloxy, hetarylthio, hetarylsulfinyl or hetarylsulfonyl, where all the aforementioned radicals may optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or represent ($C_3$-$C_6$)cycloalkyl($C_1$-$C_3$)alkyl, ($C_3$-$C_6$)cycloalkyloxy, ($C_3$-$C_6$)cycloalkyl($C_1$-$C_3$)alkoxy, ($C_3$-$C_6$) cycloalkylthio, ($C_3$-$C_6$)cycloalkyl($C_1$-$C_3$)alkylthio, ($C_3$-$C_6$)cycloalkylsulfinyl, ($C_3$-$C_6$)cycloalkyl($C_1$-$C_3$) alkylsulfinyl, ($C_3$-$C_6$)cycloalkylsulfonyl, ($C_3$-$C_6$)cycloalkyl($C_1$-$C_3$)alkylsulfonyl or ($C_3$-$C_6$)cycloalkenyl, where the aforementioned radicals may each optionally be mono- to trisubstituted by halogen, cyano, nitro, amino, hydroxyl, methyl, ethyl, trifluoromethyl, difluoromethyl, trifluoroethyl, difluoroethyl, methoxy, ethoxy, trifluoromethoxy, trifluoroethoxy or optionally methyl-, fluorine-, chlorine-, cyano-substituted cyclopropyl; or represent NR'R", where R' and R" each independently of one another represent hydrogen, cyano, ($C_1$-$C_6$)alkyl, halo($C_1$-$C_6$) alkyl, cyano($C_1$-$C_6$)alkyl, hydroxy($C_1$-$C_6$)alkyl, ($C_1$-$C_6$)alkoxy($C_1$-$C_6$)alkyl, ($C_1$-$C_6$)alkylthio($C_1$-$C_6$)alkyl, ($C_2$-$C_6$)alkenyl, halo($C_2$-$C_6$)alkenyl, cyano ($C_2$-$C_6$)alkenyl, ($C_2$-$C_6$)alkynyl, halo($C_2$-$C_6$)alkynyl, cyano($C_2$-$C_6$)alkynyl, acyl or ($C_1$-$C_6$) alkoxycarbonyl; or R' and R" together with the nitrogen atom to which they are attached may form a saturated or unsaturated five- to seven-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl and which is optionally interrupted by heteroatoms from the group consisting of O, S and N; or represent ($C_3$-$C_6$)cycloalkyl, oxetanyl, oxolanyl, oxanyl, ($C_3$-$C_6$)cycloalkenyl, phenyl, pyridyl, pyrimidyl, pyridazinyl, pyrazinyl, triazinyl, thiazolyl, thiadiazolyl, oxazolyl, oxadiazolyl, pyrazolyl or triazolyl, which may optionally be mono- or polysubstituted by identical or different substituents S1 selected from the group consisting of halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or X and Z, or Y and Z, may form the following 5 or 6-membered rings which are optionally substituted by identical or different substituents from the group consisting of hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

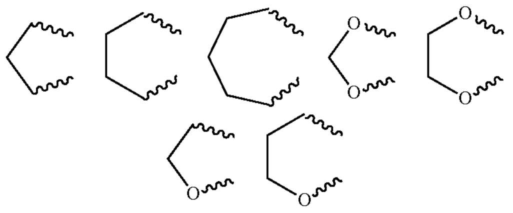

or X and Z, or Y and Z, may form the following fused rings which are optionally mono- or polysubstituted by identical or different substituents, where the substituents may each independently of one another be selected from hydrogen, halogen, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl:

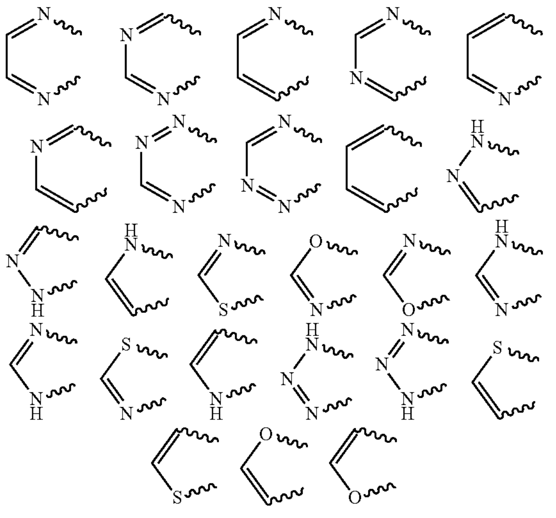

Further preferred isolated embodiments are described in more detail below:

First Embodiment (I-a)

In a first embodiment of the present invention, the compounds according to the invention have a structure of the general formula (I) in which A and B together with the atoms to which they are attached represent a substructure of the formula (I-A)

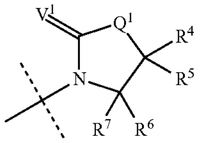

(I-A)

where $V^1$ represents oxygen, sulfur, $NR_{11}$ or a salt of $NR^{11}$;

$Q^1$ represents oxygen, sulfur, $NR^1$ or $CR^2R^3$;

$R^1$ represents hydrogen, cyano or nitro; or represents ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylsulfanyl($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, halo($C_1$-$C_6$)alkylsulfanyl($C_1$-$C_6$)alkyl, halo($C_1$-$C_6$)alkylsulfinyl($C_1$-$C_6$)alkyl, halo($C_1$-$C_6$)alkylsulfonyl($C_1$-$C_6$)alkyl, ($C_1$-$C_6$)alkoxy($C_1$-$C_6$)alkylsulfanyl($C_1$-$C_6$)alkyl, ($C_1$-$C_6$)alkoxy($C_1$-$C_6$)alkylsulfinyl($C_1$-$C_6$)alkyl, ($C_1$-$C_6$)alkoxy($C_1$-$C_6$)alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$)alkyl, hetaryl($C_1$-$C_6$)alkyl, hetaryloxy($C_1$-$C_6$)alkyl, hetarylsulfanyl($C_1$-$C_6$)alkyl, hetarylsulfinyl($C_1$-$C_6$)alkyl, hetarylsulfonyl($C_1$-$C_6$)alkyl, ($C_1$-$C_6$)alkoxycarbonyl, aryloxycarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated ($C_3$-$C_6$)cycloalkyl which may optionally be interrupted by one or more heteroatoms; or represents halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represents optionally substituted phenyl or optionally substituted hetaryl; or represents ($C_1$-$C_6$)alkoxy, halo($C_1$-$C_6$)alkoxy, ($C_3$-$C_6$)cycloalkyloxy, aryloxy, aryl($C_1$-$C_6$)alkyloxy or carbonyloxy, where the aforementioned radicals may each optionally be substituted, or represents hydroxyl; or represents ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_3$-$C_6$)cycloalkyl($C_1$-$C_6$)alkylamino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represents ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, arylsulfanyl, arylsulfinyl, arylsulfonyl, aryl($C_1$-$C_6$)alkylsulfanyl, aryl($C_1$-$C_6$)alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^{11}$ represents hydrogen, cyano or nitro; or represent ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylsulfanyl($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, halo($C_1$-$C_6$)alkylsulfanyl($C_1$-$C_6$)alkyl, halo($C_1$-$C_6$)alkylsulfinyl($C_1$-$C_6$)alkyl, halo($C_1$-$C_6$)alkylsulfonyl($C_1$-$C_6$)alkyl, ($C_1$-$C_6$)alkoxy($C_1$-$C_6$)alkylsulfanyl($C_1$-$C_6$)alkyl, ($C_1$-$C_6$)alkoxy($C_1$-$C_6$)alkylsulfinyl($C_1$-$C_6$)alkyl, ($C_1$-$C_6$)alkoxy($C_1$-$C_6$)alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$)alkyl, hetaryl($C_1$-$C_6$)alkyl, hetaryloxy($C_1$-$C_6$)alkyl, hetarylsulfanyl($C_1$-$C_6$)alkyl, hetarylsulfinyl($C_1$-$C_6$)alkyl, hetarylsulfonyl($C_1$-$C_6$)alkyl, ($C_1$-$C_6$)alkoxycarbonyl, aryloxycarbonyl, ($C_1$-$C_6$)alkylcarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated ($C_3$-$C_6$)cycloalkyl which may optionally be interrupted by one or more heteroatoms; or represents halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, halo($C_1$-$C_6$)alkoxycarbonyl, aryloxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$(C_1-C_6)$alkylamino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^2$, $R^3$, $R^4$, $R^5$, $R^6$ and $R^7$ each independently of one another represent hydrogen, cyano, halogen or nitro; or represent $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylthio$(C_1-C_6)$alkyl, halo$(C_1-C_6)$alkylthio$(C_1-C_6)$alkyl, $(C_1-C_6)$alkoxy$(C_1-C_6)$alkylthioalkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl or hetarylthio$(C_1-C_6)$alkyl, where the aforementioned radicals may each be saturated or unsaturated and/or optionally be substituted; or represent optionally substituted saturated or unsaturated $(C_3-C_6)$cycloalkyl which may optionally be interrupted by one or more heteroatoms; or represent $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl($(C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represent carbonyl or carboxyl; or represent optionally substituted phenyl or optionally substituted hetaryl;

represent $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or represent hydroxyl; or represent $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl($(C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^4$ and $R^5$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^6$ and $R^7$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or W represents hydrogen, fluorine or chlorine;

X, Y and Z each independently of one another represent hydrogen, fluorine, chlorine, bromine, cyano, nitro, amino, hydroxyl, $(C_1-C_4)$alkyl, $(C_1-C_4)$haloalkyl, $(C_2-C_4)$ alkenyl, $(C_2-C_4)$alkynyl, $(C_1-C_4)$alkoxy, $(C_1-C_4)$haloalkoxy or aminothiocarbonyl;

or represent a benzyl, phenoxy, phenylthio, cyclopropylmethyl, cyclopropyloxy or cyclopropylthio, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or represent cyclopropyl, cyclobutyl, cyclopentyl, cyclohexyl or phenyl, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl; and n represents the number 0 or 1.

In a preferred configuration of this first embodiment, the substructure of the formula (I-A) represents a substructure which is selected from the group consisting of (I-A-1)

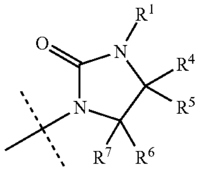

(I-A-2)

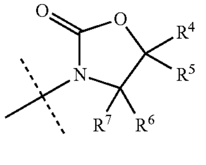

-continued (I-A-3)

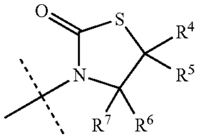

(I-A-4)

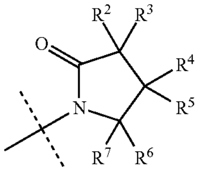

(I-A-5)

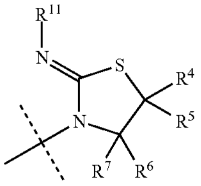

(I-A-6)

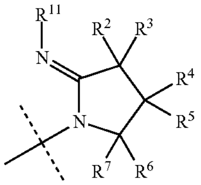

where $R^1$ represents hydrogen; or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may optionally be substituted; or represents optionally substituted $(C_3-C_6)$cycloalkyl, $(C_3-C_6)$cycloalkenyl, which may optionally be interrupted by one or more heteroatoms from the group of O, S and N; or represents halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or are carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulfonylamino, $(C_2-C_6)$alkenylamino, $(C_3-C_6)$cycloalkenyl $(C_1-C_6)$alkylamino, $(C_2-C_6)$alkynylamino, where the aforementioned radicals may each optionally be substituted, or represents amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo $(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl $(C_1-C_6)$alkylsulfinyl, $(C_3-C_6)$cycloalkyl$(C_1-C_6)$ alkylsulfonyl, aminosulfonyl, $(C_1-C_6)$ alkylaminosulfonyl, di$(C_1-C_6)$alkylaminosulfonyl or arylaminosulfonyl, where the aforementioned radicals may each optionally be substituted, or represents sulfanyl; and $R^{11}$ represents hydrogen or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, $(C_1-C_6)$alkoxy $(C_1-C_6)$alkyl, $(C_1-C_6)$alkoxycarbonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$ alkyl, $(C_2-C_6)$alkynyl, where the aforementioned radicals may optionally be substituted; or represents optionally substituted $(C_3-C_6)$cycloalkyl, $(C_3-C_6)$cycloalkenyl, which may optionally be interrupted by one or more heteroatoms from the group of O, S and N; or represents $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$ alkoxycarbonyl, halo$(C_1-C_6)$alkoxycarbonyl, aminocarbonyl, $(C_1-C_6)$alkylaminocarbonyl, di$(C_1-C_6)$ alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or represent carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulfonylamino, $(C_2-C_6)$alkenylamino, $(C_3-C_6)$cycloalkenyl $(C_1-C_6)$alkylamino, $(C_2-C_6)$alkynylamino, where the aforementioned radicals may each optionally be substituted, or represents amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo $(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl $(C_1-C_6)$alkylsulfinyl, $(C_3-C_6)$cycloalkyl$(C_1-C_6)$ alkylsulfonyl, aminosulfonyl, $(C_1-C_6)$ alkylaminosulfonyl, di$(C_1-C_6)$alkylaminosulfonyl or arylaminosulfonyl, where the aforementioned radicals may each optionally be substituted, or represents sulfanyl; and $R^2$, $R^3$, $R^4$, $R^5$, $R^6$ and $R^7$ each independently of one another represent hydrogen, cyano, halogen or nitro; or represent $(C_1-C_6)$alkyl, $(C_3-C_6)$cycloalkyl$(C_1-C_6)$alkyl, halo$(C_1-C_6)$alkyl, cyano$(C_1-C_6)$alkyl, $(C_1-C_6)$alkoxy $(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$ alkyl, $(C_2-C_6)$alkynyl, where the aforementioned radicals may each optionally be substituted, or represent optionally substituted $(C_3-C_6)$cycloalkyl, $(C_3-C_6)$cycloalkenyl, which may optionally be interrupted by one or more heteroatoms from the group consisting of O, S and N; or represent $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$ alkoxycarbonyl, halo$(C_1-C_6)$alkoxycarbonyl, aminocarbonyl, $(C_1-C_6)$alkylaminocarbonyl, di$(C_1-C_6)$ alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or represent carbonyl or carboxyl; or represent optionally substituted phenyl or optionally substituted hetaryl;

represent $(C_1-C_6)$alkoxy, halo$(C_1-C_6)$alkoxy, $(C_1-C_6)$ alkoxy$(C_1-C_6)$alkoxy, $(C_3-C_6)$cycloalkyloxy, $(C_3-C_6)$ cycloalkyl$(C_1-C_6)$alkyloxy, $(C_2-C_6)$alkenyloxy, $(C_3-C_6)$cycloalkenyl$(C_1-C_6)$alkoxy, $(C_2-C_6)$alkynyloxy or carbonyloxy, where the aforementioned radicals may each optionally be substituted, or represent hydroxyl; or represent $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulfonylamino, $(C_2-C_6)$alkenylamino, $(C_3-C_6)$cycloalkenyl $(C_1-C_6)$alkylamino, $(C_2-C_6)$alkynylamino, where the aforementioned radicals may each optionally be substituted, or represents amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$ alkylsulfonyl, aminosulfonyl, $(C_1-C_6)$ alkylaminosulfonyl, di$(C_1-C_6)$alkylaminosulfonyl or arylaminosulfonyl, where the aforementioned radicals may each optionally be substituted, or represent sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^4$ and $R^5$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N; or $R^6$ and $R^7$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N; or W represents hydrogen or fluorine;

X and Y independently of one another represent hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z represents hydrogen; and n represents the number 0 or 1.

Here, in particular in substructures (I-A-5) and (I-A-6), E and Z isomers of the exocyclic double bond to the nitrogen are included. Also included are the salts of the nitrogen located at the exocyclic double bond of substructures (I-A-5) and (I-A-6). These are preferably the salts formed by addition of haloacids. Very particularly preferably, these are hydrochlorides.

In this context, it is especially preferable that $R^1$ and $R^{11}$ each independently of one another represent hydrogen; or represent ($C_1$-$C_6$)alkyl, ($C_3$-$C_6$)cycloalkyl($C_1$-$C_3$)alkyl, ($C_2$-$C_6$)alkenyl, ($C_2$-$C_6$)alkynyl, halo($C_2$-$C_6$)alkyl, ($C_1$-$C_6$)alkoxy($C_1$-$C_6$)alkyl or phenyl($C_1$-$C_3$)alkyl, where the aforementioned radicals may each optionally be substituted; or represent optionally substituted saturated or unsaturated ($C_3$-$C_6$)cycloalkyl or optionally substituted phenyl;

$R^2$, $R^3$, $R^4$, $R^5$, $R^6$ and $R^7$ each independently of one another represent hydrogen;

represent ($C_1$-$C_6$)alkyl, ($C_3$-$C_6$)cycloalkyl($C_1$-$C_3$)alkyl, ($C_2$-$C_6$)alkenyl, ($C_2$-$C_6$)alkynyl, halo($C_1$-$C_6$)alkyl, ($C_1$-$C_6$)alkoxy($C_1$-$C_6$)alkyl or phenyl($C_1$-$C_3$)alkyl, where the aforementioned radicals may each optionally be substituted; or represent optionally substituted saturated or unsaturated ($C_3$-$C_6$)cycloalkyl or optionally substituted phenyl; or W represents hydrogen or fluorine;

X and Y independently of one another represent hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z represents hydrogen; and n represents the number 0 or 1.

Preferably, the substructure of the formula (I-A) represents a substructure which is selected from the group consisting of (I-A-1)

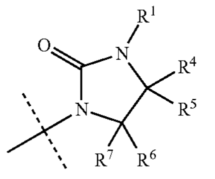

-continued (I-A-6)

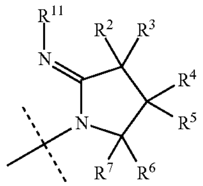

where $R^1$ and $R^{11}$ each independently of one another represent hydrogen, methyl, ethyl, propyl, isopropyl, cyclopropyl, cyclopropylmethyl, $CH_2CF_3$, $CH_2CHF_2$, $CH(CH_3)CF_3$, $CH_2CH_2CF_3$, $CH_2CH_2CHF_2$; or $R^2$, $R^3$, $R^4$, $R^5$, $R^6$ and $R^7$ each independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl, fluorine or methoxy;

X and Y represent in particular the following (Y,X) combinations: (Me, F), (Me,H), (Me,Cl), (Me,Me), (Cl,Cl), (Cl,F), (CN,F), (MeO,F), (MeO,H), (Cl,H), (Me,H), (Br, H), (Br,F), (CN,H), (F,F), ($CF_3$,H);

Z represents hydrogen; and n represents the number 0 or 1.

Also included are the salts of the nitrogen located at the exocyclic double bond of substructure (I-A-6). These are preferably the salts formed by addition of haloacids. Very particularly preferably, these are hydrochlorides.

Likewise preferably, the substructure of the formula (I-A) represents a substructure which is selected from the group consisting of (I-A-1)

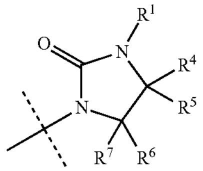

(I-A-2)

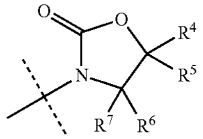

(I-A-6)

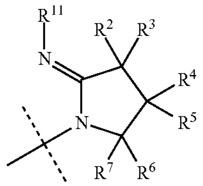

where $R^1$ and $R^{11}$ each independently of one another represent hydrogen, methyl, ethyl, propyl, isopropyl, cyclopropyl, cyclopropylmethyl, $CH_2CF_3$, $CH_2CHF_2$, $CH(CH_3)CF_3$, $CH_2CH_2CF_3$, $CH_2CH_2CHF_2$; or $R^2$, $R^3$, $R^4$, $R^5$, $R^6$ and $R^7$ each independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), ($CF_3$,H);

Z represents hydrogen; and n represents the number 0 or 1.

If the substructure of the formula (I-A) is the substructure formula (I-A-1), it is preferable that $R^1$ represents hydrogen, methyl, ethyl, $CH_2CF_3$, cyclopropyl or cyclopropylmethyl;

$R^4$, $R^5$, $R^6$ and $R^7$ each independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl, fluorine or methoxy;

X and Y represent in particular the following (Y,X) combinations: (Me, F), (Me,H), (Me,Cl), (Me,Me), (Cl,Cl), (Cl,F), (CN,F), (MeO,F), (MeO,H), (Cl,H), (Me,H), (Br, H), (Br,F), (CN,H), (F,F), ($CF_3$,H);

Z represents hydrogen; and n represents the number 0 or 1.

In this context, it is particularly preferable that $R^1$ represents hydrogen;

$R^4$, $R^5$, $R^6$ and $R^7$ represent hydrogen;

W represents fluorine;

X represents methyl or fluorine;

Y represents methyl;

X and Y represent in particular the following (Y,X) combinations: (Me, F), (Me, Me)

Z represents hydrogen; and n represents the number 0 or 1.

If the substructure of the formula (I-A) is the substructure formula (I-A-1), it is likewise preferable that $R^1$ represents hydrogen, methyl, ethyl, $CH_2CF_3$, cyclopropyl or cyclopropylmethyl;

$R^4$, $R^5$, $R^6$ and $R^7$ each independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), ($CF_3$,H);

Z represents hydrogen; and n represents the number 0 or 1.

In this context, it is particularly preferable that $R^1$ represents hydrogen or methyl;

$R^4$, $R^5$, $R^6$ and $R^7$ represent hydrogen;

W represents fluorine;

X represents methyl or fluorine;

Y represents methyl;

X and Y represent in particular the following (Y,X) combinations: (Me, F), (Me, Me)

Z represents hydrogen; and n represents the number 0 or 1.

If the substructure of the formula (I-A) is the substructure formula (I-A-2), it is preferable that $R^4$, $R^5$, $R^6$ and $R^7$ each independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), ($CF_3$,H);

Z represents hydrogen; and n represents the number 0 or 1.

In this context, it is particularly preferable that $R^4$ represents hydrogen or methyl;

$R^5$ represents hydrogen;

$R^6$ represents hydrogen or methyl, $R^7$ represents hydrogen;

W represents fluorine;

X represents fluorine;

Y represents methyl;

Z represents hydrogen; and n represents the number 0 or 1.

If the substructure of the formula (I-A) is the substructure formula (I-A-6), it is preferable that $R^{11}$ represents hydrogen, methyl, ethyl, $CH_2CF_3$, $CH_2CHF_2$, $CH(CH_3)CF_3$, $CH_2CH_2CF_3$ or $CH_2CH_2CHF_2$, cyclopropyl or cyclopropylmethyl;

$R^2$, $R^3$, $R^4$, $R^5$, $R^6$ and $R^7$ each independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl, fluorine or methoxy;

X and Y represent in particular the following (Y,X) combinations: (Me, F), (Me,H), (Me,Cl), (Me,Me), (Cl,Cl), (Cl,F), (CN,F), (MeO,F), (MeO,H), (Cl,H), (Me,H), (Br, H), (Br,F), (CN,H), (F,F), ($CF_3$,H);

Z represents hydrogen; and n represents the number 0 or 1, where the nitrogen located at the exocyclic double bond may also be present as hydrohalide.

In this context, it is particularly preferable that $R^{11}$ represents $CH_2CF_3$ or $CH(CH_3)CF_3$;

$R^2$, $R^3$, $R^4$, $R^5$, $R^6$ and $R^7$ represent hydrogen;

W represents fluorine;

X represents methyl or fluorine;

Y represents methyl;

X and Y represent in particular the following (Y,X) combinations: (Me, F), (Me, Me)

Z represents hydrogen; and n represents the number 0 or 1, where the nitrogen located at the exocyclic double bond may also be present as hydrochloride.

Second Embodiment (I-B)

In a second embodiment of the present invention, the compounds according to the invention have a structure of the general formula (I) in which A and B together with the atoms to which they are attached represent a substructure of the formula (I-B)

(I-B)

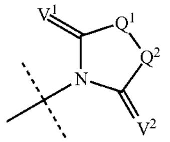

where $V^1$ and $V^2$ each independently of one another represent oxygen; sulfur, $NR^{11}$ or a salt of $NR^{11}$;

$Q^1$ represents oxygen, sulfur, $NR^1$ or $CR^2R^3$;

$Q^2$ represents $NR^{10}$ or $CR^8R^9$;

$R^1$ represents hydrogen, cyano or nitro; or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl, hetarylsulfanyl$(C_1-C_6)$alkyl, hetarylsulfinyl$(C_1-C_6)$alkyl, hetarylsulfonyl$(C_1-C_6)$alkyl, $(C_1-C_6)$alkoxycarbonyl, aryloxycarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated $(C_3-C_6)$cycloalkyl which may optionally be interrupted by one or more heteroatoms; or represents halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl($(C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represents carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$(C_1-C_6)$alkylamino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^{10}$ and $R^{11}$ each independently of one another represent hydrogen, cyano or nitro; or represent $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl, hetarylsulfanyl$(C_1-C_6)$alkyl, hetarylsulfinyl$(C_1-C_6)$alkyl, hetarylsulfonyl$(C_1-C_6)$alkyl, $(C_1-C_6)$alkoxycarbonyl, aryloxycarbonyl, $(C_1-C_6)$alkylcarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represent optionally substituted saturated or unsaturated $(C_3-C_6)$cycloalkyl which may optionally be interrupted by one or more heteroatoms; or represent halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl($(C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represents carbonyl or carboxyl; or represent optionally substituted phenyl or optionally substituted hetaryl; or represent $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or represents hydroxyl; or represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_3$-$C_6$)cycloalkyl($C_1$-$C_6$)alkylamino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, arylsulfanyl, arylsulfinyl, arylsulfonyl, aryl($C_1$-$C_6$)alkylsulfanyl, aryl($C_1$-$C_6$)alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^2$, $R^3$, $R^8$ and $R^9$ each independently of one another represent hydrogen, cyano, halogen or nitro; or represent ($C_1$-$C_6$)alkyl, ($C_3$-$C_6$)cycloalkyl($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylthio($C_1$-$C_6$)alkyl, halo($C_1$-$C_6$)alkylthio($C_1$-$C_6$)alkyl, ($C_1$-$C_6$)alkoxy($C_1$-$C_6$)alkylthioalkyl, ($C_1$-$C_6$)alkylsulfanyl($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, halo($C_1$-$C_6$)alkylsulfanyl($C_1$-$C_6$)alkyl, halo($C_1$-$C_6$)alkylsulfinyl($C_1$-$C_6$)alkyl, halo($C_1$-$C_6$)alkylsulfonyl($C_1$-$C_6$)alkyl, ($C_1$-$C_6$)alkoxy($C_1$-$C_6$)alkylsulfanyl($C_1$-$C_6$)alkyl, ($C_1$-$C_6$)alkoxy($C_1$-$C_6$)alkylsulfinyl($C_1$-$C_6$)alkyl, ($C_1$-$C_6$)alkoxy($C_1$-$C_6$)alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$)alkyl, hetaryl($C_1$-$C_6$)alkyl, hetaryloxy($C_1$-$C_6$)alkyl or hetarylthio($C_1$-$C_6$)alkyl, where the aforementioned radicals may each be saturated or unsaturated and/or optionally be substituted; or represent optionally substituted saturated or unsaturated ($C_3$-$C_6$)cycloalkyl which may optionally be interrupted by one or more heteroatoms; or represent ($C_1$-$C_6$)alkylcarbonyl, halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, ($C_1$-$C_6$)alkoxycarbonyl, halo($C_1$-$C_6$)alkoxycarbonyl, aryloxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represent carbonyl or carboxyl; or represent optionally substituted phenyl or optionally substituted hetaryl;

represent ($C_1$-$C_6$)alkoxy, halo($C_1$-$C_6$)alkoxy, ($C_1$-$C_6$)alkoxy($C_1$-$C_6$)alkoxy, aryloxy, aryl($C_1$-$C_6$)alkyloxy, ($C_3$-$C_6$)cycloalkyloxy, ($C_3$-$C_6$)cycloalkyl($C_1$-$C_6$)alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or represent hydroxyl; or represent ($C_1$-$C_6$)alkylamino, di($C_1$-$C_6$)alkylamino, halo($C_1$-$C_6$)alkylamino, dihalo($C_1$-$C_6$)alkylamino, ($C_3$-$C_6$)cycloalkylamino, di($C_3$-$C_6$)cycloalkylamino, ($C_3$-$C_6$)cycloalkyl(($C_1$-$C_6$)alkyl)amino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, arylsulfanyl, arylsulfinyl, arylsulfonyl, aryl($C_1$-$C_6$)alkylsulfanyl, aryl($C_1$-$C_6$)alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N;

W represents hydrogen, fluorine or chlorine;

X, Y and Z each independently of one another represent hydrogen, fluorine, chlorine, bromine, cyano, nitro, amino, hydroxyl, ($C_1$-$C_4$)alkyl, ($C_1$-$C_4$)haloalkyl, ($C_2$-$C_4$) alkenyl, ($C_2$-$C_4$)alkynyl, ($C_1$-$C_4$)alkoxy, ($C_1$-$C_4$)haloalkoxy or aminothiocarbonyl;

or represent a benzyl, phenoxy, phenylthio, cyclopropylmethyl, cyclopropyloxy or cyclopropylthio, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or represent cyclopropyl, cyclobutyl, cyclopentyl, cyclohexyl or phenyl, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl; and n represents the number 0 or 1.

In a preferred configuration of this second embodiment, the substructure of the formula (I-B) represents a substructure which is selected from the group consisting of (I-B-1)

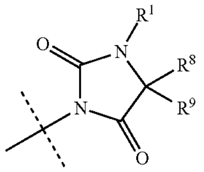

(I-B-2)

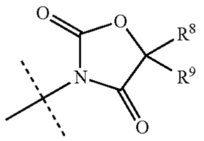

(I-B-3)

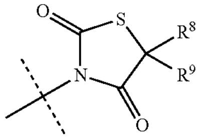

(I-B-4)

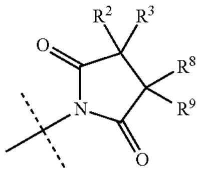

-continued (I-B-5)

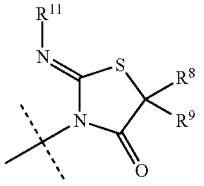

(I-B-6)

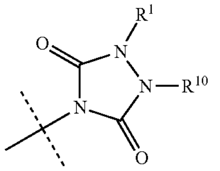

(I-B-7)

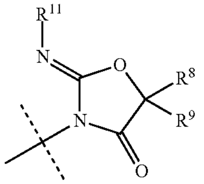

where $R^1$ represents hydrogen or represents ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, ($C_1$-$C_6$)alkoxy ($C_1$-$C_6$)alkyl, ($C_1$-$C_6$)alkoxycarbonyl($C_1$-$C_6$)alkyl, phenyl($C_1$-$C_6$)alkyl, hetaryl($C_1$-$C_6$)alkyl, ($C_2$-$C_6$)alkenyl, halo($C_2$-$C_6$)alkenyl, ($C_3$-$C_6$)cycloalkenyl($C_1$-$C_6$) alkyl, ($C_2$-$C_6$)alkynyl, where the aforementioned radicals may optionally be substituted; or represents optionally substituted ($C_3$-$C_6$)cycloalkyl, ($C_3$-$C_6$)cycloalkenyl, which may optionally be interrupted by one or more heteroatoms from the group of O, S and N; or represents halo($C_1$-$C_6$)alkylcarbonyl, ($C_1$-$C_6$)alkoxy($C_1$-$C_6$)alkylcarbonyl, ($C_1$-$C_6$)alkoxycarbonyl, halo($C_1$-$C_6$) alkoxycarbonyl, aminocarbonyl, ($C_1$-$C_6$)alkylaminocarbonyl, di($C_1$-$C_6$)alkylaminocarbonyl, ($C_3$-$C_6$) cycloalkylaminocarbonyl, ($C_1$-$C_6$) alkylaminothiocarbonyl, di($C_1$-$C_6$) alkylaminothiocarbonyl, ($C_2$-$C_6$)alkenylcarbonyl, ($C_3$-$C_6$)cycloalkenyl($C_1$-$C_6$)alkylcarbonyl, ($C_2$-$C_6$) alkynylcarbonyl or aminothiocarbonyl, where the aforementioned radicals may each optionally be substituted, or represents carbonyl or carboxyl; or represents optionally substituted phenyl or optionally substituted hetaryl; or represents ($C_1$-$C_6$)alkoxy, halo($C_1$-$C_6$)alkoxy, ($C_3$-$C_6$)cycloalkyloxy, or carbonyloxy, where the aforementioned radicals may each optionally be substituted, or represents hydroxyl; or represents ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_1$-$C_6$)alkylcarbonylamino, ($C_1$-$C_6$)alkoxycarbonylamino, ($C_1$-$C_6$)alkylcarbamoylamino, ($C_1$-$C_6$)alkylsulfonylamino, ($C_2$-$C_6$)alkenylamino, ($C_3$-$C_6$)cycloalkenyl ($C_1$-$C_6$)alkylamino, ($C_2$-$C_6$)alkynylamino, where the aforementioned radicals may each optionally be substituted, or represents amino; or represents ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo ($C_1$-$C_6$)alkylsulfinyl, halo($C_1$-$C_6$)alkylsulfanyl, ($C_3$-

$C_6$)cycloalkyl($C_1$-$C_6$)alkylsulfanyl, ($C_3$-$C_6$)cycloalkyl ($C_1$-$C_6$)alkylsulfinyl, ($C_3$-$C_6$)cycloalkyl($C_1$-$C_6$) alkylsulfonyl, aminosulfonyl, ($C_1$-$C_6$) alkylaminosulfonyl, di($C_1$-$C_6$)alkylaminosulfonyl or arylaminosulfonyl, where the aforementioned radicals may each optionally be substituted, or represents sulfanyl; and $R^{10}$ and $R^{11}$ each independently of one another
represent hydrogen; or
represent ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, ($C_1$-$C_6$)alkoxy ($C_1$-$C_6$)alkyl, ($C_1$-$C_6$)alkoxycarbonyl($C_1$-$C_6$)alkyl, phenyl($C_1$-$C_6$)alkyl, hetaryl($C_1$-$C_6$)alkyl, ($C_2$-$C_6$)alkenyl, halo($C_2$-$C_6$)alkenyl, ($C_3$-$C_6$)cycloalkenyl($C_1$-$C_6$) alkyl, ($C_2$-$C_6$)alkynyl, where the aforementioned radicals may optionally be substituted; or
represent optionally substituted ($C_3$-$C_6$)cycloalkyl, ($C_3$-$C_6$)cycloalkenyl, which may optionally be interrupted by one or more heteroatoms from the group of O, S and N; or
represent ($C_1$-$C_6$)alkylcarbonyl, halo($C_1$-$C_6$)alkylcarbonyl, ($C_1$-$C_6$)alkoxy($C_1$-$C_6$)alkylcarbonyl, ($C_1$-$C_6$) alkoxycarbonyl, halo($C_1$-$C_6$)alkoxycarbonyl, aminocarbonyl, ($C_1$-$C_6$)alkylaminocarbonyl, di($C_1$-$C_6$) alkylaminocarbonyl, ($C_3$-$C_6$)cycloalkylaminocarbonyl, ($C_1$-$C_6$)alkylaminothiocarbonyl, di($C_1$-$C_6$)alkylaminothiocarbonyl, ($C_2$-$C_6$)alkenylcarbonyl, ($C_3$-$C_6$)cycloalkenyl($C_1$-$C_6$)alkylcarbonyl, ($C_2$-$C_6$)alkynylcarbonyl or aminothiocarbonyl, where the aforementioned radicals may each optionally be substituted, or represent carbonyl or carboxyl; or
represent optionally substituted phenyl or optionally substituted hetaryl; or
represent ($C_1$-$C_6$)alkoxy, halo($C_1$-$C_6$)alkoxy, ($C_3$-$C_6$)cycloalkyloxy, or carbonyloxy, where the aforementioned radicals may each optionally be substituted, or represents hydroxyl; or
represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_1$-$C_6$)alkylcarbonylamino, ($C_1$-$C_6$)alkoxycarbonylamino, ($C_1$-$C_6$)alkylcarbamoylamino, ($C_1$-$C_6$)alkylsulfonylamino, ($C_2$-$C_6$)alkenylamino, ($C_3$-$C_6$)cycloalkenyl ($C_1$-$C_6$)alkylamino, ($C_2$-$C_6$)alkynylamino, where the aforementioned radicals may each optionally be substituted, or represents amino; or
represents ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo ($C_1$-$C_6$)alkylsulfinyl, halo($C_1$-$C_6$)alkylsulfanyl, ($C_3$-$C_6$)cycloalkyl($C_1$-$C_6$)alkylsulfanyl, ($C_3$-$C_6$)cycloalkyl ($C_1$-$C_6$)alkylsulfinyl, ($C_3$-$C_6$)cycloalkyl($C_1$-$C_6$) alkylsulfonyl, aminosulfonyl, ($C_1$-$C_6$) alkylaminosulfonyl, di($C_1$-$C_6$)alkylaminosulfonyl or arylaminosulfonyl, where the aforementioned radicals may each optionally be substituted, or represents sulfanyl; and $R^2$, $R^3$, $R^8$ and $R^9$ each independently of one another
represent hydrogen, cyano, halogen or nitro; or
represent ($C_1$-$C_6$)alkyl, ($C_3$-$C_6$)cycloalkyl($C_1$-$C_6$)alkyl, halo($C_1$-$C_6$)alkyl, cyano($C_1$-$C_6$)alkyl, ($C_1$-$C_6$)alkoxy ($C_1$-$C_6$)alkyl, ($C_1$-$C_6$)alkoxycarbonyl($C_1$-$C_6$)alkyl, ($C_1$-$C_6$)alkylsulfanyl($C_1$-$C_6$)alkyl, ($C_1$-$C_6$)alkylsulfinyl($C_1$-$C_6$)alkyl, phenyl($C_1$-$C_6$)alkyl, hetaryl($C_1$-$C_6$) alkyl, ($C_2$-$C_6$)alkenyl, halo($C_2$-$C_6$)alkenyl, ($C_3$-$C_6$)cycloalkenyl($C_1$-$C_6$)alkyl, ($C_2$-$C_6$)alkynyl, where the aforementioned radicals may each optionally be substituted; or
represent optionally substituted ($C_3$-$C_6$)cycloalkyl, ($C_3$-$C_6$)cycloalkenyl, which may optionally be interrupted by one or more heteroatoms from the group of O, S and N; or
represent ($C_1$-$C_6$)alkylcarbonyl, halo($C_1$-$C_6$)alkylcarbonyl, ($C_1$-$C_6$)alkoxy($C_1$-$C_6$)alkylcarbonyl, ($C_1$-$C_6$) alkoxycarbonyl, halo($C_1$-$C_6$)alkoxycarbonyl, aminocarbonyl, ($C_1$-$C_6$)alkylaminocarbonyl, di($C_1$-$C_6$) alkylaminocarbonyl, ($C_3$-$C_6$)cycloalkylaminocarbonyl, ($C_1$-$C_6$)alkylaminothiocarbonyl, di($C_1$-$C_6$)alkylaminothiocarbonyl, ($C_2$-$C_6$)alkenylcarbonyl, ($C_3$-$C_6$)cycloalkenyl($C_1$-$C_6$)alkylcarbonyl, ($C_2$-$C_6$)alkynylcarbonyl or aminothiocarbonyl,
where the aforementioned radicals may each optionally be substituted, or represent carbonyl or carboxyl; or
represent optionally substituted phenyl or optionally substituted hetaryl; or
represent ($C_1$-$C_6$)alkoxy, halo($C_1$-$C_6$)alkoxy, ($C_1$-$C_6$) alkoxy($C_1$-$C_6$)alkoxy, ($C_3$-$C_6$)cycloalkyloxy, ($C_3$-$C_6$) cycloalkyl($C_1$-$C_6$)alkyloxy, ($C_2$-$C_6$)alkenyloxy, ($C_3$-$C_6$)cycloalkenyl($C_1$-$C_6$)alkoxy, ($C_2$-$C_6$)alkynyloxy or carbonyloxy, where the aforementioned radicals may each optionally be substituted, or represent hydroxyl; or
represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_1$-$C_6$)alkylcarbonylamino, ($C_1$-$C_6$)alkoxycarbonylamino, ($C_1$-$C_6$)alkylcarbamoylamino, ($C_1$-$C_6$)alkylsulfonylamino, ($C_2$-$C_6$)alkenylamino, ($C_3$-$C_6$)cycloalkenyl ($C_1$-$C_6$)alkylamino, ($C_2$-$C_6$)alkynylamino, where the aforementioned radicals may each optionally be substituted, or represent amino; or
represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfanyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$) alkylsulfonyl, aminosulfonyl, ($C_1$-$C_6$) alkylaminosulfonyl, di($C_1$-$C_6$)alkylaminosulfonyl or arylaminosulfonyl, where the aforementioned radicals may each optionally be substituted, or represent sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N;

W represents hydrogen or fluorine;

X and Y independently of one another represent hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z represents hydrogen; and n represents the number 0 or 1.

In this context, it is preferable that $R^1$, $R^{10}$ and $R^{11}$ each independently of one another represent hydrogen; or represent $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_2-C_6)$alkyl, $(C_1-C_6)$alkoxy$(C_1-C_6)$alkyl or phenyl$(C_1-C_3)$alkyl, where the aforementioned radicals may each optionally be substituted; or represent optionally substituted saturated or unsaturated $(C_3-C_6)$cycloalkyl or optionally substituted phenyl;

$R^2$, $R^3$, $R^8$ and $R^9$ each independently of one another represent hydrogen; or represent $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, $(C_1-C_6)$alkoxy$(C_1-C_6)$alkyl or phenyl$(C_1-C_3)$alkyl, where the aforementioned radicals may each optionally be substituted; or represent optionally substituted saturated or unsaturated $(C_3-C_6)$cycloalkyl or optionally substituted phenyl; or W represents hydrogen or fluorine;

X and Y independently of one another represent hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z represents hydrogen; and n represents the number 0 or 1.

Preferably, the substructure of the formula (I-B) is a substructure which is selected from the group consisting of (I-B-1)

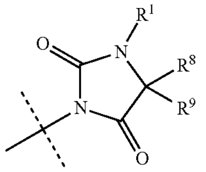

(I-B-4)

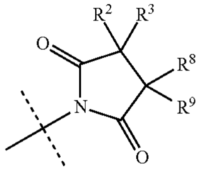

(I-B-5)

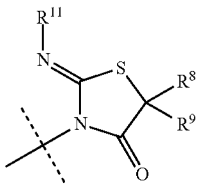

where $R^1$ and $R^{11}$ each independently of one another represent hydrogen, methyl, ethyl, propyl, isopropyl, cyclopropyl, cyclopropylmethyl, $CH_2CF_3$, $CH_2CHF_2$, $CH(CH_3)CF_3$, $CH_2CH_2CF_3$, $CH_2CH_2CHF_2$; or $R^2$, $R^3$, $R^8$ and $R^9$ each independently of one another represent hydrogen, methyl, trifluoromethyl or phenyl;

W represents hydrogen or halogen;

X, Y and Z each independently of one another represent hydrogen, halogen, cyano or nitro; or represent $(C_1-C_6)$alkyl; $(C_1-C_6)$alkoxy; halo$(C_1-C_6)$alkyl; halo$(C_1-C_6)$alkoxy, where the aforementioned radicals may optionally be substituted; and n represents the number 0 or 1.

Likewise preferably, the substructure of the formula (I-B) represents a substructure which is selected from the group consisting of (I-B-1)

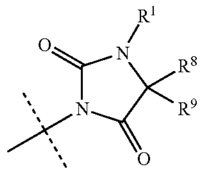

(I-B-4)

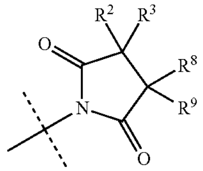

(I-B-5)

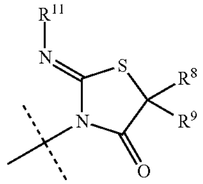

(I-B-2)

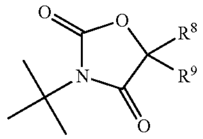

(I-B-6)

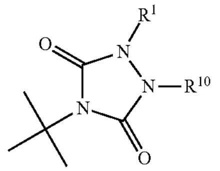

where $R^1$, $R^{10}$ and $R^{11}$ each independently of one another represent hydrogen, methyl, ethyl, propyl, isopropyl, n-butyl, cyclopropyl, cyclopropylmethyl, $CH_2CF_3$, $CH_2CHF_2$, $CH(CH_3)CF_3$, $CH_2CH_2CF_3$, $CH_2CH_2CHF_2$, $CH_2C(CH_3)_3$, $CH_2CH(CH_3)_2$, $CH_2CH{=}CH_2$ (=allyl), $CH_2CCH$ (=vinyl) or benzyl;

$R^2$, $R^3$, $R^8$ and $R^9$ each independently of one another represent hydrogen, methyl, trifluoromethyl or phenyl;

W represents hydrogen or fluorine;

X, Y and Z each independently of one another represent hydrogen; fluorine, bromine, chlorine, cyano or nitro; or represent $(C_1-C_6)$alkyl; $(C_1-C_6)$alkoxy; halo$(C_1-C_6)$alkyl; halo$(C_1-C_6)$alkoxy, where the aforementioned radicals may optionally be substituted; and n represents the number 0 or 1.

Likewise preferably, the substructure of the formula (I-B) represents a substructure which is selected from the group consisting of (I-B-1)

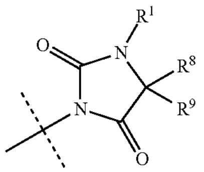

(I-B-4)

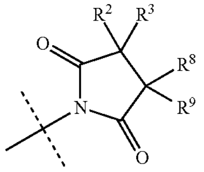

(I-B-5)

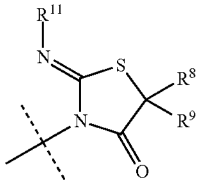

(I-B-2)

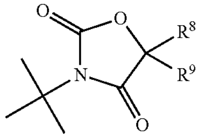

(I-B-6)

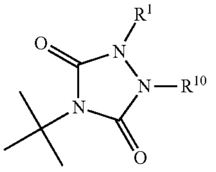

where $R^1$, $R^{10}$ and $R^{11}$ each independently of one another represent hydrogen, methyl, ethyl, propyl, isopropyl, n-butyl, cyclopropyl, cyclopropylmethyl, $CH_2CF_3$, $CH_2CHF_2$, $CH(CH_3)CF_3$, $CH_2CH_2CF_3$, $CH_2CH_2CHF_2$, $CH_2C(CH_3)_3$, $CH_2CH(CH_3)_2$, $CH_2CH{=}CH_2$ (=allyl), $CH_2CCH$ (=vinyl) or benzyl;

$R^2$, $R^3$, $R^8$ and $R^9$ each independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), $(CF_3,H)$;

Z represents hydrogen; and n represents the number 0 or 1.

If the substructure of the formula (I-B) is the substructure formula (I-B-1), it is preferable that $R^1$ represents hydrogen, methyl, ethyl, propyl, isopropyl, $CH_2CF_3$, cyclopropyl or cyclopropylmethyl;

$R^8$ and $R^9$ independently of one another represent hydrogen, methyl, trifluoromethyl or phenyl, W represents hydrogen or fluorine;

X represents hydrogen, chlorine, fluorine or methyl;

Y represents chlorine, bromine, cyano, methyl, trifluoromethyl, fluorine or methoxy;

X and Y represent in particular the following (Y,X) combinations: (Me, F), (Me,H), (Me,Cl), (Me,Me), (Cl,Cl), (Cl,F), (CN,F), (MeO,F), (MeO,H), (Cl,H), (Me,H), (Br, H), (Br,F), (CN,H), (F,F), $(CF_3,H)$;

Z represents hydrogen; and n represents the number 0 or 1.

In this context, it is particularly preferable that $R^1$ represents methyl;

$R^8$ and $R^9$ each represent methyl;

W represents fluorine;

X represents hydrogen or fluorine;

Y represents methyl;

Z represents hydrogen; and n represents the number 0 or 1.

If the substructure of the formula (I-B) is the substructure formula (I-B-1), it is likewise preferable that $R^1$ represents hydrogen, methyl, ethyl, propyl, isopropyl, n-butyl, $CH_2CF_3$, $CH_2CH{=}CH_2$, cyclopropyl, cyclopropylmethyl or benzyl;

$R^8$ and $R^9$ independently of one another represent hydrogen, methyl, trifluoromethyl or phenyl, W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), $(CF_3,H)$;

Z represents hydrogen; and n represents the number 0 or 1.

In this context, it is particularly preferable that $R^1$ represents methyl, n-butyl, $CH_2CH{=}CH_2$ or benzyl;

$R^8$ and $R^9$ each represent hydrogen or methyl;

W represents fluorine;

X represents hydrogen or fluorine;

Y represents methyl;

Z represents hydrogen; and n represents the number 0 or 1.

If the substructure of the formula (I-B) is the substructure formula (I-B-2), it is preferable that $R^8$ and $R^9$ independently of one another represent hydrogen, methyl, trifluoromethyl or phenyl, W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), $(CF_3,H)$;

Z represents hydrogen; and n represents the number 0 or 1.

In this context, it is particularly preferable that $R^8$ and $R^9$ independently of one another represent hydrogen or methyl;

W represents fluorine;

X represents fluorine;

Y represents methyl;

Z represents hydrogen; and n represents the number 0 or 1.

If the substructure of the formula (I-B) is the substructure formula (I-B-4), it is preferable that $R^2$, $R^3$, $R^8$ and $R^9$ each independently of one another independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl, fluorine or methoxy;

X and Y represent in particular the following (Y,X) combinations: (Me, F), (Me,H), (Me,Cl), (Me,Me), (Cl,Cl), (Cl,F), (CN,F), (MeO,F), (MeO,H), (Cl,H), (Me,H), (Br, H), (Br,F), (CN,H), (F,F), ($CF_3$,H);

Z represents hydrogen; and n represents the number 0 or 1.

In this context, it is particularly preferable that $R^2$, $R^3$, $R^8$ and $R^9$ represent hydrogen;

W represents fluorine;

X represents fluorine;

Y represents methyl;

Z represents hydrogen; and n represents the number 0 or 1.

If the substructure of the formula (I-B) is the substructure formula (I-B-5), it is preferable that $R^{11}$ represents hydrogen, methyl, ethyl, propyl, isopropyl, cyclopropyl, cyclopropylmethyl, $CH_2CF_3$, $CH_2CHF_2$, $CH(CH_3)CF_3$, $CH_2CH_2CF_3$, $CH_2CH_2CHF_2$;

$R^8$ and $R^9$ each independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl, fluorine or methoxy;

X and Y represent in particular the following (Y,X) combinations: (Me, F), (Me,H), (Me,Cl), (Me,Me), (Cl,Cl), (Cl,F), (CN,F), (MeO,F), (MeO,H), (Cl,H), (Me,H), (Br, H), (Br,F), (CN,H), (F,F), ($CF_3$,H);

Z represents hydrogen; and n represents the number 0 or 1.

In this context, it is particularly preferable that $R^{11}$ represents $CH_2CF_3$ or cyclopropyl;

$R^8$ and $R^9$ each represent methyl;

W represents fluorine;

X represents methyl or fluorine;

Y represents methyl;

Z represents hydrogen; and n represents the number 0 or 1.

If the substructure of the formula (I-B) is the substructure formula (I-B-5), it is likewise preferable that $R^1$ represents hydrogen, methyl, ethyl, propyl, isopropyl, $CH_2C(CH_3)_3$, $CH_2CH(CH_3)_2$, cyclopropyl, cyclopropylmethyl, $CH_2CF_3$, $CH_2CHF_2$, $CH(CH_3)CF_3$, $CH_2CH_2CF_3$, $CH_2CH_2CHF_2$;

$R^8$ and $R^9$ each independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), ($CF_3$,H);

Z represents hydrogen; and n represents the number 0 or 1.

In this context, it is likewise very particularly preferable that $R^{11}$ represents $CH_2C(CH_3)_3$, $CH_2CH(CH_3)_2$, $CH_2CF_3$ or cyclopropyl;

$R^8$ and $R^9$ each represent methyl;

W represents fluorine;

X represents methyl or fluorine;

Y represents methyl;

Z represents hydrogen; and n represents the number 0 or 1.

If the substructure of the formula (I-B) is the substructure formula (I-B-6), it is preferable that $R^1$ and $R^{10}$ each independently of one another represent hydrogen, methyl, ethyl, propyl, isopropyl, $CH_2CH{=}CH_2$, $CH_2CCH$, $CH_2CF_3$, cyclopropyl or cyclopropylmethyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), ($CF_3$,H);

Z represents hydrogen; and n represents the number 0 or 1.

In this context, it is particularly preferable that $R^1$ represents methyl, ethyl or $CH_2CH{=}CH_2$;

$R^{10}$ represents methyl, ethyl, isopropyl, $CH_2CH{=}CH_2$, $CH_2CCH$ or cyclopropylmethyl;

W represents fluorine;

X represents fluorine;

Y represents methyl;

Z represents hydrogen; and n represents the number 0 or 1.

Third Embodiment (I-C)

In a third embodiment of the present invention, the compounds according to the invention have a structure of the general formula (I) in which A and B together with the atoms to which they are attached represent a substructure of the formula (I-C)

(I-C)

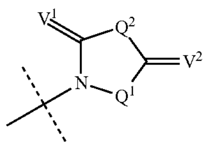

where $V^1$ and $V^2$ each independently of one another represent oxygen; sulfur, $NR_{11}$ or a salt of $NR_{11}$;

$Q^1$ represents oxygen, sulfur, $NR_1$ or $CR_2R_3$;

$Q^2$ represents $NR^{10}$ or $CR_8R_9$;

$R^1$ represents hydrogen, cyano or nitro; or represents $(C_1\text{-}C_6)$alkyl, $(C_3\text{-}C_6)$cycloalkyl$(C_1\text{-}C_6)$alkyl, halo$(C_2\text{-}C_6)$alkyl, cyano$(C_1\text{-}C_6)$alkyl, hydroxy$(C_1\text{-}C_6)$alkyl, $(C_1\text{-}C_6)$alkoxy$(C_1\text{-}C_6)$alkyl, amino$(C_1\text{-}C_6)$alkyl, $(C_1\text{-}C_6)$alkoxycarbonyl$(C_1\text{-}C_6)$alkyl, $(C_1\text{-}C_6)$alkylsulfanyl$(C_1\text{-}C_6)$alkyl, $(C_1\text{-}C_6)$alkylsulfinyl$(C_1\text{-}C_6)$alkyl, $(C_1\text{-}C_6)$alkylsulfonyl$(C_1\text{-}C_6)$alkyl, halo$(C_1\text{-}C_6)$alkylsulfanyl$(C_1\text{-}C_6)$alkyl, halo$(C_1\text{-}C_6)$alkylsulfinyl$(C_1\text{-}C_6)$alkyl, halo$(C_1\text{-}C_6)$alkylsulfonyl$(C_1\text{-}C_6)$alkyl, $(C_1\text{-}C_6)$alkoxy$(C_1\text{-}C_6)$alkylsulfanyl$(C_1\text{-}C_6)$alkyl, $(C_1\text{-}C_6)$alkoxy$(C_1\text{-}C_6)$alkylsulfinyl$(C_1\text{-}C_6)$alkyl, $(C_1\text{-}C_6)$ alkoxy($C_1$-$C_6$)alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$)alkyl, hetaryl($C_1$-$C_6$)alkyl, hetaryloxy($C_1$-$C_6$)alkyl, hetarylsulfanyl($C_1$-$C_6$)alkyl, hetarylsulfinyl($C_1$-$C_6$)alkyl, hetarylsulfonyl($C_1$-$C_6$)alkyl, ($C_1$-$C_6$)alkoxycarbonyl, aryloxycarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represent optionally substituted saturated or unsaturated ($C_3$-$C_6$)cycloalkyl which may optionally be interrupted by one or more heteroatoms; or represents halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represent optionally substituted phenyl or optionally substituted hetaryl; or represents ($C_1$-$C_6$)alkoxy, halo($C_1$-$C_6$)alkoxy, ($C_3$-$C_6$)cycloalkyloxy, aryloxy, aryl($C_1$-$C_6$)alkyloxy or carbonyloxy, where the aforementioned radicals may each optionally be substituted, or represents hydroxyl; or represents ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_3$-$C_6$)cycloalkyl($C_1$-$C_6$)alkylamino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represents ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, arylsulfanyl, arylsulfinyl, arylsulfonyl, aryl($C_1$-$C_6$)alkylsulfanyl, aryl($C_1$-$C_6$)alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^{10}$ and $R^{11}$ each independently of one another represent hydrogen, cyano or nitro; or represent ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylsulfanyl($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, halo($C_1$-$C_6$)alkylsulfanyl($C_1$-$C_6$)alkyl, halo($C_1$-$C_6$)alkylsulfinyl($C_1$-$C_6$)alkyl, halo($C_1$-$C_6$)alkylsulfonyl($C_1$-$C_6$)alkyl, ($C_1$-$C_6$)alkoxy($C_1$-$C_6$)alkylsulfanyl($C_1$-$C_6$)alkyl, ($C_1$-$C_6$)alkoxy($C_1$-$C_6$)alkylsulfinyl($C_1$-$C_6$)alkyl, ($C_1$-$C_6$)alkoxy($C_1$-$C_6$)alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$)alkyl, hetaryl($C_1$-$C_6$)alkyl, hetaryloxy($C_1$-$C_6$)alkyl, hetarylsulfanyl($C_1$-$C_6$)alkyl, hetarylsulfinyl($C_1$-$C_6$)alkyl, hetarylsulfonyl($C_1$-$C_6$)alkyl, ($C_1$-$C_6$)alkoxycarbonyl, aryloxycarbonyl, ($C_1$-$C_6$)alkylcarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represent optionally substituted saturated or unsaturated ($C_3$-$C_6$)cycloalkyl which may optionally be interrupted by one or more heteroatoms; or represent halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represent optionally substituted phenyl or optionally substituted hetaryl; or represent ($C_1$-$C_6$)alkoxy, halo($C_1$-$C_6$)alkoxy, ($C_3$-$C_6$)cycloalkyloxy, aryloxy, aryl($C_1$-$C_6$)alkyloxy or carbonyloxy, where the aforementioned radicals may each optionally be substituted, or represents hydroxyl; or represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_3$-$C_6$)cycloalkyl($C_1$-$C_6$)alkylamino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^2$, $R^3$, $R^8$ and $R^9$ each independently of one another represent hydrogen, cyano, halogen or nitro; or represent $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylthio$(C_1-C_6)$alkyl, halo$(C_1-C_6)$alkylthio$(C_1-C_6)$alkyl, $(C_1-C_6)$alkoxy$(C_1-C_6)$alkylthioalkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl or hetarylthio$(C_1-C_6)$alkyl, where the aforementioned radicals may each be saturated or unsaturated and/or optionally be substituted; or represent optionally substituted saturated or unsaturated $(C_3-C_6)$cycloalkyl which may optionally be interrupted by one or more heteroatoms; or represent $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represent carbonyl or carboxyl; or represent optionally substituted phenyl or optionally substituted hetaryl;

represent $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or represent hydroxyl; or represent $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N;

W represents hydrogen, fluorine or chlorine;

X, Y and Z each independently of one another represent hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;

or represent a benzyl, phenoxy, phenylthio, cyclopropylmethyl, cyclopropyloxy or cyclopropylthio, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or represent cyclopropyl, cyclobutyl, cyclopentyl, cyclohexyl or phenyl, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl; and n represents the number 0 or 1.

In a preferred configuration of this third embodiment, the substructure of the formula (I-C) represents a substructure which is selected from the group consisting of (I-C-1)

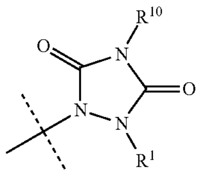

(I-C-2)

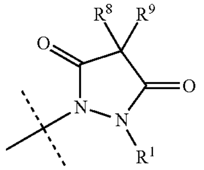

(I-C-3)

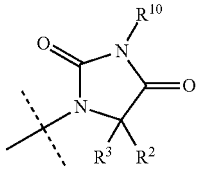

(I-C-4)

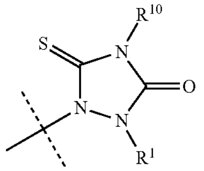

(I-C-5)

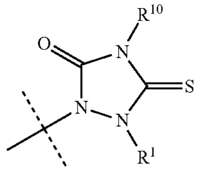

(I-C-6)

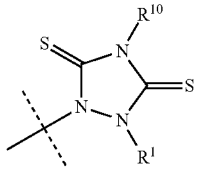

$R^1$ represents hydrogen or represents ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, ($C_1$-$C_6$)alkoxy($C_1$-$C_6$)alkyl, ($C_1$-$C_6$)alkoxycarbonyl($C_1$-$C_6$)alkyl, phenyl($C_1$-$C_6$)alkyl, hetaryl($C_1$-$C_6$)alkyl, ($C_2$-$C_6$)alkenyl, halo($C_2$-$C_6$)alkenyl, ($C_3$-$C_6$)cycloalkenyl($C_1$-$C_6$)alkyl, ($C_2$-$C_6$)alkynyl, where the aforementioned radicals may optionally be substituted; or represents optionally substituted ($C_3$-$C_6$)cycloalkyl, ($C_3$-$C_6$)cycloalkenyl, which may optionally be interrupted by one or more heteroatoms from the group of O, S and N; or represents halo($C_1$-$C_6$)alkylcarbonyl, ($C_1$-$C_6$)alkoxy($C_1$-$C_6$)alkylcarbonyl, ($C_1$-$C_6$)alkoxycarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, ($C_1$-$C_6$)alkylaminothiocarbonyl, di($C_1$-$C_6$)alkylaminothiocarbonyl, ($C_2$-$C_6$)alkenylcarbonyl, ($C_3$-$C_6$)cycloalkenyl($C_1$-$C_6$)alkylcarbonyl, ($C_2$-$C_6$)alkynylcarbonyl or aminothiocarbonyl, where the aforementioned radicals may each optionally be substituted, or represents carbonyl or carboxyl; or represent optionally substituted phenyl or optionally substituted hetaryl; or represents ($C_1$-$C_6$)alkoxy, halo($C_1$-$C_6$)alkoxy, ($C_3$-$C_6$)cycloalkyloxy, or carbonyloxy, where the aforementioned radicals may each optionally be substituted, or represents hydroxyl; or represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_1$-$C_6$)alkylcarbonylamino, ($C_1$-$C_6$)alkoxycarbonylamino, ($C_1$-$C_6$)alkylcarbamoylamino, ($C_1$-$C_6$)alkylsulfonylamino, ($C_2$-$C_6$)alkenylamino, ($C_3$-$C_6$)cycloalkenyl($C_1$-$C_6$)alkylamino, ($C_2$-$C_6$)alkynylamino, where the aforementioned radicals may each optionally be substituted, or represents amino; or represents ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfanyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted, or represents sulfanyl; and $R^{10}$ represents hydrogen; or represents ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, ($C_1$-$C_6$)alkoxy($C_1$-$C_6$)alkyl, ($C_1$-$C_6$)alkoxycarbonyl($C_1$-$C_6$)alkyl, phenyl($C_1$-$C_6$)alkyl, hetaryl($C_1$-$C_6$)alkyl, ($C_2$-$C_6$)alkenyl, halo($C_2$-$C_6$)alkenyl, ($C_3$-$C_6$)cycloalkenyl($C_1$-$C_6$)alkyl, ($C_2$-$C_6$)alkynyl, where the aforementioned radicals may optionally be substituted; or represents optionally substituted ($C_3$-$C_6$)cycloalkyl, ($C_3$-$C_6$)cycloalkenyl, which may optionally be interrupted by one or more heteroatoms from the group of O, S and N; or represents ($C_1$-$C_6$)alkylcarbonyl, halo($C_1$-$C_6$)alkylcarbonyl, ($C_1$-$C_6$)alkoxy($C_1$-$C_6$)alkylcarbonyl, ($C_1$-$C_6$)alkoxycarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, ($C_1$-$C_6$)alkylaminothiocarbonyl, di($C_1$-$C_6$)alkylaminothiocarbonyl, ($C_2$-$C_6$)alkenylcarbonyl, ($C_3$-$C_6$)cycloalkenyl($C_1$-$C_6$)alkylcarbonyl, ($C_2$-$C_6$)alkynylcarbonyl or aminothiocarbonyl, where the aforementioned radicals may each optionally be substituted, or represent carbonyl or carboxyl; or represent optionally substituted phenyl or optionally substituted hetaryl; or represents $(C_1-C_6)$alkoxy, halo$(C_1-C_6)$alkoxy, $(C_3-C_6)$cycloalkyloxy, or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulfonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or represents amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted, or represents sulfanyl; and $R^2$, $R^3$, $R^8$ and $R^9$ each independently of one another represent hydrogen, cyano, halogen or nitro; or represent $(C_1-C_6)$alkyl, $(C_3-C_6)$cycloalkyl$(C_1-C_6)$alkyl, halo$(C_1-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may each optionally be substituted; or represent optionally substituted $(C_3-C_6)$cycloalkyl, $(C_3-C_6)$cycloalkenyl, which may optionally be interrupted by one or more heteroatoms from the group of O, S and N; or represent $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or represent carbonyl or carboxyl; or represent optionally substituted phenyl or optionally substituted hetaryl; or represent $(C_1-C_6)$alkoxy, halo$(C_1-C_6)$alkoxy, $(C_1-C_6)$alkoxy$(C_1-C_6)$alkoxy, $(C_3-C_6)$cycloalkyloxy, $(C_3-C_6)$cycloalkyl$(C_1-C_6)$alkyloxy, $(C_2-C_6)$alkenyloxy, $(C_3-C_6)$cycloalkenyl$(C_1-C_6)$alkoxy, $(C_2-C_6)$alkynyloxy or carbonyloxy, where the aforementioned radicals may each optionally be substituted, or represent hydroxyl; or represent $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulfonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or represent amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted, or represent sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N;

W represents hydrogen or fluorine;

X and Y each independently of one another represent hydrogen, fluorine, chlorine, bromine, methyl, ethyl, trifluoromethyl, (2,2)-difluoromethyl, difluoromethoxy, trifluoromethoxy, cyclopropyl, cyano, amino, hydroxyl or nitro;

Z represents hydrogen; and n represents the number 0 or 1.

In this context, it is preferable that $R^1$ and $R^{10}$ each independently of one another represent hydrogen; or represent $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_2-C_6)$alkyl, $(C_1-C_6)$alkoxy$(C_1-C_6)$alkyl or phenyl$(C_1-C_3)$alkyl, where the aforementioned radicals may each optionally be substituted; or represents optionally substituted saturated or unsaturated $(C_3-C_6)$cycloalkyl or optionally substituted phenyl;

$R^2$, $R^3$, $R^8$ and $R^9$ each independently of one another represent hydrogen; or represent $(C_1-C_6)$alkyl, $(C_3-C_6)$cycloalkyl$(C_1-C_3)$alkyl, $(C_2-C_6)$alkenyl, $(C_2-C_6)$alkynyl, halo$(C_1-C_6)$alkyl, $(C_1-C_6)$alkoxy$(C_1-C_6)$alkyl or phenyl$(C_1-C_3)$alkyl, where the aforementioned radicals may each optionally be substituted; or represent optionally substituted saturated or unsaturated $(C_3-C_6)$cycloalkyl or optionally substituted phenyl; or W represents hydrogen or fluorine;

X and Y each independently of one another represent hydrogen, fluorine, chlorine, bromine, methyl, ethyl, trifluoromethyl, (2,2)-difluoromethyl, difluoromethoxy, trifluoromethoxy, cyclopropyl, cyano, amino, hydroxyl or nitro;

Z represents hydrogen; and n represents the number 0 or 1.

Preferably, the substructure of the formula (I-C) represents the substructure (I-C-I)

(I-C-1)

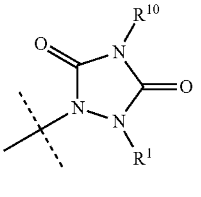

where $R^1$ and $R^{10}$ each independently of one another represent hydrogen, $(C_1\text{-}C_4)$alkyl, $(C_1\text{-}C_4)$haloalkyl or $(C_2\text{-}C_4)$alkenyl; or represent saturated or unsaturated $(C_3\text{-}C_6)$cycloalkyl, $(C_3\text{-}C_6)$cycloalkyl$(C_1\text{-}C_2)$alkyl, phenyl or phenyl$(C_1\text{-}C_2)$ alkyl, where the aforementioned radicals may each be mono- or polysubstituted by halogen, cyano, nitro, amino, hydroxy, methyl, ethyl, trifluoromethyl, difluoromethyl, trifluoroethyl, difluoroethyl, methoxy, ethoxy, trifluoromethoxy, trifluoroethoxy, trifluoroethylsulfanyl or optionally methyl-, fluorine-, chlorine-, cyano-substituted cyclopropyl;

W represents hydrogen or fluorine;

X represents hydrogen, chlorine, fluorine or methyl;

Y represents chlorine, bromine, cyano, methyl, trifluoromethyl, fluorine or methoxy;

X and Y represent in particular the following (Y,X) combinations: (Me, F), (Me,H), (Me,Cl), (Me,Me), (Cl,Cl), (Cl,F), (CN,F), (MeO,F), (MeO,H), (Cl,H), (Me,H), (Br, H), (Br,F), (CN,H), (F,F), $(CF_3,H)$;

Z represents hydrogen; and n represents the number 0 or 1.

Likewise preferably, the substructure of the formula (I-C) represents a substructure which is selected from the group consisting of (I-C-1)

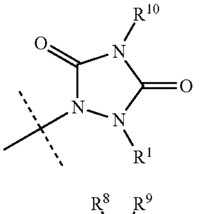

(I-C-2)

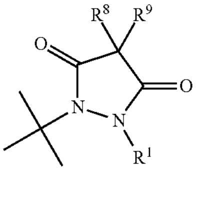

-continued (I-C-3)

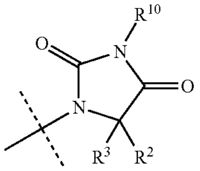

(I-C-5)

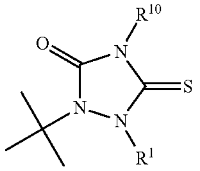

(I-C-6)

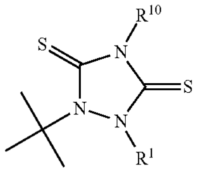

where $R^1$ and $R^{10}$ each independently of one another represent hydrogen, $(C_1\text{-}C_4)$alkyl, $(C_2\text{-}C_4)$haloalkyl, $(C_1\text{-}C_3)$alkoxy$(C_1\text{-}C_4)$alkyl or $(C_2\text{-}C_4)$alkenyl; or represent saturated or unsaturated $(C_3\text{-}C_6)$cycloalkyl, $(C_3\text{-}C_6)$cycloalkyl$(C_1\text{-}C_2)$alkyl, phenyl or phenyl$(C_1\text{-}C_2)$ alkyl, where the aforementioned radicals may each be mono- or polysubstituted by halogen, cyano, nitro, amino, hydroxy, methyl, ethyl, trifluoromethyl, difluoromethyl, trifluoroethyl, difluoroethyl, methoxy, ethoxy, trifluoromethoxy, trifluoroethoxy, trifluoroethylsulfanyl or optionally methyl-, fluorine-, chlorine-, cyano-substituted cyclopropyl;

$R^2$, $R^3$, $R^8$ and $R^9$ each independently of one another represent hydrogen; or represent $(C_1\text{-}C_6)$alkyl, $(C_2\text{-}C_6)$alkenyl, $(C_2\text{-}C_6)$alkynyl, halo$(C_1\text{-}C_6)$alkyl or phenyl$(C_1\text{-}C_3)$alkyl, where the aforementioned radicals may each be mono- or polysubstituted by halogen, cyano, nitro, amino, hydroxy, methyl, ethyl, trifluoromethyl, difluoromethyl, trifluoroethyl, difluoroethyl, methoxy, ethoxy, trifluoromethoxy, trifluoroethoxy, trifluoroethylsulfanyl or optionally methyl-, fluorine-, chlorine-, cyano-substituted cyclopropyl;

represent $(C_3\text{-}C_6)$cycloalkyl, or phenyl, where the aforementioned radicals may each be mono- or polysubstituted by halogen, cyano, nitro, amino, hydroxy, methyl, ethyl, trifluoromethyl, difluoromethyl, trifluoroethyl, difluoroethyl, methoxy, ethoxy, trifluoromethoxy, trifluoroethoxy, trifluoroethylsulfanyl or optionally methyl-, fluorine-, chlorine-, cyano-substituted cyclopropyl;

$R^2$ and $R^3$ together with the atom to which they are attached may form a cyclopropyl, cyclobutyl, cyclopentyl or cyclohexyl ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3\text{-}C_6)$cycloalkyl; or $R^8$ and $R^9$ together with the atom to which they are attached may form a cyclopropyl, cyclobutyl, cyclopentyl or cyclohexyl ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Me,H), (Br,H), (Br,F), (CN,H), (F,F), ($CF_3$,H);

Z represents hydrogen; and n represents the number 0 or 1.

If the substructure of the formula (I-C) is the substructure formula (I-C-1), it is preferable that $R^1$ represents hydrogen, methyl, ethyl, propyl, isopropyl, butyl, tert-butyl, isobutyl, 2-butyl, allyl, $CH_2CF_3$; or represents saturated or unsaturated cyclopropyl, cyclobutyl, cyclopentyl, cyclohexyl, cyclopentenyl, cyclohexenyl, cyclopropylmethyl, phenyl, benzyl, where the aforementioned radicals may each optionally be mono- or polysubstituted by halogen, methyl, ethyl, trifluoromethyl, difluoromethyl, trifluoroethyl, difluoroethyl, methoxy, ethoxy, trifluoromethoxy, trifluoroethoxy, trifluoroethylsulfanyl or optionally methyl-, fluorine-, chlorine-, cyano-substituted cyclopropyl;

$R^{10}$ represents methyl, ethyl, propyl, isopropyl, butyl, tert-butyl, isobutyl, 2-butyl, allyl, cyclopropyl, cyclopropylmethyl or phenyl which is optionally mono- or polysubstituted by halogen, methyl, trifluoromethyl, cyclopropyl, cyano;

W represents hydrogen or fluorine;

X represents hydrogen, chlorine, fluorine or methyl;

Y represents chlorine, bromine, cyano, methyl, trifluoromethyl, fluorine or methoxy;

X and Y represent in particular the following (Y,X) combinations: (Me, F), (Me,H), (Me,Cl), (Me,Me), (Cl,Cl), (Cl,F), (CN,F), (MeO,F), (MeO,H), (Cl,H), (Me,H), (Br, H), (Br,F), (CN,H), (F,F), ($CF_3$,H);

Z represents hydrogen; and n represents the number 0 or 1.

In this context, it is particularly preferable that $R^1$ represents hydrogen, cyclopentyl, cyclohex-2-en-1-yl, methyl, ethyl, $CH_2CH(CH_3)_2$, $CH(CH_3)CH_2CH_3$, $CH(CH_3)_2$, $CH_2$-cyclopropyl, $CH_2CH{=}CH_2$, benzyl, 4-cyano-2,5-difluorophenyl, 3-(2,2,2-trifluoroethylsulfinyl)-4-methylphenyl, 3-(2,2,2-trifluoroethylsulfanyl)-4-methylphenyl or (2-chlorophenyl)methyl;

$R^{10}$ represents methyl, ethyl, $CH_2CH{=}CH_2$, $CH(CH_3)_2$, $C(CH_3)_3$, cyclopropyl, phenyl or 3-(trifluoromethyl)phenyl;

W represents fluorine;

X represents hydrogen, fluorine or methyl;

Y represents bromine, chlorine, fluorine, cyano, methyl, methoxy or $CF_3$;

Z represents hydrogen; and n represents the number 0 or 1.

If the substructure of the formula (I-C) is the substructure formula (I-C-1), it is likewise preferable that $R^1$ represents hydrogen, methyl, ethyl, propyl, isopropyl, butyl, tert-butyl, isobutyl, 2-butyl, allyl, $CH_2CF_3$; or represents saturated or unsaturated cyclopropyl, cyclobutyl, cyclopentyl, cyclohexyl, cyclopentenyl, cyclohexenyl, cyclopropylmethyl, phenyl or benzyl, where the aforementioned radicals may each optionally be mono- or polysubstituted by cyano, halogen, methyl, ethyl, trifluoromethyl, difluoromethyl, trifluoroethyl, difluoroethyl, methoxy, ethoxy, trifluoromethoxy, trifluoroethoxy, trifluoroethylsulfanyl, trifluoroethylsulfinyl or optionally methyl-, fluorine-, chlorine-, cyano-substituted cyclopropyl;

$R^{10}$ represents methyl, ethyl, propyl, isopropyl, butyl, tert-butyl, isobutyl, 2-butyl, $CH_2CHF_2$, $CH_2CH_2CH_2OCH_3$, allyl, cyclopropyl, cyclohexyl, cyclopropylmethyl or phenyl which is optionally mono- or polysubstituted by halogen, methyl, trifluoromethyl, cyclopropyl, cyano;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), ($CF_3$,H);

Z represents hydrogen; and n represents the number 0 or 1.

In this context, it is likewise very particularly preferable that $R^1$ represents hydrogen, cyclopentyl, cyclohex-2-en-1-yl, methyl, ethyl, propyl, $CH_2CH(CH_3)_2$, $CH(CH_3)CH_2CH_3$, $CH(CH_3)_2$, $C(CH_3)_3$, cyclopropylmethyl, $CH_2CH{=}CH_2$, $CH_2CF_3$, benzyl, 4-cyano-2,5-difluorophenyl, 3-(2,2,2-trifluoroethylsulfinyl)-4-methylphenyl, 3-(2,2,2-trifluoroethylsulfanyl)-4-methylphenyl or (2-chlorophenyl)methyl;

$R^{10}$ represents methyl, ethyl, propyl, $CH_2CH{=}CH_2$, $CH(CH_3)_2$, $C(CH_3)_3$, $CH_2CHF_2$, $CH_2CH_2CH_2OCH_3$, cyclopropyl, cyclohexyl, phenyl, 3-chlorophenyl or 3-(trifluoromethyl)phenyl;

W represents fluorine;

X represents hydrogen, fluorine or methyl;

Y represents bromine, chlorine, fluorine, cyano, methyl or $CF_3$;

X and Y represent in particular the following (Y,X) combinations: (Me, F), (Me,H), (Me,Me), (Cl,F), (Cl,H), (Br, H), (Br,F), (CN,H), (F,F), ($CF_3$,H);

Z represents hydrogen; and n represents the number 0 or 1.

If the substructure of the formula (I-C) is the substructure formula (I-C-2), it is preferable that $R^1$ represents hydrogen, methyl, ethyl, propyl, isopropyl, butyl, tert-butyl, isobutyl, 2-butyl, allyl, $CH_2CF_3$; or represents saturated or unsaturated cyclopropyl, cyclobutyl, cyclopentyl, cyclohexyl, cyclopentenyl, cyclohexenyl, cyclopropylmethyl, phenyl, benzyl, where the aforementioned radicals may each optionally be mono- or polysubstituted by cyano, halogen, methyl, ethyl, trifluoromethyl, difluoromethyl, trifluoroethyl, difluoroethyl, methoxy, ethoxy, trifluoromethoxy, trifluoroethoxy, trifluoroethylsulfanyl or optionally methyl-, fluorine-, chlorine-, cyano-substituted cyclopropyl;

$R^8$ and $R^9$ independently of one another represent hydrogen, methyl, ethyl, trifluoromethyl or phenyl; or form a cyclobutyl ring;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), $(CF_3,H)$;

Z represents hydrogen; and n represents the number 0 or 1.

In this context, it is particularly preferable that $R^1$ represents methyl, benzyl or phenyl;

$R^8$ and $R^9$ each represent methyl or ethyl; or form a cyclobutyl ring;

W represents fluorine;

X represents hydrogen, fluorine or methyl;

Y represents bromine, chlorine, fluorine, cyano, methyl or $CF_3$;

Z represents hydrogen; and n represents the number 0 or 1.

If the substructure of the formula (I-C) is the substructure formula (I-C-3), it is preferable that $R^{10}$ represents methyl, ethyl, propyl, isopropyl, butyl, tert-butyl, isobutyl, 2-butyl, $CH_2CHF_2$, $CH_2CH_2CH_2OCH_3$, allyl, cyclopropyl, cyclohexyl, cyclopropylmethyl or phenyl which is optionally mono- or polysubstituted by halogen, methyl, trifluoromethyl, cyclopropyl, cyano;

$R^2$ and $R^3$ independently of one another represent hydrogen, methyl, ethyl, trifluoromethyl or phenyl; or form a cyclopropyl or a cyclobutyl ring;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), $(CF_3,H)$;

Z represents hydrogen; and n represents the number 0 or 1.

In this context, it is particularly preferable that $R^{10}$ represents methyl or cyclopropyl;

$R^2$ and $R^3$ independently of one another represent hydrogen or methyl;

W represents fluorine;

X represents fluorine;

Y represents methyl;

Z represents hydrogen; and n represents the number 0 or 1.

If the substructure of the formula (I-C) is the substructure formula (I-C-5), it is preferable that $R^1$ represents hydrogen, methyl, ethyl, isopropyl, tert-butyl, isobutyl or trifluoromethyl; or represents cyclopropyl, cyclobutyl, cyclopropylmethyl, phenyl or benzyl, where the aforementioned radicals may each optionally be mono- or polysubstituted by cyano, halogen, methyl, ethyl, trifluoromethyl, difluoromethyl, trifluoroethyl, difluoroethyl, methoxy, ethoxy, trifluoromethoxy, trifluoroethoxy, trifluoroethylsulfanyl, trifluoroethylsulfinyl or cyclopropyl which is optionally monosubstituted by methyl, fluorine, chlorine or cyano;

$R^{10}$ represents hydrogen, methyl, ethyl, propyl, isopropyl, tert-butyl, isobutyl, trifluoromethyl or allyl; or represents saturated or unsaturated cyclopropyl, cyclobutyl, cyclopropylmethyl, phenyl or benzyl, where the aforementioned radicals may each optionally be mono- or polysubstituted by cyano, halogen, methyl, ethyl, trifluoromethyl, difluoromethyl, trifluoroethyl, difluoroethyl, methoxy, ethoxy, trifluoromethoxy, trifluoroethoxy, trifluoroethylsulfanyl, or optionally methyl-, fluorine-, chlorine-, cyano-substituted cyclopropyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), $(CF_3,H)$;

Z represents hydrogen; and n represents the number 0 or 1.

In this context, it is particularly preferable that $R^1$ represents methyl;

$R^{10}$ represents cyclopropyl;

W represents fluorine;

X represents fluorine;

Y represents methyl;

Z represents hydrogen; and n represents the number 0 or 1.

If the substructure of the formula (I-C) is the substructure formula (I-C-6), it is preferable that $R^1$ represents hydrogen, methyl, ethyl, isopropyl, tert-butyl, isobutyl or trifluoromethyl; or represents cyclopropyl, cyclobutyl, cyclopropylmethyl, phenyl or benzyl, where the aforementioned radicals may each optionally be mono- or polysubstituted by cyano, halogen, methyl, ethyl, trifluoromethyl, difluoromethyl, trifluoroethyl, difluoroethyl, methoxy, ethoxy, trifluoromethoxy, trifluoroethoxy, trifluoroethylsulfanyl, trifluoroethylsulfinyl or cyclopropyl which is optionally monosubstituted by methyl, fluorine, chlorine or cyano;

$R^{10}$ represents hydrogen, methyl, ethyl, propyl, isopropyl, tert-butyl, isobutyl, trifluoromethyl or allyl; or represents saturated or unsaturated cyclopropyl, cyclobutyl, cyclopropylmethyl, phenyl or benzyl, where the aforementioned radicals may each optionally be mono- or polysubstituted by cyano, halogen, methyl, ethyl, trifluoromethyl, difluoromethyl, trifluoroethyl, difluoroethyl, methoxy, ethoxy, trifluoromethoxy, trifluoroethoxy, trifluoroethylsulfanyl, or optionally methyl-, fluorine-, chlorine-, cyano-substituted cyclopropyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), $(CF_3,H)$;

Z represents hydrogen; and n represents the number 0 or 1.

In this context, it is particularly preferable that $R^1$ represents methyl;

$R^{10}$ represents cyclopropyl;

W represents fluorine;

X represents fluorine;

Y represents methyl;

Z represents hydrogen; and n represents the number 0 or 1.

Fourth Embodiment (I-D)

In a fourth embodiment of the present invention, the compounds according to the invention have a structure of the general formula (I) in which A and B together with the atoms to which they are attached represent a substructure of the formula (I-D)

(I-D)

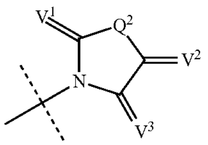

where $V^1$, $V^2$ and $V^3$ each independently of one another represent oxygen; sulfur, $NR_{11}$ or a salt of $NR_{11}$;

$Q^2$ represents $NR^{10}$ or $CR^8R^9$;

$R^{10}$ represents hydrogen, cyano or nitro; or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl, hetarylsulfanyl$(C_1-C_6)$alkyl, hetarylsulfinyl$(C_1-C_6)$alkyl, hetarylsulfonyl$(C_1-C_6)$alkyl, $(C_1-C_6)$alkoxycarbonyl, aryloxycarbonyl, $(C_1-C_6)$alkylcarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated $(C_3-C_6)$cycloalkyl which may optionally be interrupted by one or more heteroatoms; or represents halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl($(C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represents carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$(C_1-C_6)$alkylamino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represents amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represents sulfanyl; and $R^8$ and $R^9$ each independently of one another represent hydrogen, cyano, halogen or nitro; or represent $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylthio$(C_1-C_6)$alkyl, halo$(C_1-C_6)$alkylthio$(C_1-C_6)$alkyl, $(C_1-C_6)$alkoxy$(C_1-C_6)$alkylthioalkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl or hetarylthio$(C_1-C_6)$alkyl, where the aforementioned radicals may each be saturated or unsaturated and/or optionally be substituted; or represent optionally substituted saturated or unsaturated $(C_3-C_6)$cycloalkyl which may optionally be interrupted by one or more heteroatoms; or represent $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl($(C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represent carbonyl or carboxyl; or represent optionally substituted phenyl or optionally substituted hetaryl;

represent $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or represent hydroxyl; or represent $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl($(C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N;

W represents hydrogen, fluorine or chlorine;

X, Y and Z each independently of one another represent hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;

or represent a benzyl, phenoxy, phenylthio, cyclopropylmethyl, cyclopropyloxy or cyclopropylthio, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or represent cyclopropyl, cyclobutyl, cyclopentyl, cyclohexyl or phenyl, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl; and n represents the number 0 or 1.

In a preferred configuration of this fourth embodiment, the substructure of the formula (I-D) is a substructure which is selected from the group consisting of (I-D-1)

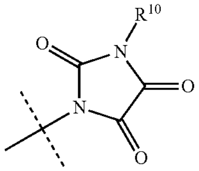

(I-D-2)

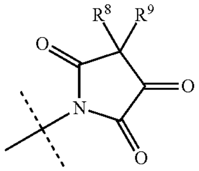

(I-D-3)

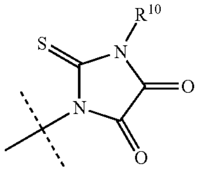

where $R^{10}$ represents hydrogen or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may optionally be substituted; or represents optionally substituted $(C_3-C_6)$cycloalkyl, $(C_3-C_6)$cycloalkenyl, which may optionally be interrupted by one or more heteroatoms from the group of O, S and N; or represents $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or represents carbonyl or carboxyl; or represents optionally substituted phenyl or optionally substituted hetaryl; or represents ($C_1$-$C_6$)alkoxy, halo($C_1$-$C_6$)alkoxy, ($C_3$-$C_6$)cycloalkyloxy, or carbonyloxy, where the aforementioned radicals may each optionally be substituted, or represents hydroxyl; or represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_1$-$C_6$)alkylcarbonylamino, ($C_1$-$C_6$)alkoxycarbonylamino, ($C_1$-$C_6$)alkylcarbamoylamino, ($C_1$-$C_6$)alkylsulfonylamino, ($C_2$-$C_6$)alkenylamino, ($C_3$-$C_6$)cycloalkenyl ($C_1$-$C_6$)alkylamino, ($C_2$-$C_6$)alkynylamino, where the aforementioned radicals may each optionally be substituted, or represents amino; or represents ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo ($C_1$-$C_6$)alkylsulfinyl, halo($C_1$-$C_6$)alkylsulfanyl, ($C_3$-$C_6$)cycloalkyl($C_1$-$C_6$)alkylsulfanyl, ($C_3$-$C_6$)cycloalkyl ($C_1$-$C_6$)alkylsulfinyl, ($C_3$-$C_6$)cycloalkyl($C_1$-$C_6$) alkylsulfonyl, aminosulfonyl, ($C_1$-$C_6$) alkylaminosulfonyl, di($C_1$-$C_6$)alkylaminosulfonyl or arylaminosulfonyl, where the aforementioned radicals may each optionally be substituted, or represents sulfanyl; and $R^8$ and $R^9$ each independently of one another represent hydrogen, cyano, halogen or nitro; or represent ($C_1$-$C_6$)alkyl, ($C_3$-$C_6$)cycloalkyl($C_1$-$C_6$)alkyl, halo($C_1$-$C_6$)alkyl, cyano($C_1$-$C_6$)alkyl, ($C_1$-$C_6$)alkoxy ($C_1$-$C_6$)alkyl, ($C_1$-$C_6$)alkoxycarbonyl($C_1$-$C_6$)alkyl, ($C_1$-$C_6$)alkylsulfanyl($C_1$-$C_6$)alkyl, ($C_1$-$C_6$)alkylsulfinyl($C_1$-$C_6$)alkyl, phenyl($C_1$-$C_6$)alkyl, hetaryl($C_1$-$C_6$) alkyl, ($C_2$-$C_6$)alkenyl, halo($C_2$-$C_6$)alkenyl, ($C_3$-$C_6$)cycloalkenyl($C_1$-$C_6$)alkyl, ($C_2$-$C_6$)alkynyl, where the aforementioned radicals may each optionally be substituted; or represent optionally substituted ($C_3$-$C_6$)cycloalkyl, ($C_3$-$C_6$)cycloalkenyl, which may optionally be interrupted by one or more heteroatoms from the group of O, S and N; or represent ($C_1$-$C_6$)alkylcarbonyl, halo($C_1$-$C_6$)alkylcarbonyl, ($C_1$-$C_6$)alkoxy($C_1$-$C_6$)alkylcarbonyl, ($C_1$-$C_6$) alkoxycarbonyl, halo($C_1$-$C_6$)alkoxycarbonyl, aminocarbonyl, ($C_1$-$C_6$)alkylaminocarbonyl, di($C_1$-$C_6$) alkylaminocarbonyl, ($C_3$-$C_6$)cycloalkylaminocarbonyl, ($C_1$-$C_6$)alkylaminothiocarbonyl, di($C_1$-$C_6$)alkylaminothiocarbonyl, ($C_2$-$C_6$)alkenylcarbonyl, ($C_3$-$C_6$)cycloalkenyl($C_1$-$C_6$)alkylcarbonyl, ($C_2$-$C_6$)alkynylcarbonyl or aminothiocarbonyl, where the aforementioned radicals may each optionally be substituted, or represent carbonyl or carboxyl; or represent optionally substituted phenyl or optionally substituted hetaryl; or represent ($C_1$-$C_6$)alkoxy, halo($C_1$-$C_6$)alkoxy, ($C_1$-$C_6$) alkoxy($C_1$-$C_6$)alkoxy, ($C_3$-$C_6$)cycloalkyloxy, ($C_3$-$C_6$) cycloalkyl($C_1$-$C_6$)alkyloxy, ($C_2$-$C_6$)alkenyloxy, ($C_3$-$C_6$)cycloalkenyl($C_1$-$C_6$)alkoxy, ($C_2$-$C_6$)alkynyloxy or carbonyloxy, where the aforementioned radicals may each optionally be substituted, or represent hydroxyl; or represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_1$-$C_6$)alkylcarbonylamino, ($C_1$-$C_6$)alkoxycarbonylamino, ($C_1$-$C_6$)alkylcarbamoylamino, ($C_1$-$C_6$)alkylsulfonylamino, ($C_2$-$C_6$)alkenylamino, ($C_3$-$C_6$)cycloalkenyl ($C_1$-$C_6$)alkylamino, ($C_2$-$C_6$)alkynylamino, where the aforementioned radicals may each optionally be substituted, or represents amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfanyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$) alkylsulfonyl, aminosulfonyl, ($C_1$-$C_6$) alkylaminosulfonyl, di($C_1$-$C_6$)alkylaminosulfonyl or arylaminosulfonyl, where the aforementioned radicals may each optionally be substituted, or represent sulfanyl; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N;

W represents hydrogen or fluorine;

X and Y each independently of one another represent hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z represents hydrogen; and n represents the number 0 or 1.

In this context, it is preferable that $R^{10}$ represents hydrogen; or represents ($C_1$-$C_6$)alkyl, ($C_3$-$C_6$)cycloalkyl($C_1$-$C_3$)alkyl, ($C_2$-$C_6$)alkenyl, ($C_2$-$C_6$)alkynyl, halo($C_2$-$C_6$)alkyl, ($C_1$-$C_6$)alkoxy($C_1$-$C_6$)alkyl or phenyl($C_1$-$C_3$)alkyl, where the aforementioned radicals may each optionally be substituted; or represents optionally substituted saturated or unsaturated ($C_3$-$C_6$)cycloalkyl or optionally substituted phenyl;

$R^8$ and $R^9$ each independently of one another represent hydrogen; or represent ($C_1$-$C_6$)alkyl, ($C_3$-$C_6$)cycloalkyl($C_1$-$C_3$)alkyl, ($C_2$-$C_6$)alkenyl, ($C_2$-$C_6$)alkynyl, halo($C_1$-$C_6$)alkyl, ($C_1$-$C_6$)alkoxy($C_1$-$C_6$)alkyl or phenyl($C_1$-$C_3$)alkyl, where the aforementioned radicals may each optionally be substituted; or represent optionally substituted saturated or unsaturated ($C_3$-$C_6$)cycloalkyl or optionally substituted phenyl; or W represents hydrogen or fluorine;

X and Y independently of one another represent hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z represents hydrogen; and n represents the number 0 or 1.

Preferably, the substructure of the formula (I-D) represents the substructure (I-D-I)

(I-D-1)

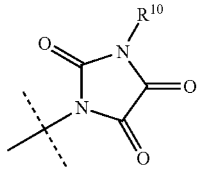

where $R^{10}$ represents hydrogen, methyl, ethyl, propyl, isopropyl, cyclopropylmethyl, $CH_2CF_3$, $CH_2CHF_2$, $CH(CH_3)CF_3$, $CH_2CH_2CF_3$, $CH_2CH_2CHF_2$ or optionally methyl-, fluorine-, chlorine-, cyano-substituted cyclopropyl;

W represents hydrogen or fluorine;

X represents hydrogen, chlorine, fluorine or methyl;

Y represents chlorine, bromine, cyano, methyl, trifluoromethyl, fluorine or methoxy;

X and Y represent in particular the following (Y,X) combinations: (Me, F), (Me,H), (Me,Cl), (Me,Me), (Cl,Cl), (Cl,F), (CN,F), (MeO,F), (MeO,H), (Cl,H), (Me,H), (Br, H), (Br,F), (CN,H), (F,F), ($CF_3$,H);

Z represents hydrogen; and n represents the number 0 or 1.

Likewise preferably, the substructure of the formula (I-D) represents a substructure which is selected from the group consisting of (I-D-1)

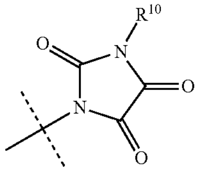

(I-D-3)

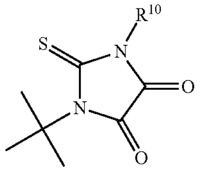

where $R^{10}$ represents hydrogen, methyl, ethyl, propyl, isopropyl, tert-butyl, cyclopropylmethyl, $CH_2CH(CH_3)_2$, $CH_2C(CH_3)_3$, $CH_2CF_3$, $CH_2CHF_2$, $CH(CH_3)CF_3$, $CH_2CH_2CF_3$, $CH_2CH_2CHF_2$ or optionally methyl-, fluorine-, chlorine-, cyano-substituted cyclopropyl or optionally methyl-, fluorine-, chlorine-, cyano-substituted cyclohexyl or optionally methyl-, fluorine-, chlorine-, cyano-substituted cyclopropylmethyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Me,H), (Br,H), (Br,F), (CN,H), (F,F), ($CF_3$,H);

Z represents hydrogen; and n represents the number 0 or 1.

If the substructure of the formula (I-D) is the substructure formula (I-D-1), it is preferable that $R^{10}$ represents hydrogen, methyl, ethyl, $CH_2CF_3$, $CH_2CHF_2$, $CH(CH_3)CF_3$, $CH_2CH_2CF_3$, $CH_2CH_2CHF_2$, cyclopropyl or cyclopropylmethyl;

W represents hydrogen or fluorine;

X represents hydrogen, chlorine, fluorine or methyl;

Y represents chlorine, bromine, cyano, methyl, trifluoromethyl, fluorine or methoxy;

X and Y represent in particular the following (Y,X) combinations: (Me, F), (Me,H), (Me,Cl), (Me,Me), (Cl,Cl), (Cl,F), (CN,F), (MeO,F), (MeO,H), (Cl,H), (Me,H), (Br, H), (Br,F), (CN,H), (F,F), ($CF_3$,H);

Z represents hydrogen;

n represents the number 0 or 1.

In this context, it is particularly preferable that $R^{10}$ represents $CH_2CHF_2$ or cyclopropyl;

W represents fluorine;

X represents hydrogen or fluorine;

Y represents methyl;

Z represents hydrogen; and n represents the number 0 or 1.

If the substructure of the formula (I-D) is the substructure formula (I-D-1), it is likewise preferable that $R^{10}$ represents hydrogen, methyl, ethyl, $CH_2CF_3$, $CH_2CHF_2$, $CH(CH_3)CF_3$, $CH_2CH_2CF_3$ or $CH_2CH_2CHF_2$, cyclopropyl, cyclohexyl or cyclopropylmethyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), ($CF_3$,H);

Z represents hydrogen;

n represents the number 0 or 1.

In this context, it is likewise very particularly preferable that $R^{10}$ represents $CH_2CHF_2$, cyclopropyl or cyclohexyl;

W represents fluorine;

X represents hydrogen, methyl or fluorine;

Y represents methyl;

X and Y represent in particular the following (Y,X) combinations: (Me, F), (Me,H), (Me,Me);

Z represents hydrogen; and n represents the number 0 or 1.

If the substructure of the formula (I-D) is the substructure formula (I-D-3), it is preferable that $R^{10}$ represents hydrogen, methyl, ethyl, tert-butyl, $CH_2CH(CH_3)_2$, $CH_2C(CH_3)_3$, $CH_2CF_3$, $CH_2CHF_2$, $CH(CH_3)CF_3$, $CH_2CH_2CF_3$, $CH_2CH_2CHF_2$, cyclopropyl or cyclopropylmethyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me,Cl), (Me,Me), (Cl,Cl), (Cl,F), (CN,F), (Cl,H), (Br,H), (Br,F), (CN,H), (F,F), ($CF_3$,H);

Z represents hydrogen;

n represents the number 0 or 1.

In this context, it is particularly preferable that $R^{10}$ represents tert-butyl, $CH_2CH(CH_3)_2$, $CH_2C(CH_3)_3$ or $CH_2CF_3$;

W represents fluorine;

X represents methyl or fluorine;

Y represents methyl;

X and Y represent in particular the following (Y,X) combinations: (Me,F), (Me,Me);

Z represents hydrogen; and n represents the number 0 or 1.

The above-recited general radical definitions and elucidations or those recited in preference ranges may be combined arbitrarily with one another, in other words including combinations between the respective ranges and preference ranges. They apply both to the end products and, correspondingly, to the precursors and intermediates.

Preference according to the invention is given to the compounds of the formula (I) which contain a combination of the meanings listed above as being preferred.

Process P1

Process P1 includes all the methods which—usually in a multistage process—enable formation of the 5-membered ring, especially proceeding from the anilines of the general formula (IVa), according to the following scheme:

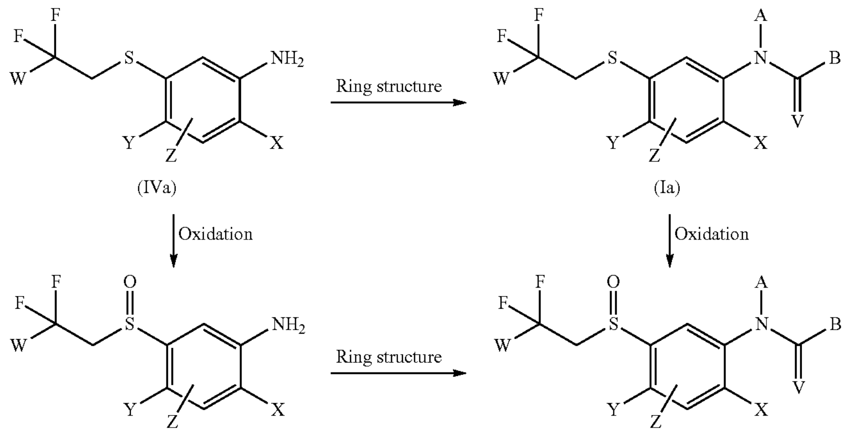

(IVa) (Ia)
(IVb) (Ib)

Particular preference according to the invention is given to the compounds of the formula (I) which contain a combination of the meanings listed above as being particularly preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Unless indicated otherwise, optionally substituted radicals may be mono- or polysubstituted, where the substituents in the case of polysubstitutions may be the same or different.

In the context of the present invention, halogen is fluorine, chlorine, bromine and iodine, more preferably fluorine, chlorine and bromine and most preferably fluorine and chlorine.

In addition, alkyl is straight-chain or branched $C_1$- to $C_8$-alkyl, preferably straight-chain or branched $C_1$- to $C_6$-alkyl, further preferably straight-chain or branched $C_1$- to $C_4$-alkyl, especially methyl and ethyl.

Alkoxy is straight-chain or branched $C_1$- to $C_8$-alkoxy, preferably straight-chain or branched $C_1$- to $C_6$-alkoxy, further preferably straight-chain or branched $C_1$- to $C_4$-alkoxy, in particular methoxy.

Haloalkyl and haloalkoxy arise from substituted alkyl and alkoxy radicals in accordance with the above definition.

Alkyl radicals in cycloalkyl, alkoxycarbonyl, alkylthioalkyl, alkylsulfinylalkyl, phenylalkyl, hetarylalkyl and alkylsulfonylalkyl likewise arise from the above definition of alkyl.

Preparation Processes

The compounds of the general formula (I) can be divided into compounds with n=0 (Ia) and n=1 (Ib) and can be prepared according to the following schemes.

The compounds of the general formula (I) can be divided into compounds with n=0 (Ia) and n=1 (Ib) and can in principle be prepared by the general processes P1, P2, P3 and P3'.

where X, Y, Z, A, B and V are as defined above.

By oxidation of the thioethers of the general formula (Ia) by methods known from the literature, it is possible to obtain the sulfoxides of the general formula (Ib).

Alternatively, some of the methods described in Process P1 can also be employed proceeding from sulfoxides of the general formula (IVb) to give the sulfoxides of the general formula (Ib). The sulfoxides of the formula (IVb) can be prepared from the sulfides (IVa) by methods known from the literature.

Process P1 is especially suitable for preparation of embodiments I-A to I-D.

Process P2

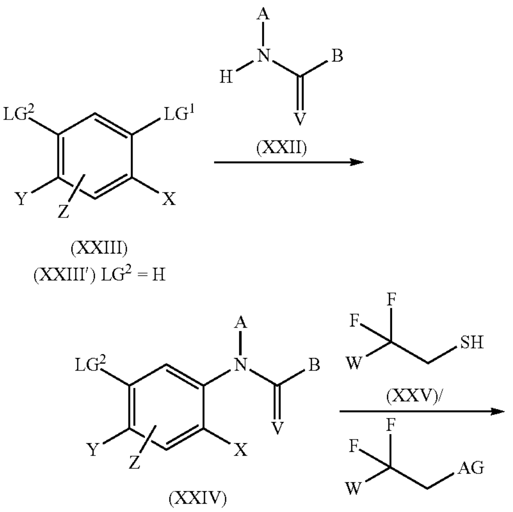

(XXIII)
(XXIII') $LG^2$ = H
(XXIV)
(XXIV') $LG^2$ = H
(XV)

-continued

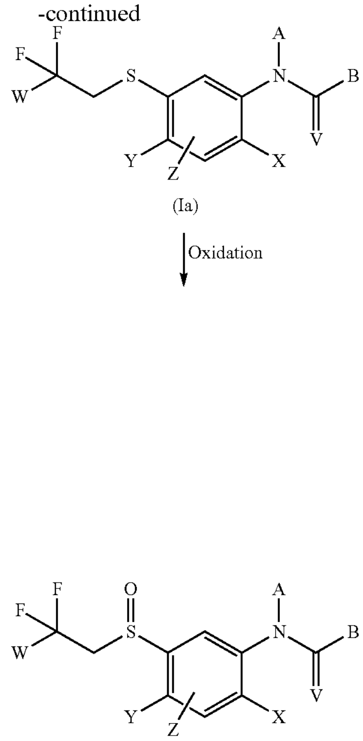

(Ia)
(Ib)

where Z, A, B, V and W are as defined above, X represents hydrogen or an electron-withdrawing group (especially nitro, chlorine, fluorine, cyano), Y represents electron-withdrawing substituents (especially nitro, chlorine, fluorine, cyano), $LG^1$ represents typical leaving groups in nucleophilic substitution reactions (especially fluoride, chloride) and $LG^2$ may represent hydrogen or typical leaving groups in nucleophilic substitution reactions (especially fluoride, chloride).

The reaction of compounds of the general formula (XXIII) with heterocyclic compounds of the general formula (XXII), usually under basic reaction conditions as, for example, in U.S. Pat. No. 6,906,006 and DE 19500439 for triazolinones, WO 2010/0119194 for hydantoins, DE 4431218 for pyrimidin(ethi) ones, WO 2009/012275 and WO 2008/155034 for pyridones or DE 19528305 for uracils, gives the compounds of the general formula (XXIV). Through another nucleophilic aromatic substitution with thiols of the general formula (XXV), the thioethers of the formula (Ia) can be prepared. Suitable reaction conditions for such reactions are described in WO 2007/131680 and WO 2008/086226.

By oxidation of the thioethers of the general formula (Ia) by methods known from the literature, it is possible to obtain the sulfoxides of the general formula (Ib).

Compounds of the formula (XXIII) in which $LG^2$ is hydrogen are referred to as (XXIII') and can be reacted in a manner similar to that described above with compounds of the formula (XXII), in this case to give compounds of the formula (XXIV').

Some compounds of the formula (XXIV') are commercially available.

The compounds of the formula (XXIV') can be converted in a multistage process to the compounds (Ia) according to the invention. The steps required include chlorosulfonation, reduction and alkylation with haloalkyl electrophiles of the formula (XV), all possible by methods known from the literature. The chlorosulfonation of the compounds (XXIV') with chlorosulfonic acid gives the corresponding sulfonyl chlorides and these can be converted to their disulfides by methods known from the literature, for example iron in hydrochloric acid or iodide. The reaction of the disulfides with haloalkyl electrophiles of the formula (XV) gives the sulfides (Ia).

By oxidation of the thioethers of the general formula (Ia) by methods known from the literature, it is possible to obtain the sulfoxides of the general formula (Ib).

Here, $LG^1$ and $LG^2$ represent typical leaving groups in nucleophilic substitution reactions such as, for example, fluoride or chloride, X and Y in Process P3 represent electron-withdrawing substituents such as, for example, nitro, chloride, fluoride, cyano.

Process P2 is especially suitable for preparation of embodiments I-A to I-D in which X is hydrogen or represents electron-withdrawing substituents (especially nitro, chloride, fluoride, cyano) and Y represents electron-withdrawing substituents (especially nitro, chloride, fluoride, cyano).

Process P3 & Process P3'

Alternatively, the compounds of the general formula (Ia) can be prepared by Processes P3 and P3', as shown in the following scheme:

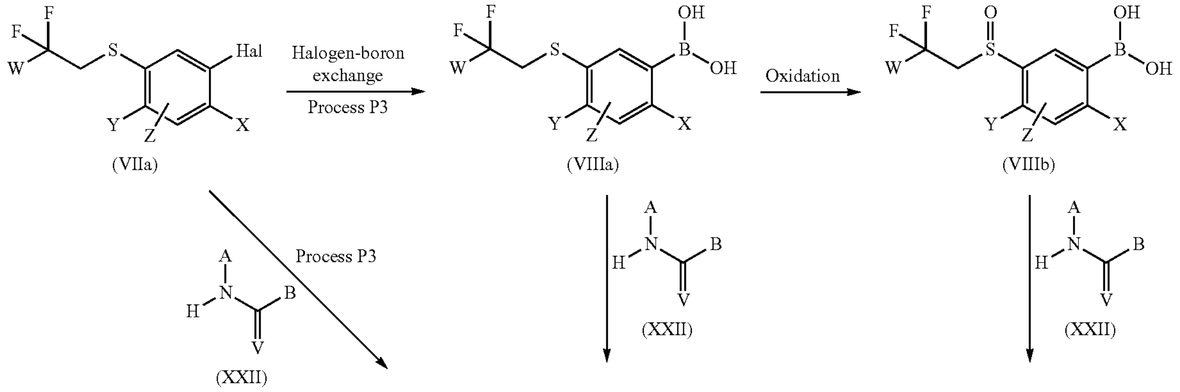

(VIIa)
(VIIIa)
(VIIIb)
(XXII)
(XXII)
(XXII)

-continued

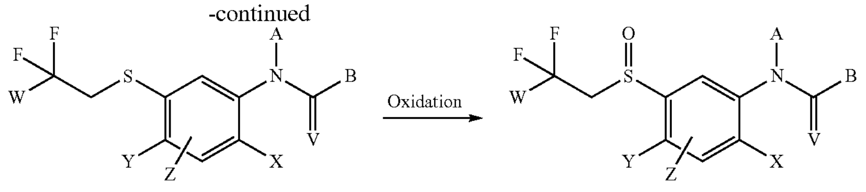

(Ia) (Ib)

where X, Y, Z, W, A, B and V are as defined above and Hal is halogen (preferably chlorine, bromine, iodine).

Process P3

According to Process P3, compounds of the general formula (Ia) can be prepared by methods known from the literature by reaction of aryl halides of the general formula (VIIa) with heterocyclic compounds of the general formula (XXII). The reaction preferably takes place through transition metal catalysis or mediation. Numerous illustrative sets of reaction conditions are known in the literature, for example in WO 2006/117657 A1, in US 2010/99725 A1, in WO 2010/47956 A1, in Chem. Pharm. Bull. 1997, Vol. 45, No. 4, 719-721, in J. Amer. Chem. Soc. 2003, Vol. 125, No. 37, 11253-11258 or else in Bull. Korean Chem. Soc. 2010, Vol. 31, No. 8, 2143-2146. Preference is given to using copper or copper salts, for example copper(I) iodide, copper (I) oxide, copper(I) triflate or copper(II) triflate, as catalyst, frequently in the presence of a ligand, for example diamine ligands such as N,N'-dimethylethylenediamine, N,N-dimethylethylenediamine or trans-N,N'-dimethyl-1,2-cyclohexanediamine. An overview is found, for example, in Chem. Sci. 2010, Vol. 1, 13-31. As an alternative, it is possible to use 1,3-diketones, for example 2,4-pentanedione, 2,2,6,6-tetramethyl-3,5-heptanedione or dibenzoylmethane, amino acids such as, for example, L-proline or glycine, or other compounds such as 8-hydroxyquinoline (Tetrahedron Lett. 2009, Vol. 50, 7293-7296), dibenzylidene acetone, bipyridine or phenanthroline. In general, the reaction is performed in the presence of a base, frequently carbonate or phosphate bases, for example potassium carbonate, sodium carbonate, cesium carbonate or potassium phosphate, in suitable solvents, for example dioxane, toluene, dimethyl sulfoxide or N,N-dimethylformamide. It is additionally possible to use other additives, for example potassium iodide, cesium fluoride or other salts.

Alternatively, it is possible to perform reactions of this kind under palladium catalysis, for instance using catalysts, for example palladium acetate, tetrakis(triphenylphosphine) palladium, bis(triphenylphosphine)palladium(II) chloride, tris(dibenzylideneacetone)dipalladium(0) in the presence of ligands, for example 2,2'-bis(diphenylphosphino)-1,1'-binaphthyl, 9,9-dimethyl-4,5-bis(diphenylphosphino)xanthene, 1,1'-bis(diphenylphosphino)ferrocene, and bases, for example potassium carbonate, sodium carbonate, cesium carbonate or potassium phosphate, in suitable solvents, for example dioxane, toluene, dimethyl sulfoxide or N,N-dimethylformamide.

Process P3 is particularly suitable for preparing embodiments I-A-1, I-A-2, I-A-3, I-A-4 and I-C-1.

Process P3'

Compounds of the general formula (Ia) can alternatively be prepared by Process P3' by reaction of boronic acids of the general formula (VIIIa) with heterocyclic compounds of the general formula (XXII).

In general, the reactions take place under catalysis or mediation by copper(II) salts, for example copper(II) acetate, copper(II) triflate, or else by copper(I) salts, for example copper(I) chloride, copper(I) acetate, under an air or oxygen atmosphere, frequently under dehydrating conditions (for example with molecular sieve). Bases used are, for example, triethylamine, N-ethyldiisopropylamine, pyridine, 2,6-lutidine, N-methylmorpholine or 1,8-diazabicycloundec-7-ene in suitable solvents, for example dichloromethane, dichloroethane, methanol, N,N-dimethylformamide, tetrahydrofuran, dioxane, acetonitrile, ethyl acetate or toluene. The literature describes numerous examples, inter alia in Bioorg. Med. Chem. Lett. 2010, Vol. 20, No. 13, 3920-3924, in Proc. Natl. Acad. Sci. USA 2011, Vol. 108, No. 17, 6781-6786, in Chem. Eur. J. 2009, Vol. 15, No. 29, 7044-7047, in Synlett 2004, Vol. 6, 1095-97, in J. Org. Chem. 2005, 70, 4, 1486-1489, in Tetrahedron Lett. 1998, Vol. 39, 2933-2936, in WO 2005/85226 A1 or in WO 2008/62905 A2. Summarizing overviews are found, for example, in Synthesis 2011, No. 6, 829-856 or in Tetrahedron 2012, vol. 68, 7735-7754. Instead of the boronic acid, it is also possible to use other boron compounds, for instance potassium trifluoroborate, boronic esters, etc., or else other organometallic compounds, for instance stannanes, silanes or bismuthanes.

By oxidation of the thioethers of the general formula (Ia) by methods known from the literature, it is possible to obtain the sulfoxides of the general formula (Ib). Alternatively, the oxidative transition metal-mediated carbon-nitrogen coupling to give aryl sulfoxides of the general formula (Ib) can be enabled proceeding from boronic sulfoxides of the general formula (VIIIb), which are obtainable by oxidation of the boronic acids (VIIIa), for example with sodium periodate, or analogous derivatives.

Process P3' is particularly suitable for preparing embodiments I-B-1, I-B-4, I-C-1 and I-C-2.

Processes Pa1-Pa8 are suitable for preparation of embodiment I-A of the compounds of the formula (I).

Process Pa1 (for the Preparation of I-A-1)

The imidazolidinones of the general formula (I-A-1) can be subdivided into (I-A-1a) (for n=0) and (I-A-1b) (for n=1). They can be prepared, for example, in accordance with process Pa1.

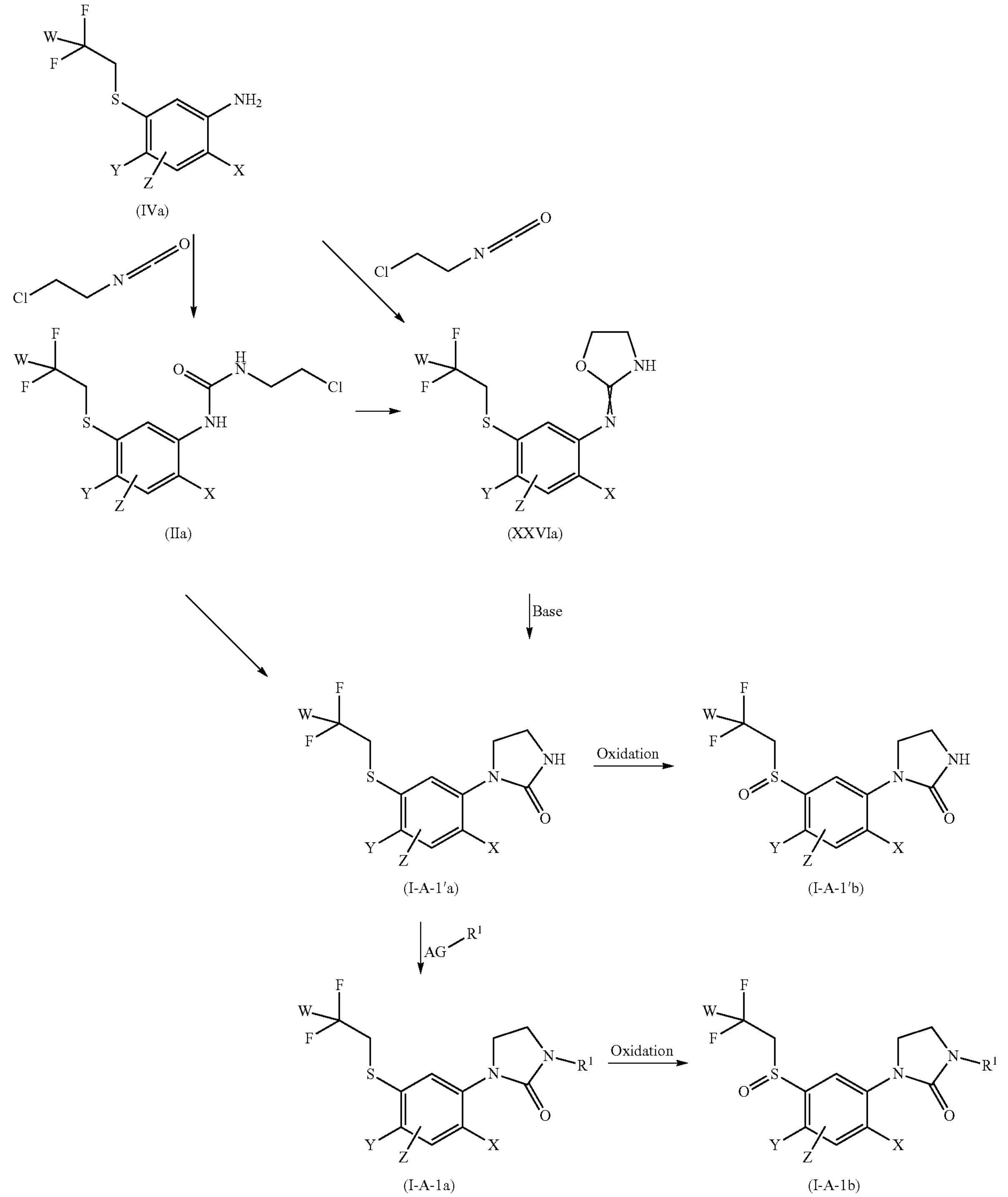

(IVa)

(IIa)

(XXVIa)

(I-A-1'a)

(I-A-1'b)

(I-A-1a)

(I-A-1b)

where W, X, Y, Z and $R^1$ have the meaning given above and AG represents a leaving group such as, for example, chloride, bromide, iodide, triflate and mesylate.

Anilines of the formula (IVa) can be converted by reaction with 2-chloroethyl isocyanate into the cyclic amidines of the general formula (XXVIa)—optionally with intermediate isolation of the ureas of the formula (IIa).

The preparation of ureas is known from the literature, for example from JP 2011/042611.

1,3-Oxazolidin-2-ylideneanilines of the general formula (XXVIa) are converted in the presence of bases into the 1-arylimidazolidin-2-ones of the general formula (I-A-1'a).

The thioethers (I-A-1'a) can then be converted by methods known from the literature into the compounds of the general formula (I-A-1a). Suitable alkylating agents are, for example, alkyl electrophiles of the formula $R^1$-AG, where AG represents, for example, chloride, bromide, iodide, triflate and mesylate.

Further preparation examples and the use of 1-arylimidazolidin-2-ones as intermediates have been published, for example, in the following patents: WO 2012149413, WO 2011110575, WO 2011098776, WO 2010149755, WO 2008077597, WO 2008057254, WO 2007038367, US 20070066588, WO 2005111038 or WO 2005092890.

The preparation of 1-arylimidazolidin-2-ones by reduction of 1-arylimidazolin-2-ones is described in J. Med. Chem. 1966, 9(6), 858-860.

N-Alkylations of 1-arylimidazolidin-2-ones and the preparation of 1-arylimidazolidin-2-ones by reaction of N-aryl-1,2-diamines in the presence of, for example, 1,1'-carbonyldiimidazole are described in Can. J. Chem. 2004, 82, 1649.

Process Pa 2 (for the Preparation of I-A-2)

The oxazolidinones of the general formula (I-A-2) can be subdivided into (I-A-2a) (for n=0) and (I-A-2b) (for n=1). They can be prepared, for example, in accordance with process Pa2.

The thiazolidinones of the general formula (I-A-3) can be subdivided into (I-A-3a) (for n=0) and (I-A-3b) (for n=1). They can also be prepared, for example, in accordance with process Pa3

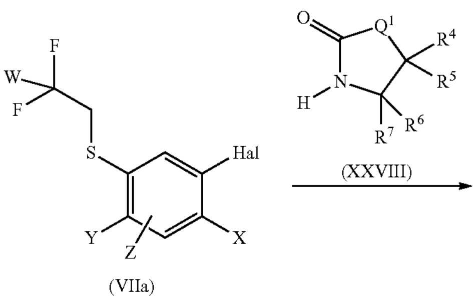
(VIIa)
(XXVIII)

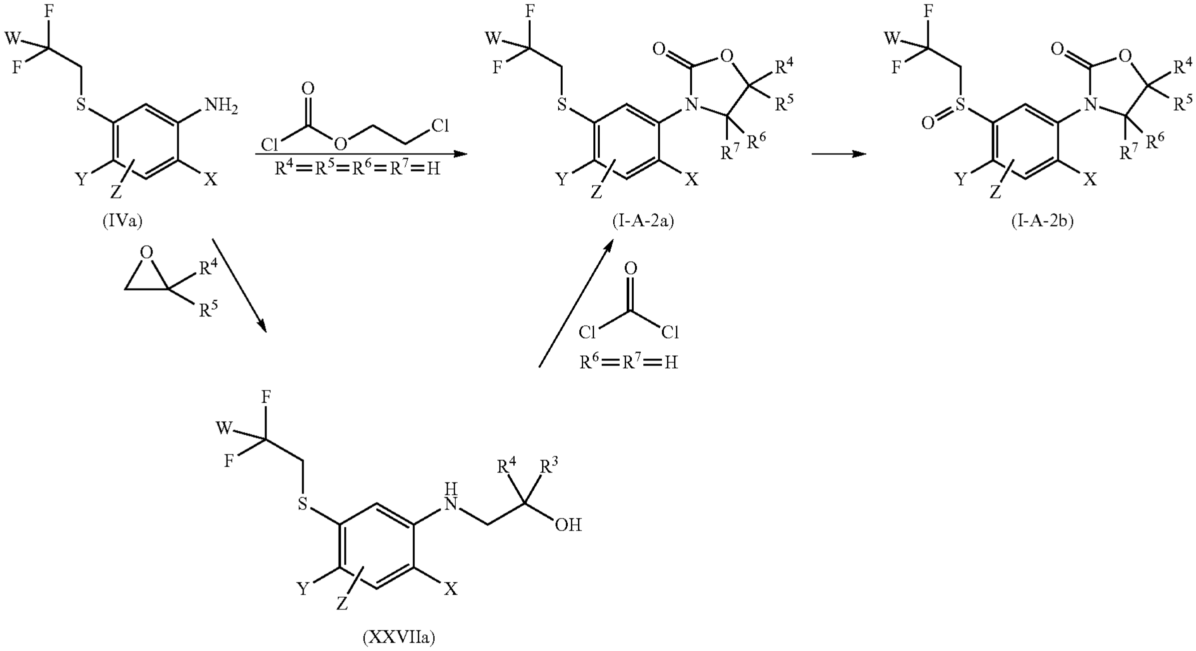

(IVa)
(I-A-2a)
(I-A-2b)
(XXVIIa)

where W, X, Y, z, $R^3$, $R^4$, $R^5$ and $R^6$ have the meaning given above.

Anilines of the formula (IVa) can be converted into the oxazolidinones of the formula (I-A-2a) by methods known from the literature, for example by reaction with 2-chloroethyl chloroformate, for example analogously to Molecules 2012, 17, 1233-1240.

Alternatively, anilines of the formula (IVa) can react with an epoxide to give aminoalcohols of the formula (XXVIIa) which can be reacted with phosgene to give oxazolidinones of the formula (I-A-2a), for example analogously to Organic Process Research and Development 2010, 14, 1457-1463 and Journal of Heterocyclic Chemistry 1986, 23, 1427-1429.

Process Pa3 (for the Preparation of I-A-2 and I-A-3)

The oxazolidinones of the general formula (I-A-2) can be subdivided into (I-A-2a) (for n=0) and (I-A-2b) (for n=1). They can be prepared, for example, in accordance with process Pa3.

-continued

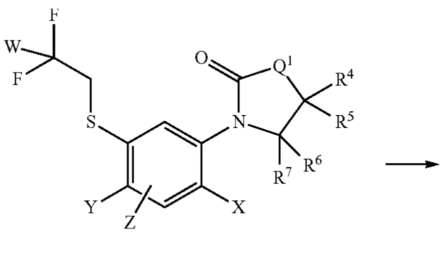
$Q^1$ = O (I-A-2a)
$Q^1$ = S (1-A-3a)

-continued

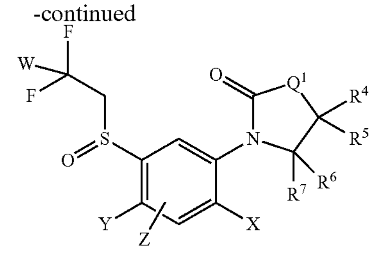

$Q^1$ = O (I-A-2b)
$Q^1$ = S (1-A-3b)

where W, X, Y, z, $R^4$, $R^5$, $R^6$ and $R^7$ have the meaning given above, $Q^1$ represents oxygen or sulfur and Hal represents a halogen from the group consisting of Cl, Br and iodine.

Halides of the formula (VIIa) can be converted with oxazolidinones ($Q^1$=O) or thiazolidinones ($Q^1$=S) of the formula (XXVIII) with the aid of a catalyst into the oxazolidinones of the formula (I-A-2a) or thiazolidinones of the formula (I-A-3a), for example analogously to Chemical Biology & Drug Design 2007, 70, 100-112.

1,3-Oxazolidin-2-ones (XXVIII, $Q^1$=O), which are known as auxiliaries (Evans auxiliary) in preparative chemistry, are commercially available or can be prepared by known methods.

1,3-Thiazolidin-2-ones (XXVIII, $Q^1$=S), such as, for example, 1,3-thiazolidin-2-ones, 5-methyl-1,3-thiazolidin-2-ones or 5,5-dimethyl-1,3-thiazolidin-2-ones, are commercially available or can be prepared by known methods.

Process Pa4 (for the Preparation of I-A-4)

The pyrrolidin-2-ones of the general formula (I-A-4) can be subdivided into (I-A-4a) (for n=0) and (I-A-4b) (for n=1). They can be prepared, for example, in accordance with process Pa4.

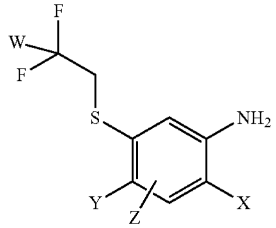

(IVa)

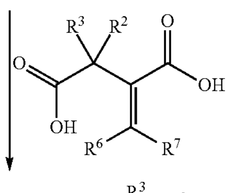

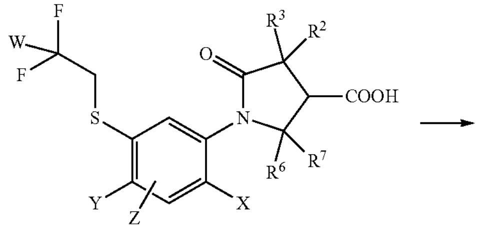

(XXIX)

-continued

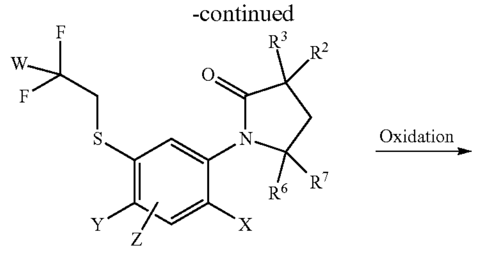

(I-A-4a)

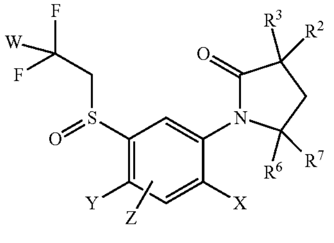

(I-A-4b)

where W, X, Y, z, $R^2$, $R^3$, $R^5$ and $R^6$ have the meaning given above.

The preparation of the compounds of the general formula I-A-4 is carried out, for example, by the process described in DE 2650604.

Anilines of the general formula (IVa) are converted by reaction of optionally substituted itaconic acids into the 5-oxo-1-arylpyrrolidine-3-carboxylic acids of the general formula (XXIX). Their decarboxylation affords the 1-arylpyrrolidin-2-ones of the general structure (I-A-4a).

A further general preparation process for the 1-arylpyrrolidin-2-ones comprises the reaction of dihydrofuran-2(3H)-one with anilines. This process is described, for example, in WO 2004/037787 or in J. Het. Chem. 3, 311 (1966). Analogous reactions are known, for example from Tetrahedron Lett., 1990, 31 (21) 2991.

The cyclization of 4-chloro-N-arylbutanamides to give the 1-arylpyrrolidin-2-ones is described in a Spanish patent, ES 1982-516898.

Process Pa5 (for the Preparation of I-A-5)

The 2-imino-1,3-thiazolidines of the general formula (I-A-5) can be subdivided into (I-A-5a) (for n=0) and (I-A-5b) (for n=1). They can be prepared, for example, in accordance with process Pa5.

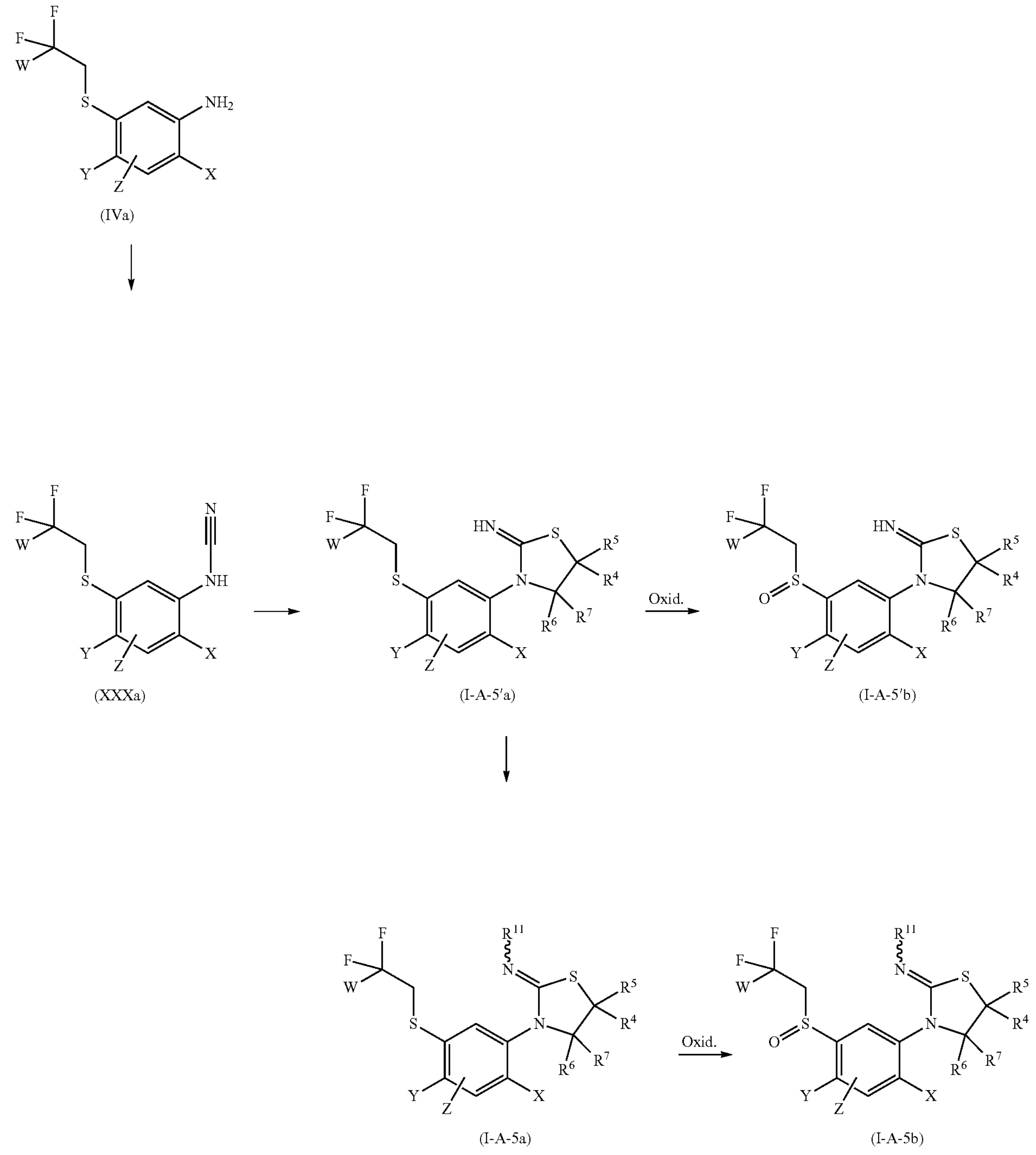

(IVa)

(XXXa) (I-A-5'a) (I-A-5'b)

(I-A-5a) (I-A-5b)

where W, X, Y, Z, $R^4$, $R^5$, $R^6$, $R^7$ and $R^{11}$ have the meaning given above.

Anilines of the formula (IVa) can be converted into arylcyanamides of the formula (XXXa) using halocyano compounds such as, for example, cyanogen bromide, according to the method described in US2007/27125. Alternatively, the anilines (IVa) can initially be converted by methods known from the literature into their thioureas, and these are then converted into arylcyanamides (XXXa), for example by transition metal-catalyzed reactions as described by S. K. Sahoo in Adv. Synth. and Catal. 2010, 352, 2538-2548. The arylcyanamides (XXXa) can react, for example, with suitable thiiranes, as in U.S. Pat. No. 5,266,701, forming the unsubstituted 2-imino-1,3-thiazolidines (I-A-5'). Compounds of the formula (I-A-5'a) can be substituted at the nitrogen atom using methods known from the literature, for example with alkyl iodides as described by Y. V. Raschkes in J. Org. Chem. USSR (Engl.) 1981, 17, 529-536.

Process Pa6 (for the Preparation of I-A-5)

Alternatively, the 2-imino-1,3-thiazolidines (I-A-5) can be synthesized according to process Pa6.

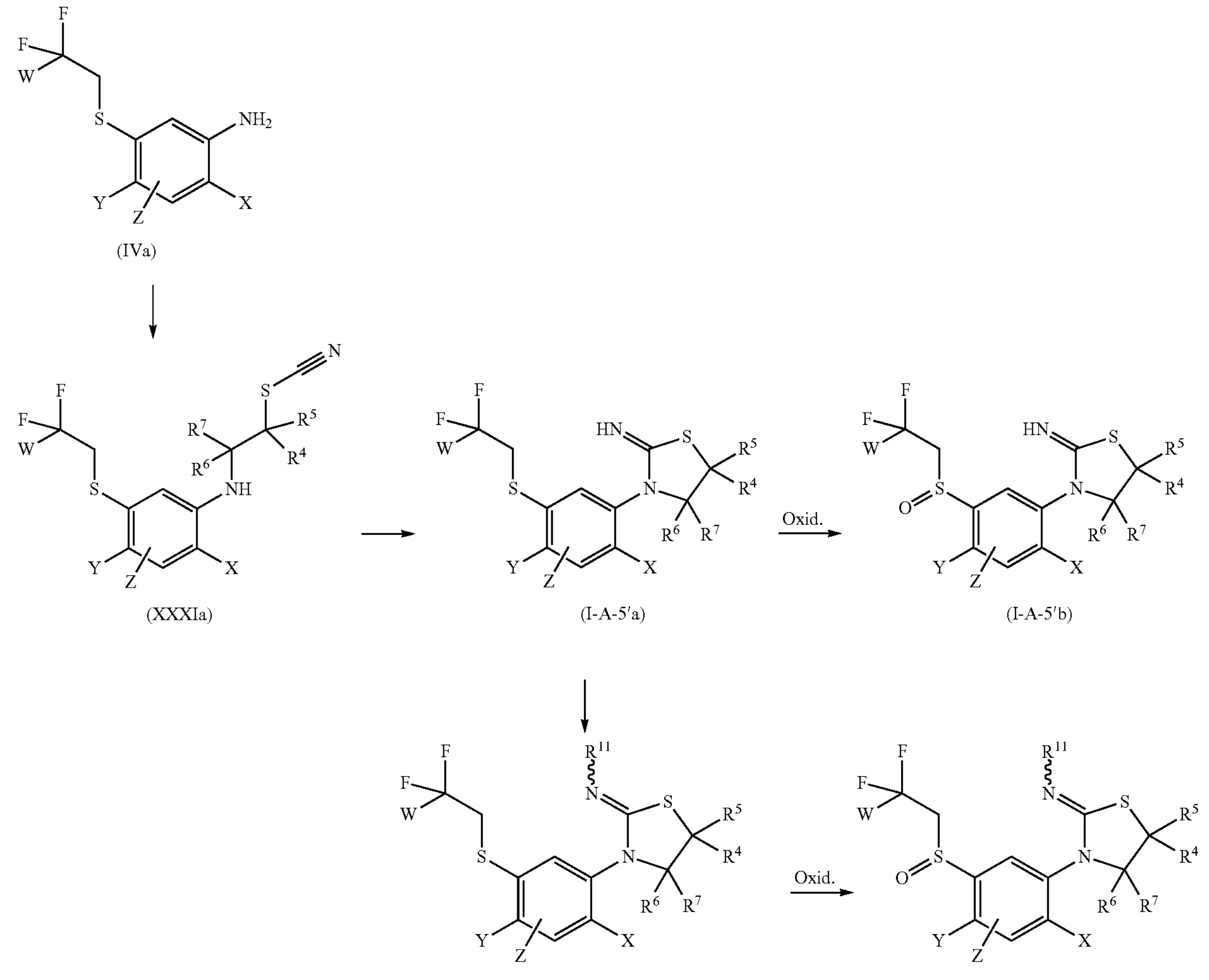

(IVa)
(XXXIa)
(I-A-5'a)
(I-A-5'b)
(I-A-5a)
(I-A-5b)

Anilines of the formula (IVa) can be converted, for example, with N-alkylthiocyanates into the products (XXXIa), for example in an alcohol as solvent and with hydrochloric acid as acidic medium, as described in U.S. Pat. No. 4,665,083.

Process Pa7 (for the Preparation of I-A-5)

An alternative is the synthesis of the 2-imino-1,3-thiazolidines (I-A-5) via thioureas of the formula (II') according to process Pa7.

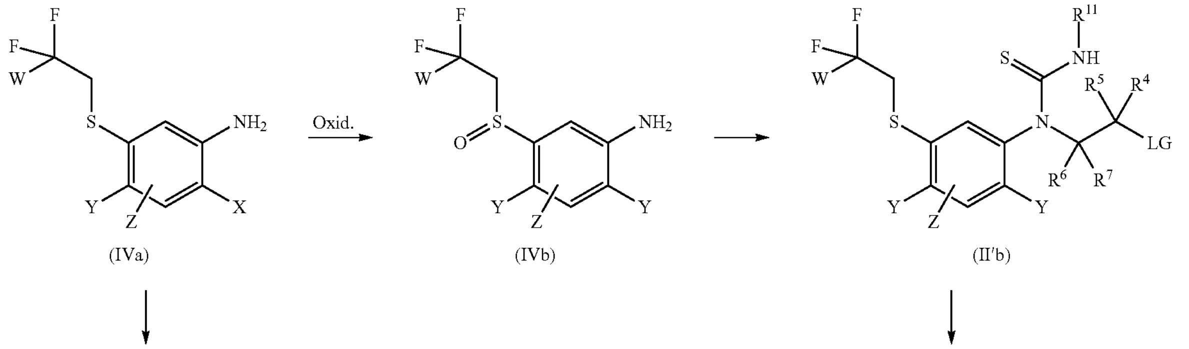

(IVa)
(IVb)
(II'b)

-continued

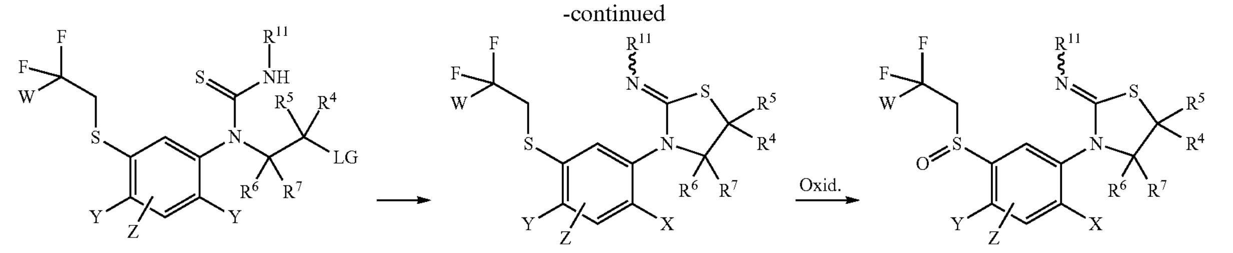

(II'a) (I-A-5a) (I-A-5b)

where W, X, Y, Z, $R^4$, $R^5$, $R^6$, $R^7$ and $R^{11}$ have the meanings given above and LG represents a leaving group (preferably halogen and alkoxy).

(II)

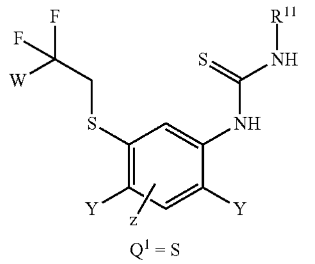

$Q^1 = S$

Thioureas of the formula (II') can be prepared from anilines (IV) by methods known from the literature, for example via thioureas (II) and suitable alkylating agents or via alkylated anilines and isothiocyanates, for example as in the U.S. Pat. No. 6,353,006. Subsequent cyclization to the thiazolidines (I-A-5) can be spontaneous or optionally with the aid of an activator. Here, mesylates, tosylates or triflates may be formed as intermediates. The patent WO2003/97605 describes the reaction of an alcohol with mesyl chloride in the presence of triethylamine and dichloromethane as solvent.

The order of the synthesis steps is variable, and it is therefore possible, for example using 1,2-dibromoethane ($R^4$=$R^5$=$R^6$=$R^7$) according to H. G. Hoker in Synthesis 2009, 7, 1195-1203, to carry out the cyclizations to the thiazolidines (I-A-5) directly from the ureas (II), without isolation of the synthesis intermediates (II').

Process Pa8 (for the Preparation of I-A-6)

The N-arylylpyrrolidin-2-ylidenethanamines of the general formula (I-A-6) can be subdivided into (I-A-6a) (for n=0) and (I-A-6b) (for n=1). They can be prepared, for example, in accordance with process Pa8.

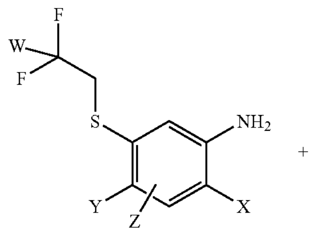

(IVa)

-continued

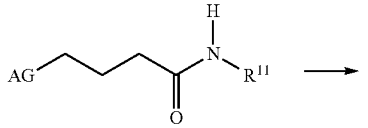

(XXXII)

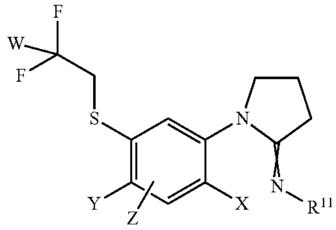

(I-A-6a)

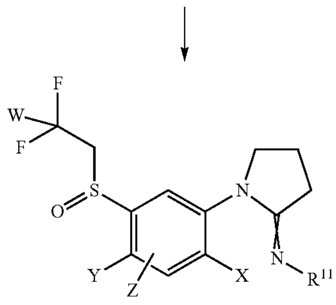

(I-A-6b)

where W, X, Y, Z and $R^{11}$ have the meaning given above and AG represents a leaving group such as chloride, bromide, iodide, triflate or tosylate.

The N-arylylpyrrolidin-2-ylidenethanamines of the general formula (I-A-6a) according to the invention are obtained by reacting anilines of the formula (IVa) with butanamides of the formula (XXXII) in the presence of phosphoryl chloride. Some of the butanamides of the formula (XXXII) are commercially available or can be prepared by known processes.

Processes Pb1-Pb9 are suitable for preparing embodiment I-B of the compounds of the formula (I).

Processes Pb1 and Pb2 (for the Preparation of I-B-1)

The imidazolidine-2,4-diones of the general formula (I-B-1) can be subdivided into (I-B-1a) (for n=0) and (I-B-1b) (for n=1). They can be prepared, for example, in accordance with process Pb1 and process Pb2.

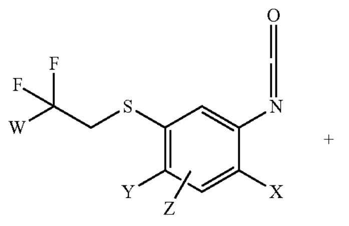

(IIIa)

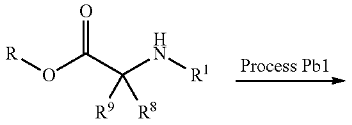

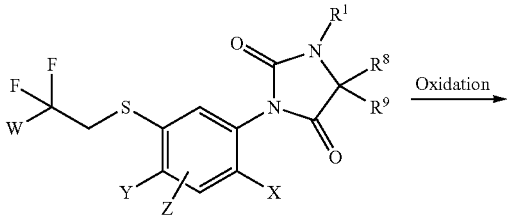

(I-B-1a)

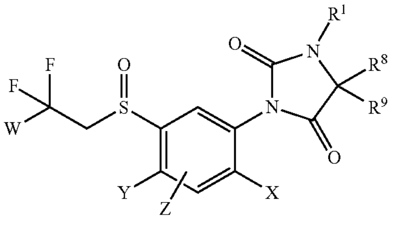

(I-B-1b)

where W, X, Y, z, $R^1$, $R^8$ and $R^9$ have the meaning given above.

Alternatively, imidazolidine-2,4-diones of the general formula (I-B-1a) can be prepared by process Pb1 by condensation of isocyanates of the formula (IIIa) with various α-amino esters or their surrogates, for example according to J. Med. Chem. 2012, 55, 8225-8235, Synth. Commun. 2010, 40, 1377-1390 or Tetrahedron Lett. 2012, 53, 5593-5596. Alternatively, α-amino esters can also be prepared and employed by reductive amination as described in J. Org. Chem. 1997, 62, 3230-3235. Furthermore, isocyanates of the formula (IIIa) can be prepared in situ by reaction with phosgene, diphosgene or triphosgene, as described, for example, in J. Med. Chem. 2012, 55, 8236-8247, in US2011/53947 A1 or in WO2005/103054 A2, and used directly.

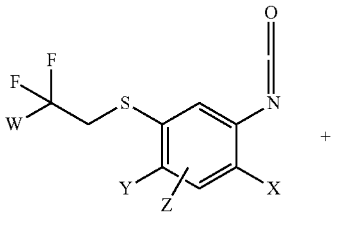

(IIIa)

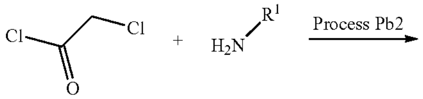

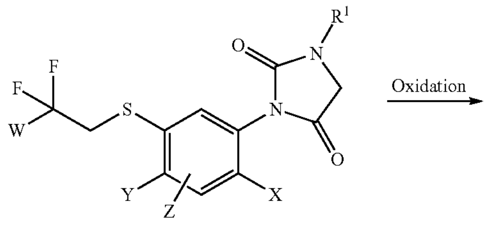

(I-B-1a)

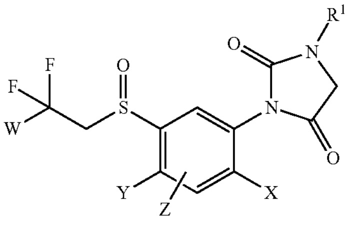

(I-B-1b)

Alternatively, the imidazolidine-2,4-diones of the general formula (I-B-1a) can be prepared according to process Pb2 by condensation of isocyanates of the formula (IIIa) with chloroacetyl chloride and amines (R'—$NH_2$) using polymer supports and microwave irradiation according to Tetrahedron Lett. 2004, 45, 437-440.

Process Pb3 (I-B-2)

The oxazolidinediones of the general formula (I-B-2) can be subdivided into (I-B-2a) (for n=0) and (I-B-2b) (for n=1). They can be prepared, for example, in accordance with process Pb3

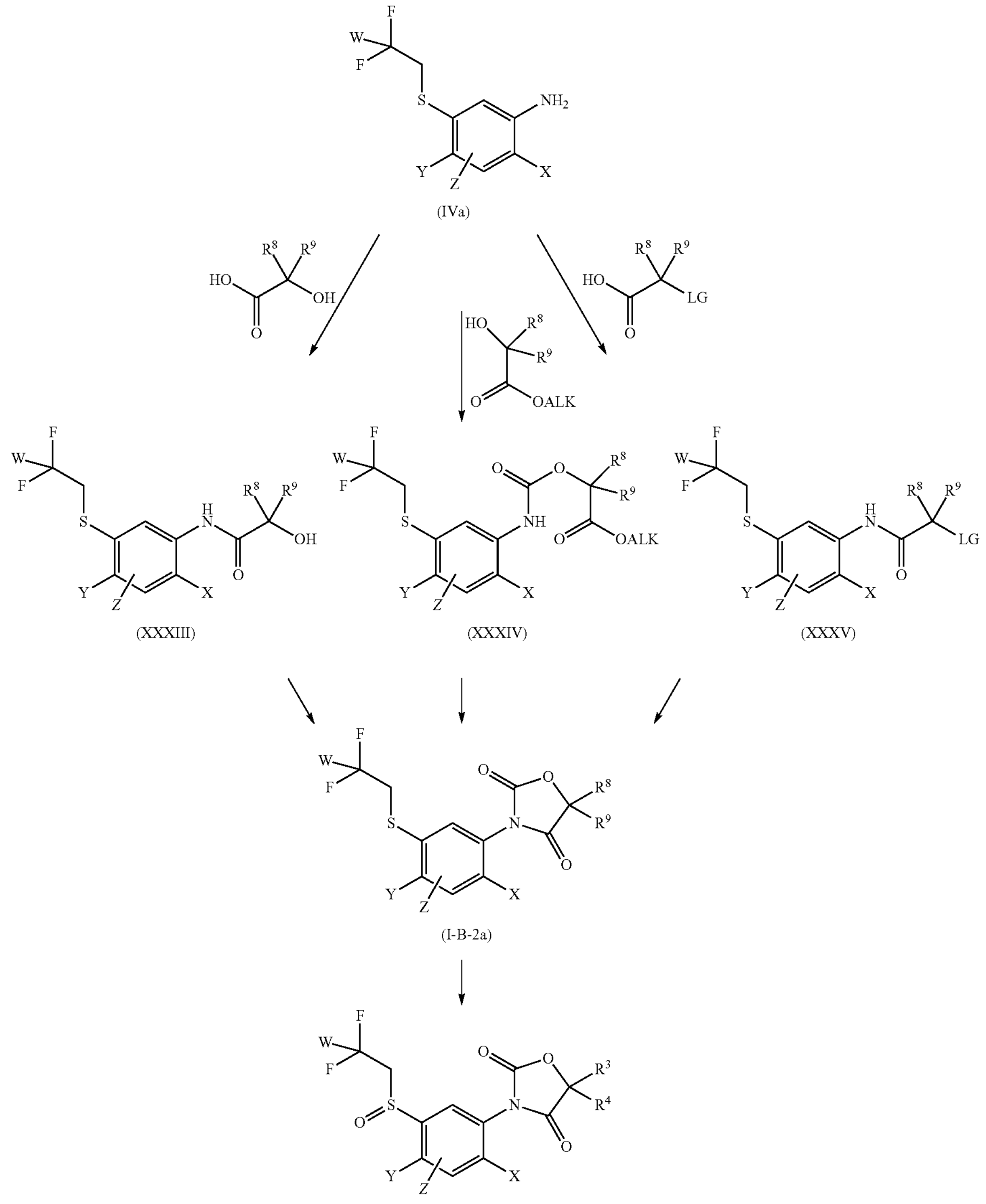

(IVa)

(XXXIII) (XXXIV) (XXXV)

(I-B-2a)

(I-B-2b)

where X, Y, z, $R^8$ and $R^9$ have the meaning given above, LG represents a leaving group such as, for example, chlorine, bromine, iodine, tosylate, mesylate or triflate and ALK represents a small alkyl group such as, for example, methyl or ethyl.

Anilines of the formula (IVa) can be converted into the α-hydroxycarboxamides of the formula (XXXIII) by reaction with an α-hydroxycarboxylic acid using a chlorinating agent such as, for example, thionyl chloride and a base such as, for example triethylamine. Alternatively, it is possible to activate the anilines (IVa), for example using trimethylaluminum, followed by conversion with α-hydroxycarboxylic esters into the carboxamides of the formula (XXXIII). α-Hydroxycarboxamides of the formula (XXXIII) can be converted by methods known from the literature into the oxazolidinediones of the formula (I-B-2a), for example by reaction with carbonyldiimidazole in the presence of a base, for example analogously to Bioorg. & Med. Chem 2002, 3267-3276.

Anilines of the formula (IVa) can be converted into the carbamates of the formula (XXXIV) by reaction with an α-hydroxy ester with the aid of, for example, carbonyldiimidazole and a base such as, for example, triethylamine. Carbamates of the formula (XXXIV) can be converted into the oxazolidinediones of the formula (I-B-2a) by methods known from the literature, for example by reaction with a base such as sodium methoxide, for example analogously to Bioorg. & Med. Chem 2012, 3242-3254.

Anilines of the formula (IVa) can be converted into the carboxamides of the formula (XXXV) by reaction with a coupling agent or a chlorinating agent. Carboxamides of the formula (XXXV) can be converted into the oxazolidinediones of the formula (I-B-2a) according to methods known from the literature, for example analogously to Tetrahedron 1999, 193-200, Tetrahedron Letters 2009, 50, 5123-5125 or Pharmazie 1992, 47, 340.

A general synthesis of oxazolidinediones is described in JACS 1959, 6498-6503.

Process Pb4 (for the Preparation of I-B-3)

The thiazolidinediones of the general formula (I-B-3) can be subdivided into (I-B-3a) (for n=0) and (I-B-3b) (for n=1). They can be prepared, for example, in accordance with process Pb4.

where X, Y, z, W, $R^3$ and $R^4$ each have the meaning given above and LG represents a leaving group such as, for example, chlorine, bromine, iodine, tosylate, mesylate, triflate.

Anilines of the formula (IV) can be converted into the carboxamides of the formula (XXXV) by reaction with a coupling agent or a chlorinating agent. Carboxamides of the formula (XXXV) can be converted into the thiocyanates of the formula (XXXVI) by reaction with potassium thiocyanate. Thiocyanates of the formula (XXXVI) can be converted into the thiazolidinediones of the formula (I-B-3a) according to methods known from the literature, for example analogously to Pharmazie 1992, 47, 340.

Process Pb5 (for the Preparation of I-B-4)

The N-arylpyrrolidine-2,5-diones of the general formula (I-B-4) can be subdivided into (I-B-4a) (for n=0) and (I-B-4b) (for n=1). They can be prepared, for example, in accordance with process Pb5.

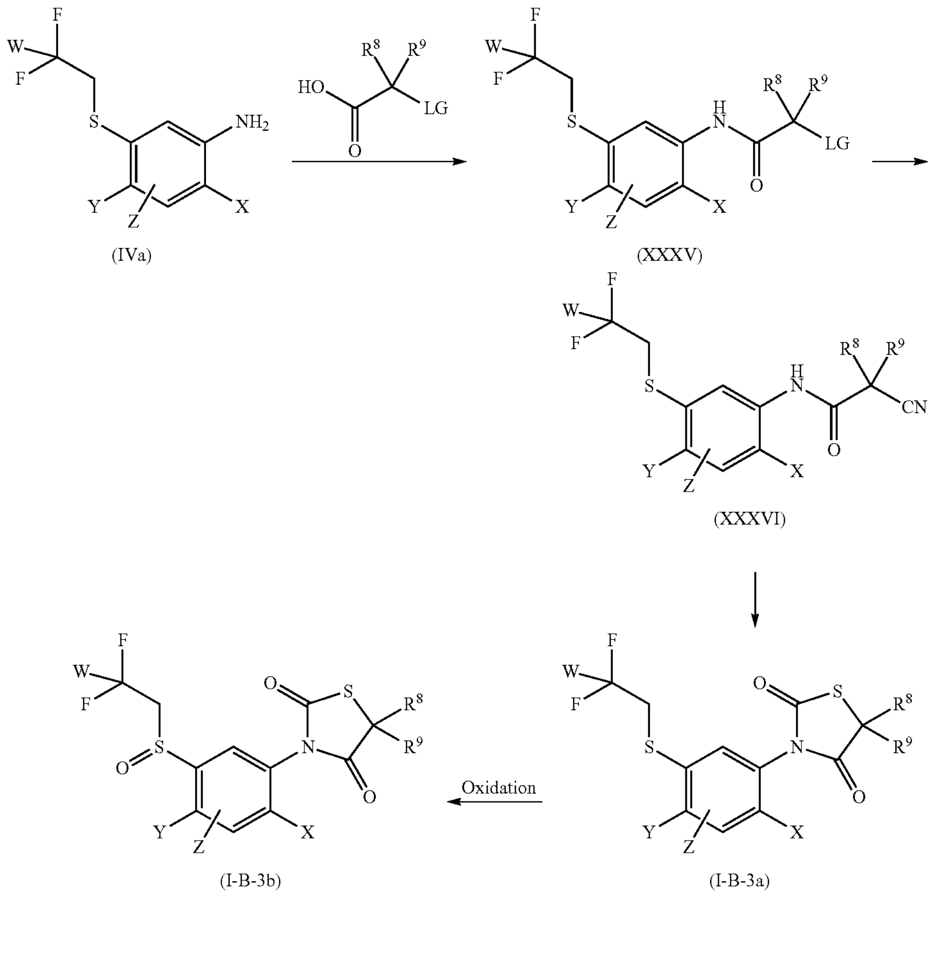

(IVa) (XXXV) (XXXVI) (I-B-3a) (I-B-3b)

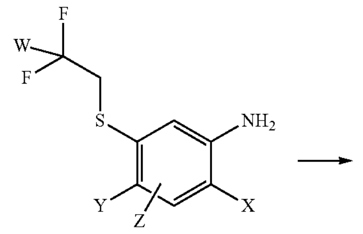

(IVa)

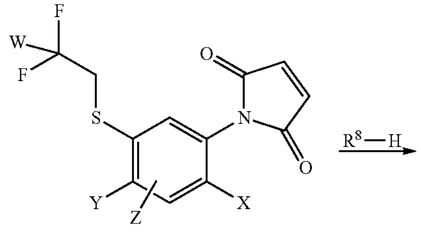

(XXXVII)

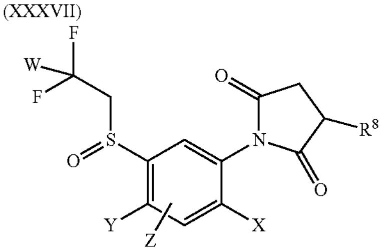

(I-B-4a)

Oxidation

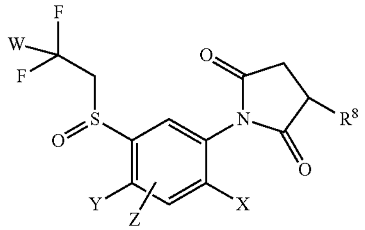

(I-B-4b)

where W, X, Y, z, R' and R" have the meaning given above and $R^8$ represents an optionally substituted amino group.

The preparation of the compounds of the general formula (I-B-4) is carried out by converting anilines of the formula (IV) with furan-2,5-diones according to Angewandte Makromolekulare Chemie (1988), 157, 59-78 or U.S. Pat. No. 3,853,912 into the N-arylmaleimides of the general formula (I-B-4a).

The N-arylpyrrolidine-2,5-diones of the general formula (I-B-4a) or (I-B-4b) according to the invention are obtained from N-arylmaleimides of the general formula (XXXVII) by reaction with amines of the formula ($R^8$—H), optionally in the presence of an inert organic solvent.

The reaction of maleimides with amines is known from the literature, for example from Biochemistry, 1966, 5 (9), 2963-2971 or J. Org. Chem. (2007), 43(3), 393-396.

Further synthesis variants are described, for example, in Tetrahedron (1999), 55(40), 11859-11870 or Acta Chem. Scand. (1999), 53(1), 48-56 or Indian Drugs (1992), 29(7), 306-307 or Bioorg. Med. Chem. Lett. (2006), 16(3), 525-528 or Arzneimittel-Forsch. (2003), 53(4), 280-288.

Process Pb6 (for the Preparation of I-B-4)

Alternatively, the N-arylpyrrolidine-2,5-diones of the general formula (I-B-4) can be prepared by process Pb6

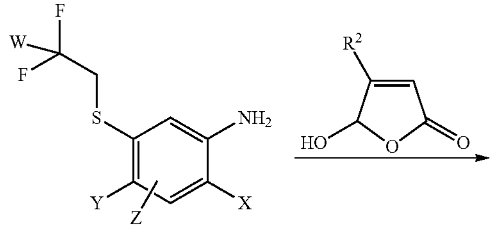

(IVa)

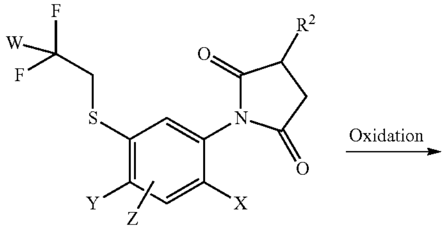

(I-B-4a)

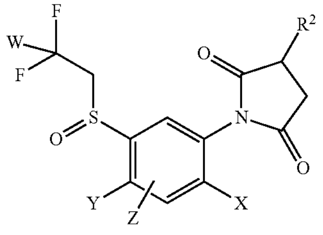

(I-B-4b)

where W, X, Y and Z have the meaning given above.

The N-arylpyrrolidine-2,5-diones of the general formula (I-B-4) according to the invention are obtained by reacting anilines of the general formula (IVa) with 5-hydroxyfuran-2(5H)-one in the presence of a solvent.

Further synthesis variants are described, for example, in Bioorg. Med. Chem. Lett. (2012), 22(23), 7019-7023 or in Tetrahedron Lett. (2010), 51, 2215-2217 or in Revue Roumaine de Chimie (2005), 50(7-8), 655-661 or J. Am. Chem. Soc. 1924, 46, 2069-2078. (for $R^2$=H)

Process Pb7 (for the Preparation of I-B-5 and I-B-7)

The 3-arylimino-1,3-thiazolidin-4-ones ($Q^1$=S) of the general formula (I-B-5) can be subdivided into (I-B-5a) (for n=0) and (I-B-5b) (for n=1).

The 3-arylimino-1,3-oxazolidin-4-ones ($Q^1$=O) of the general formula (I-B-7) can be subdivided into (I-B-7a) (for n=0) and (I-B-7b) (for n=1).

I-B-5 and I-B-7 can be prepared, for example, according to process Pb7

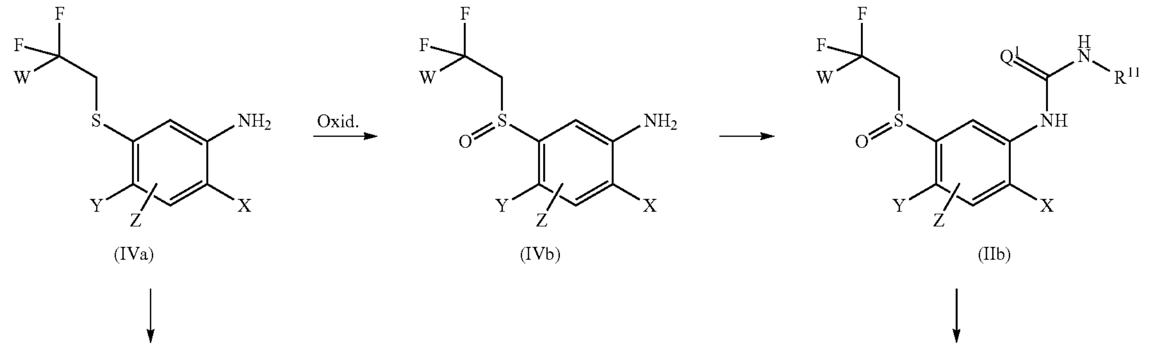

(IVa) (IVb) (IIb)

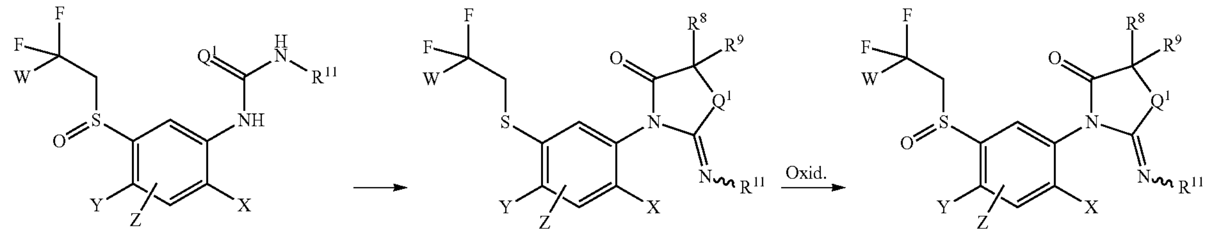

(IIb)
$Q^1$ = O, S $Q^1$ = S: (I-B-5a)
$Q^1$ = O: (I-B-7a)

$Q^1$ = S: (I-B-5b)
$Q^1$ = O: (I-B-7b)

where W, X, Y, Z, A, $R^8$, $R^9$ and $R^{11}$ each have the meanings given above.

Anilines of the formula (IV) can be converted to the ureas ($Q^1$=O) and thioureas ($Q^1$=S) of the formula (II) by methods known from the literature, for example according to JP2011/042611, by mixing them with isocyanates (for $Q^1$=O) and isothiocyanates (for $Q^1$=S), optionally in the presence of a base and optionally in the presence of an organic solvent, or by converting them by generally known methods into their isocyanates ($Q^1$=O) and isothiocyanates ($Q^1$=S) and reacting the latter with amines to give the ureas or thioureas.

From the ureas ($Q^1$=O) and thioureas ($Q^1$=S) of the general formula (II), it is possible to synthesize the 3-arylimino-1,3-oxazolidin-4-ones ($Q^1$=O) and -thiazolidin-4-ones ($Q^1$=S), respectively, of the general formulae (I-B-7) and (I-B-5), respectively, for example by cycloacylation with an adequate halocarbonyl derivative in an inert solvent, in most cases at temperatures of more than 100° C. Suitable halocarbonyl derivatives are, for example, chloroacetic acid and its acid chloride, bromoacetic acid and its acid chloride or bromide; as described by C. F. Howell in J. Org. Chem. 1962, 27, 1691 for conversions into oxazolidinones and V. N. Britsun in Russ. J. Org. Chem. 2006, 41 (11), 1719-1729 for thiazolidinones.

Process Pb8 and Pb9 (for the Preparation of I-B-6)

The 4-aryl-1,2,4-triazolidine-3,5-diones of the general formulae (I-B-6) and (I-B-6') can be subdivided into (I-B-6a) and (I-B-6'a) (for n=0) and (I-B-6b) and (I-B-6'b) (for n=1), respectively. They can be prepared, for example, in accordance with process Pb8, Pb9 and Pb10.

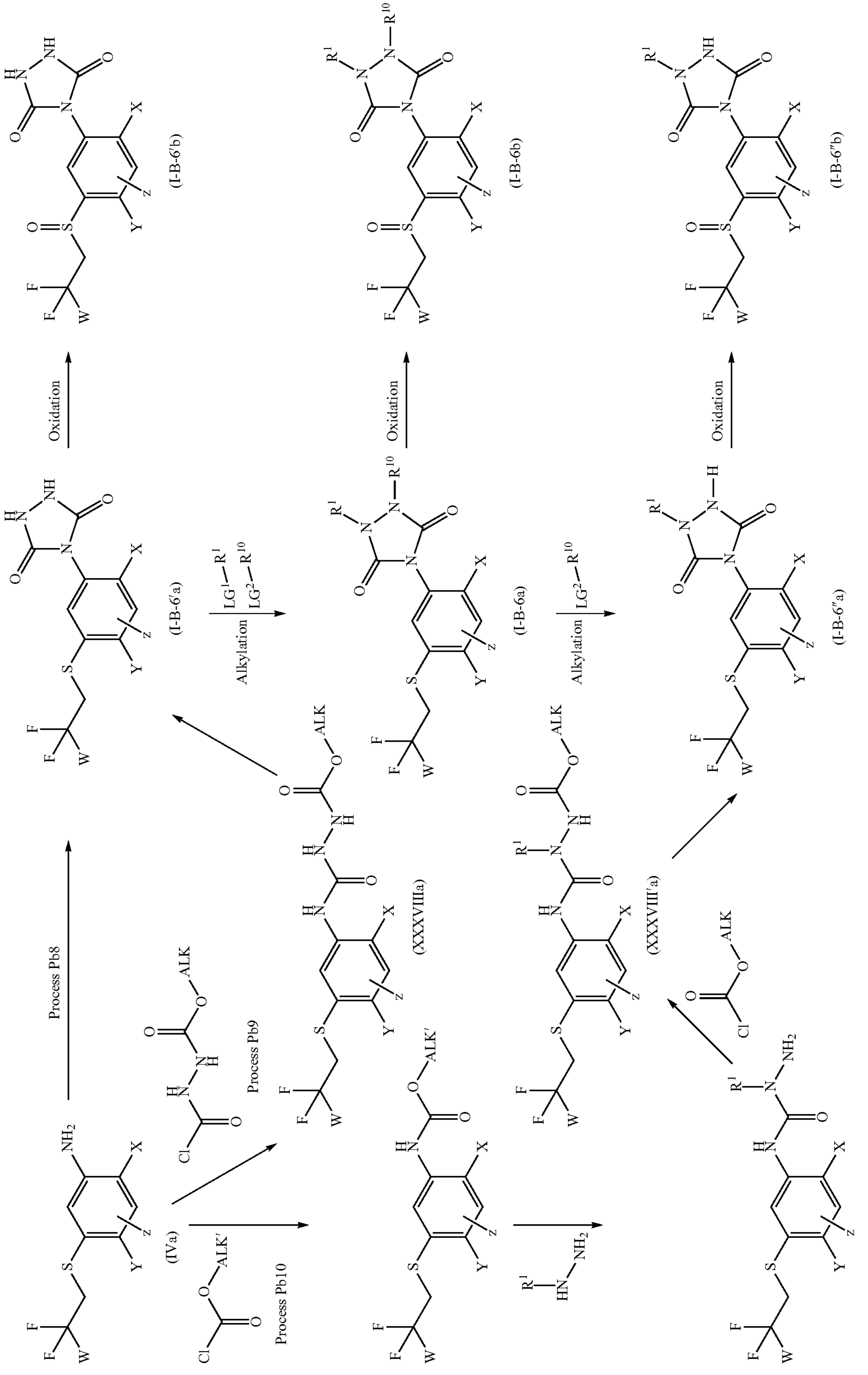
(IVa)
(XXXVIIIa)
(XXXVIII'a)
(I-B-6'a)
(I-B-6a)
(I-B-6"a)
(I-B-6'b)
(I-B-6b)
(I-B-6"b)

where W, X, Y, z, $R^1$ and $R^{10}$ have the meaning given above and ALK and ALK' represent a small alkyl group such as methyl or ethyl.

Alternatively, 4-aryl-1,2,4-triazolidine-3,5-diones of the general formula (I-B-6'a) can be obtained according to process Pb8 by reacting the anilines (IVa) with chloroformic esters and semicarbazides as described, for example, in Synlett 2007, 8, 1255-1256 or in Synth. Commun. 2007, 37, 1927-1934.

Alternatively, 4-aryl-1,2,4-triazolidine-3,5-diones of the general formula (I-B-6'a) can be prepared by condensation of the anilines (IVa) with diurea according to process Pb8, as described, for example, in Phamaceutical Bulletin 1954, 2, 403-411.

Synthesis 1982, 2, 159-160 describes the synthesis of 4-aryl-1,2,4-triazolidine-3,5-diones of the general formula (I-B-6'a) by acylation with alkyl 2-(chlorocarbonyl)hydrazinecarboxylates to give compounds of the general formula (XXXVIIIa) and subsequent cyclization according to process Pb9.

Subsequent alkylation of (I-B-6'a) with the appropriate alkylating agent $R^1$-$LG^1$ or $R^{10}$-$LG^2$ gives 4-aryl-1,2,4-triazolidine-3,5-diones of the general formula (I-B-6a), where $LG^1$ and $LG^2$ represent classical leaving groups such as iodide, bromide, chloride, tosylate, mesylate or triflate.

Alternatively, 4-aryl-1,2,4-triazolidine-3,5-diones of the general formula (I-B-6"a) can be prepared according to process Pb10 by cyclization of compounds of the general formula (XXXVIII'a) which for their part are accessible by reacting the anilines (IVa) with chloroformic esters, substituted hydrazines and another acylation with chloroformic esters.

Subsequent alkylation of (I-B-6"a) with the appropriate alkylating agent $R^{10}$-$LG^2$ gives 4-aryl-1,2,4-triazolidine-3,5-diones of the general formula (I-B-6a), where $LG^2$ represents classical leaving groups such as iodide, bromide, chloride, tosylate, mesylate or triflate.

Processes Pc1-Pc11 are suitable for preparing embodiment I-C of the compounds of the formula (I).

Processes Pc1 & Pc2 (for the Preparation of I-C-1)

The 2-aryl-1,2,4-triazolidine-3,5-diones of the general formula (I-C-1) can be subdivided into (I-C-1a) (for n=0) and (I-C-1b) (for n=1).

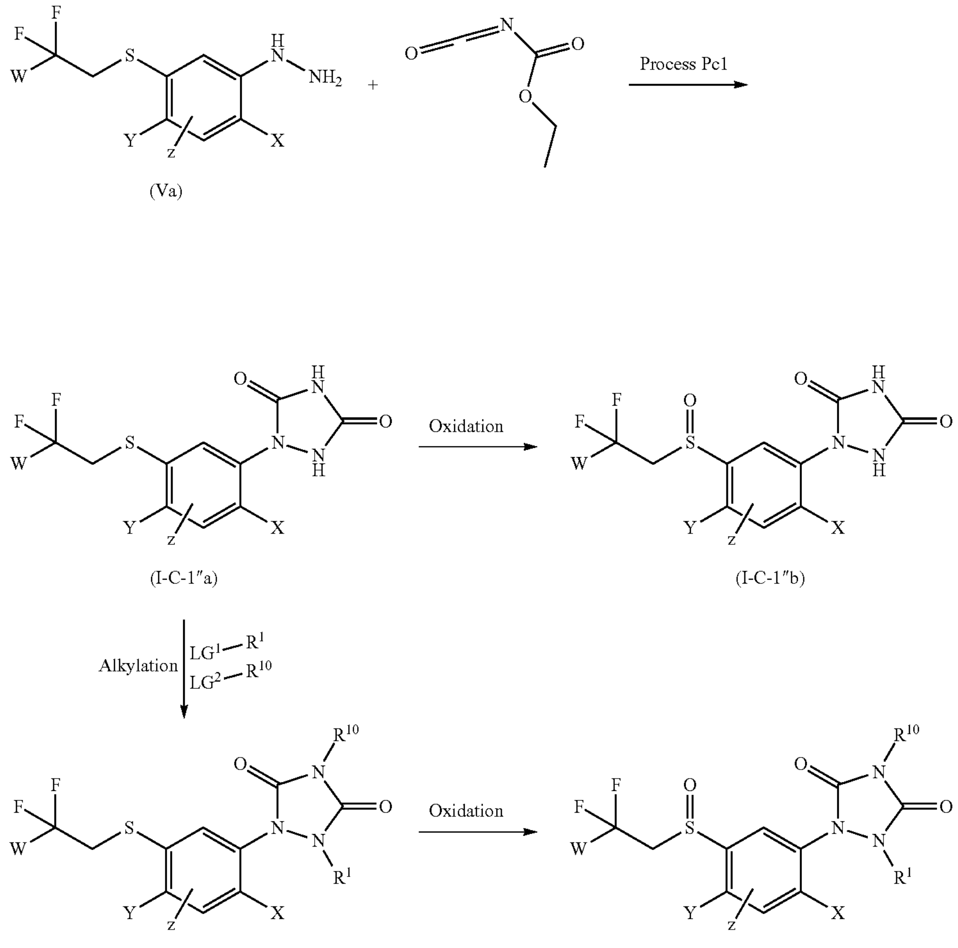

(Va)

(I-C-1"a)

(I-C-1"b)

(I-C-1a)

(I-C-1b)

Alternatively, 2-aryl-1,2,4-triazolidine-3,5-diones of the general formula (I-C-1"a) or (I-C-1a) can be prepared according to process Pc1 by condensation of hydrazines of the formula (Va) with ethyl isocyanatocarbonate, as described, for example, in Monatsh. Chem. 1999, 130, 2, 327-332.

Process Pc2

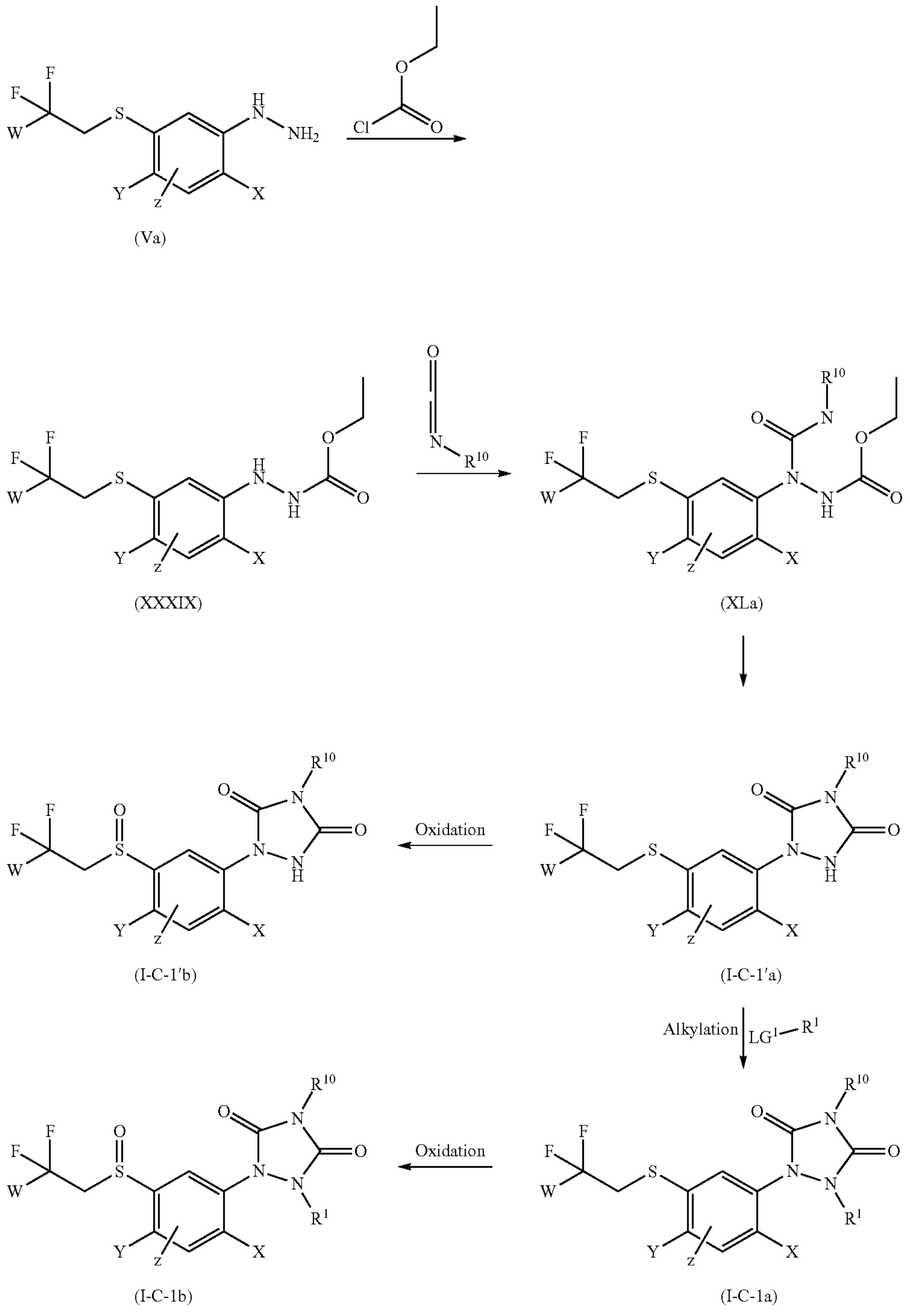

(Va) (XXXIX) (XLa) (I-C-1'b) (I-C-1'a) (I-C-1b) (I-C-1a)

According to J. Org. Chem. 1991, 56, 5643-5651, 2-aryl-1,2,4-triazolidine-3,5-diones of the general formula (I-C-1a) can alternatively be prepared by process Pc2. Condensation of hydrazines of the formula (Va) with chloroformic esters affords the corresponding ethyl phenylhydrazinecarboxylates (XXXIXa), which can then be reacted with isocyanates to give the corresponding substituted ethyl 2-(carbamoyl)-2-phenylhydrazinecarboxylates of the general formula (XLa) and then cyclized with strong bases such as, for example, potassium hydroxide to give the 2-aryl-1,2,4-triazolidine-3,5-diones of the general formula (I-C-1'a).

Subsequent alkylation with the appropriate alkylating agent $R^1$-$LG^1$ gives 2-aryl-1,2,4-triazolidine-3,5-diones of the general formula (I-C-1a), where $LG^1$ represents a classical leaving group such as iodide, bromide, chloride, tosylate, mesylate or triflate. Literature procedures for the alkylation can be found, for example, in J. Org. Chem. 1991, 56, 5643-5651, in Amer. Chem. J. 1910, 43, 532-543 or in Amer. Chem. J. 1910, 43, 380.

Processes Pc3 & Pc4 (for the Preparation of I-C-1)

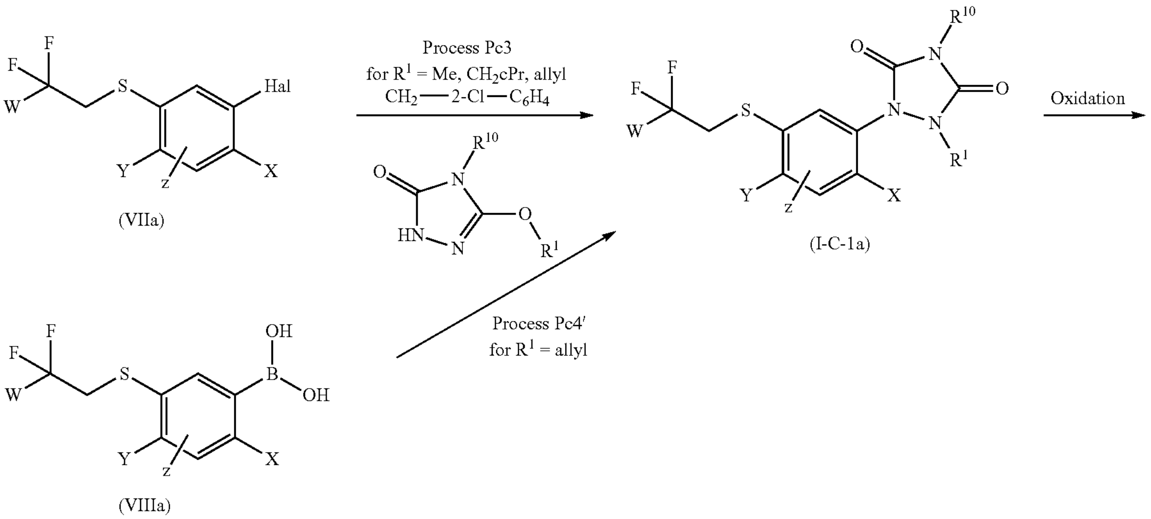

(VIIa)

(VIIIa)

(I-C-1a)

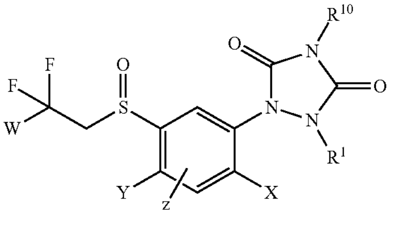

(I-C-1b)

Alternatively, 2-aryl-1,2,4-triazolidine-3,5-diones of the general formula (I-C-1a) can be prepared by process Pc3 by reacting aryl halides of the formula (VIIa) with triazolinones, where in this case $R^1$ may represent methyl, cycloalkylalkyl or substituted benzyl. Preferably, the reaction is carried out using transition metal catalysis or mediation, for example using copper such as, for example, copper(I) iodide in the presence of ligands such as, for example, N,N'-dimethyl-1,2-cyclohexanediamine and a base such as potassium carbonate in suitable solvents such as dioxane or toluene.

For $R^1$=allyl, 2-aryl-1,2,4-triazolidine-3,5-diones of the general formula (I-C-1a) can alternatively be prepared by process Pc4 by reacting boronic acids of the formula (VIII) with triazolinones. Preferably, the reactions are carried out with catalysis or mediation by copper(II) salts such as, for example, copper(II) acetate, under air or oxygen atmosphere, under dehydrating conditions (using, for example, a molecular sieve). The bases used are, for example, triethylamine or pyridine in suitable solvents such as, for example, dichloromethane.

Processes Pc5 & Pc6 (for the Preparation of I-C-2)

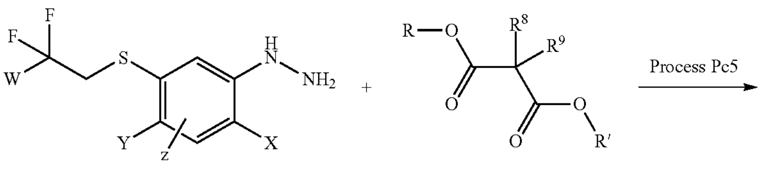

(Va)

-continued

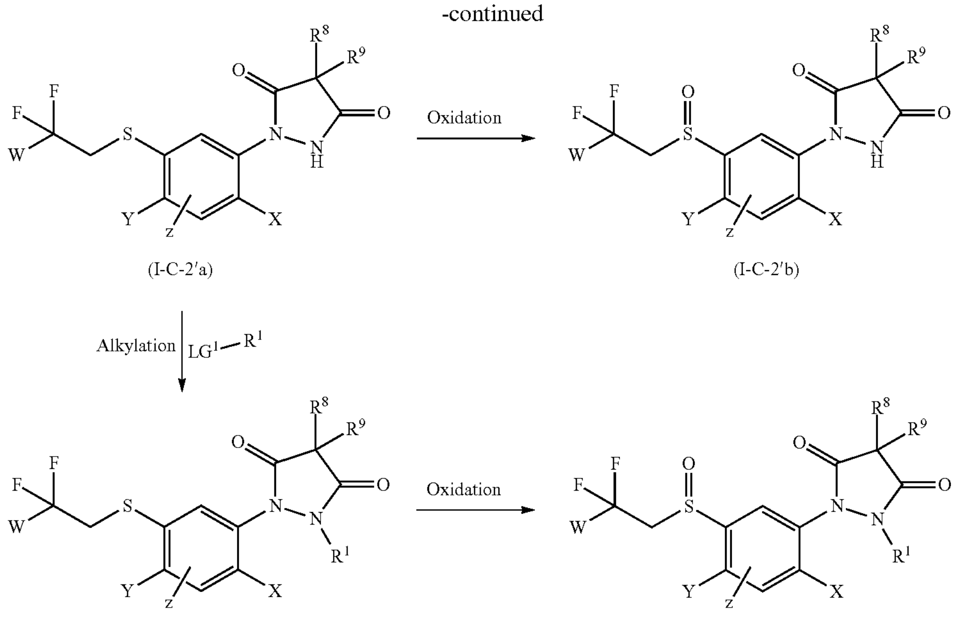

(I-C-2'a) (I-C-2'b) (I-C-2a) (I-C-2b)

Alternatively, pyrazole-3,5(2H,4H)-diones of the general formula (I-C-2a) can be prepared by process Pc5 by condensation of hydrazines of the formula (Va) with malonic acids or malonic diesters, as described, for example, in Helv. Chim. Acta 1953, 36, 75-81, Can. J. of Research, Section B 1950, 28, 720-725 or Tetrahedron Letters 2010, 51, 5328-5332.

Alternatively, pyrazole-3,5(2H,4H)-diones of the general formula (I-C-2a) can be prepared by process Pc6 as described, for example, in Arch. Pharm. 1980, 313, 577-582. Here, condensation of hydrazines of the formula (Va) with cyanoacetic acids using dicyclohexylcarbodiimide initially affords the respective 2-cyano-N'-arylacetohydrazides which are cyclized under acidic conditions such as, for example, dilute sulfuric acid to give the corresponding iminopyrazolidinones (XLIa). Hydrolysis with dilute base such as, for example, sodium hydroxide affords pyrazole-3,5(2H,4H)-diones of the general formula (I-C-2'a).

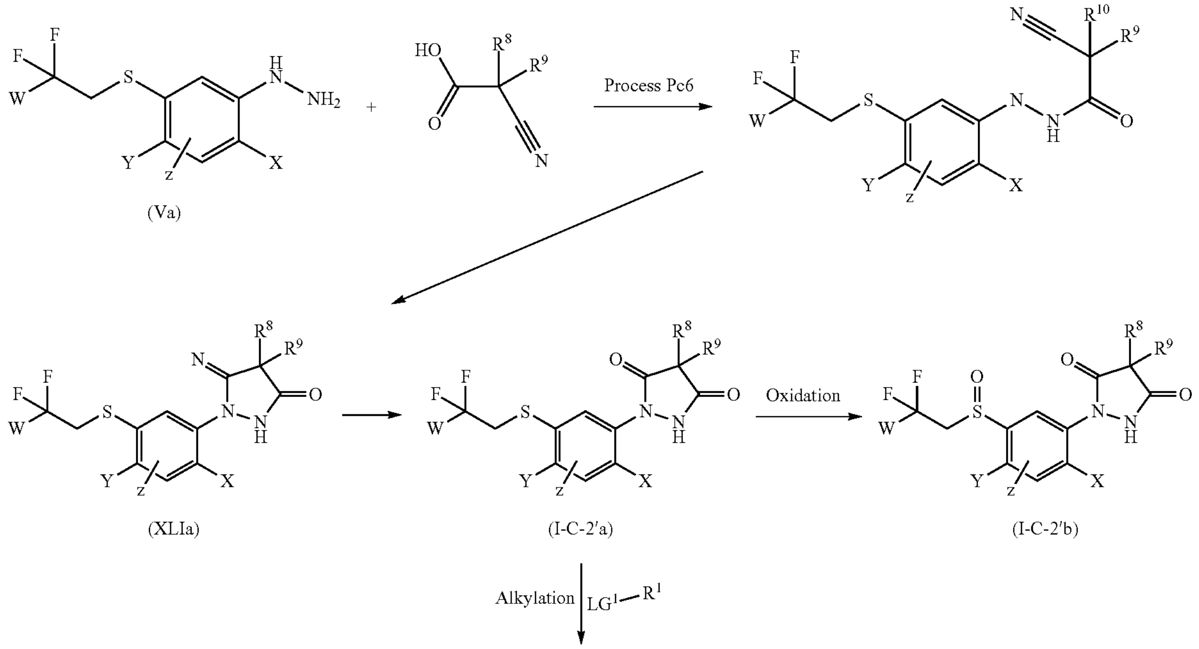

(Va) (XLIa) (I-C-2'a) (I-C-2'b)

-continued

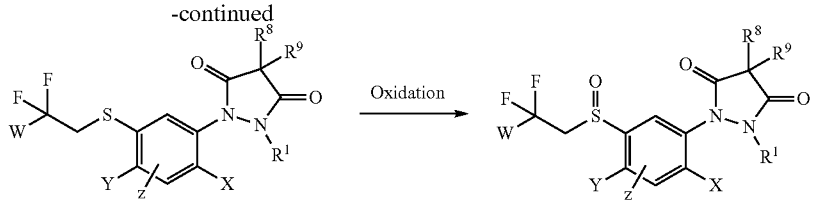

(I-C-2a) (I-C-2b)

Subsequent alkylation with the appropriate alkylating agent $R^1$-$LG^1$ gives pyrazole-3,5(2H,4H)-diones of the general formula (I-C-2a), where $LG^1$ represents a classical leaving group such as iodide, bromide, chloride, tosylate, mesylate or triflate. Literature procedures for the alkylation can be found, for example, in Arch. Pharm. 1958, 291, 404 or in Chem. Ber. 1908, 41, 3872.

Processes Pc7 and Pc8 (I-C-3)

For preparing the imidazolidine-2,4-diones of the general formula (I-C-3), it is possible to use, for example, process Pc7 and process Pc8.

The imidazolidine-2,4-diones of the general formula (I-C-3) can be subdivided into (I-C-3a) (for n=0) and (I-C-3b) (for n=1).

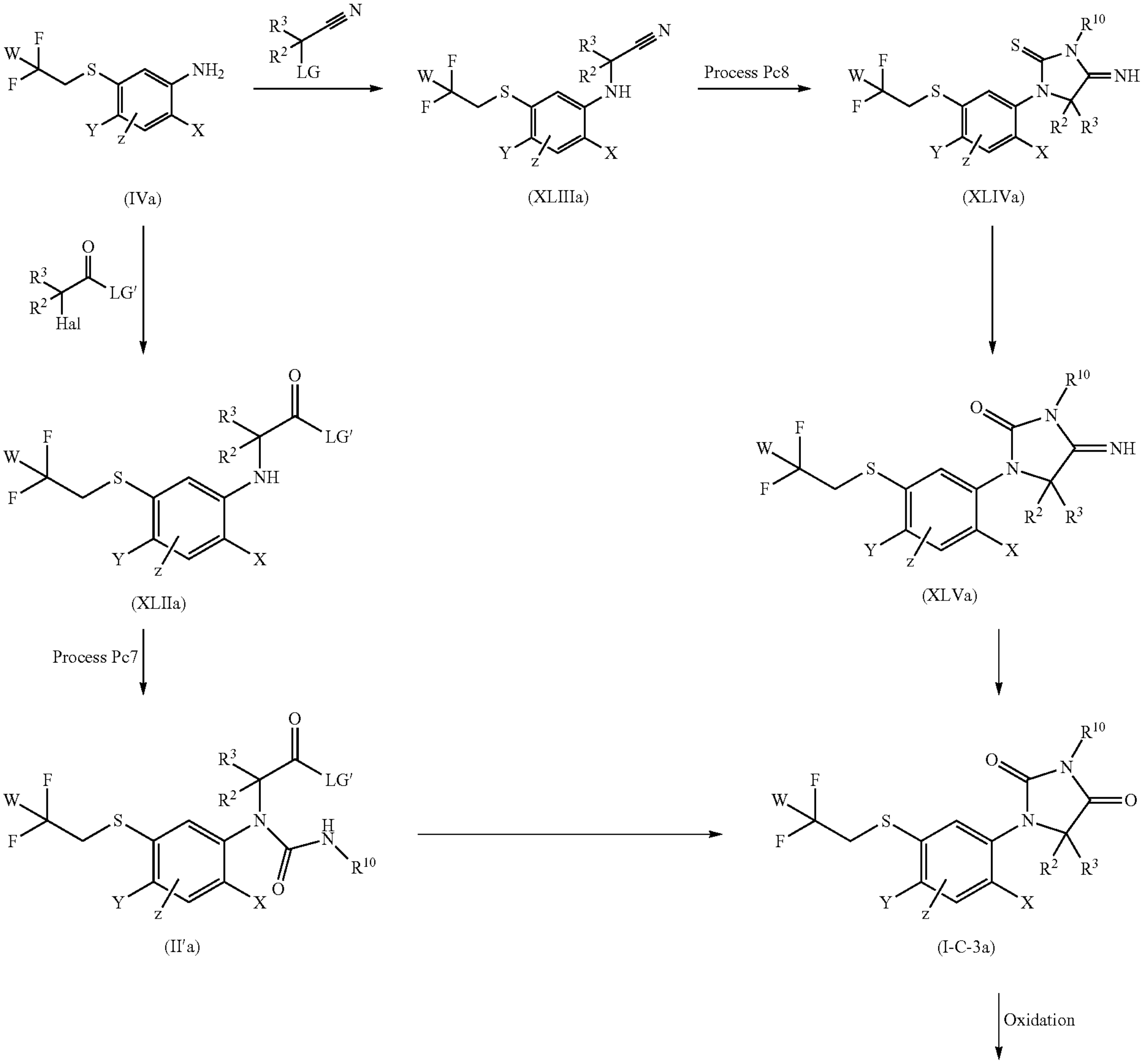

(IVa) (XLIIIa) (XLIVa) (XLIIa) (XLVa) (II'a) (I-C-3a)

-continued

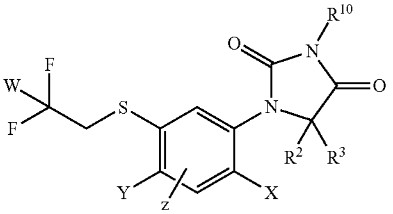

(I-C-3b)

where W, X, Y, Z, $R^2$, $R^3$ and $R^{10}$ have the meanings given above, n may represent 0 or 1, Hal represents halogen (preferably chlorine and bromine) and LG and LG' represent a leaving group (e.g. halogen, hydroxy, alkoxy).

Process Pc7

Anilines of the formula (IVa) can be alkylated with adequate halocarbonyl compounds according to methods known from the literature. For example, for $R^2$=$R^3$=hydrogen the reaction can be carried out using ethyl bromoacetate according to US2012/277273. The alkylated anilines of the formula (XLIIa) can be converted with isocyanates or 4-nitrophenyl alkylcarbamates into the ureas of the formula (II'a), optionally with the aid of a base, as in US2012/277273. Subsequently, there was ring closure to give the imidazolidine-2,4-diones (I), for example according to US2012/277273, where the alkylated ureas (II'a) are treated with a base in an inert organic solvent, optionally at elevated temperature. Alternatively, the cyclization can be carried out by treating the ureas (II'a) with neutral aluminum oxide, optionally in a solvent.

Alternatively, the imidazolidine-2,4-diones of the general formula (I) can also be prepared by Process Pc8, according to WO2006/124118.

Anilines of the formula (IV) can be alkylated with adequate nitrile compounds to give the compounds (XLIIIa). For example, for $R^2$=$R^3$=methyl the reaction can be carried out using 2-hydroxy-2-methylpropanonitrile. Alternatively, the preparation of the alkylated anilines (XLIIIa) from the anilines (IVa) can be carried out by reaction with a cyanide source and a ketone using, for example, potassium cyanide and acetone in acetic acid as in Bull. Chem. Soc. Japan 1926, 1, 202. The alkylated anilines of the formula (XLIIIa) can be converted with isothiocyanates into the 3-aryl-5-iminoimidazolidinethiones of the formula (XLIVa), optionally with the aid of a base, in an inert organic solvent, as in US2012/277273. The imidazolidinethiones (XLIVa) can afford the imidazolidinones (XLVa) when treated with an acid (for example hydrochloric acid). By reaction with an oxidizing agent, the imidazolidinones (XLVa) can then be converted into the imidazolidinediones (I-C-3a).

Process Pc9 (for the Preparation of I-C-3)

Imidazolidine-2,4-diones of the formula (I-C-3) where $R^4$ represents hydrogen can also be prepared by process Pc9.

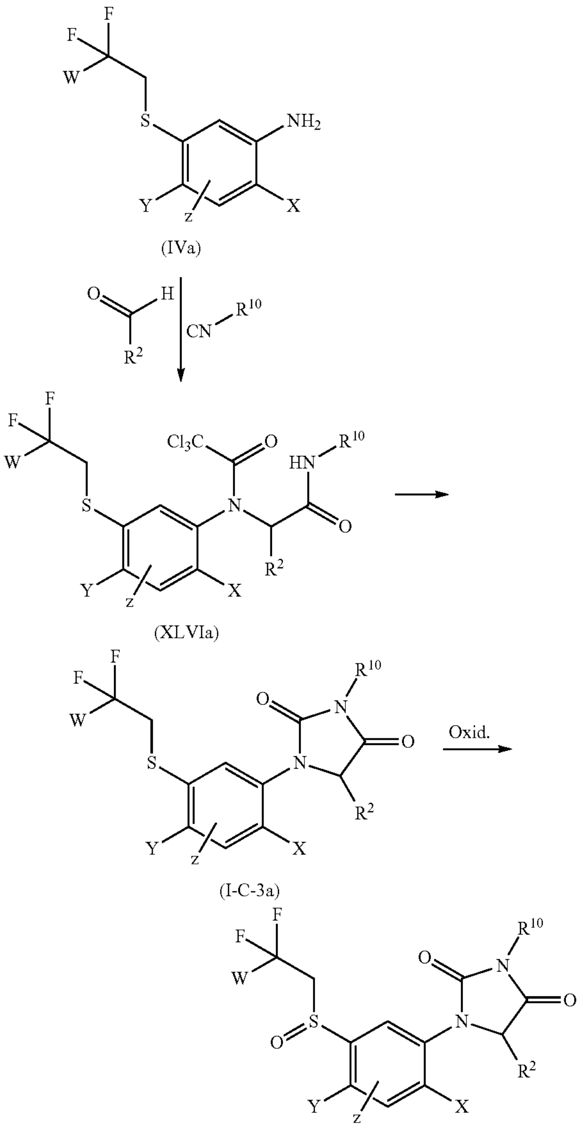

(IVa)

(XLVIa)

(I-C-3a)

(I-C-3b)

Anilines of the formula (IVa) can be converted into the 2-N-trichloroacetylaminoacetamides of the formula (XLVIa) using methods known from the literature, for example according to Tetrahedron 2012, 68, 2621-2629. To this end, the aniline (IVa) is added to the required aldehyde, for example in methanol at room temperature, and the resulting imine is reacted with an isocyanide and trichloroacetic acid. The 2-N-trichloroacetylaminoacetamides (XLVIa) can be used to prepare the imidazolidine-2,4-diones of the general formula (I-C-3a), for example by reaction with sodium ethoxide in methanol, as described in the article mentioned above.

Process Pc10 (for the Preparation of I-C-4)

The 5-thioxo-1,2,4-triazolidin-3-ones of the general formula (I-C-4) can be subdivided into (I-C-4a) (for n=0) and (I-C-4b) (for n=1) and can be prepared, for example, by process Pc10.

also described in DE 2554866. If isothiocyanates are used, the corresponding 1-aryl-5-thioxo-1,2,4-triazolidin-3-ones are obtained.

In Berichte der Deutschen Chemischen Gesellschaft (1910), 42, 4763-4769 and (1911), 44, 560-583, 1-aryl-5-thioxo-1,2,4-triazolidin-3-ones are prepared by reaction of specific thiosemicarbazides with phosgene.

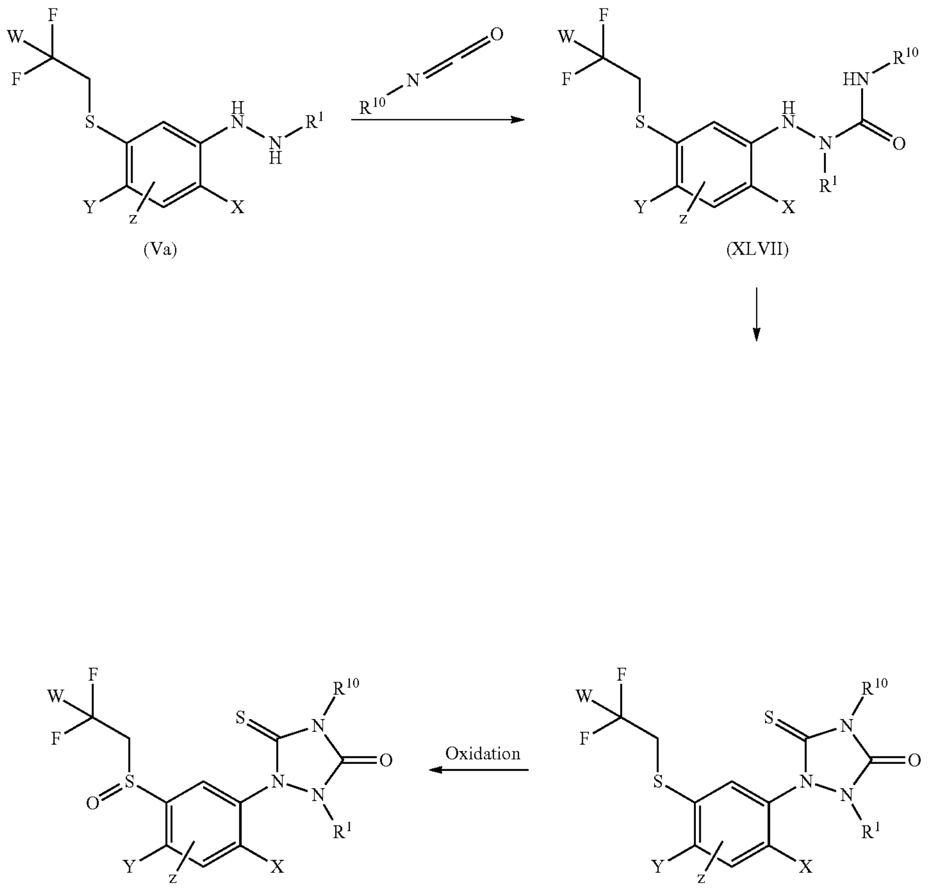

(Va) (XLVII) (I-C-4b) (I-C-4a)

where W, X, Z, z, $R^1$ and $R^{10}$ have the meaning given above.

Reaction of hydrazines of the general formula (Va) with isocyanates ($R^{10}$—NCO) gives the semicarbazides of the formula (XLVII) which are converted by subsequent reaction with, for example, 1,1'-thiocarbonyldiimidazole, into the 1-aryl-5-thioxo-1,2,4-triazolidin-3-ones of the formula (I-C-4a).

The semicarbazides of the formula (XLVII) are prepared by processes described, for example, in Rec. Trav. Chim. 52, 979 (1933) or in den Chem. Ber. 36, 1362 (1903).

A further preparation process for 1-aryl-5-thioxo-1,2,4-triazolidin-3-ones consists in the selective conversion of a carbonyl group of corresponding 1-aryl-1,2,4-triazolin-3,5-diones into the thiocarbonyl group using suitable sulfurizing agents such as, for example, phosphorus pentasulfide or Lawesson's reagent in a suitable solvent, for example xylene or cumene. This process is described, for example, in DE 2554866.

The synthesis of 1-aryl-1,2,4-triazoline-3,5-diones by reaction of 1-alkoxycarbonylhydrazines with isocyanates is The preparation and use of 1-aryl-1,2,4-triazoline-3,5-diones as herbicides and insecticides are described in WO 9726248.

The preparation of further 1-aryl-1,2,4-triazoline-3,5-dione precursors is also described in U.S. Pat. No. 3,663,564 and U.S. Pat. No. 3,621,099.

Process Pc11 (for the Preparation of I-C-5 and I-C-6)

The 1-aryl-5-thioxo-1,2,4-triazolidin-3-ones of the general formula (I-C-5) can be subdivided into (I-C-5a) (for n=0) and (I-C-5b) (for n=1) and can be prepared, for example, by process Pc11.

1-Aryl-1,2,4-triazolidine-3,5-diones of the general formula (I-C-6) can be subdivided into (I-C-6a) (for n=0) and (I-C-6b) (for n=1) and can be prepared, for example, by process Pc11.

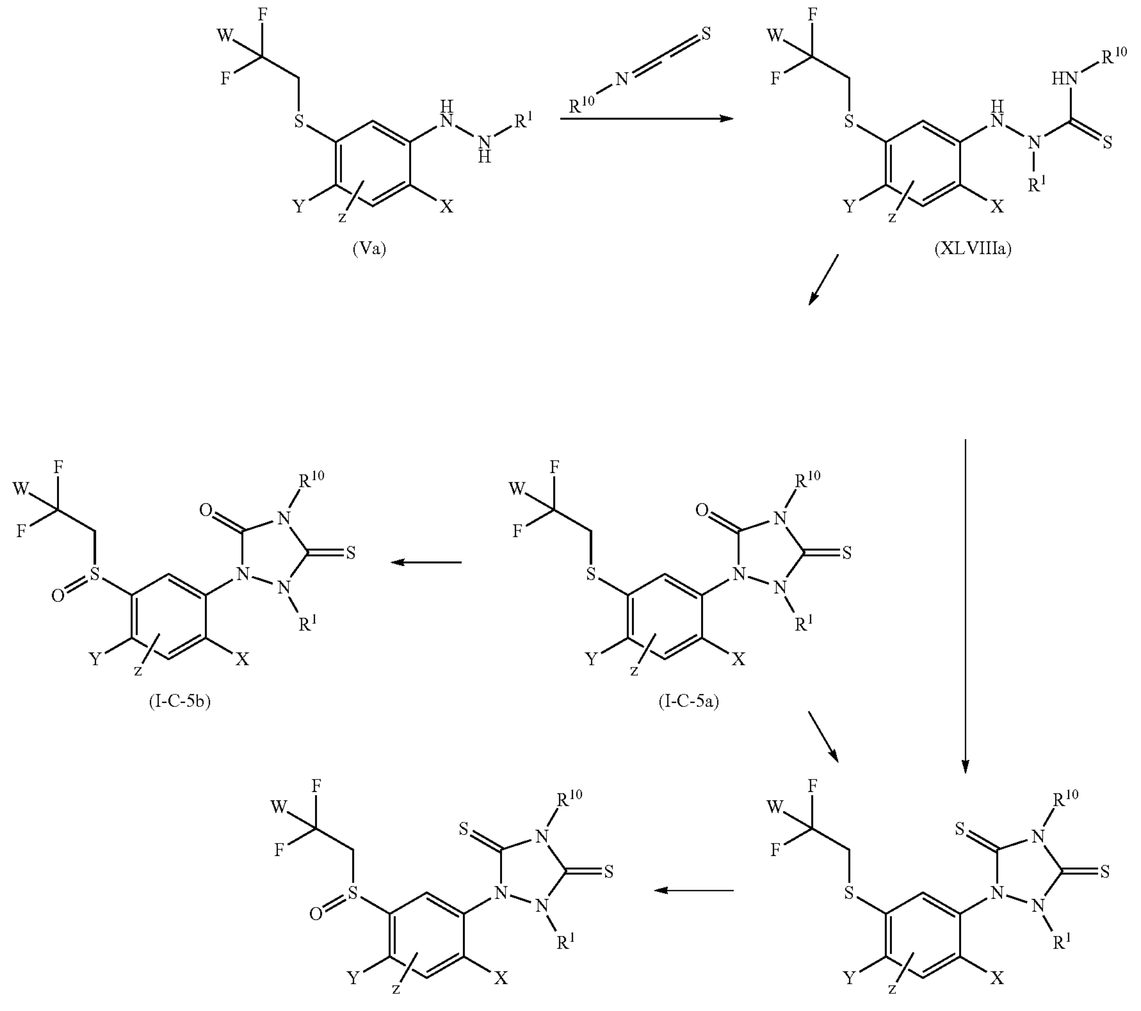

(Va) (XLVIIIa) (I-C-5b) (I-C-5a) (I-C-6b) (I-C-6a)

where W, X, Z, z, $R^1$ and $R^{10}$ have the meaning given above.

Reaction of hydrazines of the general formula (Va) with isothiocyanates ($R^{10}$—NCS) gives the thiosemicarbazides of the general formula (XLVIIIa) which, by subsequent reaction with, for example, 1,1'-carbonyldiimidazole are converted into the 1-aryl-5-thioxo-1,2,4-triazolidin-3-ones of the formula (I-C-5a) or by subsequent reaction with, for example, 1,1'-thiocarbonyldiimidazole are converted into the 1-aryl-1,2,4-triazolidine-3,5-dithiones of the formula (I-C-6a).

The thiosemicarbazides of the formula (XLVIII) are prepared by processes described, for example, in Rec. Trav. Chim. 55, 101 (1936), in J. Am. Chem. Soc. 1552 (1931) or in Chem. Ber. 34, 320 (1901).

A further general preparation process for the 2-aryl-5-thioxo-1,2,4-triazolidin-3-ones and the 2-aryl-1,2,4-triazolidine-3,5-dithiones consists in the selective conversion of a carbonyl group of corresponding 1-aryl-1,2,4-triazolin-3,5-diones into the thiocarbonyl group using suitable sulfurizing agents such as, for example, phosphorus pentasulfide or Lawesson's reagent in a suitable solvent, for example xylene or cumene. This process is described, for example, in DE 2554866.

The synthesis of the corresponding 1-aryl-1,2,4-triazoline-3,5-diones by reaction of 1-alkoxycarbonylhydrazines with isocyanates is also described in DE 2554866. When 1-alkoxythiocarbonylhydrazines are employed, 1-aryl-5-thioxo-1,2,4-triazolidin-3-ones are obtained.

In Berichte der Deutschen Chemischen Gesellschaft (1910), 42, 4763-4769 and (1911), 44, 560-583, the 1-aryl-5-thioxo-1,2,4-triazolidin-3-ones are prepared by reaction of specific thiosemicarbazides with phosgene.

By oxidation of the thioethers of the formula (I-C-5a) or (I-C-6a) by methods known from the literature, the sulfoxides of the formula (I-C-5b) and (I-C-6b), respectively, are obtained.

Processes Pd1-Pd3 are suitable for preparation of embodiment I-D of the compounds of the formula (I).

Process Pd1 (I-D-1)

The 3-arylimidazolidine-2,4,5-triones of the general formula (I-D-1) can be subdivided into (I-D-1a) (for n=0) and (I-D-1b) (for n=1) and can be prepared, for example, by process Pd1.

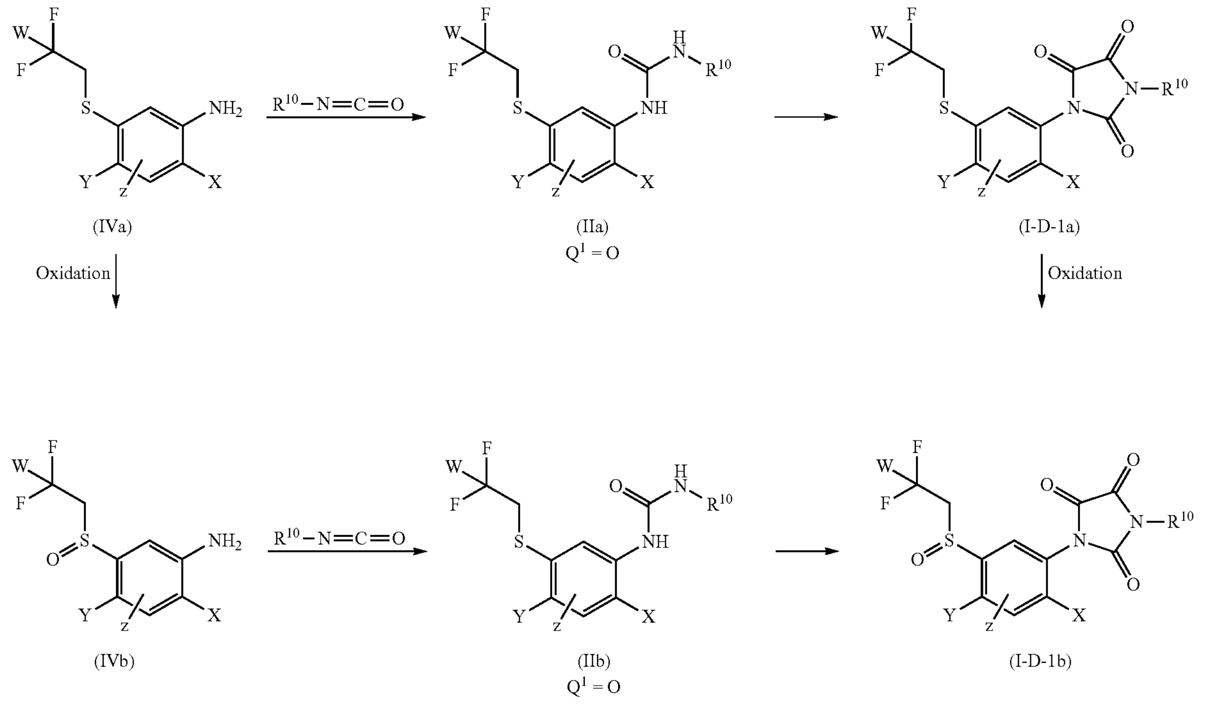

(IVa) (IIa) $Q^1 = O$ (I-D-1a)

(IVb) (IIb) $Q^1 = O$ (I-D-1b)

Phenylureas of the formula (II, $Q^1$=O) are prepared by methods known from the literature described, for example, in the patent JP2011/042611.

Reaction of phenylureas of the formula (II) with oxalyl chloride gives the 1-R-3-arylimidazolidine-2,4,5-triones of the formula (I-D-1), analogously to the procedures from J. Korean Chem. Soc. (1999), 43(4), 491-493 or JP 1976-92865 or Tetrahedron Lett. 2012, 53, 4758-4762.

Further synthesis variants are described in Synthesis (1977), (9), 641-2 or Liebigs Ann. Chem. (1927), 458, 76-92 or Recl. Trav. Chim. Pays-Bas (1915), 34 289-325 or J. Fluorine Chem. 2011, 132, 596-611 or Bioorg. Med. Chem. Lett. (2009), 19(9), 2570-2573 or Asian J. Chem. (2007), 19(2), 1455-1460 or J. Het. Chem. 2003, 40(5), 885-893 or US 20030119889 or US 20030119890 or J. Het. Chem. (1994), 31(6), 1535-9 or J. Het. Chem. (1971), 8(4), 669-70 or Pharmazie (1990), 45(10), 795-6 or Zeitschrift f. Chemie (1989), 29(8), 281-3 or J. Org. Chem., 1979, 44 (22), 3858-3861 or Synthesis (1977), (9), 641-2 or in DE 1969-1916932 or DE 19660523.

A number of 3-arylimidazolidine-2,4,5-triones are also commercially available, for example 1-[3 (methylsulfanyl) phenyl]imidazolidine-2,4,5-trione [CAS-RN: 1152595-83-9].

Process Pd2 (for the Preparation of I-D-2)

The pyrrolidine-2,3,5-triones of the general formula (I-D-2) can be subdivided into (I-D-2a) (for n=0) and (I-D-2b) (for n=1). They can be prepared, for example, in accordance with process Pd2

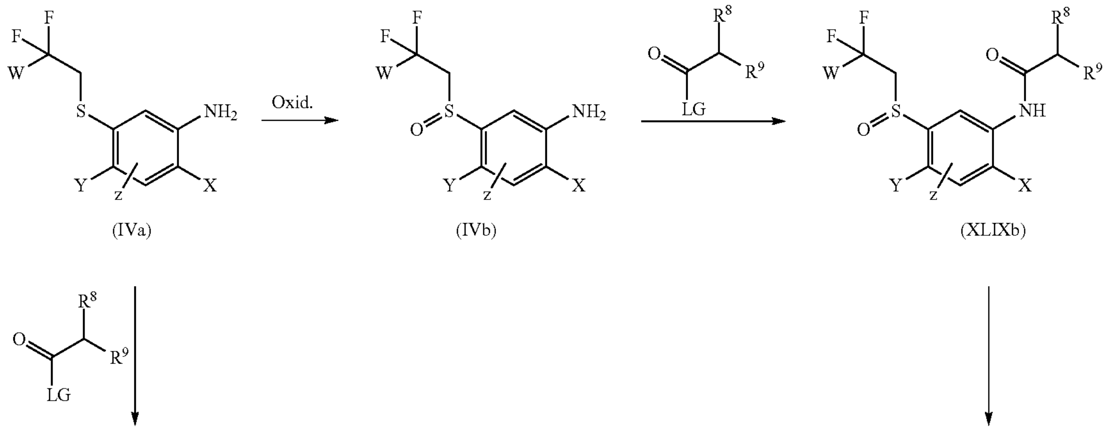

(IVa) (IVb) (XLIXb)

-continued

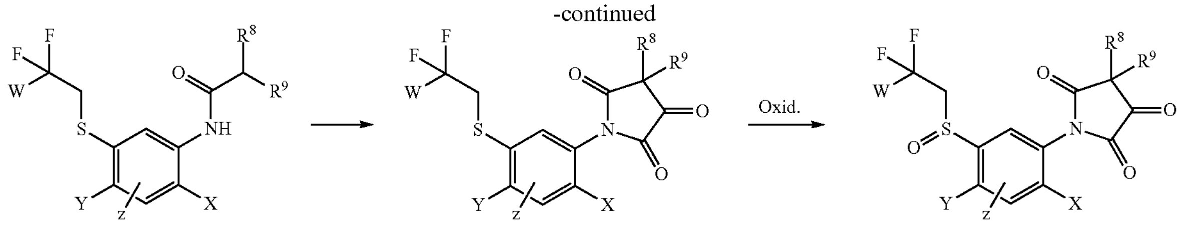

(XLIXa) (I-D-2a) (I-D-2b)

where W, X, Y, Z, $R^8$ and $R^9$ have the meanings given above and LG represents OH or halogen (in particular chlorine).

Anilines of the formula (IV) can be reacted with carboxylic acids or carboxylic acid derivatives (in particular chlorides) to give the amides of the formula (XLIX), optionally in the presence of a base and optionally in the presence of an organic solvent as described, for example, by G. S. Skinner in J. Amer. Chem. Soc. 1950, 72, 5569-5573. The amides (XLIX) can be treated, for example, with oxalyl chloride or ethyl oxalate to afford the pyrrolidine-2,3,5-triones (I). As described by G. S. Skinner, the reaction can be carried out in an inert organic solvent such as toluene at 60° C. Alternatively and depending on the nature of the $R^8$ and $R^9$ radicals, the amides (XLIX) can be converted with ethyl oxalate into oxazolidinediones which then re-arrange in an alcohol to give the desired pyrrolidinetriones of the formula (I-D-2). This was published by G. S. Skinner in J. Amer. Chem. Soc. 1956, 77, 4656-4659.

Process Pd3 (for the Preparation of I-D-3)

The 2-thioxoimidazolidine-4,5-diones of the general formula (I-D-3) can be subdivided into (I-D-3a) (for n=0) and (I-D-3b) (for n=1). They can be prepared, for example, in accordance with process Pd3.

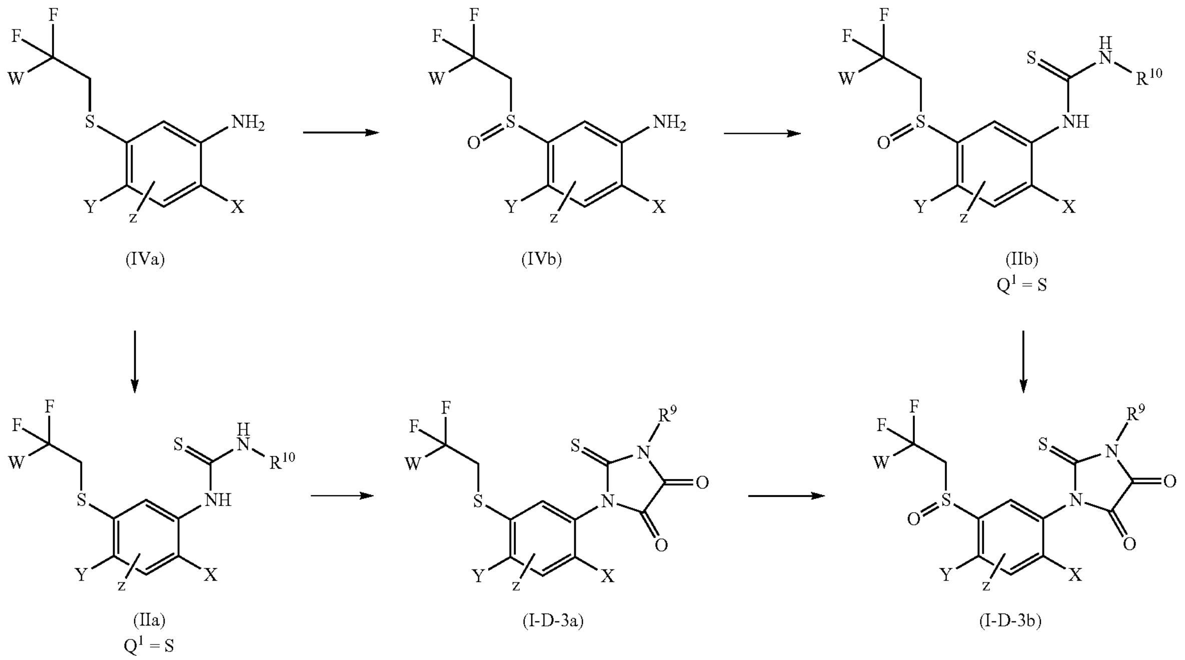

(IVa) (IVb) (IIb) $Q^1 = S$ (IIa) $Q^1 = S$ (I-D-3a) (I-D-3b)

where W, X, Y, Z, A and $R^{10}$ are each as defined above.

Anilines of the formula (IV) can be converted into the thioureas of the formula (II) by methods known from the literature, for example according to JP2011/042611, by treating them with isothiocyanates, optionally in the presence of a base and optionally in the presence of an organic solvent, or by converting them by generally known methods into their isothiocyanates and then reacting these with amines to give the thioureas.

From the thioureas of the general formula (II), it is possible to synthesize the 2-thioxoimidazolidine-4,5-diones of the general formula (I-D-3a) or (I-D-3b), for example by reaction with oxalyl chloride or ethyl oxalyl chloride in an inert solvent such as chloroform, dichloromethane or acetonitrile, optionally at elevated temperature. Examples of such reactions can be found inter alia in J. Med. Chem. 2004, 47, 681-695 and US2003/119889.

Reactions in the Microwave

When carrying out the processes according to the invention, it is optionally possible to use any commercial microwave apparatus suitable for these reactions (e.g. Anton Paar Monowave 300, CEM Discover S, Biotage Initiator 60).

Thionation

A further general process for preparing the compounds of the general formula (Ia) or (Ib) according to the invention in which V is sulfur involves the conversion of the carbonyl in corresponding precursors to the thiocarbonyl group with the aid of suitable thionating reagents, for example phosphorus pentasulfide or Lawesson's reagent in a suitable solvent, for example pyridine, xylene or cumene. This variant is described in numerous publications, for example in J. Amer. Chem. Soc. 1956, 1938-1941, Chem. Pharm. Bull. 1962, 10, 647-652, U.S. Pat. No. 3,007,927, DE 2554866 or WO 2000026194.

General Preparation Processes for Oxidizing Thioethers to Sulfoxides

Compounds of the general formula (Ib) can be prepared through oxidation by processes known from the literature from compounds of the general formula (Ia), for example by means of an oxidizing agent in a suitable solvent and diluent. Suitable oxidizing agents are, for example, dilute nitric acid, hydrogen peroxide and peroxycarboxylic acids, for example meta-chloroperbenzoic acid. Suitable solvents are inert organic solvents, typically acetonitrile and halogenated solvents such as dichloromethane, chloroform or dichloroethane.

A large number of different methods are suitable for generating enantiomerically enriched sulfoxides, as described by A. R. Maguire in ARKIVOC, 2011(i), 1-110: metal-catalysed asymmetric oxidations of thioethers, for example with titanium and vanadium as the most frequently employed catalyst sources, in the form of $Ti(O^iPr_4)$ and $VO(acac)_2$, together with a chiral ligand and an oxidizing agent such as tert-butyl hydroperoxide (TBHP), 2-phenylpropan-2-yl hydroperoxide (CHP) or hydrogen peroxide; non-metal-catalysed asymmetric oxidations employing chiral oxidizing agents or chiral catalysts; electrochemical or biological asymmetric oxidations and also kinetic resolution of sulfoxides and nucleophilic shift (according to Andersen's method).

The enantiomers can also be obtained from the racemate, for example by separating them on a preparative scale by chiral HPLC.

Description of the Starting Materials and Intermediates

Anilines of the formula (IV), halides of the formula (VII), boronic acids of the formula (VIII), hydrazines of the formula (V) and isocyanates of the formula (III) are central building blocks for preparing the compounds of the formula (I).

The anilines of the general formula (IV) can be classified into compounds where n=0 (IVa) and n=1 (IVb).

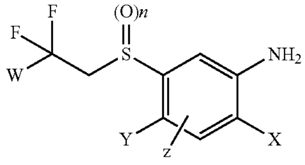

(IVa) n = 0
(IVb) n = 1

Some of the anilines of the formula (IVa) are known from the literature, for example from JP 2007/284356, or they can be synthesized by processes known from the literature, especially under the conditions specified in the preparation examples.

The compounds of the formula (IVb) are novel and can be prepared by oxidation, especially under the conditions specified in the preparation examples.

The anilines of the general formula (IVa) can be prepared, for example, as in the scheme below;

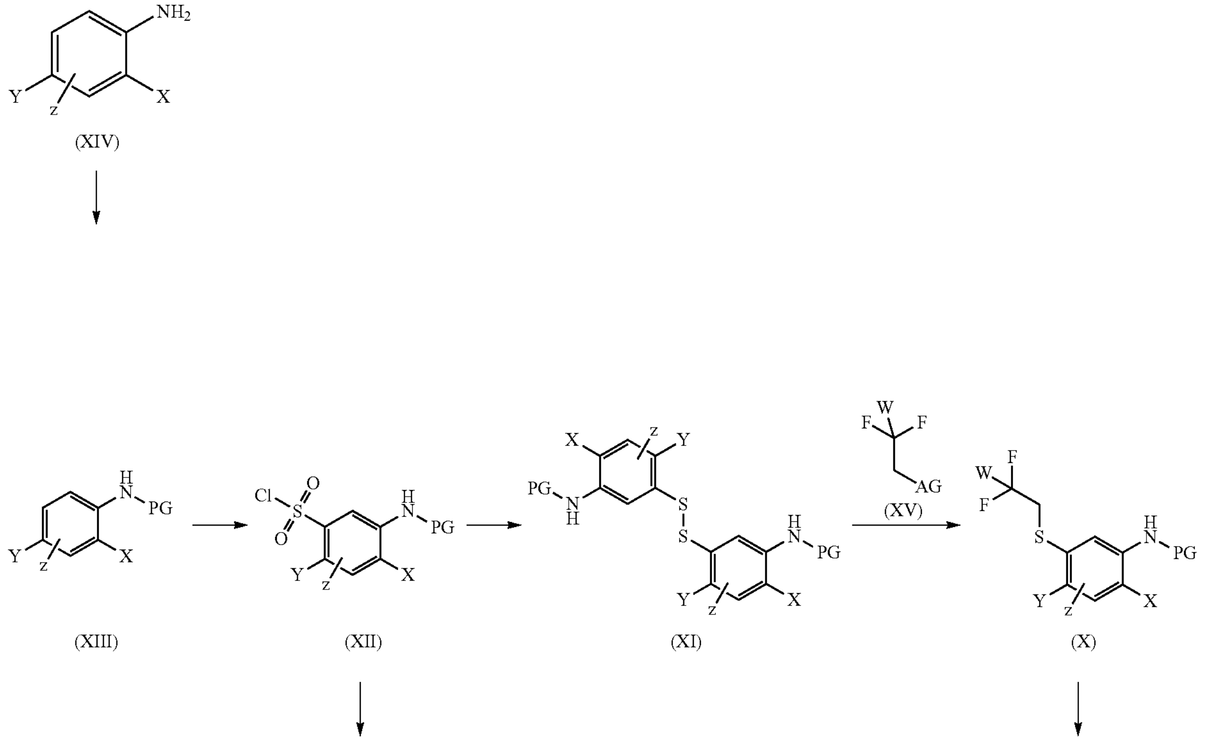

(XIV)

(XIII) (XII) (XI) (XV) (X)

-continued

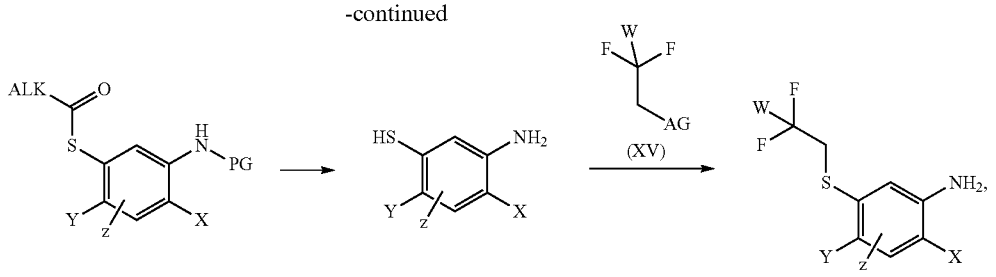

(XVII) (XVI) (IVa)

where X, Y, Z and W are as defined above, AG is a leaving group and PG is a protecting group.

Anilines of the formula (XIV) are either commercially available or can be prepared by known methods. They can be protected with a suitable protective group, for example an acetyl group, to give compounds of the formula (XIII). In the presence of acids, acid anhydrides or acid chlorides, for example, the anilines (XIV) can be converted to the corresponding anilides (XIII). The chlorosulfonation of the protected anilines (XIII) with chlorosulfonic acid gives the corresponding sulfonyl chlorides (XII). The reduction of the sulfonyl chlorides (XII) to the disulfides (XI) is possible by methods known from the literature, for example iron in hydrochloric acid or iodide. The reaction of the disulfides (XI) with haloalkyl electrophiles of the formula (XV) where AG is a leaving group, for example chlorine, bromine, tosylate, mesylate or triflate, gives the sulfides (X). The protecting group can be removed by suitable methods known from the literature, so as to obtain anilines of the formula (IVa).

Instead of the reduction to the disulfide (XI), the sulfonyl chloride (XII) can be reduced with a suitable reducing agent, for example iodine/phosphorus, to give the alkyl thioate (XVII), and then deprotected by a suitable method, for example the reaction with potassium hydroxide solution, to give thiols of the formula (XVI). Reaction of the thiols (XVI) with haloalkyl electrophiles of the formula (XV) where AG represents a leaving group such as, for example, chlorine, bromine, tosylate, mesylate or triflate affords the sulfides (IVa).

The compounds of the formulae (X), (XI), (XII), (XIII), (XVI) and (XVII) are novel and can be prepared particularly under the conditions specified in the preparation examples.

Likewise preferably, the thioethers of the formula (IVa) can alternatively be prepared according to the following scheme:

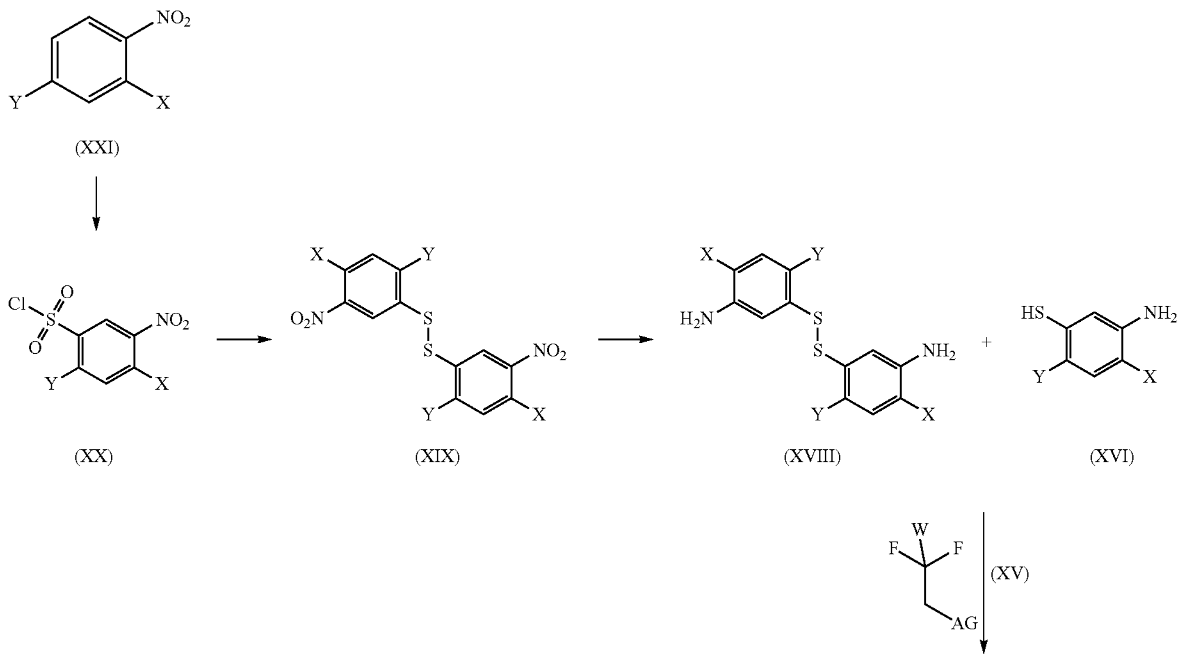

(XXI) (XX) (XIX) (XVIII) (XVI)

-continued

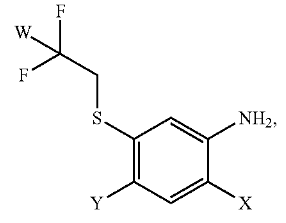

(IVa)

where X, Y, Z and W are as defined above, AG is a leaving group and PG is a protecting group.

The chlorosulfonation of the nitroaromatics of the formula (XXI) with chlorosulfonic acid gives the corresponding sulfonyl chlorides (XX). The reduction of the sulfonyl chlorides (XX) to the bis(nitroaryl) disulfides (XIX) is possible by methods known from the literature, for example iodide. The reduction of the disulfides (XXI) to the disulfanediyldianilines (XIX), some of which are formed as a mixture with the corresponding aminoarylthiols (XVI), is possible with commonly known reducing agents, for example hydrogen, optionally with the aid of heterogeneous catalysts, for example, Raney nickel, platinum on activated carbon or palladium on activated carbon. Reaction of the disulfides (XVIII) or thiophenols (XVI) with haloalkyl electrophiles of the formula (XV) where AG represents a leaving group such as, for example, chlorine, bromine, iodine, tosylate, mesylate or triflate affords the 3-[(2,2,2-trifluoroethyl)sulfanyl]anilines of the formula (IVa).

The compounds of the formulae (XVI), (XVIII), (XIX) and (XX) are novel and can be prepared in particular under the conditions mentioned in the Preparation Examples.

Halides of the General Formula (VIIa)

(VIIa)

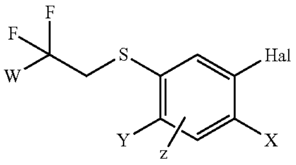

in which X, Y, Z and W are as defined above and Hal is chlorine, bromine or iodine are known from the literature, from WO 2007/034755, JP 2007/081019, JP 2007/284385, JP 2008/260706, JP 2008/308448, JP 2009/023910 or WO 2012/176856, or can be synthesized by processes known from the literature, which may optionally be slightly modified, especially as described in the specific synthesis examples.

Suitable starting materials for the synthesis of the iodides of the general formula (VIIa) are bromides having the same formula, for example in halogen exchange reactions according to methods known from the literature, if appropriate with metal catalysis (see H. Suzuki, Chem. Let. 1985, 3, 411-412; S. L. Buchwald, J. Amer. Chem. Soc. 2002, 124 (50), 14844-14845). Synthesis is likewise possible proceeding from anilines of the formula (IVa) under Sandmeyer reaction conditions, as described by E. B. Merkushev in Synthesis 1988, 12, 923-937.

Boronic Acids of the General Formula (VIIIa) and (VIIIb)

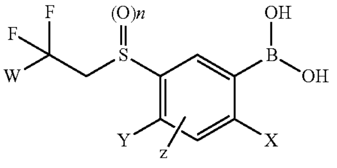

(VIIIa) n = 0
(VIIIb) n = 1 in which X, Y, Z and W are as defined above are known from the literature, for example from WO2007/034755, JP2007/284385, JP2009/023910 and WO2012/176856, or can be synthesized by processes known from the literature, especially as in the specific synthesis examples.

Hydrazines of the General Formula (Va)

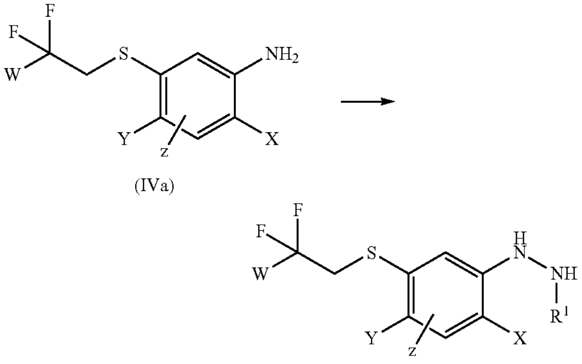

(IVa)

(Va)

Some hydrazines of the general formula (Va) are known from the literature, for example from EP 1803712 A1 and WO 2006043635, or they can be synthesized by processes known from the literature, as described, for example, in J. Med. Chem. 2003, 46, 4405-4418.

Isocyanates of the Formula (IIIa)

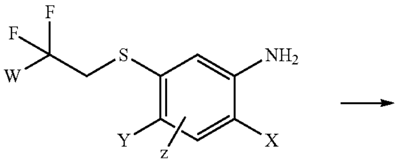

(IVa)

-continued

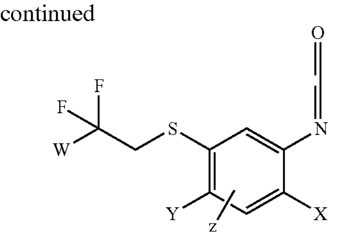

(IIIa)

Some isocyanates of the general formula (IIIa) are known from the literature, for example from JP 2011/042611 A, or they can be synthesized by processes known from the literature, as described, for example, in EP 1183229 B1, in J. Amer. Chem. Soc. 1940, 62, 2965-2966, in Angew. Chem. 1995, 107, 2746-2749 or in US2010/160388 A1, in particular as described in the specific synthesis examples.

Heterocyclic Compounds of the Formula (XXII)

(XXII)

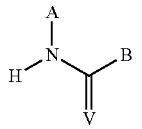

in which A and B are as defined above are commercially available or known from the literature, or they can be synthesized by processes known from the literature. As examples, the different heterocyclic compounds are divided into and specified in their subclasses.

Imidazolidine-2,4-Diones of the General Formula (XXII-B-1)

(XXII-B-1)

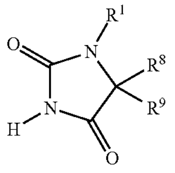

Imidazolidine-2,4-ones of the general formula (XXII-B-1) are commercially available or known from the literature, or can be synthesized by processes known from the literature. One example is: 1,5,5-trimethylimidazolidine-2,4-dione (commercially available)

Pyrrolidine-2,5-diones of the General Formula (XXII-B-4)

(XXII-B-4)

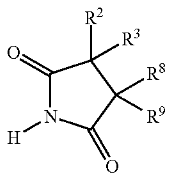

Pyrrolidine-2,5-diones of the general formula (XXII-B-4) are commercially available or known from the literature, or can be synthesized by processes known from the literature. One example is: pyrrolidine-2,5-dione (commercially available)

1,2,4-Triazolidine-3,5-diones of the General Formula (XXII-C-1)

(XXII-C-1)

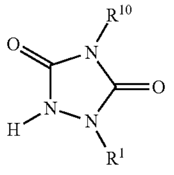

1,2,4-Triazolidine-3,5-diones of the general formula (XXII-C-1) are commercially available or known from the literature, or can be synthesized by processes known from the literature. (see also the synthesis examples). Examples include: 4-methyl-1,2,4-triazolidine-3,5-dione, [16312-79-1](commercially available), 4-ethyl-1,2,4-triazolidine-3,5-dione (see, for example, Bioorg. Med. Chem. 2010, 18, 1573-1582), 1,4-diethyl-1,2,4-triazolidine-3,5-dione (see, for example, J. Org. Chem. 1986, 51, 1719-1723; J. Org. Chem. 1973, 38, 2442-2446; see synthesis examples), 1-ethyl-4-phenyl-1,2,4-triazolidine-3,5-dione (see, for example, JP 53053655 A; WO 2012149335 A2; see synthesis examples), 1-benzyl-4-methyl-1,2,4-triazolidine-3,5-dione (see, for example, WO 2012149335 A2), 1-ethyl-4-methyl-1,2,4-triazolidine-3,5-dione (see, for example, JP 53053655 A; WO 2012149335 A2), 2,5-difluoro-4-(4-methyl-3,5-dioxo-1,2,4-triazolidin-1-yl)benzonitrile (see, for example, WO 9726248 A1), 1-(cyclohex-2-en-1-yl)-4-methyl-1,2,4-triazolidine-3,5-dione (see, for example, Org. Lett. 2000, 2, 1295-1297; J. Org. Chem. 1980, 45, 3472-3476), 1,4-dimethyl-1,2,4-triazolidine-3,5-dione (see, for example, Arch. Pharm. 1971, 304, 706-712; J. Org. Chem. 1991, 56, 5643-5651), 1-allyl-4-methyl-1,2,4-triazolidine-3,5-dione (see, for example, J. Org. Chem. 1981, 46, 614-9), 4-cyclopropyl-1-isobutyl-1,2,4-triazolidine-3,5-dione, 4-tert-butyl-1-methyl-1,2,4-triazolidine-3,5-dione, 4-tert-butyl-1-ethyl-1,2,4-triazolidine-3,5-dione, 1-cyclopentyl-4-methyl-1,2,4-triazolidine-3,5-dione, 1-ethyl-4-isopropyl-1,2,4-triazolidine-3,5-dione, 1-benzyl-4-cyclopropyl-1,2,4-triazolidine-3,5-dione, 4-isopropyl-1-methyl-1,2,4-triazolidine-3,5-dione, 1-methyl-4-[3-(trifluoromethyl)phenyl]-1,2,4-triazolidine-3,5-dione, 4-cyclopropyl-1-isopropyl-1,2,4-triazolidine-3,5-dione, 4-cyclopropyl-1,2,4-triazolidine-3,5-dione, 1-isopropyl-4-methyl-1,2,4-triazolidine-3,5-dione, 1-sec-butyl-4-cyclopropyl-1,2,4-triazolidine-3,5-dione, 4-ethyl-1-methyl-1,2,4-triazolidine-3,5-dione.

2,4-Dihydro-3H-1,2,4-triazol-3-ones

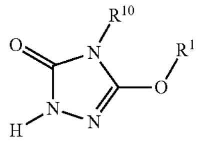

2,4-Dihydro-3H-1,2,4-triazol-3-ones are commercially available or known from the literature, or they can be synthesized by processes known from the literature. Examples include: 4-allyl-5-methoxy-2,4-dihydro-3H-1,2,4-triazol-3-one (see, for example, U.S. Pat. No. 5,541,337 A1; EP 507171 A1), 4-cyclopropyl-5-methoxy-2,4-dihydro-3H-1,2,4-triazol-3-one (see, for example, U.S. Pat. No. 5,541,337 A1; EP 507171 A1; WO 2010063402 A1), 5-(allyloxy)-4-cyclopropyl-2,4-dihydro-3H-1,2,4-triazol-3-one (see, for example, U.S. Pat. No. 5,541,337 A1), 5-(cyclopropylmethoxy)-4-methyl-2,4-dihydro-3H-1,2,4-triazol-3-one, 5-[(2-chlorobenzyl)oxy]-4-methyl-2,4-dihydro-3H-1,2,4-triazol-3-one.

Use

The active compounds according to the invention, in combination with good plant tolerance and favorable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection agents. They are effective against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus mactans, Metatetranychus* spp., *Nuphersa* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Psylliodes* spp., *Ptinus* spp., *Rhizobius ventralis, Rhizopertha dominica, Sitophilus* spp., *Sphenophorus* spp., *Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Diplopoda, for example, *Blaniulus guttulatus.*

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Cochliomyia* spp., *Contarinia* spp., *Cordylobia anthropophaga, Culex* spp., *Cuterebra* spp., *Dacus oleae, Dasyneura* spp., *Delia* spp., *Dermatobia hominis, Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia* spp., *Phorbia* spp., *Prodiplosis* spp., *Psila rosae, Rhagoletis* spp., *Stomoxys* spp., *Tabanus* spp., *Tannia* spp., *Tetanops* spp., *Tipula* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti.*

It is also possible to control protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum*

*solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example, *Athalia* spp., *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber.*

From the order of the Isoptera, for example, *Acromyrmex* spp., *Atta* spp., *Cornitermes cumulans, Microtermes obesi, Odontotermes* spp., *Reticulitermes* spp.

From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia kuehniella, Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina.*

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (*mycoplasma*-like organisms) and RLO (*rickettsia*-like organisms). If appropriate, they can also be used as intermediates or precursors for the synthesis of other active compounds.

The present invention further relates to formulations and use forms prepared therefrom as crop protection compositions and/or pesticides, for example drench, drip and spray liquors, comprising at least one of the inventive active ingredients. The use forms optionally comprise further crop protection agents and/or pesticides and/or action-improving adjuvants, such as penetrants, e.g. vegetable oils, for example rapeseed oil, sunflower oil, mineral oils, for example paraffin oils, alkyl esters of vegetable fatty acids, for example rapeseed oil methyl ester or soybean oil methyl ester, or alkanol alkoxylates, and/or spreaders, for example alkylsiloxanes, and/or salts, for example organic or inorganic ammonium or phosphonium salts, for example ammonium sulfate or diammonium hydrogenphosphate, and/or retention promoters, for example dioctyl sulfosuccinate or hydroxypropyl guar polymers, and/or humectants, for example glycerol, and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more active compounds according to the invention, optionally comprise further agrochemical active compounds.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which improves the biological activity of the formulation without having biological activity itself. Examples of adjuvants are agents which promote retention, the spreading characteristics, adhesion to the leaf surface or penetration.

These formulations are produced in a known manner, for example by mixing the active compounds with auxiliaries, for example extenders, solvents and/or solid carriers and/or further auxiliaries, for example surfactants. The formulations are produced either in suitable facilities or else before or during application.

Auxiliaries used may be those substances which are suitable for imparting particular properties, such as particular physical, technical and/or biological properties, to the formulation of the active compound or to the use forms prepared from these formulations (for example ready-to-use crop protection compositions such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons such as xylene, toluene or alkylnaphthalenes, chlorinated aromatic or aliphatic hydrocarbons such as chlorobenzene, chloroethylene or methylene chloride, aliphatic hydrocarbons such as cyclohexane, paraffins, petroleum fractions, mineral and vegetable oils, alcohols such as methanol, ethanol, isopropanol, butanol or glycol and their ethers and esters, ketones such as acetone, methyl ethyl ketone, methyl isobutyl ketone or cyclohexanone, strongly polar solvents such as dimethyl sulfoxide, and water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Especially suitable are those extenders or carriers which are gaseous at standard temperature and under standard pressure, for example aerosol propellants such as halogenated hydrocarbons, and also butane, propane, nitrogen and carbon dioxide.

Examples of emulsifiers and/or foam formers, dispersants or wetting agents with ionic or nonionic properties, or mixtures of these surfactants, are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkyl sulfonates, alkyl sulfates, arylsulfonates, protein hydrolyzates, lignosulfite waste liquors and methylcellulose. The presence of a surfactant is advantageous when one of the active compounds and/or one of the inert carriers is insoluble in water and when application is carried out in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components may be stabilizers, such as cold stabilizers, preservatives, antioxidants, light stabilizers, or other agents which improve the chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the active compounds can be combined with any solid or liquid additive which is commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of agrochemically active compounds into plants. Penetrants are defined in this context by their ability to penetrate from the (generally aqueous) application liquor and/or from the spray coating into the cuticle of the plant and hence increase the mobility of the active compounds in the cuticle. The method described in the literature (Baur et al., 1997, Pesticide Science 51, 131-152) can be used for determining this property. Examples include alcohol alkoxylates, for example coconut fat ethoxylate (10) or isotridecyl ethoxylate (12), fatty acid esters, for example rapeseed oil methyl ester or soya oil methyl ester, fatty amine alkoxylates, for example tallowamine ethoxylate (15) or ammonium salts and/or phosphonium salts, for example ammonium sulfate or diammonium hydrogenphosphate.

The formulations contain preferably between 0.00000001% and 98% by weight of active compound or more preferably between 0.01% and 95% by weight of active compound, more preferably between 0.5% and 90% by weight of active compound, based on the weight of the formulation.

The active compound content of the use forms (crop protection compositions) prepared from the formulations can vary within wide limits. The active compound concentration of the use forms may typically be between 0.00000001% and 95% by weight of active compound, preferably between 0.00001% and 1% by weight, based on the weight of the use form. Application is accomplished in a customary manner appropriate to the use forms.

The active compounds according to the invention can be used as such or in formulations thereof, including in a mixture with one or more suitable fungicides, bactericides, acaricides, nematicides, insecticides, microbiologicals, fertilizers, attractants, phytotonics, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. In addition, plant growth can be improved by those combinations which enhance tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products. In general, combination of the active compounds according to the invention and mixing partners gives synergistic effects, meaning that the efficacy of the mixture in question is greater than the efficacy of the individual components. It is generally possible to use the combinations in premixes, tankmixes or readymixes, and also in seed applications.

Particularly favourable mixing partners are, for example, the following:

Insecticides/Acaricides/Nematicides

The active compounds mentioned here under their "common names" are known and are described for example in The Pesticide Manual, 14th Ed., British Crop Protection Council 2006, or can be searched for on the Internet (e.g. http://www.alanwood.net/pesticides).

(1) Acetylcholinesterase (AChE) inhibitors, for example carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel antagonists, for example cyclodiene organochlorines, for example chlordane and endosulfan; or phenylpyrazoles (fiproles), for example ethiprole and fipronil.

(3) Sodium channel modulators/voltage-dependent sodium channel blockers, for example pyrethroids, for example acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrine (pyrethrum), resmethrin, silafluofen, tefluthrin, tetramethrin, tetramethrin [(1R) isomers], tralomethrin and transfluthrin; or DDT; or methoxychlor.

(4) Nicotinergic acetylcholine receptor (nAChR) agonists, for example neonicotinoids, for example acetamiprid, clothianidin, dinotefuran, imidacloprid, nitenpyram, thiacloprid and thiamethoxam; or nicotine.

(5) Nicotinergic acetylcholine receptor (nAChR) allosteric activators, for example spinosyns, for example spinetoram and spinosad.

(6) Chloride channel activators, for example avermectins/milbemycins, for example abamectin, emamectin benzoate, lepimectin and milbemectin.

(7) Juvenile hormone imitators, for example juvenile hormone analogs, for example hydroprene, kinoprene and methoprene; or fenoxycarb; or pyriproxyfen.

(8) Active compounds having unknown or nonspecific mechanisms of action, for example alkyl halides, for example methyl bromide and other alkyl halides; or chloropicrin; or sulfuryl fluoride; or borax; or tartar emetic.

(9) Selective antifeedants, for example pymetrozine; or flonicamid.

(10) Mite growth inhibitors, for example clofentezine, hexythiazox and diflovidazin; or etoxazole.

(11) Microbial disruptors of the insect gut membrane, e.g. *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron; or organotin compounds, e.g. azocyclotin, cyhexatin and fenbutatin oxide; or propargite; or tetradifon.

(13) Oxidative phosphorylation decouplers that interrupt the H proton gradient, for example chlorfenapyr, DNOC and sulfluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Molting disruptors, dipteran, for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon; or acequinocyl; or fluacrypyrim.

(21) Complex-I electron transport inhibitors, for example METI acaricides, e.g. fenazaquin, fenpyroximate, pyrimidifen, pyridaben, tebufenpyrad and tolfenpyrad; or rotenone (Derris).

(22) Voltage-gated sodium channel blockers, for example indoxacarb; or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, for example aluminum phosphide, calcium phosphide, phosphine and zinc phosphide; or cyanide.

(25) Complex-II electron transport inhibitors, for example cyenopyrafen.

(28) Ryanodine receptor effectors, for example diamides, for example chlorantraniliprole and flubendiamide;

further active compounds having an unknown mechanism of action, for example amidoflumet, azadirachtin, benclothiaz, benzoximate, bifenazate, bromopropylate, chinomethionat, cryolite, cyantraniliprole (Cyazypyr), cyflumetofen, dicofol, diflovidazin, fluensulfone, flufenerim, flufiprole, fluopyram, fufenozide, imidaclothiz, iprodione, meperfluthrin, pyridalyl, pyrifluquinazon, tetramethylfluthrin and iodomethane; and additionally preparations based on *Bacillus firmus* (particularly strain CNCM 1-1582, for example VOTiVO™, BioNem), and the following known active compounds:

3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyrid-3-yl)methyl](2-fluoroethyl)amino}furan-2(5H)-one (known from WO2007/115644), 4-{[(6-fluoropyrid-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chloropyrid-3-yl)methyl](2-fluoroethyl)amino}furan-2(5H)-one (known from WO2007/115644), flupyradifurone, 4-{[(6-chloro-5-fluoropyrid-3-yl)methyl](methyl)amino}furan-2(5H)-one (known from WO2007/115643), 4-{[(5,6-dichloropyrid-3-yl)methyl](2-fluoroethyl)amino}furan-2(5H)-one (known from WO2007/115646), 4-{[(6-chloro-5-fluoropyrid-3-yl)methyl](cyclopropyl)amino}furan-2(5H)-one (known from WO2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), {[1-(6-chloropyridin-3-yl)ethyl](methyl)oxido-$\lambda^4$-sulfanylidene}cyanamide (known from WO2007/149134) and diastereomers thereof {[(1R)-1-(6-chloropyridin-3-yl)ethyl](methyl)oxido-$\lambda^4$-sulfanylidene}cyanamide (A) and {[(1S)-1-(6-chloropyridin-3-yl)ethyl](methyl)oxido-$\lambda^4$-sulfanylidene}cyanamide (B) (likewise known from WO2007/149134) and sulfoxaflor and diastereomers thereof [(R)-methyl(oxido){(1R)-1-[6-(trifluoromethyl)pyridin-3-yl]ethyl}-$\lambda^4$-sulfanylidene]cyanamide (A1) and [(S)-methyl(oxido){(1S)-1-[6-(trifluoromethyl)pyridin-3-yl]ethyl}-$\lambda^4$-sulfanylidene]cyanamide (A2), designated as diastereomer group A (known from WO 2010/074747, WO 2010/074751), [(R)-methyl(oxido){(1S)-1-[6-(trifluoromethyl)pyridin-3-yl]ethyl}-$\lambda^4$-sulfanylidene]cyanamide (B 1) and [(S)-methyl(oxido){(1R)-1-[6-(trifluoromethyl)pyridin-3-yl]ethyl}-$\lambda^4$-sulfanylidene] cyanamide (B2), designated as diastereomer group B (likewise known from WO 2010/074747, WO 2010/074751) and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluoroethyl)sulfinyl]phenyl}-3-(trifluoromethyl)-1H-1,2,4-triazole-5-amine (known from WO2006/043635), [(3S,4aR,12R,12aS,12bS)-3-[(cyclopropylcarbonyl)oxy]-6,12-dihydroxy-4, 12b-dimethyl-11-oxo-9-(pyridin-3-yl)-1,3,4,4a,5,6,6a,12,12a, 12b-decahydro-2H,11H-benzo[f]pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazole-2-amine (known from WO2008/104503), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl) malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1] octane (known from WO2007/040280), flometoquin, PF1364 (CAS Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2(5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502), (1E)-N-[(6-chloropyridin-3-yl)methyl]-N'-cyano-N-(2,2-difluoroethyl)ethanimidamide (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925) and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233), Fungicides (1) Inhibitors of ergosterol biosynthesis such as, for example, (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifin (65472-88-0), (1.33) nuarimol (63284-71-9), (1.34) oxpoconazole (174212-12-5), (1.35) paclobutrazole (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafin (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) 0-[1-(4-methoxyphenoxy)-3,3-dimethylbutan-2-yl]1H-imidazole-1-carbothioate (111226-71-2).

(2) Respiration inhibitors (respiratory chain inhibitors) such as, for example, (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam mixture of the syn-epimeric racemate 1RS,4SR,9RS and the anti-epimeric racemate 1RS,4SR,9SR (881685-58-1), (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamid (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7), (2.28) 5,8-difluoro-N-[2-(2-fluoro-4-{[4-(trifluoromethyl)pyridin-2-yl]oxy}phenyl)ethyl]quinazoline-4-amine (1210070-84-0)

(known from WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) Respiration inhibitors (respiratory chain inhibitors) acting on complex III of the respiratory chain such as, for example, (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.5) dimoxystrobin (141600-52-4), (3.6) enestroburin (238410-11-2) (known from WO 2004/058723), (3.9) famoxadone (131807-57-3) (known from WO 2004/058723), (3.10) fenamidone (161326-34-7) (known from WO 2004/058723), (3.11) fenoxystrobin (918162-02-4), (3.12) fluoxastrobin (361377-29-9) (known from WO 2004/058723), (3.13) kresoxim-methyl (143390-89-0) (known from WO 2004/058723), (3.14) metominostrobin (133408-50-1) (known from WO 2004/058723), (3.15) orysastrobin (189892-69-1) (known from WO 2004/058723), (3.16) picoxystrobin (117428-22-5) (known from WO 2004/058723), (3.17) pyraclostrobin (175013-18-0) (known from WO 2004/058723), (3.18) pyrametostrobin (915410-70-7) (known from WO 2004/058723), (3.19) pyraoxystrobin (862588-11-2) (known from WO 2004/058723), (3.20) pyribencarb (799247-52-2) (known from WO 2004/058723), (3.21) triclopyricarb (902760-40-1), (3.22) trifloxystrobin (141517-21-7) (known from WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (known from WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (known from WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolid (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds having multisite activity, for example (5.1) Bordeaux mixture (8011-63-0), (5.2) captafol (2425-06-1), (5.3) captan (133-06-2) (known from WO 02/12172), (5.4) chlorothalonil (1897-45-6), (5.5) copper preparations such as copper hydroxide (20427-59-2), (5.6) copper naphthenate (1338-02-9), (5.7) copper oxide (1317-39-1), (5.8) copper oxychloride (1332-40-7), (5.9) copper sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) zinc metiram (9006-42-2), (5.27) copper-oxine (10380-28-6), (5.28) propamidine (104-32-5), (5.29) propineb (12071-83-9), (5.30) sulfur and sulfur preparations, for example calcium polysulfide (7704-34-9), (5.31) thiram (137-26-8), (5.32) tolylfluanid (731-27-1), (5.33) zineb (12122-67-7) and (5.34) ziram (137-30-4).

(6) Resistance inductors, for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of amino acid and protein biosynthesis such as, for example, (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (known from WO2005070917).

(8) ATP production inhibitors, for example (8.1) fentin acetate (900-95-8), (8.2) fentin chloride (639-58-7), (8.3) fentin hydroxide (76-87-9) and (8.4) silthiofam (175217-20-6).

(9) Inhibitors of cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Melanin biosynthesis inhibitors such as, for example, (11.1) carpropamid (104030-54-8), (11.2) diclocymet (139920-32-4), (11.3) fenoxanil (115852-48-7), (11.4) fthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (known from WO2005042474).

(12) Inhibitors of nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazole (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Signal transduction inhibitors, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Decouplers, for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds such as, for example, (15.1) benthiazole (21564-17-0), (15.2) bethoxazine (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulfate (43222-48-6), (15.17) diphenylamine (122-39-4), (15.18) EcoMate, (15.19) fenpyrazamine (473798-59-3), (15.20) flumetover (154025-04-4), (15.21) fluoromid (41205-21-4), (15.22) flusulfamide (106917-52-6), (15.23) flutianil (304900-25-2), (15.24) fosetyl-aluminum (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and its salts (87-86-5), (15.40) phenothrin, (15.41) phosphoric acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl) prop-2-en-1-one (1231776-28-5), (15.45z) (2Z)-3-(4-tert-butylphenyl)-3-(2-chloropyridin-4-yl)-1-(morpholin-4-yl) prop-2-en-1-one (1231776-29-6), (15.46) pyrrolnitrin (1018-71-9) (known from EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (known from WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9), (15.57) 1-(4-methoxyphenoxy)-3,3-dimethylbutan-2-yl 1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and its salts (90-43-7), (15.67) 3-(4,4,5-trifluoro-3,3-dimethyl-3,4-dihydroisoquinolin-1-yl)quinoline (861647-85-0) (known from WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiole, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidine-4-amine (1174376-11-4) (known from WO2009094442), (15.75) 5-fluoro-2-[(4-methylbenzyl)oxy]pyrimidine-4-amine (1174376-25-0) (known from WO2009094442), (15.76) 5-methyl-6-octyl[1,2,4]triazolo[1,5-a]pyrimidine-7-amine, (15.77) ethyl-(2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6), (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide (922514-48-5), (15.90) pentyl-{6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulfate (2:1) (134-31-6) and (15.94) tert-butyl {6-[({[(1-methyl-1H-tetrazol-5-yl)(phenyl)methylene]amino}oxy) methyl]pyridin-2-yl}carbamate.

(16) Further compounds such as, for example, (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl) biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide, (16.7) 5-fluoro-1,3-dimethyl-N-[4'-(prop-1-yn-1-yl)biphenyl-2-yl]-1H-pyrazole-4-carboxamide, (16.8) 2-chloro-N-[4'-(prop-1-yn-1-yl)biphenyl-2-yl]pyridine-3-carboxamide, (16.9) 3-(difluoromethyl)-N-[4'-(3,3-dimethylbut-1-yn-1-yl)biphenyl-2-yl]-1-methyl-1H-pyrazole-4-carboxamide, (16.10) N-[4'-(3,3-dimethylbut-1-yn-1-yl) biphenyl-2-yl]-5-fluoro-1,3-dimethyl-1H-pyrazole-4-carboxamide, (16.11) 3-(difluoromethyl)-N-(4'-ethynylbiphenyl-2-yl)-1-methyl-1H-pyrazole-4-carboxamide, (16.12) N-(4'-ethynylbiphenyl-2-yl)-5-fluoro-1,3-dimethyl-1H-pyrazole-4-carboxamide, (16.13) 2-chloro-N-(4'-ethynylbiphenyl-2-yl)pyridine-3-carboxamide, (16.14) 2-chloro-N-[4'-(3,3-dimethylbut-1-yn-1-yl)biphenyl-2-yl]pyridine-3-carboxamide (known from EP-A 1 559 320), (16.15) 4-(difluoromethyl)-2-methyl-N-[4'-(trifluoromethyl)biphenyl-2-yl]-1,3-thiazole-5-carboxamide, (16.16) 5-fluoro-N-[4'-(3-hydroxy-3-methylbut-1-yn-1-yl) biphenyl-2-yl]-1,3-dimethyl-1H-pyrazole-4-carboxamide, (16.17) 2-chloro-N-[4'-(3-hydroxy-3-methylbut-1-yn-1-yl) biphenyl-2-yl]pyridine-3-carboxamide, (16.18) 3-(difluoromethyl)-N-[4'-(3-methoxy-3-methylbut-1-yn-1-yl)biphenyl-2-yl]-1-methyl-1H-pyrazole-4-carboxamide, (16.19) 5-fluoro-N-[4'-(3-methoxy-3-methylbut-1-yn-1-yl)biphenyl-2-yl]-1,3-dimethyl-1H-pyrazole-4-carboxamide, (16.20) 2-chloro-N-[4'-(3-methoxy-3-methylbut-1-yn-1-yl) biphenyl-2-yl]pyridine-3-carboxamide, (16.21) (5-bromo-2-methoxy-4-methylpyridin-3-yl)(2,3,4-trimethoxy-6-methylphenyl)methanone, (16.22) N-[2-(4-{[3-(4-chlorophenyl) prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid and (16.24) but-3-yn-1-yl {6-[({[(Z)-(1-methyl-1H-tetrazol-5-yl)(phenyl) methylene]amino}oxy)methyl]pyridin-2-yl}carbamate.

All the mixing partners mentioned in classes (1) to (16), as the case may be, may form salts with suitable bases or acids if they are capable of doing so on the basis of their functional groups.

Another possibility is a mixture with other known active compounds, such as herbicides, fertilizers, growth regulators, safeners, semiochemicals, or else with agents for improving the plant properties.

When used as insecticides, the active compounds according to the invention may also be present in their commercially available formulations and in the use forms, prepared from these formulations, in a mixture with synergists. Synergists are compounds which increase the action of the active compounds, without it being necessary for the synergist added to be active itself.

When used as insecticides, the active compounds according to the invention can furthermore be present in their commercially available formulations and in the use forms, prepared from these formulations, in mixtures with inhibitors which reduce degradation of the active compound after use in the environment of the plant, on the surface of parts of plants or in plant tissues.

All plants and plant parts can be treated in accordance with the invention. Plants in this context are understood to include all plants and plant populations, such as desired and unwanted wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plant parts are to be understood as meaning all above-ground and below-ground parts and organs of plants, such as shoot, leaf, flower and root, examples which may be mentioned being leaves, needles, stems, trunks, flowers, fruit bodies, fruits and seeds and also roots, tubers and rhizomes. Parts of plants also include harvested material and vegetative and generative propagation material, for example cuttings, tubers, rhizomes, slips and seed.

The treatment according to the invention of the plants and plant parts with the active compounds is carried out directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding techniques, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts" and "parts of plants" or "plant parts" have been elucidated above.

Particular preference is given in accordance with the invention to treating plants of the respective commercially customary plant cultivars or those that are in use. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergistic") effects. For example, the following effects extending beyond the effects that are actually to be expected are possible: reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, increased storage life and/or processability of the harvested products.

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are an improved defense of the plants against animal and microbial pests, such as against insects, mites, phytopathogenic fungi, bacteria and/or viruses, and also increased tolerance of the plants to certain herbicidally active compounds. Examples of transgenic plants include the important crop plants, such as cereals (wheat, rice), maize, soya, potatoes, sugarbeet, tomatoes, peas and other vegetable types, cotton, tobacco, oilseed rape, and also fruit plants (with the following fruits: apples, pears, citrus fruits and grapes), particular emphasis being given to maize, soya, potatoes, cotton, tobacco and oilseed rape. Traits that are particularly emphasized are the improved defense of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIA, CryIIIB2, Cry9c, Cry2Ab, Cry3Bb and CryIF, and also combinations thereof) (referred to hereinafter as "Bt plants"). Traits that are also particularly emphasized are the improved defense of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain herbicidally active compounds, for example imidazolinones, sulfonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants include maize varieties, cotton varieties and soya varieties which are sold under the commercial names Roundup Ready® (tolerance to glyphosate e.g. maize, cotton, soya), Liberty Link® (tolerance to phosphinothricin, e.g. oilseed rape), IMI® (tolerance to imidazolinones) and STS® (tolerance to sulfonylureas, e.g. maize). Herbicide-resistant plants (bred conventionally for herbicide tolerance) also include the varieties sold under the Clearfield® name (e.g. maize). Of course, these statements also apply to plant cultivars which have these genetic traits or genetic traits which are yet to be developed and will be developed and/or marketed in the future.

The plants listed can be treated in accordance with the invention in a particularly advantageous manner with the compounds of the general formula I and/or the active compound mixtures according to the invention. The areas of preference stated above for the active compounds or mixtures also apply to the treatment of these plants. Particular emphasis is given to the treatment of plants with the compounds or mixtures specifically mentioned in the present text.

The inventive active ingredients are not just active against plant pests, hygiene pests and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The inventive active ingredients of the formula (I) are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals, for example dogs, cats, caged birds, aquarium fish, and experimental animals, for example hamsters, guinea pigs, rats and mice. The control of these arthropods is intended to reduce or prevent cases of deaths and reductions in performance (in the case of meat, milk, wool, hides, eggs, honey and the like), such that more economical and simpler animal husbandry is possible through the use of the inventive active ingredients.

The application of the inventive active ingredients in the veterinary sector and in animal husbandry is accomplished in a known manner by enteral administration in the form of, for example, tablets, capsules, potions, drenches, granules, pastes, boluses, the feed-through method and suppositories, by parenteral administration, for example by injections (intramuscular, subcutaneous, intravenous, intraperitoneal and the like), implants, by nasal administration, by dermal use in the form, for example, of dipping or bathing, spraying, pouring-on and spotting-on, washing and powdering, and also with the aid of active ingredient-containing molded articles, such as collars, ear marks, tail marks, limb bands, halters, marking devices and the like.

When used for livestock, poultry, domestic animals and the like, the active ingredients of the formula (I) can be used as formulations (for example powders, emulsions, flowables) comprising the active ingredients in an amount of from 1 to 80% by weight, either directly or after 100 to 10 000-fold dilution, or they may be used as a chemical bath.

It has also been found that the compounds according to the invention have strong insecticidal action against insects which destroy industrial materials.

The following insects may be mentioned as examples and as preferred—but without limitation:

beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus;*

Dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;* bristletails, such as *Lepisma saccharina.*

Industrial materials in the present context are understood to mean inanimate materials, such as preferably plastics, adhesives, sizes, papers and cards, leather, wood, processed wood products and coating compositions.

The ready-to-use compositions may optionally also comprise other insecticides, and optionally also one or more fungicides.

Moreover, the compounds according to the invention can be employed for protecting objects which come into contact with saltwater or brackish water, in particular hulls, screens, nets, buildings, moorings and signaling systems, against fouling.

In addition, the compounds according to the invention can be used as antifouling compositions, alone or in combinations with other active compounds.

The active compounds are also suitable for controlling animal pests in the domestic sector, in the hygiene sector and in the protection of stored products, in particular insects, arachnids and mites, which are found in enclosed spaces, for example homes, factory halls, offices, vehicle cabins and the like. They can be used to control these pests alone or in combination with other active compounds and auxiliaries in domestic insecticide products. They are effective against sensitive and resistant species, and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the *Blattaria*, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of domestic insecticides, they are used alone or in combination with other suitable active compounds, such as phosphoric esters, carbamates, pyrethroids, neonicotinoids, growth regulators or active compounds from other known classes of insecticides.

Application is effected in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

EXAMPLES

Preparation Examples Including the Further Description of the Processes and Intermediates The preparation and use examples which follow illustrate the invention without limiting it. The products were characterized by 1H NMR spectroscopy and/or LC-MS (liquid chromatography-mass spectrometry) and/or GC-MS (gas chromatography-mass spectrometry).

The log P values were determined analogously to OECD Guideline 117 (EC Directive 92/69/EEC) by HPLC (high-performance liquid chromatography) using reversed-phase columns (C 18), by the following methods:

[a] The LC-MS determination in the acidic range was effected at pH 2.7 with 0.1% aqueous formic acid and acetonitrile (contains 0.1% formic acid) as eluents; linear gradient from 10% acetonitrile to 95% acetonitrile. log P[a] is also referred to as log P(HCOOH).

[b] LC-MS determination in the neutral range was effected at pH 7.8 with 0.001 molar aqueous ammonium hydrogencarbonate solution and acetonitrile as eluents; linear gradient from 10% acetonitrile to 95% acetonitrile. log P[b] is also referred to as log P(neutral).

Calibration is effected with solutions of a homologous series of unbranched alkan-2-ones (having 3 to 16 carbon atoms) with known log P values (log P values determined on the basis of the retention times by linear interpolation between two successive alkanones).

The NMR spectra were measured with a Bruker II Avance 400 equipped with a 1.7 mm TCI probe head. In isolated cases, the NMR spectra were determined using a Bruker Avance II 600.

The NMR data for selected examples are listed in conventional form (δ values, multiplet splitting, number of hydrogen atoms). The splitting of the signals was described as follows: s (singlet), d (doublet), t (triplet), q (quartet), m (multiplet), broad (for broad signals). Solvents used were $CD_3CN$, $CDCl_3$ or D6-DMSO, and tetramethylsilane (0.00 ppm) was used as reference.

The GC-MS spectra were determined using an Agilent 6890 GC, HP 5973 MSD on a dimethylsilicone phase, using a temperature gradient from 50° C. to 320° C. GC-MS indices are determined as Kovats indices using solutions of a homologous series of n-alkanes (having an even number of 8 to 38 carbon atoms).

The enantiomers were obtained from the racemate by separating them preparatively by means of HPLC using a chiral column (ChiralCel OJ-H, e.g. 5 nm 250×4.6 mm) with heptane/methanol/ethanol (95:2.5:2.5) eluent.

Synthesis of Anilines of the Formula (IVa), (IVb) and Intermediates (X), (XI), (XII), (XIII), (XVI), (XVII), (XVIII), (XIX) and (XX)

2,2,2-Trifluoro-N-(2-fluoro-4-methylphenyl)acetamide (XIII-1)

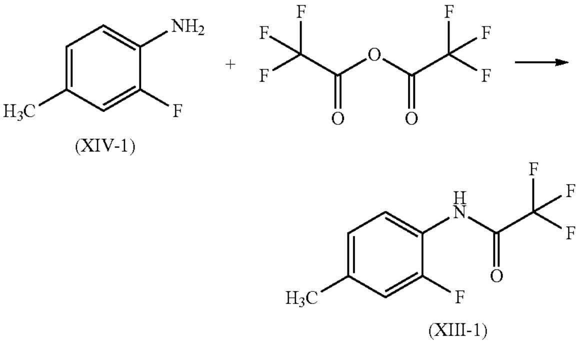

(XIV-1)

(XIII-1)

At 0° C., 27.5 g of 2-fluoro-4-methylaniline are initially charged in 300 ml of dichloromethane, 26.7 g of triethylamine are added and 50.8 g of trifluoroacetic anhydride are then added dropwise. The mixture is stirred at 0° C. for another 2 h and then concentrated by rotary evaporation. The residue is taken up in water and extracted twice with ethyl acetate. The combined organic phases are dried over sodium sulfate and filtered and the solvent is removed under reduced pressure. This gives 49.0 g (100% of theory) of the title compound. log P[a]: 2.40

The following was obtained analogously:

N-(4-Chloro-2-fluorophenyl)-2,2,2-trifluoroacetamide (XIII-2)

(XIII-2)

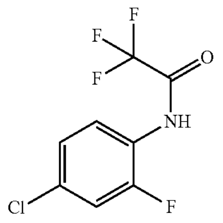

log P[a]: 2.53; log P[b]: 2.40; 1H-NMR (D6-DMSO, 400 MHz) δ ppm 11.29 (s, 1H), 7.62 (dd, 1H), 7.55 (dd, 1H), 7.37 (dd, 1H)

4-Fluoro-2-methyl-5-[(trifluoroacetyl)amino]benzenesulfonyl chloride (XII-1)

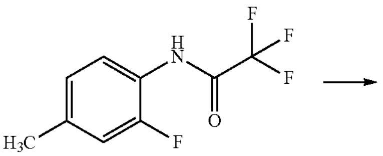

(XIII-1)

-continued

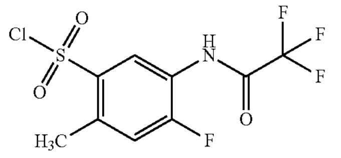

(XII-1)

258 g of chlorosulfonic acid are initially charged, and 49 g of 2,2,2-trifluoro-N-(2-fluoro-4-methylphenyl)acetamide are added in portions at room temperature. The mixture is stirred at room temperature for another 16 h. The mixture is added to ice while stirring, and extracted twice with ethyl acetate. The combined organic phases are dried over sodium sulfate and filtered and the solvent is removed under reduced pressure. This gives 70.8 g of the chlorosulfonyl (XII-1). The crude product is immediately converted further.

N,N'-[Disulfanediylbis(6-fluoro-4-methylbenzene-3,1-diyl)]bis(2,2,2-trifluoroacetamide) (XI-1)

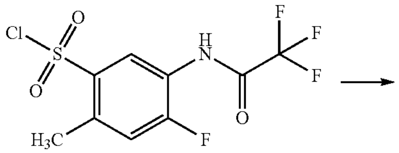

(XII-1)

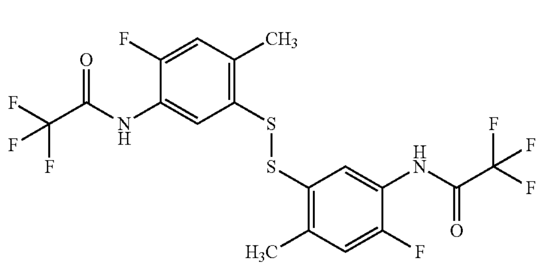

(XI-1)

298.8 g of sodium iodide are dissolved in 1000 ml of trifluoroacetic acid, and 70.8 g of 4-fluoro-2-methyl-5-[(trifluoroacetyl)amino]benzenesulfonyl chloride are added at room temperature. The mixture is stirred at room temperature for 16 h and the solvent is then removed under reduced pressure. The residue is stirred with water and filtered off with suction. This gives 62.3 g (86% of theory) of the title compound as a solid.

log P[a]: 4.41

The following was obtained analogously:

N,N'-[Disulfanediylbis(4-chloro-6-fluorobenzene-3,1-diyl)]bis(2,2,2-trifluoroacetamide) (XI-2)

(XI-2)

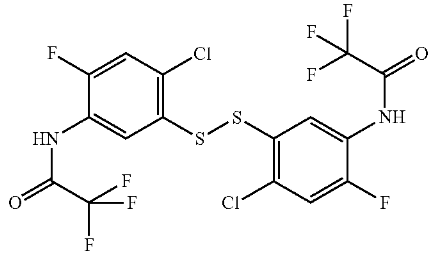

log P[a]: 4.60; log P[b]: 3.82; 1H-NMR (D6-DMSO, 400 MHz) δ ppm 11.44 (s, 2H), 7.95 (d, 2H), 7.83 (d, 2H)

2,2,2-Trifluoro-N-{2-fluoro-4-methyl-5-[(2,2,2-trifluoroethyl)sulfanyl]phenyl}acetamide (X-1)

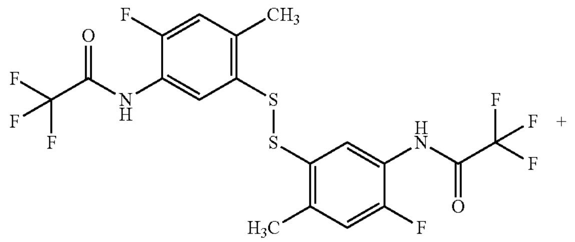

(XI-1)

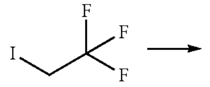

(XV-1)

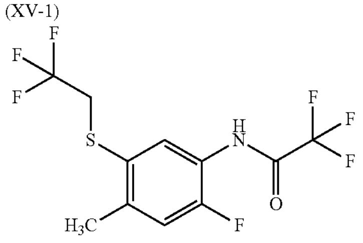

(X-1)

3.4 g of N,N'-[disulfanediylbis(6-fluoro-4-methylbenzene-3,1-diyl)]bis(2,2,2-trifluoroacetamide) are dissolved in 150 ml of N,N-dimethylformamide, and 1.86 g of potassium carbonate, 3.11 g of 1,1,1-trifluoroiodoethane, 2.39 g of Rongalit and a few drops of water are added. The reaction mixture is stirred at room temperature for 16 h. The majority of the N,N-dimethylformamide is distilled off under reduced pressure. The residue is taken up in water and extracted twice with ethyl acetate. The combined organic phases are dried over sodium sulfate and filtered, and the solvent is then removed under reduced pressure. This gives 4.48 g (90% of theory) of the title compound. log P[a]: 3.31

The following was obtained analogously:

N-{4-Chloro-2-fluoro-5-[(2,2,2-trifluoroethyl)sulfanyl]phenyl}-2,2,2-trifluoroacetamide (X-2)

(X-2)

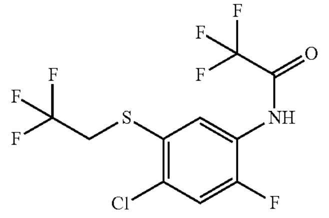

log P[a]: 3.34; log P[b]: 3.14; 1H-NMR (D6-DMSO, 400 MHz) δ ppm 11.47 (bs, 1H), 7.85 (d, 1H), 7.76 (d, 1H), 4.09 (q, 2H)

S-(5-Acetamido-4-fluoro-2-methylphenyl)ethanethioate (XVII-1)

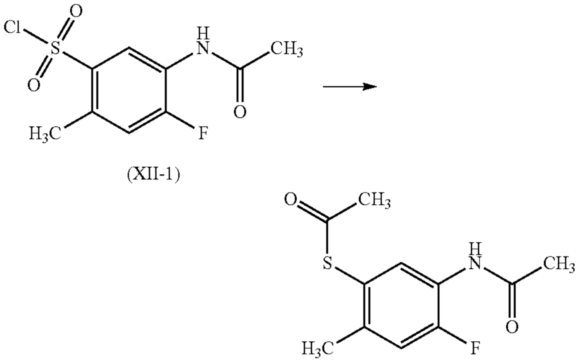

(XII-1)

(XVII-1)

99.3 g of 5-acetamido-4-fluoro-2-methylbenzenesulfonyl chloride are suspended in 700 ml of glacial acetic acid, 0.9 g of iodine and 38.7 g of red phosphorus are added, and the mixture is stirred at reflux for 5 h. After cooling, the solid is filtered off and the filtrate is concentrated by rotary evaporation. The residue is stirred with water and filtered off with suction. This gives 57.6 g (67% of theory) of the title compound as a solid. log P[a]: 1.78

5-Amino-4-fluoro-2-methylbenzenethiol (XVI-1)

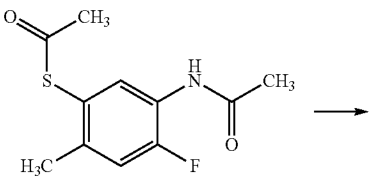

(XVII-1)

-continued

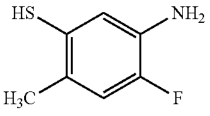

(XVI-1)

57.4 g of S-(5-acetamido-4-fluoro-2-methylphenyl)ethanethioate are dissolved in 750 ml of water and 96.6 g of potassium hydroxide. The reaction mixture is boiled at reflux for 16 hours. After cooling, the solution is adjusted to pH 2-3 with hydrochloric acid, and the precipitated solid is filtered off with suction. This gives 35.8 g (94% of theory) of the title compound as a solid. log P[a]: 3.70

2-Fluoro-4-methyl-5-[(2,2,2-trifluoroethyl)sulfinyl]aniline (IVb-1)

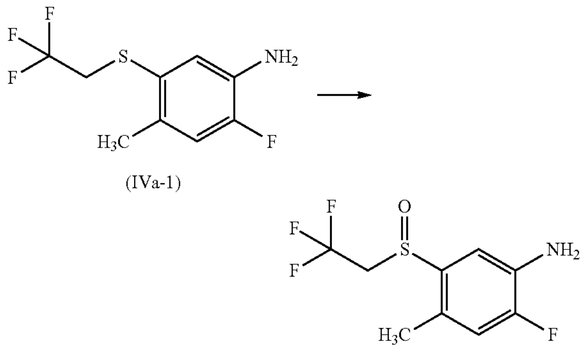

(IVa-1)

(IVb-1)

At 0-4° C., 5.00 g (0.21 mmol) of 2-fluoro-4-methyl-5-[(2,2,2-trifluoroethyl)sulfanyl]aniline are initially charged in 100 ml of dichloromethane, 6.18 g (0.25 mmol) of meta-chloroperbenzoic acid are added and the reaction mixture is stirred at room temperature for 2 h. A 33% strength sodium thiosulfate solution is then added (peroxide test carried out), and the mixture is extracted twice with dichloromethane. The combined organic phases are washed with a saturated sodium carbonate solution, dried over sodium sulfate and filtered, and the solvent is removed under reduced pressure. The residue comprises 5.10 g (90% pure, 86% of theory) of the title compound as a brown oil.

log P[a]: 1.77; log P[b]: 1.72; 1H-NMR (D6-DMSO, 400 MHz) δ ppm 7.26 (d, 1H), 7.02 (d, 1H), 5.45 (bs, 2H), 4.08-3.95 (m, 1H), 3.88-3.75 (m, 1H), 2.19 (s, 3H)

1,1'-Disulfanediylbis(2-chloro-5-nitrobenzene) (XIX-3)

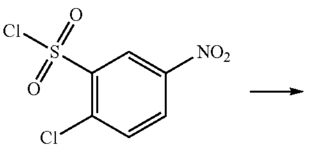

(XX-3)

-continued

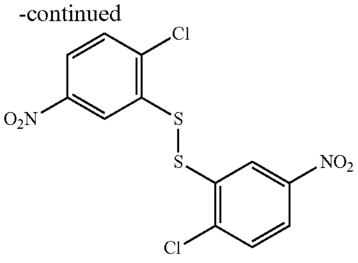

(XIX-3)

With vigorous stirring, 236.1 g (1.02 mol) of chlorosulfonic acid are added to 52.0 g (203.1 mmol) of 2-chloro-5-nitrobenzenesulfonyl chloride, and the mixture is stirred at room temperature overnight. After addition of 40% strength aqueous sodium bisulfite solution, the solid formed is filtered off with suction, washed with water and dried on a clay disk overnight. This gives 36.1 g (100% pure, 94% of theory) of the title compound as a gray-brown solid.

log P[a]: 5.03; log P[b]: 5.01; $^1$H-NMR (D6-DMSO, 400 MHz) δ ppm 8.40 (d, 2H), 8.18-8.16 (m, 2H), 7.91 (d, 2H); GC-MS: EI mass (m/z): 376 (2Cl) $[M]^+$ 1,1'-Disulfanediylbis(2,4-dichloro-5-nitrobenzene) (XIX-6)

(XIX-6)

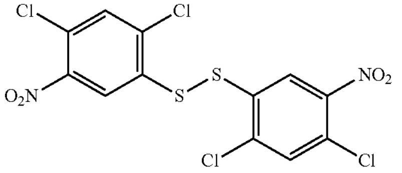

log P[a]: 5.69; log P[b]: 5.64; $^1$H-NMR (D6-DMSO 400 MHz) δ ppm 8.33 (s, 2H), 8.21 (s, 2H)

3,3'-Disulfanediylbis(4-chloroaniline) (XVIII-3)

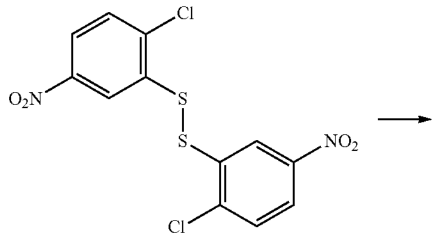

(XIX-3)

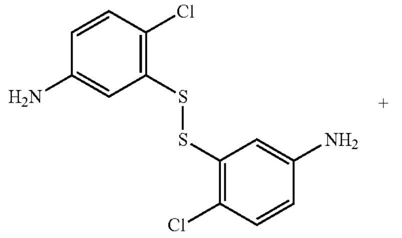

(XVIII-3)

-continued

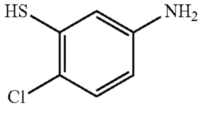

(XVI-3)

8.00 g (21.2 mmol) of 1,1'-disulfanediylbis(2-chloro-5-nitrobenzene) are dissolved in 150 ml of THF, 1.6 g of Raney nickel are added and the mixture is stirred at 50° C. under a hydrogen atmosphere (20 bar) for 72 h. Using THF, the reaction mixture is filtered through kieselguhr, and the filtrate is freed from the solvent under reduced pressure. This gives 6.64 g (90% pure, 89% of theory) of a mixture of 1,1'-disulfanediylbis(2-chloro-5-nitrobenzene) and 5-amino-2-chlorobenzenethiol which is alkylated without further purification.

1,1'-Disulfanediylbis(2-chloro-5-nitrobenzene) (XIX-3)

log P[a]: 3.31; log P[b]: 3.35; $^1$H-NMR (D6-DMSO, 400 MHz) δ ppm 7.10 (d, 2H), 6.73 (d, 2H), 6.47-6.44 (m, 2H), 5.51 (broad, 4H); GC-MS: EI mass (m/z): 316 (2Cl) $[M]^+$ 5-Amino-2-chlorobenzenethiol (XVI-3)

log P[a]: 1.64; log P[b]: not measurable; $^1$H-NMR (D6-DMSO, 400 MHz) δ ppm 7.01 (d, 1H), 6.54 (d, 1H), 6.35-6.32 (m, 1H), 5.28 (broad, 3H); GC-MS: EI mass (m/z): 159 (1Cl) $[M]^+$ The following were obtained analogously:

3,3'-Disulfanediylbis(4,6-dichloroaniline) (XVIII-6)

(XVIII-6)

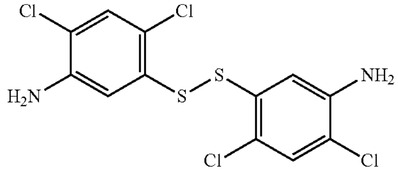

log P[a]: 5.14; log P[b]: 4.95; $^1$H-NMR (D6-DMSO, 400 MHz) δ ppm 7.41 (s, 2H), 6.95 (s, 2H), 5.78 (broad, 4H); GC-MS: EI mass (m/z): 386 (4Cl) $[M]^+$ 4-Chloro-3-[(2,2,2-trifluoroethyl)sulfanyl]aniline (IVa-3)

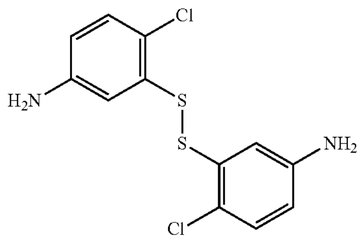

(XVIII-3)

-continued

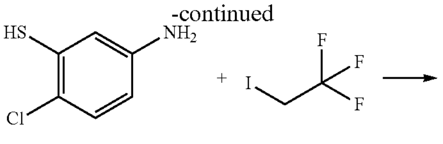

(XVI-3) (XV)

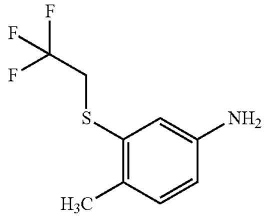

(IVa-3)

6.40 g of a mixture of disulfanediylbis(2-chloro-5-nitrobenzene) and 5-amino-2-chlorobenzenethiol (about 20 mmol) are initially charged in 100 ml of N,N-dimethylformamide, and 7.02 g (40.3 mmol) of sodium dithionite, 5.58 g (40.3 mmol) of potassium carbonate and 5.49 g (40.3 mmol) of Rongalit are added and the mixture is cooled to 0° C. 9.32 g of 1,1,1-trifluoro-2-iodoethane are added dropwise at 0° C. The reaction mixture is stirred at room temperature overnight. Most of the solvent is removed under reduced pressure, water is added to the residue and the mixture is extracted with ethyl acetate. The combined organic phases are washed successively with water and saturated aqueous sodium chloride solution, dried over magnesium sulfate, filtered and freed from the solvent under reduced pressure. Purification by column chromatography on silica gel by means of MPLC using the mobile phase cyclohexane/ethyl acetate gives 4.70 g (98% pure, 47% of theory) of the title compound as a yellow liquid.

log P[a]: 2.64; log P[b]: 2.69; $^1$H-NMR (D6-DMSO, 400 MHz) δ ppm 7.09 (d, 1H), 6.78 (d, 1H), 6.49-6.46 (m, 1H), 5.37 (broad, 2H), 3.90 (q, 2H); GC-MS: EI mass (m/z): 241 (1Cl) $[M]^+$ The following were obtained analogously:

4-Chloro-2-fluoro-5-[(2,2,2-trifluoroethyl)sulfanyl]aniline (IVa-2)

(IVa-2)

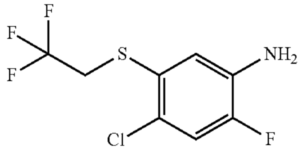

11.0 g (30.9 mmol) of N-{4-chloro-2-fluoro-5-[(2,2,2-trifluoroethyl)sulfanyl]phenyl}-2,2,2-trifluoroacetamide in 150 ml of dioxane are added carefully to a solution of 10.3 ml (186 mmol) of sulfuric acid (96% strength) in 100 ml of water. The reaction mixture is then heated under reflux overnight. After cooling, the solution is adjusted to pH 7 using a saturated sodium bicarbonate solution and a little sodium carbonate and extracted three times with ethyl acetate. The combined organic phases are washed with a saturated sodium chloride solution, dried over sodium sulfate, filtered and concentrated. The residue comprises 8.27 g (96% pure, 99% of theory) of the title compound as a black oil/solid mixture.

log P[a]: 3.02; log P[b]: 3.00; 1H-NMR (D6-DMSO 400 MHz) δ ppm 7.27 (d, 1H), 7.04 (d, 1H), 5.46 (bs, 2H), 3.85 (q, 2H)

Synthesis of Bromides of the Formula (VIIa)

(VIIa)

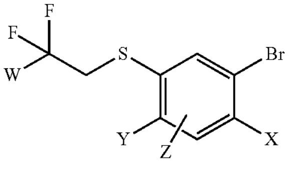

5-Bromo-2-methylphenyl-2,2,2-trifluoroethyl sulfide (VIIa-7)

Step 1: 5-Bromo-2-methylbenzenesulfonyl chloride

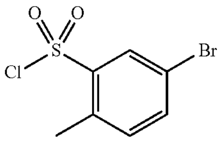

69.50 g (406.3 mmol) of 4-bromotoluene are initially charged in 250 ml of dichloromethane, and 175.33 g (1.50 mol) of chlorosulfonic acid are added dropwise at −5° C. With stirring, the reaction mixture is brought to room temperature overnight, 1000 ml of ice-water are added and the mixture is extracted with dichloromethane. The combined organic phases are washed with saturated aqueous sodium chloride solution, dried over magnesium sulfate, filtered and freed of the solvent under reduced pressure. This gives 89.54 g (95% pure, 78% of theory) of the title compound as a yellow liquid which is reacted further without further purification.

log P[a]: 3.73; log P[b]: 3.74; GC-MS: EI mass (m/z): 270 (1Cl, 1Br) $[M]^+$; $^1$H-NMR ($CDCl_3$, 400 MHz): 8.19 (d, 1H), 7.73-7.72 (m, 1H), 7.31 (d, 1H), 2.73 (s, 3H); $^1$H-NMR ($CD_3CN$, 400 MHz): 8.18 (d, 1H), 7.88-7.85 (m, 1H), 7.46 (d, 1H), 2.71 (s, 3H)

Step 2: 1,1'-Disulfanediylbis(5-bromo-2-methylbenzene)

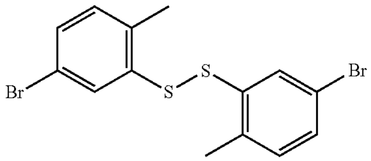 [SMILES: Cc1ccc(Br)cc1SSc1cc(Br)ccc1C]

25.00 g (92.7 mmol) of 5-bromo-2-methylbenzenesulfonyl chloride are admixed with 145.7 g of aqueous hydriodic acid (57%, 649.2 mmol) while stirring vigorously. The reaction mixture is stirred at room temperature for 3 d, then 40% aqueous sodium bisulfite solution is added. The solid is filtered off with suction, washed thoroughly with water and dried on a clay tile overnight. This gives 19.50 g (95% pure, 99% of theory) of the title compound as a yellow solid, which is converted further without further purification.

log P[a]: >7.36; log P[b]: >7.36; GC-MS: EI mass (m/z): 404 (2Br) $[M]^+$;

$^1$H-NMR (D6-DMSO): 7.56 (d, 2H), 7.46-7.43 (m, 2H), 7.26 (d, 2H), 2.35 (s, 6H)

Step 3:
5-Bromo-2-methylphenyl-2,2,2-trifluoroethyl sulfide (VIIa-7)

(VIIa-7)

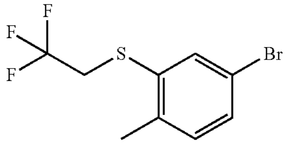

27.70 g (68.5 mmol) of 1,1'-disulfanediylbis(5-bromo-2-methylbenzene) are initially charged in 350 ml of N,N-dimethylformamide, 23.86 g (137.1 mmol) of sodium dithionite, 18.66 g (137.1 mmol) of Rongalit® and 18.94 g (137.1 mmol) of potassium carbonate are added and the mixture is cooled to 0° C. 31.65 g (150.8 mmol) of 1,1,1-trifluoro-2-iodoethane in 20 ml of N,N-dimethylformamide are added dropwise at 0° C. The reaction mixture is brought to room temperature overnight while stirring, 500 ml of water are added and the mixture is extracted with tert-butyl methyl ether. The combined organic phases are washed with water, saturated aqueous sodium bicarbonate solution and saturated aqueous sodium chloride solution, dried over magnesium sulfate, filtered and freed of the solvent under reduced pressure. Purification by column chromatography on silica gel by means of MPLC with cyclohexane/ethyl acetate as eluent gives 30.01 g (93% pure, 71% of theory) of the title compound as a colorless liquid.

log P[a]: 4.29; log P[b]: 4.26; GC-MS: EI mass (m/z): 286 (1Br) $[M]^+$;

$^1$H-NMR (D6-DMSO, 400 MHz) δ ppm: 7.70 (d, 1H), 7.39-7.36 (m, 1H), 7.21 (d, 1H), 4.09 (q, 2H), 2.30 (s, 3H)

The following were obtained analogously:

4-Bromo-1-methoxy-2-[(2,2,2-trifluoroethyl)sulfanyl]benzene (VIIa-8)

(VIIa-8)

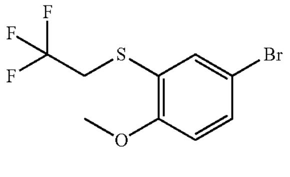

log P[a]: 3.69; log P[b]: 3.81; GC-MS: EI mass (m/z): 302 (1Br) $[M]^+$;

$^1$H-NMR (D6-DMSO, 400 MHz) δ ppm: 7.59 (d, 1H), 7.45-7.42 (m, 1H), 7.00 (d, 1H), 4.02 (q, 2H), 3.85 (s, 3H)

4-Bromo-1-chloro-2-[(2,2,2-trifluoroethyl)sulfanyl]benzene (VIIa-3)

(VIIa-3)

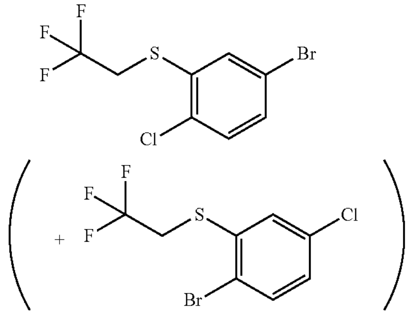

Obtained as a mixture of 60% 4-bromo-1-chloro-2-[(2,2,2-trifluoroethyl)sulfanyl]benzene and 40% 1-bromo-4-chloro-2-[(2,2,2-trifluoroethyl)sulfanyl]benzene.

log P[a]: 4.20; log P[b]: 4.21; GC-MS: EI mass (m/z): 306 (1Br, 1Cl) $[M]^+$;

$^1$H-NMR (D6-DMSO, 400 MHz) δ ppm: 7.85 (broad, 1H), 7.70 (d, 1'H), 7.67 (d, 1'H), 7.50-7.44 (m, 2H), 7.27-7.24 (m, 1'H), 4.30-4.22 (m, 2H+2'H)

1-Bromo-2-fluoro-4-methyl-5-[(2,2,2-trifluoroethyl)sulfanyl]benzene (VIIa-1)

(VIIa-1)

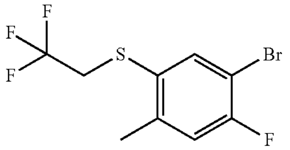

log P[a]: 4.30; log P[b]: 4.34; GC-MS: EI mass (m/z): 304 (1Br) $[M]^+$;

$^1$H-NMR (D6-DMSO, 400 MHz): 7.87 (d, 1H), 7.36 (d, 1H), 4.02 (q, 2H), 2.35 (s, 3H)

1-Bromo-2,4-dichloro-5-[(2,2,2-trifluoroethyl)sulfanyl]benzene (VIIa-6)

(VIIa-6)

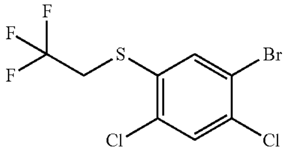

log P[a]: 4.80; log P[b]: 4.77; GC-MS: EI mass (m/z): 340 (1Br, 2Cl) $[M]^+$;

$^1$H-NMR (D6-DMSO, 400 MHz): 8.04 (s, 1H), 7.91 (s, 1H), 4.28 (q, 2H)

1-Bromo-2,4-dimethyl-5-[(2,2,2-trifluoroethyl)sulfanyl]benzene (VIIa-1)

(VIIa-11)

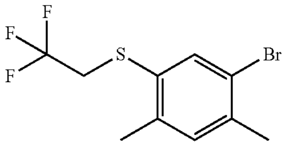

log P[a]: 4.81; log P[b]: 4.77; GC-MS: EI mass (m/z): 340 (1Br, 2Cl) $[M]^+$;

$^1$H-NMR (D6-DMSO, 400 MHz): 8.04 (s, 1H), 7.91 (s, 1H), 4.28 (q, 2H)

1-Bromo-4-chloro-2-fluoro-5-[(2,2,2-trifluoroethyl)sulfanyl]benzene (VIIa-2)

(VIIa-2)

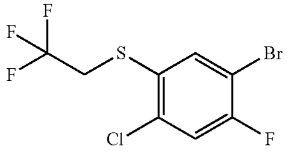

log P[a]: 4.28; log P[b]: 4.29; GC-MS: EI mass (m/z): 324 (1Cl, 1Br) $[M]^+$; $^1$H-NMR (D6-DMSO, 400 MHz): 8.04 (d, 1H), 7.77 (d, 1H), 4.20 (q, 2H)

1,4-Dibromo-2-[(2,2,2-trifluoroethyl)sulfanyl]benzene (VIIa-13)

(VIIa-13)

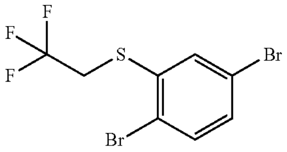

log P[a]: 4.29; log P[b]: 4.25; GC-MS: EI mass (m/z): 350 (2Br) $[M]^+$; $^1$H-NMR (D6-DMSO, 400 MHz): 7.81 (d, 1H), 7.60 (d, 1H), 7.39-7.37 (m, 1H), 4.26 (q, 2H)

1,4-Dibromo-2-fluoro-5-[(2,2,2-trifluoroethyl)sulfanyl]benzene (VIIa-14)

(VIIa-14)

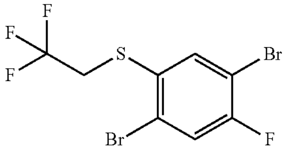

log P[a]: 4.39; log P[b]: 4.36; GC-MS: EI mass (m/z): 368 (2Br) $[M]^+$; $^1$H-NMR (D6-DMSO, 400 MHz): 8.00 (d, 1H), 7.87 (d, 1H), 4.21 (q, 2H)

1-Bromo-2,4-difluoro-5-[(2,2,2-trifluoroethyl)sulfanyl]benzene (VIIa-15)

(VIIa-15)

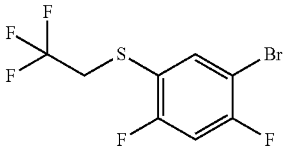

log P[a]: 3.89; log P[b]: 3.86; GC-MS: EI mass (m/z): 308 $[M]^+$; $^1$H-NMR (D6-DMSO, 400 MHz): 8.07 (t, 1H), 7.63 (t, 1H), 4.03 (q, 2H)

4-Bromo-2-[(2,2,2-trifluoroethyl)sulfanyl]benzonitrile (VIIa-9)

(VIIa-9)

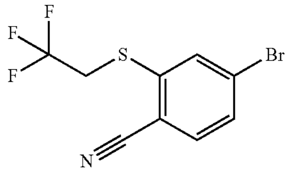

24.0 g (86.4 mmol) of sodium hydride (60% in mineral oil) are initially charged in 300 ml of N,N-dimethylformamide, and 10.0 g (86.4 mmol) of 2,2,2-trifluoroethanethiol are added dropwise at 0° C. At 0° C., the reaction mixture is added dropwise to a solution of 14.4 g (72.0 mmol) of 4-bromo-2-fluorobenzonitrile in 100 ml of N,N-dimethylformamide, and the mixture is brought to room temperature overnight while stirring. The reaction mixture is poured into water, neutralized with saturated aqueous ammonium chloride solution and extracted with tert-butyl methyl ether. The combined organic phases are washed successively with water and saturated aqueous sodium chloride solution, dried over magnesium sulfate, filtered and freed of the solvent under reduced pressure. The residue is stirred with petroleum ether, filtered off and recrystallized from diethyl ether. This gives 17.6 g (99% pure, 82% of theory) of the title compound as a colorless solid.

log P[a]: 3.21; log P[b]: 3.16; $^1$H-NMR (D6-DMSO, 400 MHz) δ ppm: 8.12 (d, 1H), 7.83 (d, 1H), 7.72-7.69 (m, 1H), 4.33 (q, 2H)

The following was obtained analogously:

4-Bromo-2-[(2,2,2-trifluoroethyl)sulfanyl]-1-(trifluoromethyl)benzene (VIIa-10)

(VIIa-10)

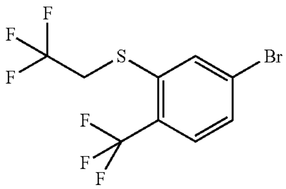

log P[a]: 4.22; log P[b]: 4.20; $^{1}$H-NMR (D6-DMSO, 400 MHz): 8.18 (s, 1H), 7.73-7.68 (m, 2H), 4.30 (q, 2H)

Synthesis of Iodides of the Formula (VIIa)

(VIIa)

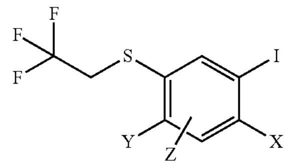

1-Fluoro-2-iodo-5-methyl-4-[(2,2,2-trifluoroethyl) sulfanyl]benzene (VIIa-1-I)

(VIIa-1-I)

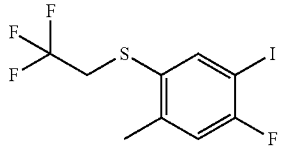

10.0 g (33.0 mmol) of 5-bromo-2-methylphenyl-2,2,2-trifluoroethyl sulfide, 9.89 g (66.0 mmol) of sodium iodide, 314 mg (1.65 mmol) of copper(I) iodide and 469 mg (3.3 mmol) of trans-N,N'-dimethylcyclohexane-1,2-diamine (racemic) were stirred in 33 ml of degassed dioxane at 110° C. overnight. Another 9.89 g (66.0 mmol) of sodium iodide, 314 mg (1.65 mmol) of copper(I) iodide and 234 mg (1.65 mmol) of trans-N,N'-dimethylcyclohexane-1,2-diamine (racemic) were added, and the mixture was stirred at 110° C. overnight. Another 9.89 g (66.0 mmol) of sodium iodide and 314 mg (1.65 mmol) of copper(I) iodide and 20 ml of dioxane were added, and the mixture was stirred at 110° C. overnight. After cooling to room temperature, the mixture was diluted with ethyl acetate, filtered through kieselguhr and concentrated. Purification by column chromatography on silica gel by means of MPLC with cyclohexane/ethyl acetate as mobile phase gives 8.77 g (97% pure, 74% of theory) of the title compound as a colorless oil.

log P[a]: 4.44; log P[b]: 4.44; GC-MS: EI mass (m/z): 350 $[M]^+$ $^{1}$H-NMR (D6-DMSO, 400 MHz): 7.97 (d, 1H), 7.24 (d, 1H), 3.96 (q, 2H), 2.35 (s, 3H)

The following was obtained analogously:

4-Iodo-1-methyl-2-[(2,2,2-trifluoroethyl)sulfanyl] benzene (VIIa-7-I)

(VIIa-7-I)

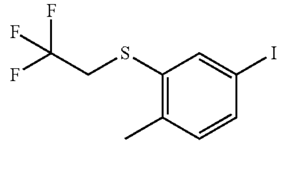

log P[a]: 4.49; log P[b]: 4.48; GC-MS: EI mass (m/z): 332 $[M]^+$ $^{1}$H-NMR (D6-DMSO, 400 MHz): 7.83 (d, 1H), 7.55-7.53 (m, 1H), 7.05 (d, 1H), 4.05 (q, 2H), 2.30 (s, 3H)

Synthesis of Boronic Acids of the Formula (VIII)

(VIII)

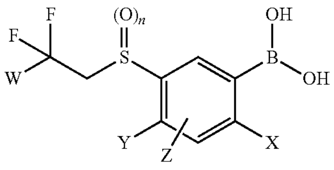

{4-Methyl-3-[(2,2,2-trifluoroethyl)sulfanyl] phenyl}boronic acid (VIIIa-7)

(VIIIa-7)

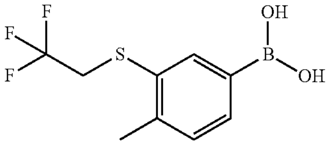

Step 1: 4,4,5,5-Tetramethyl-2-{4-methyl-3-[(2,2,2-trifluoroethyl)sulfanyl]phenyl}-1,3,2-dioxaborolane

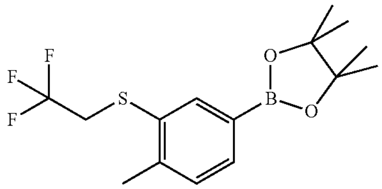 [SMILES: Cc1ccc(B2OC(C)(C)C(C)(C)O2)cc1SCC(F)(F)F]

15.0 g (52.6 mmol) of 5-bromo-2-methylphenyl-2,2,2-trifluoroethyl sulfide, 14.7 g (57.9 mmol) of 4,4,4',4',5,5,5',5'-octamethyl-2,2'-bi-1,2,3-dioxaborolane, 10.3 g (105.2 mmol) of potassium acetate and 2.15 g (2.63 mmol) of 1,1'-bis(diphenylphosphino)ferrocenepalladium(II) dichloride/methylene chloride adduct are initially charged in 78 ml of degassed dry dioxane and stirred at 160° C. under microwave irradiation (Anton Paar Multiwave) for 40 min. The reaction mixture is filtered through silica gel with ethyl acetate, and the filtrate is freed of the solvent under reduced pressure. Purification by column chromatography on silica gel by means of MPLC with cyclohexane/ethyl acetate as eluent gives 14.07 g (90% pure, 72% of theory) of the title compound as a green oil.

log P[a]: 3.73; log P[b]: 3.74; ESI mass (m/z): 333 $[M+1]^+$; GC-MS: EI mass (m/z): 332 $[M]^+$ $^{1}$H-NMR (D6-DMSO, 400 MHz) δ ppm: 7.77 (s, 1H), 7.52 (d, 1H), 7.30 (d, 1H), 3.87 (q, 2H), 2.42 (s, 3H), 1.29 (s, 12H)

Step 2: {4-Methyl-3-[(2,2,2-trifluoroethyl)sulfanyl]phenyl}boronic acid (VIIIa-7) and {4-methyl-3-[(2,2,2-trifluoroethyl)sulfinyl]phenyl}boronic acid (VIIIb-7)

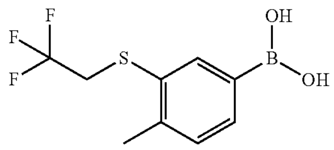

+

(VIIIa-7)

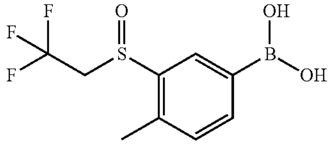

(VIIIb-7)

730 mg (2.2 mmol) of 4,4,5,5-tetramethyl-2-{4-methyl-3-[(2,2,2-trifluoroethyl)sulfanyl]phenyl}-1,3,2-dioxaborolane are initially charged in 20 ml of acetone and 20 ml of water, and 381 mg (4.9 mmol) of ammonium acetate and 1.06 g (4.9 mmol) of sodium periodate are added at 0° C. The reaction mixture is stirred at room temperature overnight and then freed from acetone under reduced pressure. The acidic aqueous phase is extracted with ethyl acetate, and the combined organic phases are washed successively with water and saturated aqueous sodium chloride solution, dried over magnesium sulfate, filtered and freed of the solvent under reduced pressure. Purification by column chromatography on silica gel by means of MPLC using the mobile phase cyclohexane/ethyl acetate gives 105 mg (96% pure, 18% of theory) of {4-methyl-3-[(2,2,2-trifluoroethyl)sulfanyl]phenyl}boronic acid and 138 mg (97% pure, 23% of theory) of {4-methyl-3-[(2,2,2-trifluoroethyl)sulfinyl]phenyl}boronic acid as colorless solids.

{4-Methyl-3-[(2,2,2-trifluoroethyl)sulfanyl]phenyl}boronic acid log P[a]: 2.30; log P[b]: 2.24; ESI mass (m/z): pos.[a]: 251 $[M+1]^+$, neg.[b]: 249 $[M-1]^-$ $^1$H-NMR (D6-DMSO, 400 MHz): 8.08 (s, 2H), 7.92 (s, 1H), 7.61-7.59 (m, 1H), 7.23 (d, 1H), 3.90 (q, 2H), 2.38 (s, 3H)

{4-Methyl-3-[(2,2,2-trifluoroethyl)sulfinyl]phenyl}boronic acid log P[a]: 1.41; log P[b]: 1.36; ESI mass (m/z): pos.[a]: 267 $[M+1]^+$;

$^1$H-NMR (D6-DMSO, 400 MHz): 8.31 (s, 1H), 8.24 (s, 2H), 7.89-7.87 (m, 1H), 7.31 (d, 1H), 4.12-4.02 (m, 1H), 3.94-3.82 (m, 1H), 2.39 (s, 3H)

The following were obtained analogously:

2-{2-Fluoro-4-methyl-5-[(2,2,2-trifluoroethyl)sulfanyl]phenyl}-4,4,5,5-tetramethyl-1,3,2-dioxaborolane

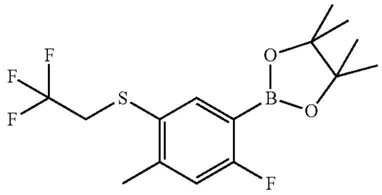 [SMILES: Cc1cc(F)c(B2OC(C)(C)C(C)(C)O2)cc1SCC(F)(F)F]

log P[a]: 4.91; log P[b]: 4.81; ESI mass (m/z): pos.[a]: 351 $[M+1]^+$; GC-MS: EI mass (m/z): 350 $[M]^+$; 1H-NMR (D6-DMSO, 400 MHz): 7.77 (d, 1H), 7.17 (d, 1H), 3.79 (q, 2H), 2.46 (s, 3H), 1.30 (s, 12H)

{2-Fluoro-4-methyl-5-[(2,2,2-trifluoroethyl)sulfanyl]phenyl}boronic acid (VIIIa-1)

(VIIIa-1)

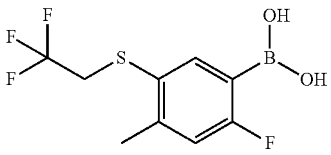

log P[a]: 2.34; log P[b]: 2.41; ESI mass (m/z): pos.[a]: 269 $[M+1]^+$, neg.[a]: 313 $[M+HCOO^-]^-$, neg.[b]: 267 $[M-1]^-$; $^1$H-NMR (D6-DMSO, 400 MHz): 8.21 (s, 2H), 7.74 (d, 1H), 7.06 (d, 1H), 3.82 (q, 2H), 2.40 (s, 3H)

2-{2,4-Dimethyl-5-[(2,2,2-trifluoroethyl)sulfanyl]phenyl}-4,4,5,5-tetramethyl-1,3,2-dioxaborolane

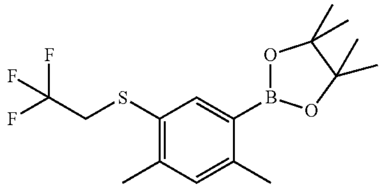 [SMILES: Cc1cc(C)c(B2OC(C)(C)C(C)(C)O2)cc1SCC(F)(F)F]

log P[a]: 5.75; log P[b]: 5.64; ESI mass (m/z): pos.[a]: 347 $[M+1]^+$; GC-MS: EI mass (m/z): 346 $[M]^+$; 1H-NMR (D6-DMSO, 400 MHz): 7.75 (s, 1H), 7.13 (s, 1H), 3.74 (q, 2H), 2.41 (s, 3H), 2.40 (s, 3H), 1.30 (s, 12H)

{2,4-Dimethyl-5-[(2,2,2-trifluoroethyl)sulfanyl]phenyl}boronic acid (VIIIa-11)

(VIIIa-11)

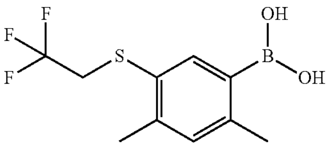

log P[a]: 2.58; log P[b]: 2.57; ESI mass (m/z): neg.[a]: 309 $[M+HCOO^-]^-$, $^1$H-NMR (D6-DMSO, 400 MHz): 8.02 (broad, 2H), 7.61 (s, 1H), 7.03 (s, 1H), 3.81 (q, 2H), 2.36 (s, 3H), 2.34 (s, 3H)

2-{2,4-Dichloro-5-[(2,2,2-trifluoroethyl)sulfanyl]phenyl}-4,4,5,5-tetramethyl-1,3,2-dioxaborolane

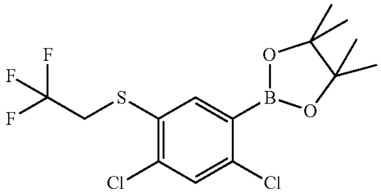 [SMILES: CC1(C)OB(c2cc(SCC(F)(F)F)c(Cl)cc2Cl)OC1(C)C]

log P[a]: 5.68; log P[b]: 5.31; ESI mass (m/z): pos.[a]: 387 $[M+1]^+$; GC-MS: EI mass (m/z): 386$[M]^+$; $^1$H-NMR (D6-DMSO, 400 MHz): 7.79 (s, 1H), 7.72 (s, 1H), 4.08 (q, 2H), 1.32 (s, 12H)

{2,4-Dichloro-5-[(2,2,2-trifluoroethyl)sulfanyl]phenyl}boronic acid (VIIIa-6)

(VIIIa-6)

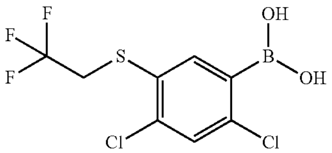

log P[a]: 2.61; log P[b]: 2.52; ESI mass (m/z): neg.[a]: 348 $[M+HCOO^-]^-$, $^1$H-NMR (D6-DMSO, 400 MHz): 8.50 (broad, 2H), 7.68 (s, 1H), 7.60 (s, 1H), 4.11 (q, 2H)

2-{4-Chloro-3-[(2,2,2-trifluoroethyl)sulfanyl]phenyl}-4,4,5,5-tetramethyl-1,3,2-dioxaborolane

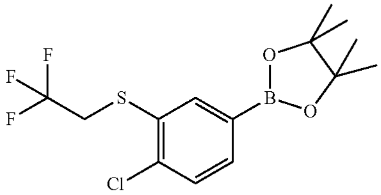 [SMILES: CC1(C)OB(c2ccc(Cl)c(SCC(F)(F)F)c2)OC1(C)C]

log P[a]: 5.27; log P[b]: 5.16; ESI mass (m/z): pos.[a]: 353 $[M+1]^+$; GC-MS: EI mass (m/z): 352$[M]^+$; 1H-NMR (D6-DMSO, 400 MHz): 7.87 (d, 1H), 7.62-7.60 (m, 1H), 7.50 (d, 1H), 3.71 (q, 2H), 1.33 (s, 12H)

{4-Chloro-3-[(2,2,2-trifluoroethyl)sulfanyl]phenyl}boronic acid (VIIIa-3)

(VIIIa-3)

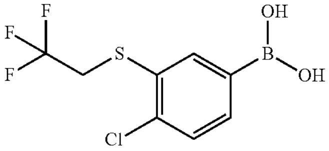

log P[a]: 2.40; log P[b]: 2.41; ESI mass (m/z): neg.[a]: 315 $[M+HCOO^-]^-$, $^1$H-NMR (D6-DMSO, 400 MHz): 8.30 (broad, 2H), 8.00 (d, 1H), 7.67-7.64 (m, 1H), 7.49 (d, 1H), 4.07 (q, 2H)

2-{4-Methoxy-3-[(2,2,2-trifluoroethyl)sulfanyl]phenyl}-4,4,5,5-tetramethyl-1,3,2-dioxaborolane

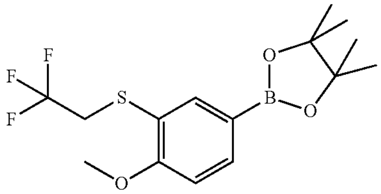 [SMILES: COc1ccc(B2OC(C)(C)C(C)(C)O2)cc1SCC(F)(F)F]

log P[a]: 4.54; log P[b]: 4.46; ESI mass (m/z): pos.[a]: 349 $[M+1]^+$; GC-MS: EI mass (m/z): 348$[M]^+$; $^1$H-NMR (D6-DMSO, 400 MHz): 7.67 (d, 1H), 7.64-7.62 (m, 1H), 7.07 (d, 1H), 3.89 (s, 3H), 3.83 (q, 2H), 1.29 (s, 12H)

{4-Methoxy-3-[(2,2,2-trifluoroethyl)sulfanyl]phenyl}boronic acid (VIIIa-8)

(VIIIa-8)

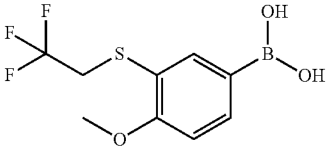

log P[a]: 1.94; log P[b]: 1.93; ESI mass (m/z): neg.[a]: 311 $[M+HCOO^-]^-$, $^1$H-NMR (D6-DMSO, 400 MHz): 7.98 (broad, 2H), 7.86 (d, 1H), 7.74-7.71 (m, 1H), 7.02 (d, 1H), 3.87 (s, 3H), 3.84 (q, 2H)

{2-Fluoro-4-methyl-5-[(2,2,2-trifluoroethyl)sulfinyl]phenyl}boronic acid (VIIIb-1)

(VIIIb-1)

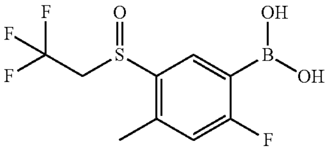

300 mg (1.12 mmol) of {2-fluoro-4-methyl-5-[(2,2,2-trifluoroethyl)sulfanyl]phenyl}boronic acid are dissolved in acetonitrile, 396.4 g (1.12 mmol) of Selectfluor® are added and the mixture is stirred at room temperature overnight. A further 39.8 mg (0.12 mmol) of Selectfluor® are added and the reaction mixture is stirred for 2 h, then diluted with ethyl acetate and washed with 1N hydrochloric acid. The organic phase is dried over magnesium sulphate, filtered and freed of the solvent under reduced pressure. Purification by column chromatography on silica gel by means of MPLC with cyclohexane/ethyl acetate as eluent gives 102 mg (97% pure, 31% of theory) of the title compound as a colorless oil which crystallizes gradually in the course of storage to give a colorless solid.

log P[a]: 1.38; log P[b]: 1.11; ESI mass (m/z): pos.[a]: 285 $[M+1]^+$, neg.[a]: 329 $[M+HCOO^-]^-$ $^1$H-NMR (D6-DMSO, 400 MHz): 8.36 (s, 2H), 8.08 (d, 1H), 7.15 (d, 1H), 4.14-3.92 (m, 2H), 2.39 (s, 3H)

The following were obtained analogously:

{2,4-Dimethyl-5-[(2,2,2-trifluoroethyl)sulfinyl]phenyl}boronic acid (VIIIb-11)

(VIIIb-11)

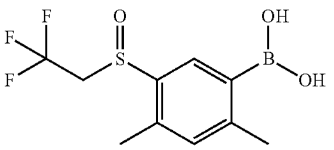

log P[a]: 1.61; log P[b]: 1.61; ESI mass (m/z): pos.[a]: 281 $[M+1]^+$; $^1$H-NMR (D6-DMSO, 400 MHz): 8.15 (s, 2H), 7.96 (s, 1H), 7.09 (s, 1H), 4.05-3.85 (m, 2H), 2.44 (s, 3H), 2.33 (s, 3H)

{2,4-Dichloro-5-[(2,2,2-trifluoroethyl)sulfinyl]phenyl}boronic acid (VIIIb-6)

(VIIIb-6)

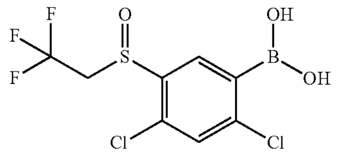

log P[a]: 1.86; log P[b]: 1.51; ESI mass (m/z): pos.[a]: 321 $[M+1]^+$; $^1$H-NMR (D6-DMSO, 400 MHz): 8.64 (broad, 2H), 7.92 (s, 1H), 7.79 (s, 1H), 4.29-4.04 (m, 2H)

{4-Chloro-3-[(2,2,2-trifluoroethyl)sulfinyl]phenyl}boronic acid (VIIIb-3)

(VIIIb-3)

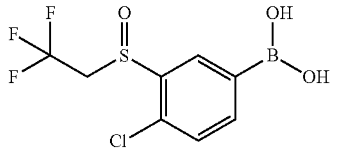

log P[a]: 1.74; log P[b]: 1.68; ESI mass (m/z): pos.[a]: 287 $[M+1]^+$; $^1$H-NMR (D6-DMSO, 400 MHz): 8.45 (broad, 2H), 8.33 (d, 1H), 8.01-7.99 (m, 1H), 7.62 (d, 1H), 4.24-4.12 (m, 1H), 4.08-3.96 (m, 1H)

{4-Methoxy-3-[(2,2,2-trifluoroethyl)sulfanyl]phenyl}boronic acid (VIIIb-8)

(VIIIb-8)

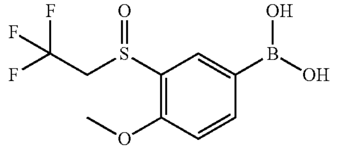

log P[a]: 1.36; log P[b]: 1.37; ESI mass (m/z): pos.[a]: 283 $[M+1]^+$; $^1$H-NMR (D6-DMSO, 400 MHz): 8.15 (s, 1H), 8.13 (s, 2H), 8.02-8.00 (m, 1H), 7.17 (d, 1H), 4.08-3.99 (m, 1H), 3.90 (s, 3H), 3.87-3.78 (m, 1H)

1,2,4-Triazolidine-3,5-diones of the General Formula (XXII-C-1)

(XXII-C-1)

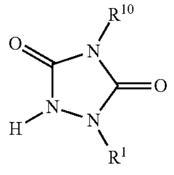

| $R^1$ | $R^{10}$ | logP [a] | logP [b] | $[M + 1]^+$ | NMR | Solvent | $M^+$ (GCMS) | GCMS index |
|---|---|---|---|---|---|---|---|---|
| $CH_2CH(CH_3)_2$ | cyclopropyl | 0.94 | n.d. | 198 | 10.36 (s, 1H), 3.17 (d, 2H), 2.60-2.56 (m, 1H), 1.96-1.89 (m, 1H), 0.85-0.78 (m, 10H) | D6-DMSO | 197 | 1651 |
| $CH_3$ | $C(CH_3)_3$ | 0.83 | n.d. | 172 | 10.15 (s, 1H), 2.94 (s, 3H), 1.52 (s, 9H) | D6-DMSO | 171 | 1380 |
| $CH_2CH_3$ | $C(CH_3)_3$ | 1.15 | n.d. | 186 | 10.11 (s, 1H), 3.36 (q, 2H), 1.52 (s, 9H), 1.07 (t, 3H) | D6-DMSO | 185 | 1436 |

-continued

| $R^1$ | $R^{10}$ | logP [a] | logP [b] | $[M+1]^+$ | NMR | Solvent | $M^+$ (GCMS) | GCMS index |
|---|---|---|---|---|---|---|---|---|
| cyclopentyl | $CH_3$ | 0.78 | n.d. | 184 | 10.25 (s, 1H), 4.38-4.30 (m, 1H), 2.87 (s, 3H), 1.81-1.75 (m, 2H), 1.66-1.56 (m, 4H), 1.53-1.48 (m, 2H) | D6-DMSO | 183 | 1672 |
| $CH_2CH_3$ | $CH(CH_3)_2$ | 0.62 | n.d. | 172 | 10.27 (s, 1H), 4.14-4.07 (m, 1H), 3.39 (q, 2H), 1.32 (d, 6H), 1.08 (t, 3H) | D6-DMSO | 171 | 1392 |
| benzyl | cyclopropyl | 1.21 | n.d. | 232 | 10.39 (s, 1H), 7.38-7.28 (m, 3H), 7.25-7.23 (m, 2H), 4.56 (s, 2H), 2.63-2.59 (m, 1H), 0.84-0.81 (m, 4H) | D6-DMSO | 231 | 2054 |
| $CH_3$ | $CH(CH_3)_2$ | 0.27 | n.d. | 158 | 10.31 (s, 1H), 4.14-4.07 (m, 1H), 2.98 (s, 3H), 1.32 (d, 6H) | D6-DMSO | 157 | 1341 |
| $CH_3$ | 3-trifluoromethylphenyl | 1.53 | n.d. | 260 | 7.86 (s, 1H), 7.82-7.80 (m, 1H), 7.70-7.67 (m, 2H), 3.16 (s, 3H) | CD3CN | 259 | 1826 |
| $CH(CH_3)_2$ | cyclopropyl | 0.50 | n.d. | 184 | 7.53 (broad, 1 H), 4.20-4.09 (m, 1H), 2.58-2.50 (m, 1H), 1.14 (d, 6H), 0.89-0.83 (m, 4H) | CD3CN | 183 | 1557 |
| H | cyclopropyl | n.d. | n.d. | 142 | 9.90 (s, 2H), 2.61-2.52 (m, 1H), 0.86-0.76 (m, 4H) | D6-DMSO | 141 | 1563 |
| $CH(CH_3)_2$ | $CH_3$ | 0.12 | n.d. | 158 | 10.20 (s, 1H), 4.16-4.08 (m, 1H), 2.87 (s, 3H), 1.11 (d, 6H) | D6-DMSO | 157 | 1359 |
| $CH(CH_3)CH_2CH_3$ | cyclopropyl | 0.82 | n.d. | 198 | 7.53 (broad, 1 H), 3.96-3.88 (m, 1H), 2.59-2.51 (m, 1H), 1.61-1.46 (m, 2H), 1.11 (d, 3H), 0.91-0.86 (m, 7H) | CD3CN | 197 | 1634 |
| $CH_3$ | $CH_2CH_3$ | n.d. | n.d. | 144 | 10.40 (s, 1H), 3.40 (q, 2H), 3.00 (s, 3H), 1.10 (t, 3H) | D6-DMSO | 143 | 1306 |

Analysis of the 2,4-dihydro-3H-1,2,4-triazol-3-ones

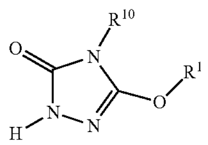

| $R^1$ | $R^{10}$ | logP [a] | logP [b] | NMR | Solvent | M+ (GCMS) | GCMS index |
|---|---|---|---|---|---|---|---|
| $CH_3$ | $CH_2CH{=}CH_2$ | 0.45 | 0.47 | 10.97(s, 1H), 5.87-5.76(m, 1H), 5.15-5.11(m, 1H), 5.03-4.97(m, 1H), 4.06-4.03(m, 2H), 3.87(s, 3H) | D6-DMSO | 155 | 1381 |

-continued

| $R^1$ | $R^{10}$ | logP [a] | logP [b] | NMR | Solvent | M+ (GCMS) | GCMS index |
|---|---|---|---|---|---|---|---|
| $CH_3$ | cyclopropyl | 0.27 | 0.31 | 10.79(s, 1H), 3.86(s, 3H), 2.68-2.61(m, 1H), 0.85-0.80(m, 1H) | D6-DMSO | 155 | 1448 |
| $CH_2CH{=}CH_2$ | cyclopropyl | 1.00 | 1.03 | 8.67(s, 1H), 6.10-6.00(m, 1H), 5.47-5.39(m, 1H), 5.33-5.28(m, 1H), 4.72-4.69(m, 2H), 2.65-2.58(m, 1H), 0.93-0.84(m, 4H) | CD3CN | 181 | 1588 |
| $CH_2$-cyclopropyl | $CH_3$ | 0.84 | 0.88 | 10.85(s, 1H), 4.04(d, 2H), 2.98(s, 3H), 1.28-1.22(m, 1H), 0.60-0.52(m, 2H), 0.39-0.30(m, 2H) | D6-DMSO | 169 | 1576 |
| 2-chlorobenzyl | $CH_3$ | 1.66 | 1.63 | 8.85(s, 1H), 7.58-7.55(m, 1H), 7.50-7.46(m, 1H), 7.42-7.35(m, 2H), 5.36(s, 2H), 3.03(s, 3H) | CD3CN | 239 | 2101 |

Preparation Example 1

2,2,2-Trifluoro-N-(1-{2-fluoro-4-methyl-5-[(2,2,2-trifluoroethyl)sulfinyl]phenyl}pyrrolidin-2-ylidene)ethanamine (Ex. No. 3)

Step 1: 2,2,2-Trifluoro-N-(1-[2-fluoro-4-methyl-5-[(2,2,2-trifluoroethyl)sulfanyl]phenyl]pyrrolidin-2-ylidene)ethanamine (Ex. No. 6)

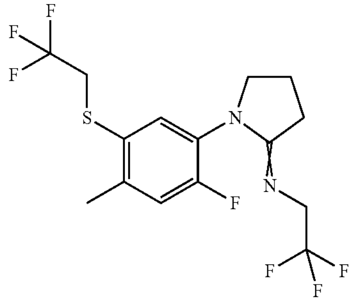 [SMILES: Cc1cc(F)c(N2CCCC2=NCC(F)(F)F)cc1SCC(F)(F)F]

200 mg (0.836 mmol) of 2-fluoro-4-methyl-5-[(2,2,2-trifluoroethyl)sulfanyl]aniline and 190 mg (0.933 mmol) of 4-chloro-N-(2,2,2-trifluoroethyl)butanamide [CAS-RN: 1017050-83-7] are stirred with 3 g (19.565 mmol) of phosphoryl chloride at 95° C. for 18 h. After removal of excess phosphoryl chloride under reduced pressure, ice-water is added to the residue and the mixture is made alkaline using potassium carbonate and extracted repeatedly with dichloromethane. The combined organic phases are dried over sodium sulfate and filtered. Removal of the solvent under reduced pressure gives 320 mg of product (98.5% of theory, purity 86.6% according to LC/MS).

1H-NMR (D6-DMSO) δ ppm: 7.64-7.62 (m, 1H), 7.29-7.26 (m, 1H), 4.30-3.87 (m, 6H), 3.33 (m, 2H), 2.38 (s, 3H), 2.33 (m, 2H)

log P (HCOOH): 1.68 log P (neutral): 4.24

Step 2: 2,2,2-Trifluoro-N-(1-[2-fluoro-4-methyl-5-[(2,2,2-trifluoroethyl)sulfinyl]phenyl]pyrrolidin-2-ylidene)ethanamine (Ex. No. 3)

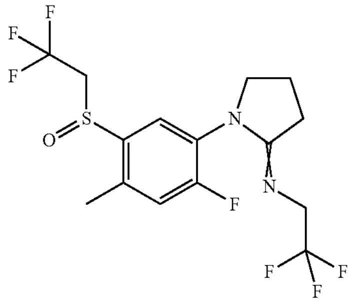 [SMILES: Cc1cc(F)c(N2CCCC2=NCC(F)(F)F)cc1S(=O)CC(F)(F)F]

At 0-4° C., 315 mg (0.81 mmol) of 2,2,2-trifluoro-N-(1-{2-fluoro-4-methyl-5-[(2,2,2-trifluoroethyl)sulfanyl]phenyl}pyrrolidin-2-ylidene)ethanamine are initially charged in 20 ml of trichloromethane. After the addition of 300 mg of buffer solution pH 7 ($KH_2PO_4$/$Na_2HPO_4$) and 55 mg of benzyltriethylammonium chloride, 25.4 mg (77%, 0.93 mmol) of meta-chloroperbenzoic acid are added a little at a time at 0-4° C. and the reaction mixture is stirred at room temperature for 24 h. After the addition of a 33% strength aqueous sodium bisulfite solution, the mixture is extracted twice with dichloromethane. The combined organic phases are washed with water, dried over sodium sulfate and filtered. After removal of the solvent under reduced pressure, the residue is purified by column chromatography using MPLC on RP(C-18) with water/acetonitrile. This gives 54.3 mg of product as a white solid (16.5% of theory, purity 96.6% according to LC/MS).

1H-NMR (D6-DMSO) δ ppm: 7.99-7.97 (m, 1H), 7.32-7.29 (m, 1H), 4.20-4.11 (m, 1H), 3.90-3.64 (m, 5H), 2.62 (t, 2H), 2.37 (s, 3H), 2.12-2.05 (m, 2H)

log P (HCOOH): 1.02 log P (neutral): 2.88

Preparation Example 2

1-{2,4-Dimethyl-5-[(2,2,2-trifluoroethyl)sulfinyl]phenyl}imidazolidin-2-one (Ex. No. 4)

Step 1: 1-(2-Chloroethyl)-3-{2,4-dimethyl-5-[(2,2,2-trifluoroethyl)sulfanyl]phenyl}urea

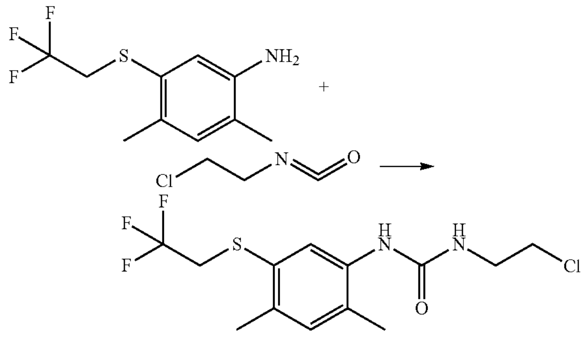

A little at a time, 1.45 g (6.16 mmol) of 2,4-dimethyl-5-[(2,2,2-trifluoroethyl)sulfanyl]aniline are added to a solution of 0.7 g (6.63 mmol) of 2-chloroethyl isothiocyanate in 50 ml of tert-butyl methyl ether and a catalytic amount of 1,8-diazabicyclo[5.4.0]undec-7-ene (DBU) and subsequently stirred at room temperature for another 18 h. Under reduced pressure, almost all of the solvent is removed from the mixture, and the resulting white solid is filtered off with suction. This leaves 2 g of product (88.5% of theory, purity 94.4% according to LC/MS).

1H-NMR (D6-DMSO) δ ppm: 8.01 (s, 1H), 7.83 (s, 1H), 7.04 (s, 1H), 7.43-7.40 (m, 1H), 6.83 (t, 1H), 3.77-3.69 (q, 2H), 3.68-3.65 (m, 2H), 3.45-3.40 (m, 2H), 2.30 (s, 3H), 2.14 (s, 3H)

Step 2: 1-{2,4-Dimethyl-5-[(2,2,2-trifluoroethyl)sulfanyl]phenyl}imidazolidin-2-one (Ex. No. 1)

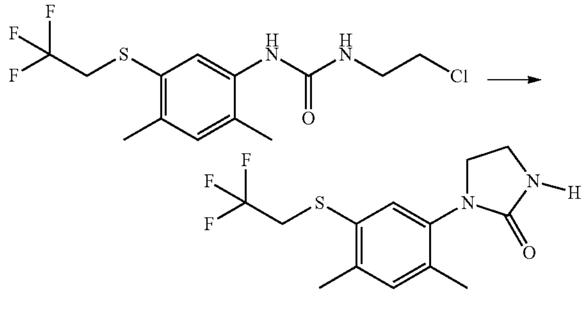

900 mg (2.64 mmol) of 1-(2-chloroethyl)-3-{2,4-dimethyl-5-[(2,2,2-trifluoroethyl)sulfanyl]phenyl}urea in a mixture of 15 ml of water and 20 ml of propionitrile with 4 g of potassium carbonate are heated under reflux for 18 h. Under reduced pressure, the mixture is freed from the solvent and the slurry of solids that remains is acidified with dilute hydrochloric acid. The mixture is then allowed to stand for 18 h, and the beige precipitate is then filtered off with suction. This gives 560 mg of crude product. Purification by column chromatography using ethyl acetate/cyclohexane 2:1 v/v as mobile phase gives 118 mg of product (14.6% of theory, purity according to LC/MS 91.1%).

1H-NMR (D6-DMSO) δ ppm: 7.37 (s, 1H), 7.14 (s, 1H), 6.64 (s, 1H), 3.92-3.87 (q, 2H), 3.73-3.70 (m, 2H), 3.42-3.39 (m, 2H), 2.33 (s, 3H), 2.15 (s, 3H)

13C-NMR (D6-DMSO) δ ppm: 160.3, 137.6, 136.7, 135.6, 132.6, 129.8, 128.9, 126.3, 47.6, 38.1, 35.1, 19.7, 17.6 log P (HCOOH): 2.43 log P (neutral): 2.39

Step 3: 1-{2,4-Dimethyl-5-[(2,2,2-trifluoroethyl)sulfinyl]phenyl}imidazolidin-2-one (Ex. No. 4)

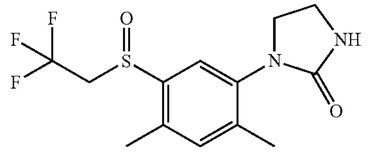 [SMILES: Cc1cc(C)c(S(=O)CC(F)(F)F)cc1N1CCNC1=O]

At 0-4° C., 30 mg (0.099 mmol) of 1-{2,4-diethyl-5-[(2,2,2-trifluoroethyl)sulfanyl]phenyl}imidazolidin-2-one are initially charged in 10 ml of trichloromethane. After the addition of 100 mg of buffer solution pH 7 ($KH_2PO_4$/$Na_2HPO_4$) and 15 mg of benzyltriethylammonium chloride, 25.4 mg (77%, 0.113 mmol) of meta-chloroperbenzoic acid are added a little at a time at 0-4° C. and the reaction mixture is stirred at room temperature for 24 h. After the addition of a 33% strength aqueous sodium bisulfite solution, the mixture is extracted twice with dichloromethane. The combined organic phases are washed with water, dried over sodium sulfate and filtered. After removal of the solvent under reduced pressure, the residue is purified by column chromatography using MPLC on RP(C-18) with water/acetonitrile. This gives 9.1 mg of product as a beige solid (28.8% of theory, purity 88.4% according to LC/MS).

13C-NMR (D6-DMSO) δ ppm: 159.9, 139.8, 138.2, 138.2, 132.8, 132.6, 121.0, 56.9, 47.1, 37.7, 17.7, 16.7

1H-NMR (D6-DMSO) δ ppm: 7.67 (s, 1H), 7.24 (s, 1H), 6.77 (broad, 1H), 4.13-3.93 (m, 2H), 3.78-3.71 (m, 2H), 3.44 (t, 2H), 2.33 (s, 3H), 2.24 (s, 3H)

log P (HCOOH): 1.51 log P (neutral): 1.52

Preparation Example 3

1-{2-Fluoro-4-methyl-5-[(2,2,2-trifluoroethyl)sulfanyl]phenyl}imidazolidin-2-one (Ex. No. 9)

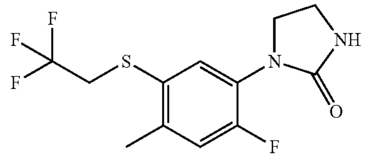 [SMILES: Cc1cc(F)c(N2CCNC2=O)cc1SCC(F)(F)F]

28 mg (0.09 mmol) of 2-fluoro-4-methyl-N-(1,3-oxazolidin-2-ylidene)-5-[(2,2,2-trifluoroethyl)sulfanyl]aniline in 5 ml of methyl tert-butyl ether are, after addition of 20 mg of triethylamine, stirred at room temperature for 24 h. After removal of the solvent under reduced pressure, 23 mg of product remain as a white solid (82.1% of theory, purity 100% according to 1H NMR).

1H-NMR (D6-DMSO) δ ppm: 7.67-7.65 (m, 1H), 7.23-7.20 (m, 1H), 6.90 (broad, 1H), 3.91-3.83 (q, 2H), 3.80 (t, 2H), 3.41 (t, 2H), 2.37 (s, 3H)

log P (HCOOH): 2.36 log P (neutral): 2.31

Preparation Example 4

3-{2-Fluoro-4-methyl-5-[(2,2,2-trifluoroethyl)sulfinyl]phenyl}-2-[(2,2,2-trifluoroethyl)imino]-1,3-thiazolidin-4-one (Ex. No. 13)

Step 1: 1-{2-Fluoro-4-methyl-5-[(2,2,2-trifluoroethyl)sulfanyl]phenyl}-3-(2,2,2-trifluoroethyl)thiourea

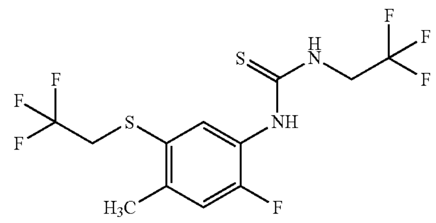 [SMILES: Cc1cc(F)c(NC(=S)NCC(F)(F)F)cc1SCC(F)(F)F]

1.00 g (4.18 mmol) of 2-fluoro-4-methyl-5-[(2,2,2-trifluoroethyl)sulfanyl]aniline is initially charged in 5 ml of dichloromethane, and 0.006 ml (0.042 mmol) of triethylamine is added. After the addition of 0.59 g (4.18 mmol) of 1,1,1-trifluoro-2-isothiocyanatoethane, the reaction mixture is stirred at room temperature overnight. The solvent is removed under reduced pressure, the residue is stirred with a little toluene and the insoluble fraction is filtered off with suction and dried. This gives 0.31 g (100% pure, 20% of theory) of the title compound as a white solid. The filtrate is freed of the solvent under reduced pressure. The residue of 1.30 g comprises the title compound in a purity of 77%.

log P (HCOOH): 3.32; log P(neutral): 3.24; 1H-NMR (D6-DMSO, 400 MHz) δ ppm 9.62 (bs, 1H), 8.34 (bs, 1H), 7.76 (d, 1H), 7.26 (d, 1H), 4.46-4.40 (m, 2H), 3.87 (q, 2H), 2.38 (s, 3H)

Step 2: 3-{2-Fluoro-4-methyl-5-[(2,2,2-trifluoroethyl)sulfanyl]phenyl}-2-[(2,2,2-trifluoroethyl)imino]-1,3-thiazolidin-4-one (Ex. No. 11)

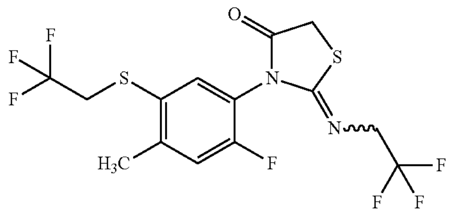 [SMILES: Cc1cc(F)c(N2C(=O)CSC2=NCC(F)(F)F)cc1SCC(F)(F)F]

3.00 g (7.89 mmol) of 1-{2-fluoro-4-methyl-5-[(2,2,2-trifluoroethyl)sulfanyl]phenyl}-3-(2,2,2-trifluoroethyl)thiourea and 1.10 g (7.89 mmol) of bromoacetic acid are initially charged in 80 ml of toluene, and the mixture is stirred at reflux for 6 h. After cooling, a saturated sodium chloride solution is added to the reaction mixture and the organic phase is separated off, dried over sodium sulfate and freed from the solvent under reduced pressure. The residue is applied to RP(C-18) material and purified by means of MPLC on RP(C-18) using water/acetonitrile. 0.30 g (95% pure, 9% of theory) of the title compound is isolated as a white solid.

log P (HCOOH): 3.60; log P(neutral): 3.50; 1H-NMR (D6-DMSO, 400 MHz) δ ppm 7.62 (d, 1H), 7.39 (d, 1H), 4.39 (d, 1H), 4.26 (d, 1H), 4.00-3.83 (m, 4H), 2.43 (s, 3H)

Step 3: 3-{2-Fluoro-4-methyl-5-[(2,2,2-trifluoroethyl)sulfinyl]phenyl}-2-[(2,2,2-trifluoroethyl)imino]-1,3-thiazolidin-4-one (Ex. No. 13)

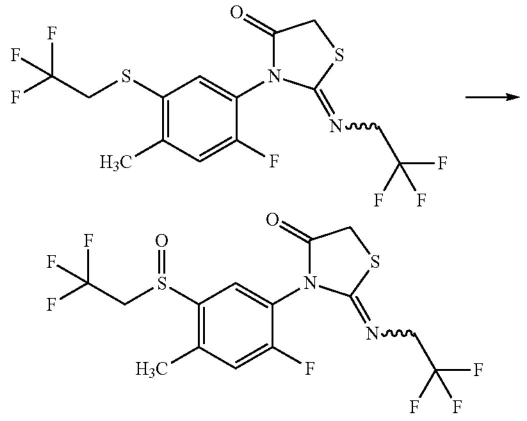

At 0-4° C., 270 mg (0.64 mmol) of 3-({2-fluoro-4-methyl-5-[(2,2,2-trifluoroethyl)sulfanyl]phenyl}-2-[(2,2,2-trifluoroethyl)imino]-1,3-thiazolidin-4-one are initially charged in 5 ml of dichloromethane, 166 mg (0.67 mmol) of meta-chloroperbenzoic acid (70%) are added and the reaction mixture is stirred at room temperature for another 2 h. A 33% strength sodium thiosulfate solution (peroxide test carried out) and a saturated sodium bicarbonate solution are then added, and the mixture is extracted twice with dichloromethane. The combined organic phases are washed with a saturated sodium carbonate solution, dried over sodium sulfate and filtered, and the solvent is removed under reduced pressure. The residue is applied to RP(C-18) material and purified by means of MPLC on RP(C-18) using water/acetonitrile. 195 mg (100% pure, 70% of theory) of the title compound are isolated as a white solid.

log P (HCOOH): 2.70; log P(neutral): 2.64; 1H-NMR (D6-DMSO, 400 MHz) δ ppm 7.92 (dd, 1H), 7.52 (dd, 1H), 4.41-4.25 (m, 3H), 4.06-3.69 (m, 3H), 2.43 (s, 3H)

Preparation Example 5

3-{2-Fluoro-4-methyl-5-[(2,2,2-trifluoroethyl)sulfanyl]phenyl}-1,5,5-trimethylimidazolidine-2,4-dione (Ex. No. 18)

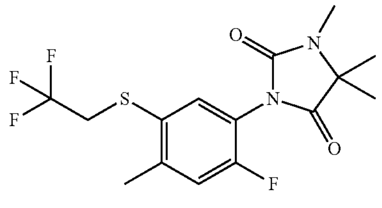 [SMILES: Cc1cc(F)c(N2C(=O)N(C)C(C)(C)C2=O)cc1SCC(F)(F)F]

268.0 mg (1.0 mmol) of {2-fluoro-4-methyl-5-[(2,2,2-trifluoroethyl)sulfanyl]phenyl}boronic acid, 284 mg (2.0 mmol) of 1,5,5-trimethylimidazolidine-2,4-dione, 272 mg (1.5 mmol) of copper(II) acetate, 158 mg (2.0 mmol) of pyridine and 0.5 g of activated 3 Å molecular sieve are stirred in 5 ml of dry dichloromethane at room temperature for 4 d. The reaction mixture is adsorbed on kieselguhr and purified by column chromatography on silica gel by means of MPLC with cyclohexane/ethyl acetate as eluent. This gives 34 mg (99% pure, 9% of theory) of the title compound as a colorless oil.

log P (HCOOH): 2.96; log P(neutral): 2.92; $^{1}$H-NMR (D6-DMSO, 400 MHz) δ ppm 7.69 (d, 1H), 7.39 (d, 1H), 3.93 (q, 2H), 2.88 (s, 3H), 2.43 (s, 3H), 1.43 (s, 6H)

Preparation Example 6

3-{2-Fluoro-4-methyl-5-[(2,2,2-trifluoroethyl)sulfinyl]phenyl}-1,5,5-trimethylimidazolidine-2,4-dione (Ex. No. 17)

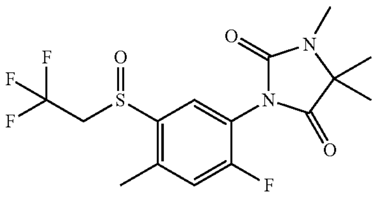 [SMILES: Cc1cc(F)c(N2C(=O)N(C)C(C)(C)C2=O)cc1S(=O)CC(F)(F)F]

At 0° C., 14.7 mg (0.07 mmol) of meta-chloroperbenzoic acid (about 77%) are added to a solution of 24.0 mg (0.07 mmol) of 3-{2-fluoro-4-methyl-5-[(2,2,2-trifluoroethyl)sulfanyl]phenyl}-1,5,5-trimethylimidazolidine-2,4-dione in 10 ml of dichloromethane. The reaction mixture is stirred at 0° C. for 2 h, washed with 1M sodium hydroxide solution and freed of the solvent under reduced pressure. This gives 25 mg (97% pure, 97% of theory) of the title compound as a colorless solid.

log P (HCOOH): 2.04; log P(neutral): 2.01; $^{1}$H-NMR (D6-DMSO, 400 MHz) δ ppm 7.97 (d, 1H), 7.51 (d, 1H), 4.32-4.20 (m, 1H), 4.00-3.89 (m, 1H), 2.89 (s, 3H), 2.43 (s, 3H), 1.45 (s, 3H), 1.44 (s, 3H)

Preparation Example 7

1-{2-Fluoro-4-methyl-5-[(2,2,2-trifluoroethyl)sulfanyl]phenyl}pyrrolidine-2,5-dione (Ex. No. 19)

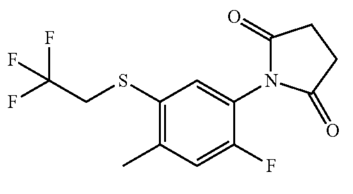 [SMILES: Cc1cc(F)c(N2C(=O)CCC2=O)cc1SCC(F)(F)F]

268 mg (1.0 mmol) of {2-fluoro-4-methyl-5-[(2,2,2-trifluoroethyl)sulfanyl]phenyl}boronic acid, 198 mg (2.0 mmol) of pyrrolidine-2,5-dione, 272 mg (1.5 mmol) of copper(II) acetate, 158 mg (2.0 mmol) of pyridine and 0.5 g of activated 3 Å molecular sieve are stirred in 5 ml of dry dichloromethane at room temperature for 4 d. The reaction mixture is adsorbed on kieselguhr and purified by column chromatography on silica gel by means of MPLC with cyclohexane/ethyl acetate as eluent. This gives 28 mg (100% pure, 9% of theory) of the title compound as a colorless oil.

log P (HCOOH): 2.52; log P(neutral): 2.45; $^{1}$H-NMR (D6-DMSO, 400 MHz) δ ppm 7.56 (d, 1H), 7.40 (d, 1H), 3.87 (q, 2H), 2.86 (broad, 4H), 2.44 (s, 3H)

Preparation Example 8

1,4-Dimethyl-2-{4-methyl-3-[(2,2,2-trifluoroethyl)sulfanyl]phenyl}-1,2,4-triazolidine-3,5-dione (Ex. No. 20)

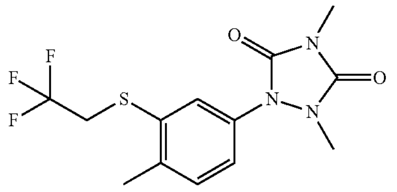 [SMILES: Cc1ccc(-n2c(=O)n(C)c(=O)n2C)cc1SCC(F)(F)F]

350 mg (1.2 mmol) of 5-bromo-2-methylphenyl-2,2,2-trifluoroethyl sulfide, 190.2 mg (1.5 mmol) of 5-methoxy-4-methyl-2,4-dihydro-3H-1,2,4-triazol-3-one, 23.4 mg (0.12 mmol) of copper(I) iodide, 34.9 mg (0.25 mmol) of trans-N,N'-dimethylcyclohexane-1,2-diamine (racemic), 61 mg (0.37 mmol) of potassium iodide and 508.9 mg (3.7 mmol) of potassium carbonate are stirred in 3 ml of dry degassed dioxane at 110° C. overnight. After cooling to room temperature, the reaction mixture is diluted with ethyl acetate and filtered through silica gel using ethyl acetate. Adsorption on kieselguhr and purification by column chromatography on silica gel by means of MPLC with cyclohexane/ethyl acetate as eluent gives 123 mg (90% pure, 27% of theory) of the title compound as a colorless oil.

log P (HCOOH): 2.59; log P(neutral): 2.58; $^{1}$H-NMR (D6-DMSO, 400 MHz) δ ppm 7.49 (d, 1H), 7.38 (d, 1H), 7.23-7.21 (m, 1H), 4.03 (q, 2H), 3.00 (s, 3H), 2.99 (s, 3H), 2.38 (s, 3H)

Preparation Example 9

1,4-Dimethyl-2-{4-methyl-3-[(2,2,2-trifluoroethyl)sulfinyl]phenyl}-1,2,4-triazolidine-3,5-dione (Ex. No. 21)

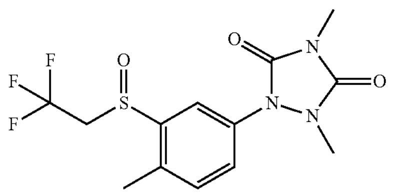 [SMILES: Cc1ccc(-n2c(=O)n(C)c(=O)n2C)cc1S(=O)CC(F)(F)F]

At 0° C., 57.1 mg (0.25 mmol) of meta-chloroperbenzoic acid (about 77%) are added to a solution of 85.0 mg (0.25 mmol) of 1,4-dimethyl-2-{4-methyl-3-[(2,2,2-trifluoroethyl)sulfanyl]phenyl}-1,2,4-triazolidine-3,5-dione in 10 ml of dichloromethane. The reaction mixture is stirred at 0° C. for 2 h, washed with 1M sodium hydroxide solution and freed of the solvent under reduced pressure. Adsorption on kieselguhr and purification by column chromatography on silica gel by means of MPLC with cyclohexane/ethyl acetate as eluent gives 80.0 mg (87% pure, 78% of theory) of the title compound as a colorless oil.

log P (HCOOH): 1.63; log P(neutral): 1.63; $^{1}$H-NMR (D6-DMSO, 400 MHz) δ ppm 7.79 (d, 1H), 7.47-7.54 (m, 2H), 4.12-4.22 (m, 1H), 4.02-4.08 (m, 1H), 3.04 (s, 3H), 3.00 (s, 3H), 2.38 (s, 3H)

Preparation Example 10

1-Ethyl-2-{2-fluoro-4-methyl-5-[(2,2,2-trifluoro-ethyl)sulfanyl]phenyl}-4-phenyl-1,2,4-triazolidine-3,5-dione (Ex. No. 87)

Step 1: 1-Ethyl-4-phenyl-1,2,4-triazolidine-3,5-dione

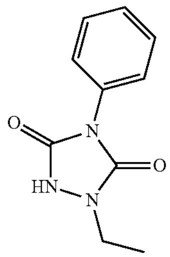

At 0° C., 3.54 g (20.0 mmol) of 4-phenylurazole are added to 1.35 g (24.0 mmol) of potassium hydroxide in 60 ml of ethanol, and the mixture is stirred at 0° C. for 30 min. At 0° C., 2.50 g (16.0 mmol) of ethyl iodide are added and the reaction mixture is stirred at room temperature overnight. Another 2.50 g (16.0 mmol) of ethyl iodide and 20 ml of ethanol are added and the mixture is stirred at room temperature for 3 d. The reaction mixture is heated at 60° C. for 3 h, then cooled, poured into water, adjusted to pH=2-3 with dilute hydrochloric acid and freed of the solvent under reduced pressure. Purification by column chromatography on RP(C-18) silica gel by means of MPLC with water/acetonitrile (1% formic acid) as eluent gives 1.54 g (100% pure, 37% of theory) of the title compound as a colorless solid.

log P (HCOOH): 0.91; $^{1}$H-NMR (D6-DMSO, 400 MHz) δ ppm 10.79 (s, 1H), 7.51-7.37 (m, 5H), 3.54 (q, 2H), 1.18 (t, 3H)

Step 2: 1-Ethyl-2-{2-fluoro-4-methyl-5-[(2,2,2-trifluoroethyl)sulfanyl]phenyl}-4-phenyl-1,2,4-triazolidine-3,5-dione (Ex. No. 87)

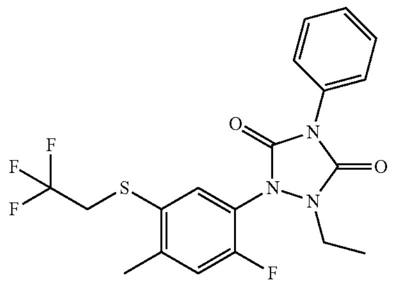 [SMILES: CCn1c(=O)n(-c2ccccc2)c(=O)n1-c1cc(SCC(F)(F)F)c(C)cc1F]

230.0 mg (0.86 mmol) of {2-fluoro-4-methyl-5-[(2,2,2-trifluoroethyl)sulfanyl]phenyl}boronic acid, 352 mg (1.72 mmol) of 1-ethyl-4-phenyl-1,2,4-triazolidine-3,5-dione, 233.8 mg (1.29 mmol) of copper(II) acetate, 136 mg (1.72 mmol) of pyridine and 0.5 g of activated 3 Å molecular sieve are stirred in 5 ml of dry dichloromethane at room temperature for 4 d. The reaction mixture is adsorbed on kieselguhr and purified by column chromatography on silica gel by means of MPLC with cyclohexane/ethyl acetate as eluent. This gives 160 mg (96% pure, 42% of theory) of the title compound as a colorless oil.

log P (HCOOH): 3.71; log P(neutral): 3.69; $^{1}$H-NMR (D6-DMSO, 400 MHz) δ ppm 7.87 (d, 1H), 7.57-7.44 (m, 6H), 4.05 (q, 2H), 3.49 (q, 2H), 2.44 (s, 3H), 1.08 (t, 3H)

Preparation Example 11

1-Ethyl-2-{2-fluoro-4-methyl-5-[(2,2,2-trifluoro-ethyl)sulfinyl]phenyl}-4-phenyl-1,2,4-triazolidine-3,5-dione (Ex. No. 88)

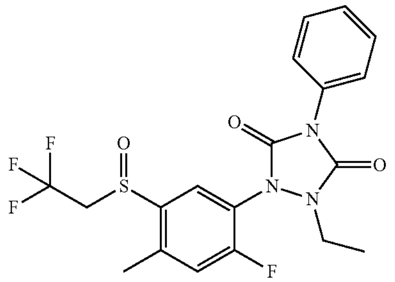 [SMILES: CCn1c(=O)n(-c2ccccc2)c(=O)n1-c1cc(S(=O)CC(F)(F)F)c(C)cc1F]

At 0° C., 44.0 mg (0.20 mmol) of meta-chloroperbenzoic acid (about 77%) are added to a solution of 80.0 mg (0.19 mmol) of 1-ethyl-2-{2-fluoro-4-methyl-5-[(2,2,2-trifluoro-ethyl)sulfanyl]phenyl}-4-phenyl-1,2,4-triazolidine-3,5-dione in 10 ml of dichloromethane. The reaction mixture is stirred at 0° C. for 2 h, washed with 1M sodium hydroxide solution and freed of the solvent under reduced pressure. Adsorption on kieselguhr and purification by column chromatography on silica gel by means of MPLC with cyclohexane/ethyl acetate as eluent gives 74 mg (100% pure, 89% of theory) of the title compound as a colorless solid.

log P (HCOOH): 2.71; log P(neutral): 2.66; $^{1}$H-NMR (D6-DMSO, 400 MHz) δ ppm 8.10 (d, 1H), 7.59 (d, 1H), 7.55-7.51 (m, 4H), 7.48-7.44 (m, 1H), 4.31-4.09 (m, 2H), 3.57-3.51 (m, 2H), 2.44 (s, 3H), 1.09 (t, 3H)

Preparation Example 12

1,4-Diethyl-2-{4-methyl-3-[(2,2,2-trifluoroethyl)sulfanyl]phenyl}-1,2,4-triazolidine-3,5-dione (Ex. No. 100)

Step 1: 1,4-Diethyl-1,2,4-triazolidine-3,5-dione

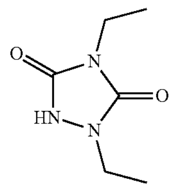

10.32 g (87.4 mmol) of diethyl carbonate are added to 5.00 g (83.2 mmol) of ethylhydrazine and the mixture is heated at reflux overnight. After cooling to room temperature, the solvent is removed under reduced pressure. The residue is taken up in 50 ml of toluene, 7.10 g (99.8 mmol) of ethyl isocyanate are added and the mixture is heated at reflux for 30 min and, after cooling to room temperature, freed from the solvent under reduced pressure. 83.2 ml of a 4N potassium hydroxide solution (332.8 mmol) are added to the residue and the mixture is heated at reflux for 20 min. After cooling to room temperature, the reaction solution is acidified with semiconcentrated hydrochloric acid and extracted with dichloromethane. The combined organic phases are dried over magnesium sulphate, filtered and freed of the solvent under reduced pressure. After freeze-drying, 4.61 g (100% pure, 35% of theory) of the title compound are obtained as a colorless solid.

log P (HCOOH): 0.14; $^{1}$H-NMR (D6-DMSO, 400 MHz) δ ppm 10.35 (s, 1H), 3.42 (q, 2H), 3.38 (q, 2H), 1.10 (t, 3H), 1.09 (t, 3H)

Step 2: 1,4-Diethyl-2-{4-methyl-3-[(2,2,2-trifluoroethyl)sulfanyl]phenyl}-1,2,4-triazolidine-3,5-dione (Ex. No. 100)

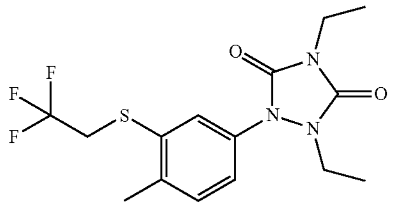 [SMILES: CCn1c(=O)n(CC)n(-c2ccc(C)c(SCC(F)(F)F)c2)c1=O]

250.0 mg (1.0 mmol) of {4-methyl-3-[(2,2,2-trifluoroethyl)sulfanyl]phenyl}boronic acid, 314.3 mg (2.0 mmol) of 1,4-diethyl-1,2,4-triazolidine-3,5-dione, 272.5 mg (1.5 mmol) of copper(II) acetate, 158 mg (2.0 mmol) of pyridine and 0.5 g of activated 3 Å molecular sieve are stirred in 5 ml of dry dichloromethane at room temperature for 4 d. The reaction mixture is adsorbed on kieselguhr and purified by column chromatography on silica gel by MPLC using the mobile phase cyclohexane/ethyl acetate and by column chromatography on RP(C-18) silica gel by MPLC using the mobile phase water/acetonitrile. This gives 177.0 mg (100% pure, 49% of theory) of the title compound as a colorless oil.

log P (HCOOH): 3.32; log P(neutral): 3.29; $^{1}$H-NMR (D6-DMSO, 400 MHz) δ ppm 7.52 (d, 1H), 7.38 (d, 1H), 7.25-7.22 (m, 1H), 4.05 (q, 2H), 3.52 (q, 2H), 3.46 (q, 2H), 2.37 (s, 3H), 1.17 (t, 3H), 0.96 (t, 3H)

Preparation Example 13

1-(2,2-Difluoroethyl)-3-{2-fluoro-4-methyl-5-[(2,2,2-trifluoroethyl)sulfinyl]phenyl}imidazolidine-2,4,5-trione (Ex. No. 103)

Step 1: 1-(2,2-Difluoroethyl)-3-{2-fluoro-4-methyl-5-[(2,2,2-trifluoroethyl)sulfanyl]phenyl}urea

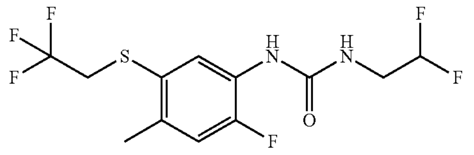 [SMILES: Cc1cc(F)c(NC(=O)NCC(F)F)cc1SCC(F)(F)F]

A little at a time, 300 mg (2.8 mmol) of 1,1-difluoro-2-isocyanatoethane are added to a solution of 600 mg (2.51 mmol) of 2-fluoro-4-methyl-5-[(2,2,2-trifluoroethyl)sulfanyl]aniline in 40 ml of methyl tert-butyl ether and a catalytic amount of 1,8-diazabicyclo[5.4.0]undec-7-ene (DBU), and the mixture is then stirred at room temperature for another 18 h. Under reduced pressure, almost all of the solvent is removed from the mixture, and the resulting white solid is filtered off with suction. This leaves 660 mg of product (76% of theory, purity 96.5% according to LC/MS).

1H-NMR (D6-DMSO) δ ppm: 8.52 (s, 1H), 8.31-8.29 (m, 1H), 7.20-7.17 (m, 1H), 6.92 (t, 1H), 6.07 (tt, 1H), 3.79-3.71 (q, 2H), 3.60-3.48 (m, 2H), 2.34 (s, 3H)

Step 2: 1-(2,2-Difluoroethyl)-3-[2-fluoro-4-methyl-5-[(2,2,2-trifluoroethyl)sulfanyl]phenyl]imidazolidine-2,4,5-trione (Ex. No. 101)

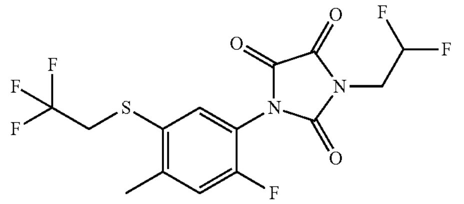 [SMILES: Cc1cc(F)c(N2C(=O)C(=O)N(CC(F)F)C2=O)cc1SCC(F)(F)F]

160 mg (1.261 mmol) of oxalyl chloride (dissolved in 5 ml of acetonitrile) are added dropwise to 200 mg (0.578 mmol) of 1-(2,2-difluoroethyl)-3-{2-fluoro-4-methyl-5-[(2,2 trifluoroethyl)sulfanyl]phenyl}urea in 20 ml of acetonitrile, and the mixture is stirred under reflux for another 18 h. The residue that remains after concentration on a rotary evaporator under reduced pressure is stirred with water and filtered off with suction. This leaves 195 mg of product as a white solid (84.4% of theory, purity >100% according to 1H-NMR) as residue.

1H-NMR (D6-DMSO) δ ppm: 7.70-7.68 (m, 1H), 7.51-7.48 (m, 1H), 6.25 (tt, 1H), 4.10-4.01 (dt, 2H), 3.90-3.82 (q, 2H), 2.48 (s, 3H)

13C-NMR (D6-DMSO) δ ppm: 156.4, 156.3, 151.6, 144.1, 133.0, 128.4, 125.3, 118.3, 115.4, 112.8, 40.4, 35.0, 19.9 log P (HCOOH): 3.22 log P (neutral): 1.73

Step 3: 1-(2,2-Difluoroethyl)-3-{2-fluoro-4-methyl-5-[(2,2,2-trifluoroethyl)sulfinyl]phenyl}imidazolidine-2,4,5-trione (Ex. No. 103)

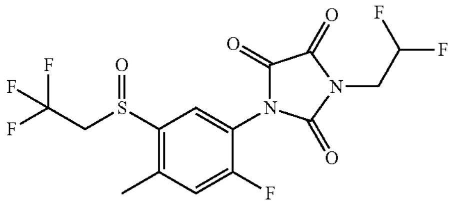 [SMILES: Cc1cc(F)c(N2C(=O)C(=O)N(CC(F)F)C2=O)cc1S(=O)CC(F)(F)F]

At 0° C., 195 mg (0.487 mmol) of 1-(2,2-difluoroethyl)-3-{2-fluoro-4-methyl-5-[(2,2,2-trifluoroethyl)sulfanyl]phenyl}imidazolidine-2,4,5-trione are initially charged in 10 ml of acetic acid. After the addition of catalytic amounts of sodium tungstate at 0-4° C., 765 mg (0.675 mmol) of 3% aqueous hydrogen peroxide solution are added thereto in portions and the reaction mixture is stirred at RT for 24 h. After the addition of a 33% strength aqueous bisulfite solution, the mixture is extracted twice with dichloromethane. The combined organic phases are washed with water, dried over sodium sulfate and filtered. After removing the solvent under reduced pressure, the residue is purified by column chromatography by means of MPLC using RP(C-18). Using water/acetonitrile, this gives 100 mg of product as a white solid (44.4% of theory, purity 90% according to 1H-NMR).

1H-NMR (D6-DMSO) δ ppm: 8.04-8.03 (m, 1H), 7.61-7.58 (m, 1H), 6.24 (tt, 1H), 4.36-4.27 (m, 1H), 4.10-4.01 (dt, 2H), 3.92-3.83 (m, 1H), 2.43 (s, 3H)

log P (HCOOH): 2.32 log P (neutral): 0.87

Preparation Example 14

3-[2-Fluoro-4-methyl-5-(2,2,2-trifluoroethylsulfinyl)phenyl]oxazolidin-2-one (Ex. No. 105)

Step 1: 2-Chloroethyl N-[2-fluoro-4-methyl-5-(2,2,2-trifluoroethylsulfanyl)phenyl]carbamate

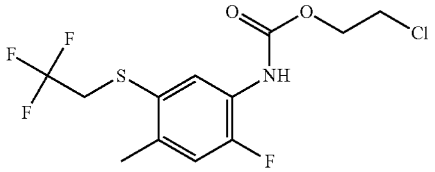 [SMILES: Cc1cc(F)c(NC(=O)OCCCl)cc1SCC(F)(F)F]

2-Fluoro-4-methyl-5-[(2,2,2-trifluoroethyl)sulfanyl]aniline (500 mg, 2.09 mmol) is initially charged in 5 ml of THF at 0° C. Triethylamine (435 μl, 2 mmol) and 2-chloroethyl chloroformate (218 μl, 2.09 mmol) are added and the reaction mixture is stirred under reflux for 4 h. The solution is cooled and water is added. After extraction with ethyl acetate, the combined organic phases are washed with water and sat. NaCl solution and then dried over $Na_2SO_4$. The solvent is removed on a rotary evaporator. Purification of the crude product by column chromatography (25% EtOAc/petroleum ether) gives 360 mg (1.04 mmol, 50% of theory) of the title compound.

1H-NMR (D6-DMSO, 400 MHz) δ ppm: 9.51 (s, 1H), 7.78 (d, 1H), 7.22 (d, 1H), 4.34 (t, 2H), 3.87-3.77 (m, 4H), 2.37 (s, 3H)

log P (HCOOH): 3.45

Step 2: 3-[2-Fluoro-4-methyl-5-(2,2,2-trifluoroethylsulfanyl)phenyl]oxazolidin-2-one (Ex. No. 104)

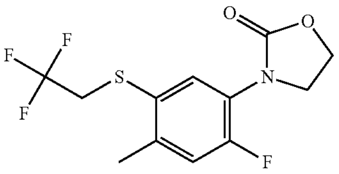 [SMILES: Cc1cc(F)c(N2CCOC2=O)cc1SCC(F)(F)F]

2-Chloroethyl N-[2-fluoro-4-methyl-5-(2,2,2-trifluoroethylsulfanyl)phenyl]carbamate (400 mg, 1.16 mmol) is dissolved in 5 ml of DMF, and cesium carbonate (565 mg, 1.74 mmol) is added. The mixture is stirred at 80° C. for 8 h. The solution is cooled to room temperature, water is added and the mixture is extracted with ethyl acetate. The combined organic phases are washed with water and sat. NaCl solution and then dried over $Na_2SO_4$. The solvent is removed on a rotary evaporator. Purification of the crude product by column chromatography (35% EtOAc/petroleum ether) gives 250 mg (0.81 mmol, 70% of theory) of the title compound.

1H-NMR ($CDCl_3$, 400 MHz) δ ppm: 7.71 (d, 1H), 7.03 (d, 1H), 4.54-4.49 (m, 2H), 4.08-4.03 (m, 2H), 3.37-3.31 (m, 2H), 2.46 (s, 3H)

log P (HCOOH): 2.66

Step 3: 3-[2-Fluoro-4-methyl-5-(2,2,2-trifluoroethylsulfinyl)phenyl]oxazolidin-2-one (Ex. No. 105)

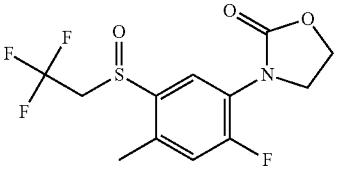 [SMILES: Cc1cc(F)c(N2CCOC2=O)cc1S(=O)CC(F)(F)F]

3-[2-Fluoro-4-methyl-5-(2,2,2-trifluoroethylsulfanyl)phenyl]oxazolidin-2-one (170 mg, 0.55 mmol) is dissolved in 3 ml of acetone/water (1:1), and Oxone (169 mg, 0.34 mmol) is added. The solution is stirred at room temperature for 2 h. The mixture is concentrated under reduced pressure and water is added to the residue. The mixture is extracted with ethyl acetate. The combined organic phases are washed with water and saturated sodium chloride solution and then dried over sodium sulfate. The solvent is removed on a rotary evaporator. Purification of the crude product by column chromatography (40% EtOAc/petroleum ether) gives 90 mg (0.23 mmol, 50% of theory) of the title compound.

1H-NMR ($CDCl_3$, 400 MHz) δ ppm: 8.11 (d, 1H), 7.19 (d, 1H), 4.58-4.49 (m, 2H), 4.18-4.10 (m, 1H), 4.04-3.96 (m, 1H), 3.59-3.33 (m, 2H), 2.41 (s, 3H)

log P (HCOOH): 1.64

Preparation Example 15

3-[2-Fluoro-4-methyl-5-(2,2,2-trifluoroethylsulfinyl)phenyl]-5-methyloxazolidin-2-one (Ex. No. 109)

Step 1: 1-[2-Fluoro-4-methyl-5-(2,2,2-trifluoroethylsulfanyl)aniline]propan-2-ol

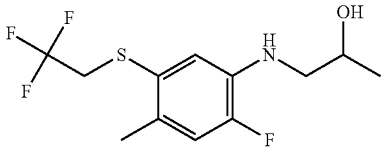 [SMILES: Cc1cc(F)c(NCC(C)O)cc1SCC(F)(F)F]

2-Fluoro-4-methyl-5-[(2,2,2-trifluoroethyl)sulfanyl]aniline (700 mg, 2.93 mmol) is initially charged in 10 ml of dichloromethane. Propylene oxide (4.39 mmol) and LiBr (76.2 mg, 0.88 mmol) are added and the reaction mixture is stirred at room temperature for 16 h. The solution is cooled and water is added. After extraction with dichloromethane, the combined organic phases are washed with water and saturated sodium chloride solution and then dried over sodium sulfate. The solvent is removed on a rotary evaporator. Purification of the crude product by column chromatography (25% EtOAc/petroleum ether) gives 200 mg (0.67 mmol, 23% of theory) of the title compound.

1H-NMR ($CDCl_3$, 400 MHz) δ ppm: 6.91 (d, 1H), 6.86 (d, 1H), 4.10-4.02 (m, 2H), 3.32-3.20 (m, 3H), 3.05-3.00 (m, 1H), 2.37 (s, 3H), 1.85-1.80 (m, 1H), 1.30-1.29 (m, 3H)

log P (HCOOH): 3.01

Step 2: 3-[2-Fluoro-4-methyl-5-(2,2,2-trifluoroethylsulfanyl)phenyl]-5-methyloxazolidin-2-one (Ex. No. 106)

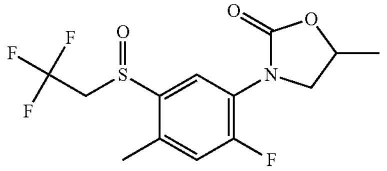 [SMILES: Cc1cc(F)c(N2CC(C)OC2=O)cc1S(=O)CC(F)(F)F]

1-[2-Fluoro-4-methyl-5-(2,2,2-trifluoroethylsulfanyl)aniline]propan-2-ol (200 mg, 0.67 mmol) is dissolved in 5 ml of THF, and phosgene (1.01 mmol, as a 20% strength solution in toluene) and DIPEA (172 μl, 1.01 mmol) are added. The mixture is stirred at room temperature for 16 h. The solution is cooled to room temperature, water is added and the mixture is extracted with ethyl acetate. The combined organic phases are washed with water and saturated sodium chloride solution and then dried over sodium sulfate. The solvent is removed on a rotary evaporator. Purification of the crude product by column chromatography (15% EtOAc/petroleum ether) gives 120 mg (0.37 mmol, 55% of theory) of the title compound.

1H-NMR (D6-DMSO, 400 MHz) δ ppm: 7.74 (d, 1H), 7.31 (d, 1H), 4.87-4.80 (m, 1H), 4.10-4.04 (m, 1H), 3.98-3.88 (m, 2H), 3.64-3.59 (m, 1H), 2.39 (s, 3H), 1.43 (d, 3H)

log P (HCOOH): 2.98

Step 3: 3-[2-Fluoro-4-methyl-5-(2,2,2-trifluoroethylsulfinyl)phenyl]-5-methyloxazolidin-2-one (Ex. No. 109)

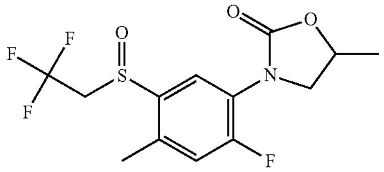

3-[2-Fluoro-4-methyl-5-(2,2,2-trifluoroethylsulfanyl)phenyl]-5-methyloxazolidin-2-one (120 mg, 0.37 mmol) is dissolved in 3 ml of acetone/water (1:1), and Oxone (184 mg, 0.37 mmol) is added. The solution is stirred at room temperature for 2 h. The mixture is concentrated under reduced pressure and water is added to the residue. The mixture is extracted with ethyl acetate. The combined organic phases are washed with water and sat. NaCl solution and then dried over $Na_2SO_4$. The solvent is removed on a rotary evaporator. Purification of the crude product by column chromatography (40% EtOAc/petroleum ether) gives 82 mg (0.24 mmol, 65% of theory) of the title compound.

1H-NMR ($CDCl_3$, 400 MHz) δ ppm 8.11 (d, 1H), 7.08 (d, 1H), 4.90-4.81 (m, 1H), 4.20-4.01 (m, 1H), 3.76-3.37 (m, 3H), 2.40 (s, 3H), 1.57-1.54 (m, 3H)

log P (HCOOH): 1.93; log P (neutral): 1.89

Preparation Example 16

3-[2-Fluoro-4-methyl-5-(2,2,2-trifluoroethylsulfinyl)phenyl]-4-methyloxazolidin-2-one (Ex. No. 107)

Step 1: Allyl N-[2-fluoro-4-methyl-5-(2,2,2-trifluoroethylsulfanyl)phenyl]carbamate

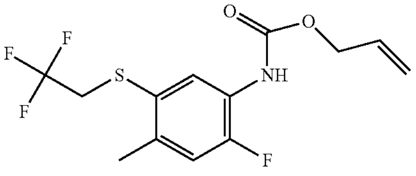 [SMILES: C=CCOC(=O)Nc1cc(SCC(F)(F)F)c(C)cc1F]

2-Fluoro-4-methyl-5-[(2,2,2-trifluoroethyl)sulfanyl]aniline (1.0 g, 4.18 mmol) is initially charged in 10 ml of THF. Allyloxycarbonyl chloride (530 μl, 5.02 mmol) and cesium carbonate (2.04 g, 6.27 mmol) are added and the reaction mixture is stirred at room temperature for 16 h. The solution is cooled and water is added. After extraction with ethyl acetate, the combined organic phases are washed with water and saturated sodium chloride solution and then dried over sodium sulfate. The solvent is removed on a rotary evaporator. Purification of the crude product by column chromatography (10% EtOAc/petroleum ether) gives 800 mg (2.47 mmol, 59% of theory) of the title compound.

1H-NMR ($CDCl_3$, 400 MHz) δ ppm 8.27 (s, 1H), 6.98-6.79 (m, 2H), 6.03-5.93 (m, 1H), 5.41-5.28 (m, 2H), 4.69 (d, 2H), 3.38 (q, 2H), 2.42 (s, 3H)

log P (HCOOH): 3.59

Step 2: 3-[2-Fluoro-4-methyl-5-(2,2,2-trifluoroethyl-sulfanyl)phenyl]-4-methyloxazolidin-2-one (Ex. No. 108)

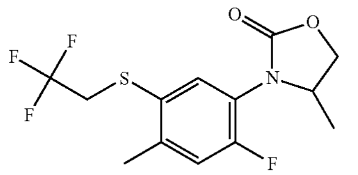 [SMILES: Cc1cc(F)c(N2C(=O)OCC2C)cc1SCC(F)(F)F]

Allyl N-[2-fluoro-4-methyl-5-(2,2,2-trifluoroethylsulfanyl)phenyl]carbamate (800 mg, 2.5 mmol) is dissolved in 10 ml of THF/DMSO/fluorobenzene (8:1:1), and IBX (12.3 mmol) is added. In a closed pressure-resistant vessel, the mixture is heated at 120° C. for 48 h. The solution is cooled to room temperature, water is added and the mixture is extracted with ethyl acetate. The combined organic phases are washed with water and saturated sodium chloride solution and then dried over sodium sulfate. The solvent is removed on a rotary evaporator. Purification of the crude product by column chromatography (25% EtOAc/petroleum ether) gives 171 mg (0.53 mmol, 21% of theory) of the title compound.

1H-NMR ($CDCl_3$, 400 MHz) δ ppm 7.56 (d, 1H), 7.06 (d, 1H), 4.65-4.60 (m, 1H), 4.45-4.38 (m, 1H), 4.06-4.01 (m, 1H), 3.35 (q, 2H), 2.48 (s, 3H), 1.26-1.22 (m, 3H)

log P (HCOOH): 2.92

Step 3: 3-[2-Fluoro-4-methyl-5-(2,2,2-trifluoroethyl-sulfinyl)phenyl]-4-methyloxazolidin-2-one (Ex. No. 107)

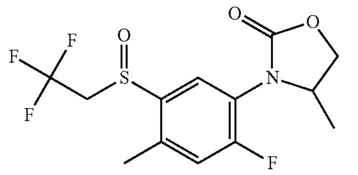 [SMILES: Cc1cc(F)c(N2C(=O)OCC2C)cc1S(=O)CC(F)(F)F]

3-[2-Fluoro-4-methyl-5-(2,2,2-trifluoroethylsulfanyl)phenyl]-4-methyloxazolidin-2-one (103 mg, 0.32 mmol) is dissolved in 3 ml of acetone/water (1:1), and Oxone (184 mg, 0.37 mmol) is added. The solution is stirred at room temperature for 2 h. The mixture is concentrated under reduced pressure and water is added to the residue. The mixture is extracted with ethyl acetate. The combined organic phases are washed with water and saturated sodium chloride solution and then dried over sodium sulfate. The solvent is removed on a rotary evaporator. Purification of the crude product by column chromatography (40% EtOAc/petroleum ether) gives 67 mg (0.20 mmol, 62% of theory) of the title compound.

1H-NMR ($CDCl_3$, 400 MHz) δ ppm 7.98 (dd, 1H), 7.26-7.07 (m, 1H), 4.68-4.62 (m, 1H), 4.51-4.42 (m, 1H), 4.11-4.02 (m, 1H), 3.53-3.39 (m, 2H), 2.41 (s, 3H), 1.26-1.23 (m, 3H)

log P (HCOOH): 1.79

Preparation Example 17

3-[2-Fluoro-4-methyl-5-(2,2,2-trifluoroethylsulfinyl)phenyl]-5,5-dimethyloxazolidine-2,4-dione (Ex. No. 110)

Step 1: N-[2-Fluoro-4-methyl-5-(2,2,2-trifluoroethylsulfanyl)phenyl]-2-hydroxy-2-methylpropanamide

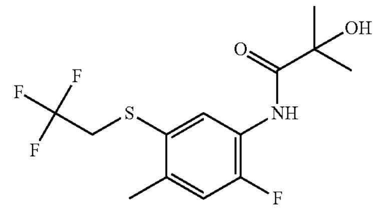 [SMILES: Cc1cc(F)c(NC(=O)C(C)(C)O)cc1SCC(F)(F)F]

2-Fluoro-4-methyl-5-[(2,2,2-trifluoroethyl)sulfanyl]aniline (1.00 g, 4.18 mmol) is initially charged in 10 ml of dichloromethane at 0° C. Ethyl 2-hydroxyisobutyrate (1.15 ml, 8.36 mmol) and $AlMe_3$ (10.5 mmol, as a 2M solution in toluene) are added and the reaction mixture is stirred in a closed pressure-resistant vessel at 65° C. for 16 h. The solution is cooled and water is added. After extraction with dichloromethane, the combined organic phases are washed with 1N HCl and saturated sodium chloride solution and then dried over sodium sulfate. The solvent is removed on a rotary evaporator. Purification of the crude product by column chromatography (15% EtOAc/petroleum ether) gives 500 mg (1.53 mmol, 37% of theory) of the title compound.

1H-NMR ($CDCl_3$, 400 MHz) δ ppm 8.89 (s, 1H), 8.57 (d, 1H), 6.98 (d, 1H), 3.40 (q, 2H), 2.43 (s, 3H), 2.15 (s, 1H), 1.57 (s, 6H)

log P (HCOOH): 2.81

Step 2: 3-[2-Fluoro-4-methyl-5-(2,2,2-trifluoroethyl-sulfanyl)phenyl]-5,5-dimethyloxazolidine-2,4-dione (Ex. No. 111)

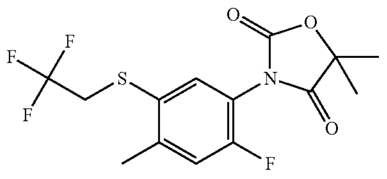 [SMILES: Cc1cc(F)c(N2C(=O)OC(C)(C)C2=O)cc1SCC(F)(F)F]

N-[2-Fluoro-4-methyl-5-(2,2,2-trifluoroethylsulfanyl)phenyl]-2-hydroxy-2-methylpropanamide (400 mg, 1.23 mmol) is dissolved in 5 ml of THF, and phosgene (1.84 mmol, as a 20% strength solution in toluene) and diisopropylethylamine (418 μl, 2.36 mmol) are added. The mixture is stirred at room temperature for 16 h. Water is added to the solution and the mixture is extracted with ethyl acetate. The combined organic phases are washed with water and saturated sodium chloride solution and then dried over sodium sulfate. The solvent is removed on a rotary evaporator. Purification of the crude product by column chromatography (10% EtOAc/petroleum ether) gives 200 mg (0.57 mmol, 46% of theory) of the title compound.

1H-NMR ($CDCl_3$, 400 MHz) δ ppm 7.50 (d, 1H), 7.16 (d, 1H), 3.39-3.32 (m, 2H), 2.53 (s, 3H), 1.71 (s, 6H)

log P (HCOOH): 3.35

Step 3: 3-[2-Fluoro-4-methyl-5-(2,2,2-trifluoroethylsulfinyl)phenyl]-5,5-dimethyloxazolidine-2,4-dione (Ex. No. 110)

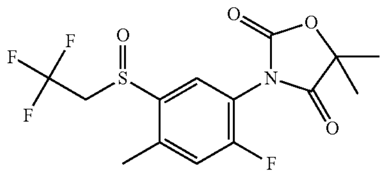 [SMILES: Cc1cc(F)c(N2C(=O)OC(C)(C)C2=O)cc1S(=O)CC(F)(F)F]

3-[2-Fluoro-4-methyl-5-(2,2,2-trifluoroethylsulfanyl)phenyl]-5,5-dimethyloxazolidine-2,4-dione (120 mg, 0.34 mmol) is dissolved in 3 ml of acetone/water (1:1), and Oxone (105 mg, 0.34 mmol) is added. The solution is stirred at room temperature for 2 h. The mixture is concentrated under reduced pressure and water is added to the residue. The mixture is extracted with ethyl acetate. The combined organic phases are washed with water and saturated sodium chloride solution and then dried over sodium sulfate. The solvent is removed on a rotary evaporator. Purification of the crude product by column chromatography (20% EtOAc/petroleum ether) gives 85 mg (0.23 mmol, 68% of theory) of the title compound.

1H-NMR ($CDCl_3$, 400 MHz) δ ppm 7.99 (d, 1H), 7.24 (d, 1H), 3.52-3.41 (m, 2H), 2.45 (s, 3H), 1.72 (s, 6H)

log P (HCOOH): 2.38

Preparation Example 18

4-{2-Fluoro-4-methyl-5-[(2,2,2-trifluoroethyl)sulfanyl]phenyl}-1,2-dimethyl-1,2,4-triazolidine-3,5-dione (Ex. No. 116)

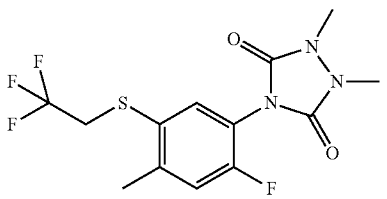 [SMILES: Cc1cc(F)c(-n2c(=O)n(C)n(C)c2=O)cc1SCC(F)(F)F]

2.1 ml (4.18 mmol) of a solution of trimethylaluminum in toluene (2M) are added to a solution of 1.0 g (4.18 mmol) of 2-fluoro-4-methyl-5-[(2,2,2-trifluoroethyl)sulfanyl]aniline in 10 ml of toluene, and the mixture is stirred under argon at room temperature for 30 min. 426.8 mg (2.09 mmol) of diethyl 1,2-dimethylhydrazine-1,2-dicarboxylate are added. The reaction mixture is stirred at room temperature for 30 min and then heated at reflux overnight. After cooling, the reaction mixture is introduced into a mixture of ethyl acetate and 1N hydrochloric acid, the phases are separated and the organic phase is dried over magnesium sulfate, filtered and concentrated. Purification by column chromatography on silica gel by means of MPLC with cyclohexane/ethyl acetate as eluent gives 486 mg (97% pure, 64% of theory) of the title compound as a beige solid.

log P[a]: 2.40; log P[b]: 2.39; $^1$H-NMR ($D^6$-DMSO, 400 MHz) ppm: 7.72 (d, 1H), 7.42 (d, 1H), 3.93 (q, 2H), 3.19 (s, 6H), 2.44 (s, 3H)

Preparation Example 19

4-{2-Fluoro-4-methyl-5-[(2,2,2-trifluoroethyl)sulfinyl]phenyl}-1,2-dimethyl-1,2,4-triazolidine-3,5-dione (Ex. No. 117)

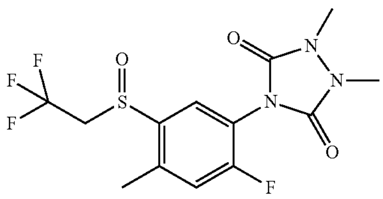 [SMILES: Cc1cc(F)c(-n2c(=O)n(C)n(C)c2=O)cc1S(=O)CC(F)(F)F]

At 0° C., 155 mg (0.69 mmol) of meta-chloroperbenzoic acid (about 77%) are added to a solution of 243 mg (0.69 mmol) of 4-{2-fluoro-4-methyl-5-[(2,2,2-trifluoroethyl)sulfanyl]phenyl}-1,2-dimethyl-1,2,4-triazolidine-3,5-dione in 10 ml of dichloromethane. The reaction mixture is stirred at 0° C. for 2 h, washed with 1M sodium hydroxide solution and freed of the solvent under reduced pressure. This gives 270 mg (100% pure, 100% of theory) of the title compound as a colorless oil.

log P[a]: 1.54; log P[b]: 1.50; $^1$H-NMR ($D^6$-DMSO, 400 MHz) δ ppm: 7.99 (d, 1H), 7.54 (d, 1H), 4.29-4.25 (m, 1H), 3.96-3.89 (m, 1H), 3.19 (s, 6H), 2.50 (s, 3H)

Preparation Example 20

1,2-Diethyl-4-{2-fluoro-4-methyl-5-[(2,2,2-trifluoroethyl)sulfanyl]phenyl}-1,2,4-triazolidine-3,5-dione (Ex. No. 118)

Step 1: Ethyl 2-({2-fluoro-4-methyl-5-[(2,2,2-trifluoroethyl)sulfanyl]phenyl}carbamoyl)hydrazinecarboxylate

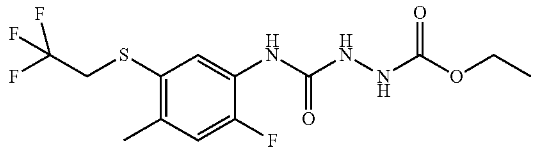 [SMILES: CCOC(=O)NNC(=O)Nc1cc(SCC(F)(F)F)c(C)cc1F]

At room temperature, 404.3 mg (3.88 mmol) of ethyl hydrazinecarboxylate are added to a solution of 1.10 g (3.53 mmol) of ethyl {2-fluoro-4-methyl-5-[(2,2,2-trifluoroethyl)sulfanyl]phenyl}carbamate (see, for example, JP2011/042611) in ethanol (15 ml). The reaction mixture is heated at reflux for 4 h and the cooled to room temperature, diluted with water and extracted with ethyl acetate. The combined organic phases are washed with water and aqueous saturated sodium chloride solution, dried over sodium sulfate, filtered and concentrated under reduced pressure. Purification by column chromatography on silica gel using the mobile phase petroleum ether/ethyl acetate (85/15) gives 850 mg (100% pure, 65% of theory) of the title compound as a beige solid.

log P[a]: 2.41; $^1$H-NMR ($D^6$-DMSO, 400 MHz) δ ppm: 9.00 (broad, 1H), 8.49 (broad, 1H), 8.25 (broad, 1H), 8.17 (broad, 1H), 7.21 (d, 1H), 4.06 (q, 2H), 3.76 (q, 2H), 2.36 (s, 3H), 1.19 (t, 3H)

Step 2: 4-{2-Fluoro-4-methyl-5-[(2,2,2-trifluoroethyl)sulfanyl]phenyl}-1, 2,4-triazolidine-3,5-dione

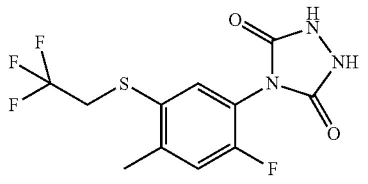 [SMILES: Cc1cc(F)c(-n2c(=O)[nH][nH]c2=O)cc1SCC(F)(F)F]

A solution of 500 mg (1.35 mmol) of ethyl 2-({2-fluoro-4-methyl-5-[(2,2,2-trifluoroethyl)sulfanyl]phenyl}carbamoyl)hydrazinecarboxylate in ethanol (8 ml) and 6N aqueous potassium hydroxide solution (2 ml) is heated at reflux for 4 h. After cooling to room temperature, the reaction mixture is poured into cold water. The solid formed is filtered off, washed with water and dried. This gives 270 mg (90% pure, 56% of theory) of the title compound as a beige solid.

log P[a]: 1.82; $^1$H-NMR ($D^6$-DMSO, 400 MHz) δ ppm: 10.58 (broad, 2H), 7.70 (d, 1H), 7.39 (d, 1H), 3.96 (q, 2H), 2.43 (s, 3H)

Step 3: 1,2-Diethyl-4-{2-fluoro-4-methyl-5-[(2,2,2-trifluoroethyl)sulfanyl]phenyl}-1,2,4-triazolidine-3,5-dione (Ex. No. 118)

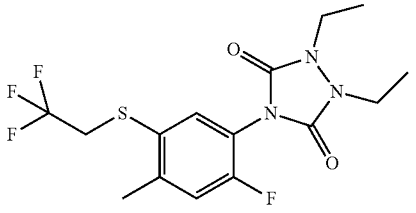 [SMILES: CCn1c(=O)n(-c2cc(SCC(F)(F)F)c(C)cc2F)c(=O)n1CC]

At 0° C., 322 mg (2.33 mmol) of potassium carbonate and 484 mg (3.10 mmol) of ethyl iodide are added to a solution of 500 mg (1.55 mmol) of 4-{2-fluoro-4-methyl-5-[(2,2,2-trifluoroethyl)sulfanyl]phenyl}-1,2,4-triazolidine-3,5-dione in N,N-dimethylformamide (5 ml). The reaction mixture is stirred at room temperature for 6 h and then poured into cold water. The solid formed is filtered off, washed with water and dried. This gives 170 mg (98% pure, 28% of theory) of the title compound as a beige solid.

log P[a]: 3.03; $^1$H-NMR ($D^6$-DMSO, 400 MHz) δ ppm: 7.72 (d, 1H), 7.40 (d, 1H), 3.96 (q, 2H), 3.61 (q, 4H), 2.42 (s, 3H), 1.10 (t, 6H)

Preparation Example 21

1,2-Diethyl-4-{2-fluoro-4-methyl-5-[(2,2,2-trifluoroethyl)sulfinyl]phenyl}-1,2,4-triazolidine-3,5-dione (Ex. No. 119)

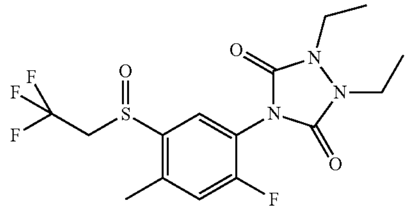 [SMILES: CCn1c(=O)n(-c2cc(S(=O)CC(F)(F)F)c(C)cc2F)c(=O)n1CC]

At room temperature, 98 mg (0.32 mmol) of Oxone are added to a solution of 120 mg (0.32 mmol) of 1,2-diethyl-4-{2-fluoro-4-methyl-5-[(2,2,2-trifluoroethyl)sulfanyl]phenyl}-1,2,4-triazolidine-3,5-dione in acetone/water (1:1). The reaction mixture is stirred at room temperature for 2 h and then concentrated under reduced pressure. The residue is diluted with water and extracted with ethyl acetate. The combined organic phases are washed with water and aqueous saturated sodium chloride solution, dried over sodium sulfate, filtered and concentrated under reduced pressure. Purification by column chromatography on silica gel using the mobile phase petroleum ether/ethyl acetate (75/25) gives 50 mg (98% pure, 39% of theory) of the title compound as a beige solid.

log P[a]: 2.07; $^1$H-NMR ($D^6$-DMSO, 400 MHz) δ ppm: 7.99 (d, 1H), 7.55 (d, 1H), 4.38-4.18 (m, 1H), 4.15-3.92 (m, 1H), 3.80-3.58 (m, 4H), 2.44 (s, 3H), 1.13 (t, 6H)

Preparation Example 22

1-Ethyl-4-{2-fluoro-4-methyl-5-[(2,2,2-trifluoroethyl)sulfanyl]phenyl}-2-methyl-1,2,4-triazolidine-3,5-dione (Ex. No. 122)

Step 1: N-[2-Fluoro-4-methyl-5-[(2,2,2-trifluoroethyl)sulfanyl]phenyl]-1-methylhydrazinecarboxamide

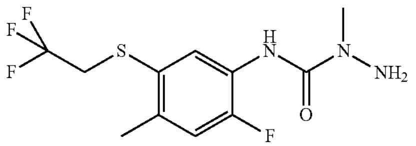 [SMILES: Cc1cc(F)c(NC(=O)N(C)N)cc1SCC(F)(F)F]

At room temperature, 2.1 g (16.1 mmol) of diisopropylethylamine and 407 mg (8.8 mmol) of methylhydrazine are added to a solution of 2.5 g (8.0 mmol) of ethyl {2-fluoro-4-methyl-5-[(2,2,2-trifluoroethyl)sulfanyl]phenyl}carbamate (see, for example, JP2011/042611) in dichloromethane (25 ml). The reaction mixture is stirred at room temperature for 6 h and then diluted with water and extracted with dichloromethane. The combined organic phases are washed with water and aqueous saturated sodium chloride solution, dried over sodium sulfate, filtered and concentrated under reduced pressure. Purification by column chromatography on silica gel using the mobile phase petroleum ether/ethyl acetate (80/20) gives 2.0 g (80% of theory) of the title compound.

Step 2: Ethyl 2-({2-fluoro-4-methyl-5-[(2,2,2-trifluoroethyl)sulfanyl]phenyl}carbamoyl)-2-methylhydrazinecarboxylate

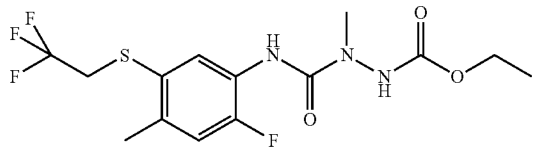 [SMILES: CCOC(=O)NN(C)C(=O)Nc1cc(SCC(F)(F)F)c(C)cc1F]

At room temperature, 4.2 g (12.8 mmol) of cesium carbonate and 764 mg (7.0 mmol) of ethyl chloroformate are added to a solution of 2.0 g (6.4 mmol) of N-{2-fluoro-4-methyl-5-[(2,2,2-trifluoroethyl)sulfanyl]phenyl}-1-methylhydrazinecarboxamide in tetrahydrofuran (20 ml). The reaction mixture is stirred at room temperature for 6 h and then diluted with water and extracted with ethyl acetate. The combined organic phases are washed with water and aqueous saturated sodium chloride solution, dried over sodium sulfate, filtered and concentrated under reduced pressure. Purification by column chromatography on silica gel using the mobile phase petroleum ether/ethyl acetate (90/10) gives 2.0 g (81% of theory) of the title compound.

Step 3: 4-[2-Fluoro-4-methyl-5-[(2,2,2-trifluoroethyl)sulfanyl]phenyl]-1-methyl-1,2,4-triazolidine-3,5-dione

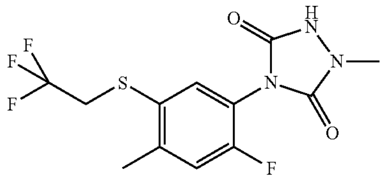 [SMILES: Cc1cc(F)c(-n2c(=O)[nH]n(C)c2=O)cc1SCC(F)(F)F]

A solution of 2.0 g (5.2 mmol) of ethyl 2-({2-fluoro-4-methyl-5-[(2,2,4-trifluoroethyl)sulfanyl]phenyl}carbamoyl)-2-methylhydrazinecarboxylate in ethanol (16 ml) and 6N aqueous potassium hydroxide solution (4 ml) is heated at reflux for 1 h. After cooling to room temperature, the reaction mixture is poured into cold water. The solid formed is filtered off, washed with water and dried. This gives 1.4 g (80% of theory) of the title compound as a beige solid.

log P[a]: 2.02; $^1$H-NMR (D$^6$-DMSO, 400 MHz) δ ppm: 10.96 (broad, 1H), 7.70 (d, 1H), 7.40 (d, 1H), 3.95 (q, 2H), 3.12 (s, 3H), 2.43 (s, 3H)

Step 4: 1-Ethyl-4-{2-fluoro-4-methyl-5-[(2,2,2-trifluoroethyl)sulfanyl]phenyl}-2-methyl-1,2,4-triazolidine-3,5-dione (Ex. No. 122)

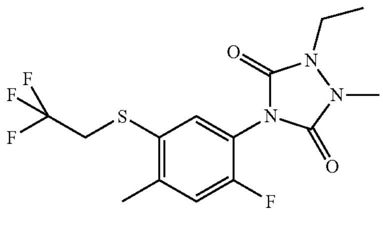 [SMILES: CCn1c(=O)n(-c2cc(SCC(F)(F)F)c(C)cc2F)c(=O)n1C]

At 0° C., 184 mg (1.33 mmol) of potassium carbonate and 207 mg (1.33 mmol) of ethyl iodide are added to a solution of 300 mg (0.89 mmol) of 4-{2-fluoro-4-methyl-5-[(2,2,2-trifluoroethyl)sulfanyl]phenyl}-1-methyl-1,2,4-triazolidine-3,5-dione in N,N-dimethylformamide (5 ml). The reaction mixture is stirred at room temperature for 16 h and then poured into cold water. The solid formed is filtered off, washed with water and dried. This gives 270 mg (98% pure, 81% of theory) of the title compound as a beige solid.

log P[a]: 2.71; $^1$H-NMR (D$^6$-DMSO, 400 MHz) δ ppm: 7.71 (d, 1H), 7.40 (d, 1H), 3.93 (q, 2H), 3.66 (q, 2H), 3.16 (s, 3H), 2.42 (s, 3H), 1.10 (t, 3H)

Preparation Example 23

1-{2-Fluoro-4-methyl-5-[(2,2,2-trifluoroethyl)sulfanyl]phenyl}-2,4,4-trimethylpyrazolidine-3,5-dione (Ex. No. 174)

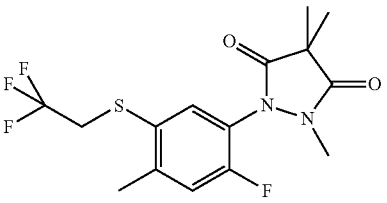 [SMILES: Cc1cc(F)c(N2C(=O)C(C)(C)C(=O)N2C)cc1SCC(F)(F)F]

268.0 mg (1.0 mmol) of {2-fluoro-4-methyl-5-[(2,2,2-trifluoroethyl)sulfanyl]phenyl}boronic acid, 284 mg (2.00 mmol) of 1,4,4-trimethylpyrazolidine-3,5-dione, 272 mg (1.5 mmol) of copper(II) acetate, 158 mg (2.0 mmol) of pyridine and 1.0 g of activated 3 Å molecular sieve are stirred in 5 ml of dry dichloromethane at room temperature for 4 d. The reaction mixture is adsorbed on kieselguhr and purified by column chromatography on silica gel by means of MPLC with cyclohexane/ethyl acetate as eluent. This gives 109 mg (99% pure, 30% of theory) of the title compound as a colorless oil.

log P[a]: 2.84; log P[b]: 2.79; $^1$H-NMR (D$^6$-DMSO, 400 MHz) δ ppm: 7.76 (d, 1H), 7.45 (d, 1H), 4.04 (q, 2H), 2.93 (s, 3H), 2.43 (s, 3H), 1.30 (s, 6H)

Preparation Example 24

1-{2-Fluoro-4-methyl-5-[(2,2,2-trifluoroethyl)sulfinyl]phenyl}-2,4,4-trimethylpyrazolidine-3,5-dione (Ex. No. 177)

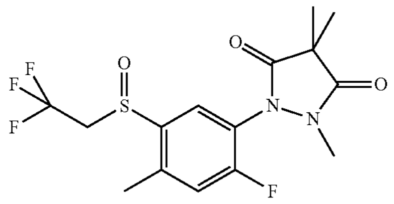 [SMILES: Cc1cc(F)c(N2C(=O)C(C)(C)C(=O)N2C)cc1S(=O)CC(F)(F)F]

At 0° C., 35.5 mg (0.16 mmol) of meta-chloroperbenzoic acid (about 77%) are added to a solution of 55.0 mg (0.15 mmol) of 1-{2-fluoro-4-methyl-5-[(2,2,2-trifluoroethyl)sulfanyl]phenyl}-2,4,4-trimethylpyrazolidine-3,5-dione in 10 ml of dichloromethane. The reaction mixture is stirred at 0° C. for 2 h, washed with 1M sodium hydroxide solution and freed of the solvent under reduced pressure. This gives 50 mg (97% pure, 84% of theory) of the title compound as a colorless oil.

log P[a]: 1.89; log P[b]: 1.85; $^1$H-NMR ($D^6$-DMSO, 400 MHz) δ ppm: 7.98 (d, 1H), 7.57 (d, 1H), 4.30-4.10 (m, 2H), 2.98 (s, 3H), 2.44 (s, 3H), 1.32 (s, 6H)

Preparation Example 25

4-Cyclopropyl-2-{2-fluoro-4-methyl-5-[(2,2,2-trifluoroethyl)sulfanyl]phenyl}-1-methyl-5-thioxo-1,2,4-triazolidin-3-one (Ex. No. 181) and 4-cyclopropyl-1-{2-fluoro-4-methyl-5-[(2,2,2-trifluoroethyl)sulfanyl]phenyl}-2-methyl-1,2,4-triazolidine-3,5-dithione (Ex. No. 182)

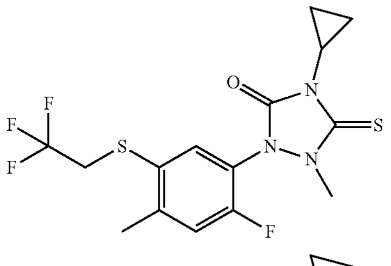

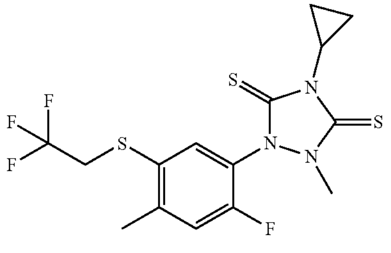

-continued

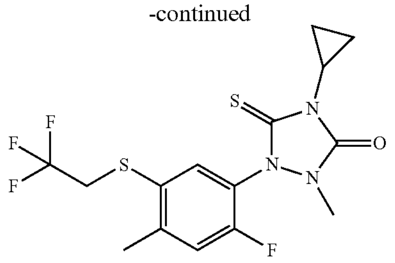

239 mg (0.59 mmol) of 2,4-bis(4-methoxyphenyl)-1,3,2,4-dithiadiphosphetane 2,4-disulfide (Lawesson's reagent) were added to a solution of 223 mg (0.59 mmol) of 4-cyclopropyl-1-{2-fluoro-4-methyl-5-[(2,2,2-trifluoroethyl)sulfanyl]phenyl}-2-methyl-1,2,4-triazolidine-3,5-dione in 10 ml of toluene. The reaction mixture is heated to reflux under argon overnight, then concentrated. This gave, after repeated purification by column chromatography by MPLC on silica gel using the mobile phase cyclohexane/ethyl acetate and on RP(C-18) using water/acetonitrile, 13 mg (85% pure, 5% of theory) of 4-cyclopropyl-2-{2-fluoro-4-methyl-5-[(2,2,2-trifluoroethyl)sulfanyl]phenyl}-1-methyl-5-thioxo-1,2,4-triazolidin-3-one, 26 mg (88% pure, 9% of theory) of 4-cyclopropyl-1-{2-fluoro-4-methyl-5-[(2,2,2-trifluoroethyl)sulfanyl]phenyl}-2-methyl-1,2,4-triazolidine-3,5-dithione and 7 mg of 4-cyclopropyl-1-{2-fluoro-4-methyl-5-[(2,2,2-trifluoroethyl)sulfanyl]phenyl}-2-methyl-5-thioxo-1,2,4-triazolidin-3-one, in each case as colorless solids.

4-Cyclopropyl-2-{2-fluoro-4-methyl-5-[(2,2,2-trifluoroethyl)sulfanyl]phenyl}-1-methyl-5-thioxo-1,2,4-triazolidin-3-one (Ex. No. 181): log P[a]: 3.44; log P[b]: 3.39; $^1$H-NMR ($D^6$-DMSO, 400 MHz) δ ppm: 7.85 (d, 1H), 7.50 (d, 1H), 4.03 (q, 2H), 3.31 (s, 3H), 2.92-2.87 (m, 1H), 2.44 (s, 3H), 1.04-0.97 (m, 4H)

4-cyclopropyl-1-{2-fluoro-4-methyl-5-[(2,2,2-trifluoroethyl)sulfanyl]phenyl}-2-methyl-1,2,4-triazolidine-3,5-dithione (Ex. No. 182): log P[a]: 3.83; log P[b]: 3.76; $^1$H-NMR ($D^6$-DMSO, 400 MHz) δ ppm: 7.96 (d, 1H), 7.55 (d, 1H), 4.11-3.95 (m, 2H), 3.39 (s, 3H), 3.00-2.91 (m, 1H), 2.46 (s, 3H), 1.25-1.10 (m, 4H)

4-cyclopropyl-1-{2-fluoro-4-methyl-5-[(2,2,2-trifluoroethyl)sulfanyl]phenyl}-2-methyl-5-thioxo-1,2,4-triazolidin-3-one: log P[a]: 3.24; log P[b]: 3.18; $^1$H-NMR ($D^6$-DMSO, 400 MHz) δ ppm: 7.81 (d, 1H), 7.48 (d, 1H), 4.10-3.92 (m, 2H), 2.98 (s, 3H), 2.92-2.87 (m, 1H), 2.44 (s, 3H), 1.11-0.99 (m, 4H)

Preparation Example 26

1-Cyclohexyl-3-{2-fluoro-4-methyl-5-[(2,2,2-trifluoroethyl)sulfanyl]phenyl}imidazolidine-2,4,5-trione (Ex. No. 185)

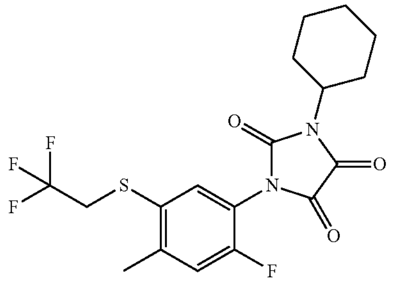 [SMILES: Cc1cc(F)c(N2C(=O)C(=O)N(C3CCCCC3)C2=O)cc1SCC(F)(F)F]

268.0 mg (1.0 mmol) of {2-fluoro-4-methyl-5-[(2,2,2-trifluoroethyl)sulfanyl]phenyl}boronic acid, 392 mg (2.00 mmol) of 1-cyclohexylimidazolidine-2,4,5-trione, 272 mg (1.5 mmol) of copper(II) acetate, 158 mg (2.0 mmol) of pyridine and 0.5 g of activated 3 Å molecular sieve are stirred in 5 ml of dry dichloromethane at room temperature for 3 d. The reaction mixture is adsorbed on kieselguhr and purified by column chromatography on silica gel by means of MPLC with cyclohexane/ethyl acetate as eluent. This gives 82 mg (96% pure, 19% of theory) of the title compound as a colorless oil.

log P[a]: 4.32; log P[b]: 4.27; $^1$H-NMR ($D^6$-DMSO, 400 MHz) δ ppm: 7.67 (d, 1H), 7.47 (d, 1H), 4.00-3.90 (m, 1H), 3.84 (q, 2H), 2.47 (s, 3H), 2.00-1.89 (m, 2H), 1.86-1.75 (m, 4H), 1.67-1.58 (m, 1H), 1.39-1.25 (m, 2H), 1.20-1.09 (m, 1H)

Preparation Example 27

1-Cyclohexyl-3-{2-fluoro-4-methyl-5-[(2,2,2-trifluoroethyl)sulfinyl]phenyl}imidazolidin-2,4,5-trion (Ex. No. 186)

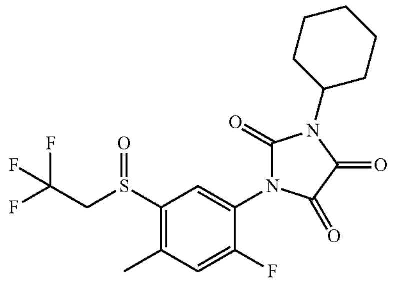 [SMILES: Cc1cc(F)c(N2C(=O)C(=O)N(C3CCCCC3)C2=O)cc1S(=O)CC(F)(F)F]

At 0° C., 23.1 mg (0.10 mmol) of meta-chloroperbenzoic acid (about 77%) are added to a solution of 41.0 mg (0.10 mmol) of 1-cyclohexyl-3-{2-fluoro-4-methyl-5-[(2,2,2-trifluoroethyl)sulfanyl]phenyl}imidazolidine-2,4,5-trione in 10 ml of dichloromethane. The reaction mixture is stirred at 0° C. for 2 h, washed with 1M sodium hydroxide solution and freed of the solvent under reduced pressure. This gives 29 mg (92% pure, 63% of theory) of the title compound as a colorless oil.

log P[a]: 3.36; log P[b]: 3.33; $^1$H-NMR ($D^6$-DMSO, 400 MHz) δ ppm: 8.03 (d, 1H), 7.57 (d, 1H), 4.35-4.26 (m, 1H), 3.99-3.83 (m, 2H), 2.43 (s, 3H), 2.00-1.90 (m, 2H), 1.86-1.75 (m, 3H), 1.69-1.60 (m, 1H), 1.39-1.22 (m, 2H), 1.22-1.09 (m, 2H)

Preparation Example 28

1-[2-Fluoro-4-methyl-5-(2,2,2-trifluoroethylsulfinyl)phenyl]-3,5,5-trimethylimidazolidine-2,4-dione (Ex. No. 216)

Step 1: Ethyl 2-[2-fluoro-4-methyl-5-(2,2,2-trifluoroethylsulfanyl)anilino]-2-methylpropanoate

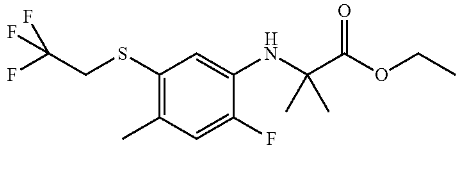 [SMILES: CCOC(=O)C(C)(C)Nc1cc(SCC(F)(F)F)c(C)cc1F]

At room temperature, 4.47 g (41.8 mmol) of 2,6-lutidine and 4.60 g (25.1 mmol) of ethyl 2-bromoisobutyrate were added to a solution of 5.00 g (20.8 mmol) of 2-fluoro-4-methyl-5-(2,2,2-trifluoroethylsulfanyl)aniline in N,N-dimethylacetamide (90 ml). The reaction mixture was stirred at 90° C. for 6 h. After cooling, the reaction mixture was diluted with water and extracted with dichloromethane. The combined organic phases were washed with saturated sodium chloride solution, dried over sodium sulfate, filtered and freed of the solvent under reduced pressure. Purification of the residue by column chromatography (20% EtOAc/petroleum ether) gave 1.50 g (20% of theory) of the title compound.

Step 2: 4-Nitrophenyl N-methylcarbamate

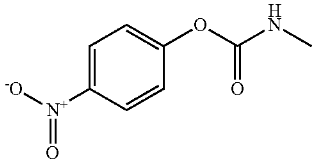

At 0° C., 3.00 ml (5.97 mmol) of methylamine were added to a solution of 1.00 g (4.97 mmol) of 4-nitrophenyl chloroformate in 50 ml of tetrahydrofuran. The reaction mixture was allowed to warm to room temperature and stirred for another 4 h. The mixture was then concentrated and the residue was diluted with water and extracted with ethyl acetate. The combined organic phases were washed with saturated sodium chloride solution, dried over sodium sulfate, filtered and freed of the solvent under reduced pressure. The crude product was purified by washing with diethyl ether. This gave 600 mg (61% of theory) of the title compound.

Step 3: Ethyl 2-[2-fluoro-4-methyl-N-(methylcarbamoyl)-5-(2,2,2-trifluoroethylsulfanyl)anilino]-2-methylpropanoate

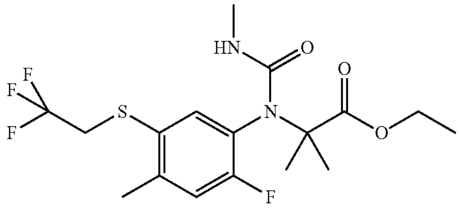 [SMILES: CCOC(=O)C(C)(C)N(C(=O)NC)c1cc(SCC(F)(F)F)c(C)cc1F]

At room temperature, 665 mg (3.11 mmol) of 4-nitrophenyl N-methylcarbamate and 379 mg (3.11 mmol) of N,N-dimethylaminopyridine were added to a solution of 1.00 g (2.83 mmol) of ethyl 2-[2-fluoro-4-methyl-5-(2,2,2-trifluoroethylsulfanyl)anilino]-2-methylpropanoate in 40 ml of methylene chloride. The reaction mixture was stirred at room temperature for 36 h. The reaction mixture was then diluted with water and extracted with methylene chloride. The combined organic phases were washed with saturated sodium chloride solution, dried over sodium sulfate, filtered and freed of the solvent under reduced pressure. 850 mg of the crude product were isolated and reacted further.

Step 4: 1-[2-Fluoro-4-methyl-5-(2,2,2-trifluoroethylsulfanyl)phenyl]-3,5,5-trimethylimidazolidine-2,4-dione (Ex. No. 217)

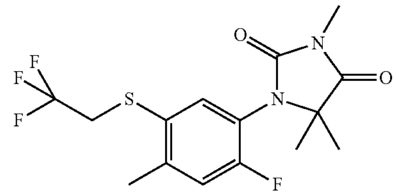 [SMILES: Cc1cc(F)c(N2C(=O)N(C)C(=O)C2(C)C)cc1SCC(F)(F)F]

At room temperature, 1 g of neutral aluminum oxide was added to a solution of 650 mg (1.78 mmol) of ethyl 2-[2-fluoro-4-methyl-N-(methylcarbamoyl)-5-(2,2,2-trifluoroethylsulfanyl)anilino]-2-methylpropanoate in 25 ml of ethyl acetate, and the mixture was stirred for 16 h. The reaction mixture was then filtered and the filtrate was concentrated. Purification of the residue by column chromatography (25% EtOAc/petroleum ether) gave 150 mg (26% of theory) of the title compound.

log P (HCOOH): 3.11; $^1$H-NMR (CDCl3, 400 MHz) δ ppm 7.41 (d, 1H), 7.14 (d, 1H), 3.32 (q, 2H), 3.12 (s, 3H), 1.41 (s, 3H), 1.40 (s, 3H)

Step 5: 1-[2-Fluoro-4-methyl-5-(2,2,2-trifluoroethylsulfinyl)phenyl]-3,5,5-trimethylimidazolidine-2,4-dione (Ex. No. 216)

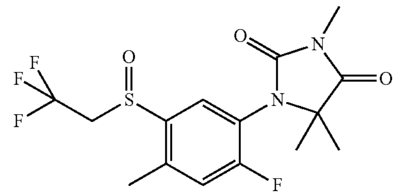 [SMILES: Cc1cc(F)c(N2C(=O)N(C)C(=O)C2(C)C)cc1S(=O)CC(F)(F)F]

At room temperature, 135 mg (0.21 mmol) of Oxone were added to a solution of 90.0 mg (0.21 mmol) of 1-[2-fluoro-4-methyl-5-(2,2,2-trifluoroethylsulfanyl)phenyl]-3,5,5-trimethylimidazolidine-2,4-dione in 8 ml of acetone/water (1:1). The solution was stirred at room temperature for 4 h and the solvent was then removed under reduced pressure. Water was added to the residue and the mixture was extracted with ethyl acetate. The combined organic phases are washed with water and saturated sodium chloride solution and then dried over sodium sulfate. The solvent is removed on a rotary evaporator. Purification of the crude product by column chromatography (40% EtOAc/petroleum ether) gave 55 mg (59% of theory) of the title compound.

log P (HCOOH): 2.05; $^1$H-NMR (CDCl3, 400 MHz) δ ppm 7.86 (d, 1H), 7.17 (d, 1H), 3.45 (q, 2H), 3.14 (s, 3H), 2.44 (s, 3H), 1.47 (s, 3H), 1.41 (s, 3H)

By the above-described processes, the following compounds of the general formula (I) were prepared:

(I) with (I-A)

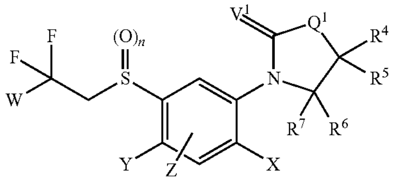

(Compound of the General Formula (I) with (I-A) with Z=H)

| Example No. | W | n | Y | X | $V^1$ | $Q^1$ | $R^4$ | $R^5$ | $R^6$ | $R^7$ |
|---|---|---|---|---|---|---|---|---|---|---|
| 1 | F | 0 | $CH_3$ | $CH_3$ | O | NH | H | H | H | H |
| 2 | F | 0 | $CH_3$ | $CH_3$ | $(NCH(CH_3)CF_3)HCl$ | $CH_2$ | H | H | H | H |
| 3 | F | 1 | $CH_3$ | F | $NCH_2CF_3$ | $CH_2$ | H | H | H | H |
| 4 | F | 1 | $CH_3$ | $CH_3$ | O | NH | H | H | H | H |
| 5 | F | 0 | $CH_3$ | $CH_3$ | $(NCH_2CF_3)HCl$ | $CH_2$ | H | H | H | H |
| 6 | F | 0 | $CH_3$ | F | $NCH_2CF_3$ | $CH_2$ | H | H | H | H |
| 7 | F | 1 | $CH_3$ | F | O | NH | H | H | H | H |
| 8 | F | 0 | $CH_3$ | F | $NCH(CH_3)CF_3$ | $CH_2$ | H | H | H | H |
| 9 | F | 0 | $CH_3$ | F | O | NH | H | H | H | H |
| 10 | F | 1 | $CH_3$ | F | $NCH(CH_3)CF_3$ | $CH_2$ | H | H | H | H |
| 104 | F | 0 | $CH_3$ | F | O | O | H | H | H | H |
| 105 | F | 1 | $CH_3$ | F | O | O | H | H | H | H |
| 106 | F | 0 | $CH_3$ | F | O | O | $CH_3$ | H | H | H |
| 107 | F | 1 | $CH_3$ | F | O | O | H | H | $CH_3$ | H |
| 108 | F | 0 | $CH_3$ | F | O | O | H | H | $CH_3$ | H |
| 109 | F | 1 | $CH_3$ | F | O | O | $CH_3$ | H | H | H |
| 198 | F | 0 | $CH_3$ | F | O | $NCH_3$ | H | H | H | H |
| 199 | F | 1 | $CH_3$ | F | O | $NCH_3$ | H | H | H | H |

(I) with (I-B)

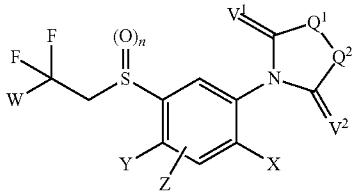

(Compound of the General Formula (I) with (I-B) with Z═H)

| Example No. | W | n | Y | X | $V^2$ | $Q^2$ | $V^1$ | $Q^1$ |
|---|---|---|---|---|---|---|---|---|
| 11 | F | 0 | $CH_3$ | F | O | $CH_2$ | $NCH_2CF_3$ | S |
| 12 | F | 1 | $CH_3$ | F | O | $CH_2$ | N-cyclopropyl | S |
| 13 | F | 1 | $CH_3$ | F | O | $CH_2$ | $NCH_2CF_3$ | S |
| 14 | F | 0 | $CH_3$ | $CH_3$ | O | $CH_2$ | N-cyclopropyl | S |
| 15 | F | 1 | $CH_3$ | $CH_3$ | O | $CH_2$ | N-cyclopropyl | S |
| 16 | F | 1 | $CH_3$ | H | O | $NCH_3$ | O | $C(CH_3)_2$ |
| 17 | F | 1 | $CH_3$ | F | O | $NCH_3$ | O | $C(CH_3)_2$ |
| 18 | F | 0 | $CH_3$ | F | O | $NCH_3$ | O | $C(CH_3)_2$ |
| 19 | F | 0 | $CH_3$ | F | O | $CH_2$ | O | $CH_2$ |
| 110 | F | 1 | $CH_3$ | F | O | $C(CH_3)_2$ | O | O |
| 111 | F | 0 | $CH_3$ | F | O | $C(CH_3)_2$ | O | O |
| 112 | F | 0 | $CH_3$ | $CH_3$ | O | $CH_2$ | N-cyclopropyl | S |
| 113 | F | 0 | $CH_3$ | F | O | $CH_2$ | N-$CH_2C(CH_3)_3$ | S |
| 114 | F | 1 | $CH_3$ | F | O | $CH_2$ | N-$CH_2C(CH_3)_3$ | S |
| 115 | F | 0 | $CH_3$ | F | O | $CH_2$ | N-$CH_2CH(CH_3)_2$ | S |
| 116 | F | 0 | $CH_3$ | F | O | $NCH_3$ | O | $NCH_3$ |
| 117 | F | 1 | $CH_3$ | F | O | $NCH_3$ | O | $NCH_3$ |
| 118 | F | 0 | $CH_3$ | F | O | $NCH_2CH_3$ | O | $NCH_2CH_3$ |
| 119 | F | 1 | $CH_3$ | F | O | $NCH_2CH_3$ | O | $NCH_2CH_3$ |
| 120 | F | 1 | $CH_3$ | F | O | $NCH_2CH{=}CH_2$ | O | $NCH_2CH{=}CH_2$ |
| 121 | F | 0 | $CH_3$ | F | O | $NCH_2CCH$ | O | $NCH_3$ |
| 122 | F | 0 | $CH_3$ | F | O | $NCH_2CH_3$ | O | $NCH_3$ |
| 123 | F | 1 | $CH_3$ | F | O | $NCH_2CCH$ | O | $NCH_3$ |
| 124 | F | 1 | $CH_3$ | F | O | $NCH_2CH{=}CH_2$ | O | $NCH_3$ |
| 125 | F | 0 | $CH_3$ | F | O | $NCH_2CH{=}CH_2$ | O | $NCH_3$ |
| 126 | F | 0 | $CH_3$ | F | O | $NCH_2$-cyclopropyl | O | $NCH_3$ |
| 200 | F | 0 | $CH_3$ | F | O | $CH_2$ | O | $NCH_3$ |
| 201 | F | 1 | $CH_3$ | F | O | $CH_2$ | O | $NCH_2CH{=}CH_2$ |
| 202 | F | 0 | $CH_3$ | F | O | $CH_2$ | O | N-nbutyl |
| 203 | F | 1 | $CH_3$ | F | O | $CH_2$ | O | N-nbutyl |
| 204 | F | 0 | $CH_3$ | F | O | $CH_2$ | O | N-benzyl |
| 205 | F | 1 | $CH_3$ | F | O | $CH_2$ | O | N-benzyl |
| 206 | F | 1 | $CH_3$ | F | O | $CH(CH_3)$ | O | O |

(I) with (I-C)

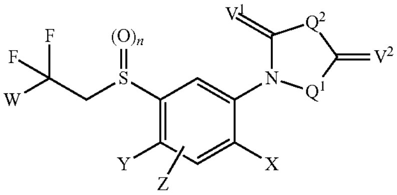

(Compound of the General Formula (I) with (I-C) with Z═H)

| Example No. | W | n | Y | X | $V^1$ | $Q^1$ | $V^2$ | $Q^2$ |
|---|---|---|---|---|---|---|---|---|
| 20 | F | 0 | $CH_3$ | H | O | $NCH_3$ | O | $NCH_3$ |
| 21 | F | 1 | $CH_3$ | H | O | $NCH_3$ | O | $NCH_3$ |
| 22 | F | 0 | $CH_3$ | F | O | $NCH_3$ | O | $NCH_3$ |
| 23 | F | 1 | $CH_3$ | F | O | $NCH_3$ | O | $NCH_3$ |
| 24 | F | 1 | Cl | H | O | $NCH_3$ | O | $NCH_3$ |
| 25 | F | 0 | $CF_3$ | H | O | $NCH_3$ | O | $NCH_3$ |

-continued

| Example No. | W | n | Y | X | $V^1$ | $Q^1$ | $V^2$ | $Q^2$ |
|---|---|---|---|---|---|---|---|---|
| 26 | F | 1 | $CF_3$ | H | O | $NCH_3$ | O | $NCH_3$ |
| 27 | F | 1 | CN | H | O | $NCH_3$ | O | $NCH_3$ |
| 28 | F | 0 | CN | H | O | $NCH_3$ | O | $NCH_3$ |
| 29 | F | 1 | Cl | F | O | $NCH_3$ | O | $NCH_3$ |
| 30 | F | 0 | Cl | F | O | $NCH_3$ | O | $NCH_3$ |
| 31 | F | 0 | Cl | H | O | $NCH_3$ | O | $NCH_3$ |
| 32 | F | 1 | $OCH_3$ | H | O | $NCH_3$ | O | $NCH_3$ |
| 33 | F | 1 | $CH_3$ | $CH_3$ | O | $NCH_3$ | O | $NCH_3$ |
| 34 | F | 1 | $CH_3$ | F | O | $NCH_3$ | O | N-cyclopropyl |
| 35 | F | 0 | $CH_3$ | F | O | $NCH_3$ | O | N-cyclopropyl |
| 36 | F | 0 | $CH_3$ | H | O | $NCH_3$ | O | N-cyclopropyl |
| 37 | F | 1 | $CH_3$ | H | O | $NCH_3$ | O | N-cyclopropyl |
| 38 | F | 1 | Cl | F | O | $NCH_3$ | O | N-cyclopropyl |
| 39 | F | 1 | Cl | H | O | $NCH_3$ | O | N-cyclopropyl |
| 40 | F | 0 | Cl | H | O | $NCH_3$ | O | N-cyclopropyl |
| 41 | F | 1 | $OCH_3$ | H | O | $NCH_3$ | O | N-cyclopropyl |
| 42 | F | 0 | $OCH_3$ | H | O | $NCH_3$ | O | N-cyclopropyl |
| 43 | F | 1 | CN | H | O | $NCH_3$ | O | N-cyclopropyl |
| 44 | F | 0 | CN | H | O | $NCH_3$ | O | N-cyclopropyl |
| 45 | F | 1 | Br | H | O | $NCH_3$ | O | N-cyclopropyl |
| 46 | F | 0 | Br | H | O | $NCH_3$ | O | N-cyclopropyl |
| 47 | F | 1 | $CH_3$ | $CH_3$ | O | $NCH_3$ | O | N-cyclopropyl |
| 48 | F | 0 | $CH_3$ | H | O | $NCH_2CH{=}CH_2$ | O | N-cyclopropyl |
| 49 | F | 1 | $CH_3$ | H | O | $NCH_2CH{=}CH_2$ | O | N-cyclopropyl |
| 50 | F | 1 | $CH_3$ | H | O | $NCH_2CH(CH_3)_2$ | O | N-cyclopropyl |
| 51 | F | 0 | $CH_3$ | H | O | $NCH_2CH_3$ | O | $NCH_3$ |
| 52 | F | 0 | $CH_3$ | H | O | $NCH_2$-cyclopropyl | O | $NCH_3$ |
| 53 | F | 0 | $CF_3$ | H | O | $NCH_3$ | O | N-cyclopropyl |
| 54 | F | 1 | $CF_3$ | H | O | $NCH_3$ | O | N-cyclopropyl |
| 55 | F | 0 | $CH_3$ | F | O | NH | O | $NCH_3$ |
| 56 | F | 0 | $CH_3$ | H | O | N-(3-(2,2,2-trifluoroethylsulfanyl)-4-methylphenyl) | O | $NCH_3$ |
| 57 | F | 0 | $CH_3$ | H | O | N-benzyl | O | $NCH_3$ |
| 58 | F | 0 | $CH_3$ | H | O | $NCH_2CH{=}CH_2$ | O | $NCH_3$ |
| 59 | F | 1 | $CH_3$ | H | O | $NCH_2CH{=}CH_2$ | O | $NCH_3$ |
| 60 | F | 0 | $CH_3$ | H | O | N-((2-chlorophenyl) methyl) | O | $NCH_3$ |
| 61 | F | 0 | $CH_3$ | H | O | $NCH(CH_3)_2$ | O | $NCH_3$ |
| 62 | F | 0 | $CH_3$ | F | O | $NCH(CH_3)_2$ | O | $NCH_3$ |
| 63 | F | 0 | $CH_3$ | H | O | $NCH(CH_3)_2$ | O | N-cyclopropyl |
| 64 | F | 1 | $CH_3$ | F | O | $NCH(CH_3)_2$ | O | N-cyclopropyl |
| 65 | F | 0 | $CH_3$ | F | O | $NCH(CH_3)_2$ | O | N-cyclopropyl |
| 66 | F | 0 | $CH_3$ | F | O | NH | O | N-cyclopropyl |
| 67 | F | 1 | Br | H | O | $NCH_3$ | O | $NCH_3$ |
| 68 | F | 0 | Br | H | O | $NCH_3$ | O | $NCH_3$ |
| 69 | F | 1 | Br | F | O | $NCH_3$ | O | $NCH_3$ |
| 70 | F | 1 | F | F | O | $NCH_3$ | O | $NCH_3$ |
| 71 | F | 0 | F | F | O | $NCH_3$ | O | N-cyclopropyl |
| 72 | F | 1 | Br | F | O | $NCH_3$ | O | N-cyclopropyl |
| 73 | F | 0 | $CH_3$ | F | O | $NCH(CH_3)CH_2CH_3$ | O | N-cyclopropyl |
| 74 | F | 1 | $CH_3$ | F | O | $NCH_3$ | O | $NCH_2CH_3$ |
| 75 | F | 1 | $CH_3$ | F | O | $NCH(CH_3)CH_2CH_3$ | O | N-cyclopropyl |
| 76 | F | 0 | $CH_3$ | F | O | $NCH_3$ | O | N-((3-(trifluoromethyl)phenyl) |
| 77 | F | 1 | $CH_3$ | F | O | $NCH_3$ | O | N-((3-(trifluoromethyl)phenyl) |
| 78 | F | 0 | $CH_3$ | F | O | N-(4-cyano-2,5-difluorophenyl) | O | $NCH_3$ |
| 79 | F | 0 | $CH_3$ | H | O | N-(3-(2,2,2-trifluoroethylsulfanyl)-4-methylphenyl) | O | $NCH_2CH{=}CH_2$ |
| 80 | F | 1 | $CH_3$ | F | O | $NCH_3$ | O | $NCH_2CH{=}CH_2$ |
| 81 | F | 0 | $CH_3$ | F | O | $NCH_3$ | O | $NCH_2CH{=}CH_2$ |
| 82 | F | 1 | $CH_3$ | H | O | N-(3-(2,2,2-trifluoroethylsulfinyl)-4-methylphenyl) | O | $NCH_3$ |
| 83 | F | 0 | $CH_3$ | F | O | $NCH_3$ | O | $NCH_2CH_3$ |
| 84 | F | 1 | $CH_3$ | H | O | N-(3-(2,2,2-trifluoroethylsulfanyl)-4-methylphenyl) | O | $NCH_3$ |

-continued

| Example No. | W | n | Y | X | $V^1$ | $Q^1$ | $V^2$ | $Q^2$ |
|---|---|---|---|---|---|---|---|---|
| 85 | F | 0 | $CH_3$ | F | O | NH | O | $NCH_2CH_3$ |
| 86 | F | 0 | $CH_3$ | F | O | N-cyclopentyl | O | $NCH_3$ |
| 87 | F | 0 | $CH_3$ | F | O | $NCH_2CH_3$ | O | N-phenyl |
| 88 | F | 1 | $CH_3$ | F | O | $NCH_2CH_3$ | O | N-phenyl |
| 89 | F | 1 | $CH_3$ | H | O | $NCH_3$ | O | $NCH_2CH_3$ |
| 90 | F | 0 | $CH_3$ | H | O | N-benzyl | O | N-cyclopropyl |
| 91 | F | 0 | $CH_3$ | F | O | $NCH_3$ | O | $NCH(CH_3)_2$ |
| 92 | F | 1 | $CH_3$ | F | O | $NCH_3$ | O | $NCH(CH_3)_2$ |
| 93 | F | 1 | $CH_3$ | F | O | $NCH_2CH_3$ | O | $NCH(CH_3)_2$ |
| 94 | F | 0 | $CH_3$ | F | O | $NCH_3$ | O | $NC(CH_3)_3$ |
| 95 | F | 1 | $CH_3$ | F | O | $NCH_3$ | O | $NC(CH_3)_3$ |
| 96 | F | 1 | $CH_3$ | F | O | N-(cyclohex-2-en-1-yl) | O | $NCH_3$ |
| 97 | F | 0 | $CH_3$ | F | O | $NCH_2CH_3$ | O | $NCH_3$ |
| 98 | F | 1 | $CH_3$ | F | O | $NCH_2CH_3$ | O | $NCH_3$ |
| 99 | F | 0 | $CH_3$ | F | O | $NCH_2CH_3$ | O | $NC(CH_3)_3$ |
| 100 | F | 0 | $CH_3$ | H | O | $NCH_2CH_3$ | O | $NCH_2CH_3$ |
| 127 | F | 0 | $CH_3$ | F | O | $NCH_2CH_3$ | O | N-cyclopropyl |
| 128 | F | 0 | $CH_3$ | F | O | $NCH_3$ | O | N-cyclopropyl |
| 129 | F | 0 | $CH_3$ | F | O | $NCH_2CF_3$ | O | N-cyclopropyl |
| 130 | F | 0 | $CH_3$ | F | O | $NCH_2CH{=}CH_2$ | O | N-cyclopropyl |
| 131 | F | 0 | $CH_3$ | H | O | $NCH_3$ | O | $NCH_2CH_3$ |
| 132 | F | 0 | $CH_3$ | H | O | $NCH_3$ | O | $NCH(CH_3)_2$ |
| 133 | F | 0 | $CH_3$ | H | O | $NCH_2CH_3$ | O | $NCH(CH_3)_2$ |
| 134 | F | 0 | $CH_3$ | H | O | $NCH_2CH_3$ | O | $NC(CH_3)_3$ |
| 135 | F | 0 | $CH_3$ | H | O | $NCH(CH_3)_2$ | O | $NC(CH_3)_3$ |
| 136 | F | 0 | $CH_3$ | F | O | $NCH_3$ | O | N-cyclohexyl |
| 137 | F | 1 | $CH_3$ | F | O | $NCH_2CH_3$ | O | $NC(CH_3)_3$ |
| 138 | F | 1 | $CH_3$ | H | O | $NCH_2CH_3$ | O | $NCH_2CH_3$ |
| 139 | F | 1 | $CH_3$ | H | O | $NCH_3$ | O | $NC(CH_3)_3$ |
| 140 | F | 1 | $CH_3$ | H | O | $NCH(CH_3)_2$ | O | $NCH_2CH_3$ |
| 141 | F | 1 | $CH_3$ | H | O | $NCH_3$ | O | $NCH(CH_3)_2$ |
| 142 | F | 0 | $CH_3$ | F | O | $NC(CH_3)_3$ | O | $NCH_2CH_3$ |
| 143 | F | 0 | $CH_3$ | F | O | $NC(CH_3)_3$ | O | $NCH(CH_3)_2$ |
| 144 | F | 0 | $CH_3$ | F | O | $NC(CH_3)_3$ | O | N-cyclopropyl |
| 145 | F | 0 | $CH_3$ | F | O | $NCH_2CF_3$ | O | $NCH_2CH_3$ |
| 146 | F | 0 | $CH_3$ | F | O | $NCH_2CF_3$ | O | $NCH(CH_3)_2$ |
| 147 | F | 0 | $CH_3$ | F | O | $NCH_2CF_3$ | O | $NC(CH_3)_3$ |
| 148 | F | 0 | $CH_3$ | F | O | $NCH_2CH(CH_3)_2$ | O | $NCH_2CH_3$ |
| 149 | F | 0 | $CH_3$ | F | O | $NCH_2CH(CH_3)_2$ | O | $NCH(CH_3)_2$ |
| 151 | F | 1 | $CH_3$ | F | O | $NCH_3$ | O | N-cyclopropyl |
| 152 | F | 1 | $CH_3$ | F | O | $NC(CH_3)_3$ | O | $NCH(CH_3)_2$ |
| 153 | F | 1 | $CH_3$ | F | O | $NCH_2CF_3$ | O | $NCH(CH_3)_2$ |
| 154 | F | 0 | $CH_3$ | F | O | $NCH_2CF_3$ | O | $NCH_2CH{=}CH_2$ |
| 155 | F | 0 | $CH_3$ | F | O | $NCH_2CF_3$ | O | N-Phenyl |
| 156 | F | 0 | $CH_3$ | F | O | $NCH_2CF_3$ | O | $NCH_2CHF_2$ |
| 157 | F | 0 | $CH_3$ | F | O | NH | O | N-(3-chlorophenyl) |
| 158 | F | 1 | $CH_3$ | F | O | NH | O | N-(3-trifluoromethylphenyl) |
| 159 | F | 0 | $CH_3$ | F | O | $NCH_3$ | O | $N(CH_2)_3OCH_3$ |
| 160 | F | 0 | $CH_3$ | F | O | $NCH_3$ | O | $NCH_2CH_2CH_3$ |
| 161 | F | 0 | $CH_3$ | F | O | $NCH_3$ | O | $NCH_2CH(CH_2)_2$ |
| 162 | F | 0 | $CH_3$ | F | O | $NCH_3$ | O | N-phenyl |
| 163 | F | 1 | $CH_3$ | F | O | $NCH_3$ | O | N-Phenyl |
| 164 | F | 1 | $CH_3$ | F | O | $NCH_2CF_3$ | O | N-cyclopropyl |
| 165 | F | 1 | $CH_3$ | F | O | $NCH_2CH{=}CH_2$ | O | N-cyclopropyl |
| 166 | F | 1 | $CH_3$ | F | O | $NCH_2CF_3$ | O | $NCH_2CH{=}CH_2$ |
| 167 | F | 1 | $CH_3$ | F | O | $NCH_2CF_3$ | O | N-phenyl |
| 168 | F | 1 | $CH_3$ | F | O | $NCH_2CF_3$ | O | $NCH_2CHF_2$ |
| 169 | F | 1 | $CH_3$ | F | O | $NCH_3$ | O | $NCH_2CH(CH_2)_2$ |
| 170 | F | 1 | $CH_3$ | F | O | $NCH_3$ | O | $N(CH_2)_3OCH_3$ |
| 171 | F | 1 | $CH_3$ | F | O | $NCH_2CH_3$ | O | N-cyclopropyl |
| 172 | F | 1 | $CH_3$ | F | O | $NCH_2CH_2CH_3$ | O | N-cyclopropyl |
| 173 | F | 0 | $CH_3$ | F | O | N-phenyl | O | $C(CH_3)_2$ |
| 174 | F | 0 | $CH_3$ | F | O | $NCH_3$ | O | $C(CH_3)_2$ |
| 175 | F | 0 | $CH_3$ | F | O | $NCH_3$ | O | $C(CH_2CH_3)_2$ |
| 176 | F | 1 | $CH_3$ | F | O | $NCH_3$ | O | $C(CH_2CH_3)_2$ |
| 177 | F | 1 | $CH_3$ | F | O | $NCH_3$ | O | $C(CH_3)_2$ |
| 178 | F | 0 | $CH_3$ | F | O | $NCH_2$phenyl | O | $C(CH_3)_2$ |
| 179 | F | 0 | $CH_3$ | F | O | $NCH_3$ | O | $C(CH_2)_3$ |
| 180 | F | 1 | $CH_3$ | F | O | $NCH_3$ | O | $C(CH_2)_3$ |
| 181 | F | 0 | $CH_3$ | F | O | $NCH_3$ | S | N-cyclopropyl |
| 182 | F | 0 | $CH_3$ | F | S | $NCH_3$ | S | N-cyclopropyl |
| 197 | F | 1 | $CH_3$ | F | O | $NCH_3$ | O | N-cyclopropyl |
| 207 | F | 0 | $CH_3$ | F | O | NH | O | N-cyclopropyl |
| 208 | F | 1 | $CH_3$ | F | O | $CH_2$ | O | $N{-}CH_3$ |

-continued

| Example No. | W | n | Y | X | $V^1$ | $Q^1$ | $V^2$ | $Q^2$ |
|---|---|---|---|---|---|---|---|---|
| 209 | F | 1 | $CH_3$ | F | O | $CH_2$ | O | N-cyclopropyl |
| 210 | F | 0 | $CH_3$ | F | O | $CH_2$ | O | N-cyclopropyl |
| 211 | F | 0 | $CH_3$ | F | O | $CH_2$ | O | N—$CH_3$ |
| 212 | F | 0 | $CH_3$ | F | O | $CH(CH_3)$ | O | N—$CH_3$ |
| 213 | F | 1 | $CH_3$ | F | O | $CH(CH_3)$ | O | N—$CH_3$ |
| 214 | F | 0 | $CH_3$ | F | O | $CH(CH_3)$ | O | N-cyclopropyl |
| 215 | F | 1 | $CH_3$ | F | O | $CH(CH_3)$ | O | N-cyclopropyl |
| 216 | F | 1 | $CH_3$ | F | O | $C(CH_3)_2$ | O | N—$CH_3$ |
| 217 | F | 0 | $CH_3$ | F | O | $C(CH_3)_2$ | O | N—$CH_3$ |

(I) with (I-D)

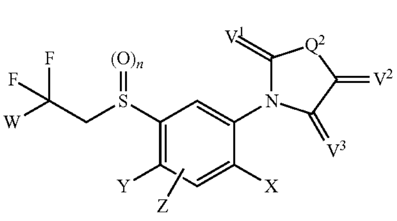

(Compound of the General Formula (I) with (I-D) with Z═H)

| Example No. | W | n | Y | X | $V^1$ | $V^2$ | $Q^2$ | $V^3$ |
|---|---|---|---|---|---|---|---|---|
| 101 | F | 0 | $CH_3$ | H | O | O | $NCH_2CHF_2$ | O |
| 102 | F | 0 | $CH_3$ | F | O | O | N-cyclopropyl | O |
| 103 | F | 1 | $CH_3$ | F | O | O | $NCH_2CHF_2$ | O |
| 183 | F | 1 | $CH_3$ | F | O | O | N-cyclopropyl | O |
| 184 | F | 1 | $CH_3$ | $CH_3$ | O | O | $NCH_2CHF_2$ | O |
| 185 | F | 0 | $CH_3$ | F | O | O | N-cyclohexyl | O |
| 186 | F | 1 | $CH_3$ | F | O | O | N-cyclohexyl | O |
| 187 | F | 0 | $CH_3$ | $CH_3$ | S | O | $NCH_2CF_3$ | O |
| 188 | F | 1 | $CH_3$ | $CH_3$ | S | O | $NCH_2CF_3$ | O |
| 189 | F | 0 | $CH_3$ | F | S | O | $NCH_2CF_3$ | O |
| 190 | F | 1 | $CH_3$ | F | S | O | $NCH_2CF_3$ | O |
| 191 | F | 0 | $CH_3$ | F | S | O | $NCH_2CH(CH_3)_2$ | O |
| 192 | F | 0 | $CH_3$ | F | S | O | $NCH_2C(CH_3)_3$ | O |
| 193 | F | 0 | $CH_3$ | F | S | O | $NC(CH_3)_3$ | O |
| 194 | F | 1 | $CH_3$ | F | S | O | $NCH_2CH(CH_3)_2$ | O |
| 195 | F | 1 | $CH_3$ | F | S | O | $NCH_2C(CH_3)_3$ | O |
| 196 | F | 1 | $CH_3$ | F | S | O | $NC(CH_3)_3$ | O |

The log P values were determined analogously to OECD Guideline 117 (EC Directive 92/69/EEC) by HPLC (high-performance liquid chromatography) using reversed-phase columns (C 18), by the following methods:

[a] The LC-MS determination in the acidic range was effected at pH 2.7 with 0.1% aqueous formic acid and acetonitrile (contains 0.1% formic acid) as eluents; linear gradient from 10% acetonitrile to 95% acetonitrile. log P[a] is also referred to as log P(HCOOH).

[b] LC-MS determination in the neutral range was effected at pH 7.8 with 0.001 molar aqueous ammonium hydrogencarbonate solution and acetonitrile as eluents; linear gradient from 10% acetonitrile to 95% acetonitrile. log P[b] is also referred to as log P(neutral).

Calibration is effected with solutions of a homologous series of unbranched alkan-2-ones (having 3 to 16 carbon atoms) with known log P values (log P values determined on the basis of the retention times by linear interpolation between two successive alkanones).

The NMR spectra were measured with a Bruker II Avance 400 equipped with a 1.7 mm TCI probe head. In isolated cases, the NMR spectra were determined using a Bruker Avance II 600.

The NMR data for selected examples are listed in conventional form (δ values, multiplet splitting, number of hydrogen atoms). The splitting of the signals was described as follows: s (singlet), d (doublet), t (triplet), q (quartet), m (multiplet), broad (for broad signals). Solvents used were $CD_3CN$, $CDCl_3$ or D6-DMSO, and tetramethylsilane (0.00 ppm) was used as reference.

The GC-MS spectra are determined using an Agilent 6890 GC, HP 5973 MSD on a dimethylsilicone phase, using a temperature gradient from 50° C. to 320° C. GC-MS indices are determined as Kovats indices using solutions of a homologous series of n-alkanes (having an even number of 8 to 38 carbon atoms).

| Ex. No. | logP (HCOOH) | logP (neutral) | NMR data | Solvent |
|---|---|---|---|---|
| 1 | 2.43 | 2.39 | 7.37(s, 1H), 7.14(s, 1H), 6.64(s, 1H), 3.92-3.87(q, 2H), 3.73-3.70(m, 2H), 3.42-3.39(m, 2H), 2.33(s, 3H), 2.15(s, 3H) | D6-DMSO |
| 2 | 2.42 | | 9.32(m, 1H), 7.64(s, 1H), 7.37(s, 1H), 4.73(m, 1H), 3.99(m, 4H), 2.38(d, 3H), 2.30(m, 2H), 2.15(s, 3H), 2.09(s, 3H), 1.34(m, 2H) | D6-DMSO |
| 3 | 1.02 | 2.88 | 7.99-7.97(m, 1H), 7.32-7.29(m, 1H), 4.20-4.11(m, 1H), 3.90-3.64(m, 5H), 2.62(t, 2H), 2.37(s, 3H), 2.12-2.05(m, 2H) | D6-DMSO |
| 4 | 1.51 | 1.52 | 7.67(s, 1H), 7.24(s, 1H), 6.77(broad, 1H), 4.13-3.93(m, 2H), 3.78-3.71(m, 2H), 3.44(t, 2H), 2.33(s, 3H), 2.24(s, 3H) | D6-DMSO |
| 5 | 1.50 | 4.38 | 9.46(t, 1H), 7.64(s, 1H), 7.37(s, 1H), 4.30-4.19(m, 2H), 4.05-3.95(m, 4H), 3.30-3.26(m, 2H), 2.38(s, 3H), 2.34-2.27(m, 2H), 2.12(s, 3H) | D6-DMSO |

-continued

| Ex. No. | logP (HCOOH) | logP (neutral) | NMR data | Solvent |
|---|---|---|---|---|
| 6 | 1.68 | 4.24 | 7.64-7.62(m, 1H), 7.29-7.26(m, 1H), 4.30-3.87(m, 6H), 3.33(m, 2H), 2.38(s, 3H), 2.33(m, 2H) | D6-DMSO |
| 7 | 1.47 | 1.43 | 7.99-7.97(m, 1H), 7.34-7.32(m, 1H), 7.03(broad, 1H), 4.16-4.10(m, 1H), 3.99-3.95(m, 1H), 3.91-3.80(m, 2H), 3.44(t, 2H), 2.35(s, 3H) | D6-DMSO |
| 8 | 1.82 | 4.63 | 7.80(broad, 1H), 7.50(broad, 1H), 4.75(broad, 1H), 4.10-3.90(m, 4H), 3.17(m, 2H), 2.42(s, 3H), 2.25(m, 2H), 1.35(broad, 3H) | D6-DMSO |
| 9 | 2.36 | 2.31 | 7.67-7.65(m, 1H), 7.23-7.20(m, 1H), 6.90(broad, 1H), 3.91-3.83(q, 2H), 3.80(t, 2H), 3.41(t, 2H), 2.37(s, 3H) | D6-DMSO |
| 10 | 1.10 | 3.20 | 7.99-7.96(m, 1H), 7.32-7.29(m, 1H), 4.21-3.59(m, 5H), 2.68-2.61(m, 2H), 2.37(s, 3H), 2.12-2.05(m, 2H), 1.11-1.09(d, 3H) | D6-DMSO |
| 11 | 3.60 | 3.50 | 7.62(d, 1H), 7.39(d, 1H), 4.39(d, 1H), 4.26(d, 1H), 4.00-3.83(m, 4H), 2.43(s, 3H) | D6-DMSO |
| 12 | 3.96 | 3.90 | 7.91(s, 1H), 7.80(s, 1H), 4.33(m, 1H), 4.23-4.00(m, 3H), 2.68-2.65(m, 1H), 0.76-0.72(m, 2H), 0.41-0.37(m, 2H) | D6-DMSO |
| 13 | 2.70 | 2.64 | 7.92(dd, 1H), 7.52(dd, 1H), 4.41-4.25(m, 3H), 4.06-3.69(m, 3H), 2.43(s, 3H) | D6-DMSO |
| 14 | 2.68 | 3.00 | 7.34(s, 1H), 7.23(s, 1H), 4.25(d, 1H), 4.14(d, 1H), 3.92-3.84(m, 2H), 2.95(s, 3H), 2.36(s, 3H), 2.00(s, 3H) | D6-DMSO |
| 15 | 2.48 | 2.48 | | D6-DMSO |
| 16 | 1.96 | 1.91 | 7.91(d, 1H), 7.55-7.52(m, 1H), 7.47(d, 1H), 4.24-4.18(m, 1H), 3.93-3.87(m, 1H), 2.89(s, 3H), 2.40(s, 3H), 1.45(s, 3H), 1.43(s, 3H) | D6-DMSO |
| 17 | 2.04 | 2.01 | 7.97(d, 1H), 7.51(d, 1H), 4.32-4.20(m, 1H), 4.00-3.89(m, 1H), 2.89(s, 3H), 2.43(s, 3H), 1.45(s, 3H), 1.44(s, 3H) | D6-DMSO |
| 18 | 2.96 | 2.92 | 7.69(d, 1H), 7.39(d, 1H), 3.93(q, 2H), 2.88(s, 3H), 2.43(s, 3H), 1.43(s, 6H) | D6-DMSO |
| 19 | 2.52 | 2.45 | 7.56(d, 1H), 7.40(d, 1H), 3.87(q, 2H), 2.86(broad, 4H), 2.44(s, 3H) | D6-DMSO |
| 20 | 2.59 | 2.58 | 7.49(d, 1H), 7.38(d, 1H), 7.23-7.21(m, 1H), 4.03(q, 2H), 3.00(s, 3H), 2.99(s, 3H), 2.38(s, 3H) | D6-DMSO |
| 21 | 1.63 | 1.63 | 7.79(d, 1H), 7.47-7.54(m, 2H), 4.12-4.22(m, 1H), 4.02-4.08(m, 1H), 3.04(s, 3H), 3.00(s, 3H), 2.38(s, 3H) | D6-DMSO |
| 22 | 2.61 | 2.56 | 7.70(d, 1H), 7.43(d, 1H), 4.01(q, 2H), 3.01(s, 3H), 2.95(s, 3H), 2.42(s, 3H) | D6-DMSO |
| 23 | 1.64 | 1.63 | 7.92(d, 1H), 7.55(d, 1H), 4.26-4.11(m, 2H), 3.01(s, 3H), 2.99(s, 3H), 2.42(s, 3H) | D6-DMSO |
| 24 | 1.97 | 1.95 | 7.81(d, 1H), 7.78(d, 1H), 7.67-7.64(m, 1H), 4.31-4.14(m, 2H), 3.07(s, 3H), 3.00(s, 3H) | D6-DMSO |
| 25 | 3.04 | 2.97 | 7.89(d, 1H), 7.81(d, 1H), 7.51-7.48(m, 1H), 4.21(q, 2H), 3.07(s, 3H), 3.01(s, 3H) | D6-DMSO |
| 26 | 2.37 | 2.31 | 8.18(d, 1H), 8.07(d, 1H), 7.85-7.82(m, 1H), 4.30-4.20(m, 2H), 3.12(s, 3H), 3.02(s, 3H) | D6-DMSO |
| 27 | 1.67 | 1.64 | 8.19(d, 1H), 7.98(d, 1H), 7.80-7.77(m, 1H), 4.42-4.32(m, 2H), 3.11(s, 3H), 3.01(s, 3H) | D6-DMSO |
| 28 | 2.18 | 2.19 | 7.99(d, 1H), 7.73(d, 1H), 7.51-7.47(m, 1H), 4.26(q, 2H), 3.07(s, 3H), 3.00(s, 3H) | D6-DMSO |
| 29 | 1.93 | 1.91 | 8.03(d, 1H), 7.94(d, 1H), 4.34-4.19(m, 2H), 3.01(s, 6H) | D6-DMSO |
| 30 | 2.71 | 2.67 | 7.86(d, 1H), 7.82(d, 1H), 4.18(q, 2H), 3.01(s, 3H), 2.97(s, 3H) | D6-DMSO |
| 31 | 2.72 | 2.69 | 8.14(d, 1H), 7.78-7.75(m, 1H), 7.59(d, 1H), 4.05(s, 3H), 4.04(q, 2H), 3.09(s, 3H) | D6-DMSO |

-continued

| Ex. No. | logP (HCOOH) | logP (neutral) | NMR data | Solvent |
|---|---|---|---|---|
| 32 | 1.58 | 1.54 | 7.64-7.59(m, 2H), 7.33(d, 1H), 4.19-4.10(m, 1H), 4.00-3.94(m, 1H), 3.92(s, 3H), 3.00(s, 3H), 2.99(s, 3H) | D6-DMSO |
| 33 | 1.75 | 1.70 | 7.77-7.74(m, 1H), 7.39(s, 1H), 4.19-4.00(m, 2H), 3.01(s, 3H), 2.97-2.90(m, 3H), 2.37(s, 3H)m 2.34(s, 3H) | D6-DMSO |
| 34 | 1.91 | 1.88 | 7.90(d, 1H), 7.53(d, 1H), 4.25-4.10(m, 2H), 2.95(s, 3H), 2.73-2.67(m, 1H), 2.42(s, 3H), 0.93-0.88(m, 4H) | D6-DMSO |
| 35 | 2.83 | 2.81 | 7.68(d, 1H), 7.42(d, 1H), 4.00(q, 2H), 2.91(s, 3H), 2.73-2.68(m, 1H), 2.42(s, 3H), 0.91-0.88(m, 4H) | D6-DMSO |
| 36 | 2.89 | 2.87 | 7.46(d, 1H), 7.37(d, 1H), 7.21-7.19(m, 1H), 4.02(q, 2H), 2.96(s, 3H), 2.70-2.65(m, 1H), 2.37(s, 3H), 0.91-0.87(m, 4H) | D6-DMSO |
| 37 | 1.89 | 1.87 | 7.77(d, 1H), 7.52-7.46(m, 2H), 4.21-4.15(m, 1H), 4.06-4.00(m, 1H), 3.01(s, 3H), 2.71-2.66(m, 1H), 2.38(s, 3H), 0.92-0.87(m, 4H) | D6-DMSO |
| 38 | 2.18 | 2.16 | 8.02(d, 1H), 7.92(d, 1H), 4.34-4.18(m, 2H), 2.97(s, 3H), 2.71-2.67(m, 1H), 0.93-0.88(m, 4H) | D6-DMSO |
| 39 | 2.20 | 2.17 | 7.80-7.76(m, 2H), 7.64-7.62(m, 1H), 4.30-4.12(m, 2H), 3.03(s, 3H), 2.71-2.66(m, 1H), 0.93-0.87(m, 4H) | D6-DMSO |
| 40 | 3.04 | 2.98 | 7.63(d, 1H), 7.55(d, 1H), 7.30-7.27(m, 1H), 4.18(q, 2H), 2.98(s, 3H), 2.70-2.67(m, 1H), 0.92-0.87(m, 4H) | D6-DMSO |
| 41 | 1.77 | 1.75 | 7.62-7.57(m, 2H), 7.32(d, 1H), 4.19-4.10(m, 1H), 4.06-3.95(m, 1H), 3.92(s, 3H), 2.97(s, 3H), 2.71-2.66(m, 1H), 0.93-0.86(m, 4H) | D6-DMSO |
| 42 | 2.51 | 2.46 | 7.42(d, 1H), 7.29-7.27(m, 1H), 7.14(d, 1H), 3.97(q, 2H), 3.89(s, 3H), 2.91(s, 3H), 2.70-2.65(m, 1H), 0.91-0.86(m, 4H) | D6-DMSO |
| 43 | 1.93 | 1.90 | 8.18(d, 1H), 7.96(d, 1H), 7.77-7.74(m, 1H), 4.42-4.30(m, 2H), 3.08(s, 3H), 2.72-2.66(m, 1H), 0.91-0.89(m, 4H) | D6-DMSO |
| 44 | 2.53 | 2.45 | 7.98(d, 1H), 7.70(d, 1H), 7.48-7.45(m, 1H), 4.25(q, 2H), 3.03(s, 3H), 2.71-2.65(m, 1H), 0.91-0.88(m, 4H) | D6-DMSO |
| 45 | 2.27 | 2.24 | 7.90(d, 1H), 7.78(d, 1H), 7.57-7.55(m, 1H), 4.26-4.10(m, 2H), 3.03(s, 3H), 2.71-2.66(m, 1H), 0.91-0.87(m, 4H) | D6-DMSO |
| 46 | 3.11 | 3.05 | 7.77(d, 1H), 7.51(d, 1H), 7.21-7.18(m, 1H), 4.19(q, 2H), 2.98(s, 3H), 2.70-2.66(m, 1H), 0.92-0.87(m, 4H) | D6-DMSO |
| 47 | 1.98 | 1.93 | 7.76-7.72(m, 1H), 7.38(s, 1H), 4.19-3.97(m, 2H), 2.93-2.86(m, 3H), 2.73-2.67(m, 1H), 2.49-2.32(m, 6H), 0.92-0.87(m, 4H) | D6-DMSO |
| 48 | 3.37 | 3.31 | 7.47(d, 1H), 7.36(d, 1H), 7.20-7.17(m, 1H), 5.75-5.67(m, 1H), 5.16-5.13(m, 1H), 5.06-5.01(m, 1H), 4.05-3.97(m, 4H), 2.74-2.67(m, 1H), 2.37(s, 3H), 0.90-0.84(m, 4H) | D6-DMSO |
| 49 | 2.28 | 2.24 | 7.78(d, 1H), 7.51-7.46(m, 2H), 5.76-5.69(m, 1H), 5.18-5.15(m, 1H), 5.08-5.04(m, 1H), 4.22-4.16(m, 1H), 4.07-3.99(m, 3H), 2.74-2.70(m, 1H), 2.38(s, 3H), 0.90-0.88(m, 4H) | D6-DMSO |
| 50 | 3.58 | 3.47 | 7.91(d, 1H), 7.73(d, 1H), 7.50-7.41(m, 1H), 4.15-3.96(m, 4H), 2.83-2.78(m, 1H), 2.43(s, 3H), 2.12-2.05(m, 1H), 1.03-0.92(m, 10H) | D6-DMSO |
| 51 | 2.82 | 2.83 | 7.53(s, 1H), 7.26(d, 1H), 7.19-7.17(m, 1H), 4.32(q, 2H), 3.95(q, 2H), 3.09(s, 3H), 2.36(s, 3H), 1.36(q, 3H) | D6-DMSO |

-continued

| Ex. No. | logP (HCOOH) | logP (neutral) | NMR data | Solvent |
|---|---|---|---|---|
| 52 | 3.34 | 3.29 | 7.51(s, 1H), 7.38(d, 1H), 7.24-7.21(m, 1H), 4.01(q, 2H), 3.33(d, 2H), 3.02(s, 3H), 2.38(s, 3H), 0.90-0.80(m, 1H), 0.41-0.32(m, 4H) | D6-DMSO |
| 53 | 3.33 | 3.23 | 7.88(d, 1H), 7.78(d, 1H), 7.48-7.46(m, 1H), 4.20(q, 2H), 3.03(s, 3H), 2.70-2.66(m, 1H), 0.92-0.88(m, 4H) | D6-DMSO |
| 54 | 2.63 | 2.58 | 8.15(d, 1H), 8.06(d, 1H), 7.82-7.80(m, 1H), 4.24-4.20(m, 2H), 3.08(s, 3H), 2.71-2.69(m, 1H), 0.93-0.89(m, 4H) | D6-DMSO |
| 55 | 2.09 | 0.60 | 10.98(s, 1H), 7.72(d, 1H), 7.39(d, 1H), 3.95(q, 2H), 2.97(s, 3H), 2.41(s, 3H) | D6-DMSO |
| 56 | 4.34 | 4.05 | 7.50(d, 2H), 7.25(d, 2H), 7.22-7.19(m, 2H), 3.86(q, 4H), 3.07(s, 3H), 2.28(s, 6H) | D6-DMSO |
| 57 | 3.62 | 3.56 | 7.44(d, 1H), 7.37(d, 1H), 7.30-7.28(m, 3H), 7.14-7.12(m, 1H), 7.04-7.02(m, 2H), 4.61(s, 2H), 3.97(q, 2H), 2.98(s, 3H), 2.39(s, 3H) | D6-DMSO |
| 58 | 3.03 | 2.88 | 7.49(d, 1H), 7.37(d, 1H), 7.22-7.19(m, 1H), 5.75-5.68(m, 1H), 5.17-5.14(m, 1H), 5.08-5.04(m, 1H), 4.06-3.98(m, 4H), 3.00(s, 3H), 2.38(s, 3H) | D6-DMSO |
| 59 | 2.03 | 2.00 | 7.80(d, 1H), 7.53-7.47(m, 2H), 5.77-5.71(m, 1H), 5.19-5.16(m, 1H), 5.11-5.06(m, 1H), 4.22-4.13(m, 1H), 4.11-4.01(m, 3H), 3.01(s, 3H), 2.39(s, 3H) | D6-DMSO |
| 60 | 3.80 | 3.75 | 7.42-7.36(m, 2H), 7.31-7.26(m, 2H), 7.24-7.16(m, 2H), 7.06-7.04(m, 1H), 4.78(s, 2H), 3.90(q, 2H), 3.02(s, 3H), 2.35(s, 3H) | D6-DMSO |
| 61 | 3.33 | 3.27 | 7.55(d, 1H), 7.37(d, 1H), 7.25-7.23(m, 1H), 4.04(q, 2H), 3.79-3.71(m, 1H), 3.97(s, 3H), 2.37(s, 3H), 1.17(d, 6H) | D6-DMSO |
| 62 | 3.29 | 3.23 | 7.77(d, 1H), 7.41(d, 1H), 4.01(q, 2H), 3.89-3.85(m, 1H), 2.99(s, 3H), 2.41(s, 3H) | D6-DMSO |
| 63 | 3.65 | 3.57 | 7.53(d, 1H), 7.36(d, 1H), 7.24-7.21(m, 1H), 4.03(q, 2H), 3.75-3.68(m, 1H), 2.71-2.66(m, 1H), 2.37(s, 3H), 1.15(d, 6H); 0.89-0.86(m, 4H) | D6-DMSO |
| 64 | 2.51 | 2.45 | 8.01(d, 1H), 7.52(d, 1H), 4.27-4.18(m, 1H), 4.12-4.02(m, 1H), 3.92-3.85(m, 1H), 2.75-2.69(m, 1H), 2.41(s, 3H), 1.12(d, 3H), 1.08(d, 3H), 0.90-0.88(m, 4H) | D6-DMSO |
| 65 | 3.59 | 3.51 | 7.76(d, 1H), 7.40(d, 1H), 4.00(q, 2H), 3.89-3.82(m, 1H), 2.74-2.67(m, 1H), 2.41(s, 3H), 1.09(d, 6H), 0.90-0.86(m, 4H) | D6-DMSO |
| 66 | 2.30 | 0.69 | 10.86(s, 1H), 7.70(d, 1H), 7.37(d, 1H), 3.94(q, 2H), 2.71-2.65(m, 1H), 2.41(s, 3H), 0.94-0.84(m, 4H) | D6-DMSO |
| 67 | 2.05 | 2.02 | 7.91(d, 1H), 7.80(d, 1H), 7.60-7.57(m, 1H), 4.26-4.11(m, 2H), 3.07(s, 3H), 3.00(s, 3H) | D6-DMSO |
| 68 | 2.83 | 2.78 | 7.77(d, 1H), 7.54(d, 1H), 7.23-7.20(m, 1H), 4.19(q, 2H), 3.02(s, 3H), 2.99(s, 3H) | D6-DMSO |
| 69 | 2.01 | 1.98 | 8.14(d, 1H), 7.91(d, 1H), 4.29-4.16(m, 2H), 3.01(s, 3H), 3.00(s, 3H) | D6-DMSO |
| 70 | 1.64 | 1.59 | 7.97(t, 1H), 7.88(d, 1H), 4.38(q, 2H), 3.01(s, 3H) 3.00(s, 3H) | D6-DMSO |
| 71 | 2.67 | 2.62 | 7.87(t, 1H), 7.69(t, 1H), 4.02(q, 2H), 2.92(s, 3H), 2.73-2.68(m, 1H), 0.91-0.88(m, 4H) | D6-DMSO |
| 72 | 2.24 | 2.18 | 8.12(d, 1H), 7.90(d, 1H), 4.29-4.14(m, 2H), 2.97(s, 3H), 2.72-2.67(m, 1H), 0.91-0.88(m, 4H) | D6-DMSO |
| 73 | 3.86 | 3.72 | 7.80(d, 1H), 7.41(d, 1H), 4.00(q, 2H), 3.64-3.58(m, 1H), 2.75-2.70(m, 1H), 2.42(s, 3H), 1.59-1.52(m, 1H), 1.43-1.36(m, 1H), 1.07(d, 3H), 0.91-0.89(m, 4H), 0.74(t, 3H) | D6-DMSO |

-continued

| Ex. No. | logP (HCOOH) | logP (neutral) | NMR data | Solvent |
|---|---|---|---|---|
| 74 | 1.93 | 1.91 | 7.92(d, 1H), 7.55(d, 1H), 4.26-4.13(m, 2H), 3.54(q, 2H), 2.99(s, 3H), 2.42(s, 3H), 1.19(t, 3H) | D6-DMSO |
| 75 | 2.73 | 2.68 | 8.03-8.00(m, 1H), 7.52(d, 1H), 4.29-4.22(m, 1H), 4.06-4.02(m, 1H), 3.70-3.55(m, 1H), 2.75-2.72(m, 1H), 2.42(s, 3H), 1.69-1.60(m, 1H), 1.55-1.45(m, 1H), 1.40(s, 3H), 1.11-1.06(m, 2H), 0.90(d, 3H), 0.80-0.75(m, 2H) | D6-DMSO |
| 76 | 4.09 | 3.94 | 7.96(s, 1H), 7.90-7.78(m, 4H), 7.49(d, 1H), 4.02(q, 2H), 3.06(s, 3H), 2.45(s, 3H) | D6-DMSO |
| 77 | 3.09 | 3.05 | 8.09(d, 1H), 7.97(s, 1H), 7.89(d, 1H), 7.85-7.78(m, 2H), 7.59(d, 1H), 4.29-4.23(m, 1H), 4.15-4.09(m, 1H), 3.10(s, 3H), 2.44(s, 3H) | D6-DMSO |
| 78 | 3.40 | 3.29 | 8.20-8.16(m, 1H), 7.85-7.81(m, 2H), 7.39(d, 1H), 3.93(q, 2H), 3.11(s, 3H), 2.34(s, 3H) | D6-DMSO |
| 79 | 4.86 | 4.67 | 7.54(d, 2H), 7.28-7.22(m, 4H), 5.94-5.87(m, 1H), 5.26-5.20(m, 2H), 4.19(d, 2H), 3.898q, 4H), 2.26(s, 6H) | D6-DMSO |
| 80 | 2.07 | 2.03 | 7.95(d, 1H), 7.56(d, 1H), 5.93-5.81(m, 1H), 5.21-5.17(m, 2H), 4.27-4.14(m, 2H), 4.14-4.11(m, 2H), 3.01(s, 3H), 2.43(s, 3H) | D6-DMSO |
| 81 | 3.05 | 3.01 | 7.73(d, 1H), 7.44(d, 1H), 5.90-5.82(m, 1H), 5.21-5.15(m, 2H), 4.13-4.11(m, 2H) 4.03(q, 2H) 2.97(s, 3H) 2.43(s, 3H) | D6-DMSO |
| 82 | 2.67 | 2.61 | 7.87(t, 2H), 7.55-7.50(m, 2H), 7.38(d, 2H), 4.14-4.04(m, 2H), 3.92-3.75(m, 2H), 3.08(d, 3H), 2.33-2.30(m, 6H) | D6-DMSO |
| 83 | 2.92 | 2.88 | 7.72-7.70(m, 1H), 7.43(d, 1H), 4.06-3.98(m, 2H), 3.53(q, 2H), 2.95(s, 3H), 2.43(s, 3H) | D6-DMSO |
| 84 | 3.46 | 3.38 | 7.88(d, 1H), 7.53(d, 1H), 7.48-7.46(m, 1H), 7.39-7.33(m, 1H), 7.29-7.23(m, 2H), 4.13-4.07(m, 1H), 3.91(q, 2H), 3.77-3.70(m, 1H), 3.07(s, 3H), 2.30(s, 3H), 2.28(s, 3H) | D6-DMSO |
| 85 | 2.43 | 0.86 | 10.97(s, 1H), 7.72(d, 1H), 7.38(d, 1H), 3.96(q, 2H), 3.50(q, 2H), 2.41(s, 3H), 1.17(t, 3H) | D6-DMSO |
| 86 | 3.75 | 3.67 | 7.77(d, 1H), 7.41(d, 1H), 4.07-3.97(m, 3H), 2.99(s, 3H), 2.41(s, 3H), 1.75-1.69(m, 2H), 1.67-1.60(m, 2H), 1.56-1.48(m, 2H), 1.46-1.40(m, 2H) | D6-DMSO |
| 87 | 3.71 | 3.69 | 7.87(d, 1H), 7.57-7.44(m, 6H), 4.05(q, 2H), 3.49(q, 2H), 2.44(s, 3H), 1.08(t, 3H) | D6-DMSO |
| 88 | 2.71 | 2.66 | 8.10(d, 1H), 7.59(d, 1H), 7.55-7.51(m, 4H), 7.48-7.44(m, 1H), 4.31-4.09(m, 2H), 3.57-3.51(m, 2H), 2.44(s, 3H), 1.09(t, 3H) | D6-DMSO |
| 89 | 1.96 | 1.91 | 7.91(d, 1H), 7.55-7.48(m, 2H), 4.22-4.15(m, 1H), 4.09-4.03(m, 1H), 3.53(q, 2H), 3.05(s, 3H), 2.33(s, 3H), 1.18(t, 3H) | D6-DMSO |
| 90 | 3.81 | 3.71 | 7.58(d, 1H), 7.33(d, 1H), 7.28-7.24(m, 3H), 7.05-7.01(m, 2H), 4.56(s, 2H), 3.92(q, 2H), 2.77-2.72(m, 1H), 2.39(s, 3H), 0.94-0.85(m, 4H) | D6-DMSO |
| 91 | 3.35 | 3.28 | 7.70(d, 1H), 7.43(d, 1H), 4.26-4.19(m, 1H), 4.03(q, 2H), 2.93(s, 3H), 2.42(s, 3H), 1.38(d, 6H) | D6-DMSO |
| 92 | 2.27 | 2.22 | 7.91(d, 1H), 7.55(d, 1H), 4.27-4.15(m, 3H), 2.97(s, 3H), 2.42(s, 3H), 1.39(d, 6H) | D6-DMSO |
| 93 | 2.58 | 2.54 | 7.93(d, 1H), 7.55(d, 1H), 4.27-4.14(m, 3H), 3.48-3.34(m, 2H), 2.42(s, 3H), 1.39(d, 6H), 1.00(t, 3H) | D6-DMSO |

-continued

| Ex. No. | logP (HCOOH) | logP (neutral) | NMR data | Solvent |
|---|---|---|---|---|
| 94 | 3.85 | 3.82 | 7.68(d, 1H), 7.42(d, 1H), 4.02(q, 2H), 2.90(s, 3H), 2.42(s, 3H), 1.58(s, 9H) | D6-DMSO |
| 95 | 2.69 | 2.65 | 7.89(d, 1H), 7.53(d, 1H), 4.26-4.12(m, 2H), 2.94(s, 3H), 2.42(s, 3H), 1.58(s, 9H) | D6-DMSO |
| 96 | 2.66 | 2.61 | 8.05-7.99(m, 1H), 7.49(d, 1H), 5.67-5.63(m, 1H), 5.39-5.28(m, 1H), 4.55-4.50(m, 1H), 4.27-4.16(m, 1H), 4.12-3.95(m, 1H), 3.01(s, 3H), 2.41(s, 3H), 1.87-1.63(m, 5H), 1.54-1.43(m, 1H) | D6-DMSO |
| 97 | 2.91 | 2.83 | 7.72(d, 1H), 7.44(d, 1H), 4.01(q, 2H), 3.38(q, 2H), 3.01(s, 3H), 2.42(s, 3H), 0.99(t, 3H) | D6-DMSO |
| 98 | 1.93 | 1.91 | 7.94(d, 1H), 7.55(d, 1H), 4.26-4.09(m, 2H), 3.50-3.38(m, 2H), 3.02(s, 3H), 2.42(s, 3H), 1.00(t, 3H) | D6-DMSO |
| 99 | 4.21 | 4.16 | 7.70(d, 1H)m 7.42(d, 1H), 4.03(q, 2H), 3.34(q, 2H), 2.42(s, 3H), 1.58(s, 9H), 0.97(t, 3H) | D6-DMSO |
| 100 | 3.32 | 3.29 | 7.52(d, 1H), 7.38(d, 1H), 7.25-7.22(m, 1H), 4.05(q, 2H), 3.52(q, 2H), 3.46(q, 2H), 2.37(s, 3H), 1.17(t, 3H), 0.96(t, 3H) | D6-DMSO |
| 101 | 3.22 | 1.73 | 7.70-7.68(m, 1H), 7.51-7.48(m, 1H), 6.25(tt, 1H), 4.10-4.01(dt, 2H), 3.90-3.82(q, 2H), 2.48(s, 3H) | D6-DMSO |
| 102 | 3.24 | | 7.64-7.62(m, 1H), 7.48-7.46(m, 1H), 3.88-3.81(q, 2H), 2.73-2.68(m, 1H), 2.47(s, 3H), 0.95-0.88(m, 4H) | D6-DMSO |
| 103 | 2.32 | 0.87 | 8.04-8.03(m, 1H), 7.61-7.58(m, 1H), 6.24(tt, 1H), 4.36-4.27(m, 1H), 4.10-4.01(dt, 2H), 3.92-3.83(m, 1H), 2.43(s, 3H) | D6-DMSO |
| 104 | 2.66 | | 7.71 (d, 1H), 7.03 (d, 1H), 4.54-4.49 (m, 2H), 4.08-4.03 (m, 2H), 3.37-3.31 (m, 2H), 2.46 (s, 3H) | D6-DMSO |
| 105 | 1.64 | | 8.11 (d, 1H), 7.19 (d, 1H), 4.58-4.49 (m, 2H), 4.18-4.10 (m, 1H), 4.04-3.96 (m, 1H), 3.59-3.33 (m, 2H), 2.41 (s, 3H) | CDCl3 |
| 106 | 2.98 | | 7.74 (d, 1H), 7.31 (d, 1H), 4.87-4.80 (m, 1H), 4.10-4.04 (m, 1H), 3.98-3.88 (m, 2H), 3.64-3.59 (m, 1H), 2.39 (s, 3H), 1.43 (d, 3H) | D6-DMSO |
| 107 | 1.79 | | 7.98 (dd, 1H), 7.26-7.07 (m, 1H), 4.68-4.62 (m, 1H), 4.51-4.42 (m, 1H), 4.11-4.02 (m, 1H), 3.53-3.39 (m, 2H), 2.41 (s, 3H), 1.26-1.23 (m, 3H). | CDCl3 |
| 108 | 2.92 | | 7.56 (d, 1H), 7.06 (d, 1H), 4.65-4.60 (m, 1H), 4.45-4.38 (m, 1H), 4.06-4.01 (m, 1H), 3.35 (q, 2H), 2.48 (s, 3H), 1.26-1.22 (m, 3H) | CDCl3 |
| 109 | 1.93 | 1.89 | 8.11 (d, 1H), 7.08 (d, 1H), 4.90-4.81 (m, 1H), 4.20-4.01 (m, 1H), 3.76-3.37 (m, 3H), 2.40 (s, 3H), 1.57-1.54 (m, 3H) | CDCl3 |
| 110 | 2.38 | | 7.99 (d, 1H), 7.24 (d, 1H), 3.52-3.41 (m, 2H), 2.45 (s, 3H), 1.72 (s, 6H) | CDCl3 |
| 111 | 3.35 | | 7.50 (d, 1H), 7.16 (d, 1H), 3.39-3.32 (m, 2H), 2.53 (s, 3H), 1.71 (s, 6H) | CDCl3 |
| 112 | 3.65 | 3.65 | 7.14(s, 1H), 7.00(s, 1H), 3.92(s, 2H), 3.82(q, 2H), 2.71(septet, 1H), 2.33(s, 3H), 2.06(s, 3H), 1.00-0.90(m, 4H) | D6-DMSO |
| 113 | 4.84 | 4.73 | 7.63(d, 1H), 7.37(d, 1H), 4.30-4.15(m, 2H), 3.89-3.86(m, 2H), 2.90(d, 2H), 2.43(s, 3H), 0.78(s, 9H) | D6-DMSO |
| 114 | 3.66 | 3.63 | 7.91-7.88(m, 1H), 7.49(d, 1H), 4.33-3.66(m, 4H), 2.97-2.87(m, 2H), 2.43(d, 3H), 0.81(d, 9H) | D6-DMSO |
| 115 | 4.33 | 4.31 | 7.63(d, 1H), 7.38(d, 1H), 4.50-4.10(m, 2H), 3.89(q, 2H), 3.02-3.00(m, 2H), 2.43(s, 3H), 1.77-1.70(m, 1H), 0.82-0.80(m, 6H) | D6-DMSO |
| 116 | 2.40 | 2.39 | 7.72(d, 1H), 7.42(d, 1H), 3.93(q, 2H), 3.19(s, 6H), 2.44(s, 3H) | D6-DMSO |
| 117 | 1.54 | 1.50 | 7.99(d, 1H), 7.54(d, 1H), 4.29-4.25(m, 1H), 3.96-3.89(m, 1H), 3.19(s, 6H), 2.50(s, 3H) | D6-DMSO |

-continued

| Ex. No. | logP (HCOOH) | logP (neutral) | NMR data | Solvent |
|---|---|---|---|---|
| 118 | 3.03 | | 7.72(d, 1H), 7.40(d, 1H), 3.96(q, 2H), 3.61(q, 4H), 2.42(s, 3H), 1.10(t, 6H) | D6-DMSO |
| 119 | 2.07 | | 7.99(d, 1H), 7.55(d, 1H), 4.38-4.18(m, 1H), 4.15-3.92(m, 1H), 3.80-3.58(m, 4H), 2.44(s, 3H), 1.13(t, 6H) | D6-DMSO |
| 120 | 2.46 | | 8.02(d, 1H), 7.56(d, 1H), 5.92-5.79(m, 2H), 5.41-5.28(m, 4H), 4.36-4.20(m, 5H), 4.09-3.96(m, 1H), 2.44(s, 3H) | D6-DMSO |
| 121 | 2.81 | | 7.72(d, 1H), 7.44(d, 1H), 4.50(d, 2H), 3.95(q, 2H), 3.20(s, 3H), 2.45-2.40(m, 4H) | D6-DMSO |
| 122 | 2.71 | | 7.71(d, 1H), 7.40(d, 1H), 3.93(q, 2H), 3.66(q, 2H), 3.16(s, 3H), 2.42(s, 3H), 1.10(t, 3H) | D6-DMSO |
| 123 | 1.96 | | 8.02(d, 1H), 7.18(d, 1H), 4.41(d, 2H), 3.54-3.38(m, 2H), 3.33(s, 3H), 2.44(s, 3H), 2.40(t, 1H) | CDCl3 |
| 124 | 2.00 | | 8.00(d, 1H), 7.55(d, 1H), 5.92-5.80(m, 1H), 5.41-5.28(m, 2H), 4.33-4.20(m, 3H), 4.04-3.91(m, 1H), 3.17(s, 3H), 2.43(s, 3H) | D6-DMSO |
| 125 | 2.91 | | 7.74(d, 1H), 7.43(d, 1H), 5.90-5.79(m, 1H), 5.41-5.28(m, 2H), 4.28(d, 2H), 3.94(q, 2H), 3.16(s, 3H), 2.44(s, 3H) | D6-DMSO |
| 126 | 3.15 | | 7.72(d, 1H), 7.43(d, 1H), 3.95(q, 2H), 3.54(d, 2H), 3.21(s, 3H), 2.44(s, 3H), 1.08-1.05(m, 1H), 0.54-0.47(m, 2H), 0.36-0.30(m, 2H) | D6-DMSO |
| 127 | 3.19 | 3.17 | 7.71(d, 1H), 7.43(d, 1H), 4.01(q, 2H), 3.35(q, 2H), 2.75-2.70(m, 1H), 2.42(s, 3H), 0.97(t, 3H), 0.91-0.87(m, 4H) | D6-DMSO |
| 128 | 3.49 | 3.45 | 7.72(d, 1H), 7.43(d, 1H), 4.01(q, 2H), 3.30(t, 2H), 2.76-2.70(m, 1H), 2.42(s, 3H), 1.42-1.34(m, 2H), 0.92-0.87(m, 4H), 0.72(t, 3H) | D6-DMSO |
| 129 | 3.48 | 3.43 | 7.79(d, 1H), 7.42(d, 1H), 4.35(q, 2H), 4.00(q, 2H), 2.81-2.73(m, 1H), 2.42(s, 3H), 0.98-0.88(m, 4H) | D6-DMSO |
| 130 | 3.31 | 3.28 | 7.67(d, 1H), 7.40(d, 1H), 5.74-5.64(m, 1H), 5.13-5.10(m, 1H), 5.07-5.02(m, 1H), 4.02-3.94(m, 4H), 2.76-2.70(m, 1H), 2.42(s, 3H), 0.92-0.89(m, 4H) | D6-DMSO |
| 131 | 3.00 | 2.97 | 7.49(d, 1H), 7.38(d, 1H), 7.23-7.21(m, 1H), 4.04(q, 2H), 3.51(q, 2H), 3.00(s, 3H), 2.37(s, 3H), 1.17(t, 3H) | D6-DMSO |
| 132 | 3.42 | 3.38 | 7.48(d, 1H), 7.38(d, 1H), 7.22-7.19(m, 1H), 4.25-4.18(m, 1H), 4.04(q, 2H), 2.98(s, 3H), 2.37(s, 3H), 1.37(d, 6H) | D6-DMSO |
| 133 | 3.77 | 3.73 | 7.52(d, 1H), 7.38(d, 1H), 7.24-7.21(m, 1H), 4.26-4.19(m, 1H), 4.05(q, 2H), 3.44(q, 2H), 2.37(s, 3H), 1.38(d, 6H), 0.95(t, 3H) | D6-DMSO |
| 134 | 4.32 | 4.27 | 7.49(d, 1H), 7.37(d, 1H), 7.22-7.20(m, 1H), 4.05(q, 2H), 3.40(q, 2H), 2.37(s, 3H), 1.58(s, 9H), 0.94(t, 3H) | D6-DMSO |
| 135 | 4.77 | 4.70 | 7.52(d, 1H), 7.35(d, 1H), 7.23-7.21(m, 1H), 4.04(q, 2H), 3.74(m, 1H), 2.37(s, 3H), 1.56(s, 9H), 1.14(d, 6H) | D6-DMSO |
| 136 | 4.17 | 4.13 | 7.71(d, 1H), 7.43(d, 1H), 4.03(q, 2H), 3.87-3.78(m, 1H), 2.93(s, 3H), 2.42(s, 3H), 2.03-1.99(m, 2H), 1.81-1.71(m, 4H), 1.64-1.61(m, 1H), 1.33-1.25(m, 2H), 1.13(m, 1H) | D6-DMSO |
| 137 | 3.02 | 2.96 | 7.90(d, 1H), 7.54(d, 1H), 4.22-4.18(m, 2H), 3.40-3.37(m, 2H), 2.42(s, 3H), 1.58(s, 9H), 0.98(t, 3H) | D6-DMSO |
| 138 | 2.20 | 2.19 | 7.82(d, 1H), 7.58-7.55(m, 1H), 7.49(d, 1H), 4.22-4.03(m, 2H), 3.59-3.45(m, 4H), 2.39(s, 3H), 1.18(t, 3H), 0.98(t, 3H) | D6-DMSO |
| 139 | 2.71 | 2.70 | 7.77(d, 1H), 7.50-7.48(m, 2H), 4.18-4.06(m, 2H), 3.00(s, 3H), 2.38(s, 3H), 1.58(s, 9H) | D6-DMSO |

-continued

| Ex. No. | logP (HCOOH) | logP (neutral) | NMR data | Solvent |
|---|---|---|---|---|
| 140 | 2.56 | 2.54 | 7.87(d, 1H), 7.57-7.55(m, 1H), 7.48(d, 1H), 4.23-4.13(m, 1H), 4.07-3.98(m, 1H), 3.80-3.74(m, 1H), 3.51(q, 2H), 2.38(s, 3H), 1.23(d, 3H), 1.21-1.15(m, 6H) | D6-DMSO |
| 141 | 2.27 | 2.24 | 7.78(d, 1H), 7.53-7.47(m, 2H), 4.26-4.15(m, 2H), 4.09-4.02(m, 1H), 3.03(s, 3H), 2.38(s, 3H), 1.38(d, 6H) | D6-DMSO |
| 142 | 4.19 | 4.13 | 7.74(d, 1H), 7.35(d, 1H), 4.12-3.86(broad, 2H), 3.52-3.41(broad, 2H), 2.39(s, 3H), 1.23(s, 9H), 1.14(t, 3H) | D6-DMSO |
| 143 | | 4.56 | 7.73(d, 1H), 7.35(d, 1H), 4.22-4.15(m, 1H), 4.11-3.85(broad, 2H), 2.39(s, 3H), 1.35(d, 6H), 1.22(s, 9H) | D6-DMSO |
| 144 | 4.08 | 4.07 | 7.73(d, 1H), 7.34(d, 1H), 4.10-3.85(broad, 2H), 2.70-2.64(m, 1H), 2.39(s, 3H), 1.20(s, 9H), 0.91-0.82(m, 4H) | D6-DMSO |
| 145 | 3.54 | 3.49 | 7.81(d, 1H), 7.43(d, 1H), 4.41(q, 2H), 4.02(q, 2H), 3.58(q, 2H), 2.43(s, 3H), 1.20(t, 3H) | D6-DMSO |
| 146 | 3.85 | 3.90 | 7.80(d, 1H), 7.43(d, 1H), 4.39(q, 2H), 4.30-4.23(m, 1H), 4.02(q, 2H), 2.43(s, 3H), 1.40(d, 6H) | D6-DMSO |
| 147 | 4.34 | 4.28 | 7.78(d, 1H), 7.42(d, 1H), 4.35(q, 2H), 4.02(q, 2H), 2.42(s, 3H), 1.59(s, 9H) | D6-DMSO |
| 148 | 3.82 | 3.78 | 7.78(d, 1H), 7.44(d, 1H), 4.04(q, 2H), 3.54(q, 2H), 3.24(d, 2H), 2.42(s, 3H), 1.75-1.65(m, 1H), 1.18(t, 3H), 0.73(d, 6H) | D6-DMSO |
| 149 | 4.27 | 4.21 | 7.76(d, 1H), 7.43(d, 1H), 4.30-4.20(m, 1H), 4.04(q, 2H), 3.21(d, 2H), 2.42(s, 3H), 1.76-1.65(m, 1H), 1.38(d, 6H), 0.73(d, 6H) | D6-DMSO |
| 151 | 1.98 | 1.88 | 7.90(d, 1H), 7.53(d, 1H), 4.25-4.10(m, 2H), 2.95(s, 3H), 2.73-2.67(m, 1H), 2.42(s, 3H), 0.93-0.88(m, 4H) | D6-DMSO |
| 152 | 3.40 | 3.35 | 8.10-7.85(broad, 1H), 7.47(d, 1H), 4.30-4.10(m, 3H), 2.44(s, 3H), 1.35(d, 6H), 1.30-1.15(broad, 9H) | D6-DMSO |
| 153 | 2.95 | 3.04 | 8.03(d, 1H), 7.55(d, 1H), 4.44(q, 2H), 4.31-4.10(m, 3H), 2.44(s, 3H), 1.40(d, 6H) | D6-DMSO |
| 154 | 3.62 | 3.64 | 7.82(d, 1H), 7.44(d, 1H), 5.94-5.82(m, 1H), 5.24-5.15(m, 2H), 4.44(q, 2H), 4.18-4.15(m, 2H), 4.03(q, 2H), 2.43(s, 3H) | D6-DMSO |
| 155 | 3.93 | 3.90 | 7.94(d, 1H), 7.60-7.44(m, 6H), 4.50(q, 2H), 4.04(q, 2H), 2.45(s, 3H) | D6-DMSO |
| 156 | 3.44 | 3.51 | 7.83(d, 1H), 7.45(d, 1H), 6.46-6.14(m, 1H), 4.46(q, 2H), 4.07-3.96(m, 4H), 2.43(s, 3H) | D6-DMSO |
| 157 | 3.31 | 1.33 | 11.55(s, 1H), 7.84(d, 1H), 7.68(s, 1H), 7.59-7.53(m, 2H), 7.52-7.50(m, 1H), 7.42(d, 1H), 3.96(q, 2H), 2.43(s, 3H) | D6-DMSO |
| 158 | 2.69 | 1.10 | | |
| 159 | 2.96 | 2.95 | 7.70(d, 1H), 7.49(d, 1H), 4.02(q, 2H), 3.56(t, 2H), 3.36(t, 2H), 3.21(s, 3H), 2.95(s, 3H), 2.43(s, 3H), 1.86-1.79(m, 2H) | D6-DMSO |
| 160 | 3.28 | 3.22 | 7.72(d, 1H), 7.44(d, 1H), 4.03(q, 2H), 3.46(t, 2H), 2.95(s, 3H), 2.43(s, 3H), 1.67-1.58(m, 2H), 0.88(t, 3H) | D6-DMSO |
| 161 | 3.39 | 3.34 | 7.73(d, 1H), 7.44(d, 1H), 4.03(q, 2H), 3.38(d, 2H), 2.97(s, 3H), 2.43(s, 3H), 1.16-1.08(m, 1H), 0.52-0.46(m, 2H), 0.35-0.29(m, 2H) | D6-DMSO |
| 162 | 3.42 | 3.27 | 7.83(d, 1H), 7.56-7.44(m, 6H), 4.04(q, 2H), 3.05(s, 3H), 2.45(s, 3H) | D6-DMSO |
| 163 | 2.44 | 2.38 | 8.07(d, 1H), 7.58(d, 1H), 7.55-7.51(m, 4H), 7.48-7.41(m, 1H), 4.31-4.10(m, 2H), 3.09(s, 3H), 2.44(s, 3H) | D6-DMSO |
| 164 | 2.58 | 2.54 | 8.03(d, 1H), 7.53(d, 1H), 4.40(q, 2H), 4.24-4.18(m, 1H), 4.15-4.04(m, 1H), 2.80-2.74(m, 1H), 2.43(s, 3H), 0.94-0.92(m, 4H) | D6-DMSO |
| 165 | 2.32 | 2.30 | 7.92(d, 1H), 7.51(d, 1H), 5.75-5.67(m, 1H), 5.16-5.14(m, 1H), 5.09-5.05(m, 1H), 4.25-4.07(m, 2H), | D6-DMSO |

-continued

| Ex. No. | logP (HCOOH) | logP (neutral) | NMR data | Solvent |
|---|---|---|---|---|
| | | | 4.00(d, 2H), 2.77-2.71(m, 1H), 2.41(s, 3H), 0.91-0.89(m, 4H) | |
| 166 | 2.72 | 2.89 | 8.05(d, 1H), 7.56(d, 1H), 5.94-5.84(m, 1H), 5.24-5.17(m, 2H), 4.48(q, 2H), 4.25-4.10(m, 4H), 2.44(s, 3H) | D6-DMSO |
| 167 | 3.05 | 3.01 | 8.20(d, 1H), 7.60-7.47(m, 6H), 4.55(q, 2H), 4.28-4.02(m, 2H), 2.45(s, 3H) | D6-DMSO |
| 168 | 2.60 | 2.58 | 8.06(d, 1H), 7.57(d, 1H), 6.45-6.16(m, 1H), 4.51-4.46(m, 2H), 4.26-3.96(m, 4H), 2.44(s, 3H) | D6-DMSO |
| 169 | 2.30 | 2.33 | 7.93(d, 1H), 7.56(d, 1H), 4.28-4.11(m, 2H), 3.38(d, 2H), 3.01(s, 3H), 2.43(s, 3H), 1.15-1.05(m, 1H), 0.51-0.45(m, 2H), 0.35-0.28(m, 2H) | D6-DMSO |
| 170 | 1.97 | 1.98 | 7.92(d, 1H), 7.55(d, 1H), 4.23-4.15(m, 2H), 3.56(t, 2H), 3.36(t, 2H), 3.21(s, 3H), 2.99(s, 3H), 2.42(s, 3H), 1.87-1.80(m, 2H) | D6-DMSO |
| 171 | 2.18 | 2.15 | 7.93(d, 1H), 7.54(d, 1H), 4.25-4.09(m, 2H), 3.43-3.37(m, 2H), 2.76-2.70(m, 1H), 2.42(s, 3H), 0.98(t, 3H), 0.91-0.87(m, 4H) | D6-DMSO |
| 172 | 2.46 | 2.42 | 7.93(d, 1H), 7.54(d, 1H), 4.27-4.08(m, 2H), 3.40-3.35(m, 2H), 2.76-2.71(m, 1H), 2.42(s, 3H), 1.45-1.36(m, 2H), 0.91-0.88(m, 4H), 0.75(t, 3H) | D6-DMSO |
| 173 | 3.64 | 3.58 | 7.74(d, 1H), 7.36-7.30(m, 5H), 7.27-7.23(m, 1H), 3.85(q, 2H), 2.30(s, 3H), 1.43(s, 6H) | D6-DMSO |
| 174 | 2.84 | 2.79 | 7.76(d, 1H), 7.45(d, 1H), 4.04(q, 2H), 2.93(s, 3H), 2.43(s, 3H), 1.30(s, 6H) | D6-DMSO |
| 175 | 3.41 | 3.40 | 7.64(d, 1H), 7.46(d, 1H), 4.04(q, 2H), 2.96(s, 3H), 2.38(s, 3H), 1.79-1.66(m, 4H), 0.83(t, 6H) | D6-DMSO |
| 176 | 2.37 | 2.31 | 7.87(d, 1H), 7.59(d, 1H), 4.27-4.18(m, 2H), 3.00(s, 3H), 2.44(s, 3H), 1.80-1.70(m, 4H), 0.84(q, 6H) | D6-DMSO |
| 177 | 1.89 | 1.85 | 7.98(d, 1H), 7.57(d, 1H), 4.30-4.10(m, 2H), 2.98(s, 3H), 2.44(s, 3H), 1.32(s, 6H) | D6-DMSO |
| 178 | 3.80 | 3.76 | 7.61(d, 1H), 7.31-7.23(m, 4H), 6.97-6.89(m, 2H), 4.65(broad, 2H), 3.96(q, 2H), 2.39(s, 3H), 1.30(s, 6H) | D6-DMSO |
| 179 | 3.00 | 2.96 | 7.71(d, 1H), 7.43(d, 1H), 4.01(q, 2H), 2.89(s, 3H), 2.43(s, 3H), 2.46-2.33(m, 4H), 2.16-2.09(m, 2H) | D6-DMSO |
| 180 | 1.99 | 1.97 | 7.92(d, 1H), 7.54(d, 1H), 4.30-4.08(m, 2H), 2.93(s, 3H), 2.48-2.31(m, 7H), 2.19-2.05(m, 2H) | D6-DMSO |
| 181 | 3.44 | 3.39 | 7.85(d, 1H), 7.50(d, 1H), 4.03(q, 2H), 3.31(s, 3H), 2.92-2.87(m, 1H), 2.44(s, 3H), 1.04-0.97(m, 4H) | D6-DMSO |
| 182 | 3.83 | 3.76 | 7.96(d, 1H), 7.55(d, 1H), 4.11-3.95(m, 2H), 3.39(s, 3H), 3.00-2.91(m, 1H), 2.46(s, 3H), 1.25-1.10(m, 4H) | D6-DMSO |
| 183 | 2.31 | | 7.98-7.96(m, 1H), 7.58-7.56(m, 1H), 4.35-4.26(m, 1H), 3.90-3.81(m, 1H), 2.73-2.67(m, 1H), 2.42(s, 3H), 0.98-0.88(m, 4H) | D6-DMSO |
| 184 | 2.44 | | 7.91-7.90(m, 1H), 7.42(s, 1H), 6.22(tt, 1H), 4.30-4.22(m, 1H), 4.08-3.99(m, 2H), 3.83-3.73(m, 1H), 2.38(s, 3H), 2.25(s, 3H) | D6-DMSO |
| 185 | 4.32 | 4.27 | 7.67(d, 1H), 7.47(d, 1H), 4.00-3.90(m, 1H), 3.84(q, 2H), 2.47(s, 3H), 2.00-1.89(m, 2H), 1.86-1.75(m, 4H), 1.67-1.58(m, 1H), 1.39-1.25(m, 2H), 1.20-1.09(m, 1H) | D6-DMSO |
| 186 | 3.36 | 3.33 | 8.03(d, 1H), 7.57(d, 1H), 4.35-4.26(m, 1H), 3.99-3.83(m, 2H), 2.43(s, 3H), 2.00-1.90(m, 2H), 1.86-1.75(m, 3H), 1.69-1.60(m, 1H), 1.39-1.22(m, 2H), 1.22-1.09(m, 2H) | D6-DMSO |

-continued

| Ex. No. | logP (HCOOH) | logP (neutral) | NMR data | Solvent |
|---|---|---|---|---|
| 187 | 4.21 | | 7.54(s, 1H), 7.32(s, 1H), 4.84-4.69(m, 2H), 3.83-3.76(q, 2H), 2.41(s, 3H), 2.13(s, 3H) | D6-DMSO |
| 188 | 3.18 | | 7.94(s, 1H), 7.41(s, 1H), 4.84-4.68(m, 2H), 4.31-4.23(m, 1H), 3.81-3.68(m, 1H), 2.39(s, 3H), 2.22(s, 3H) | D6-DMSO |
| 189 | 3.95 | | 7.70(d, 1H), 7.49(d, 1H), 4.87-4.71(m, 2H), 3.84(q, 2H), 2.49(s, 3H) | D6-DMSO |
| 190 | 3.03 | | 8.08(d, 1H), 7.59(d, 1H), 4.87-4.69(m, 2H), 4.38-3.80(m, 2H), 2.44(s, 3H) | D6-DMSO |
| 191 | 4.62 | 4.54 | 7.70(d, 1H), 7.47(d, 1H), 3.83(q, 2H), 3.75-3.66(m, 2H), 2.48(s, 3H), 2.18-2.11(m, 1H), 0.96-0.91(m, 6H) | D6-DMSO |
| 192 | 4.89 | 4.80 | 7.69(d, 1H), 7.47(d, 1H), 3.87-3.77(m, 4H), 2.48(s, 3H), 0.99(s, 9H) | D6-DMSO |
| 193 | 4.50 | 4.42 | 7.64(d, 1H), 7.44(d, 1H), 3.82(q, 2H), 2.47(s, 3H), 1.79(s, 9H) | D6-DMSO |
| 194 | 3.56 | 3.53 | 8.09-8.06(m, 1H), 7.57(d, 1H), 4.38-3.64(m, 4H), 2.44(s, 3H), 2.17-2.12(m, 1H), 0.95(d, 6H) | D6-DMSO |
| 195 | 3.85 | 3.79 | 8.08-8.05(m, 1H), 7.57(d, 1H), 4.36-4.30(m, 1H), 3.89-3.71(m, 3H), 2.44(s, 3H), 1.00(d, 9H) | D6-DMSO |
| 196 | 3.45 | 3.41 | 8.00(d, 1H), 7.54(d, 1H), 4.40-3.45(m, 2H), 2.43(d, 3H), 1.79(d, 9H) | D6-DMSO |
| 197 | 1.97 | 1.89 | 7.90(d, 1H), 7.53(d, 1H), 4.25-4.10(m, 2H), 2.95(s, 3H), 2.73-2.67(m, 1H), 2.42(s, 3H), 0.93-0.88(m, 4H) | D6-DMSO |
| 198 | 2.79 | 2.75 | 7.67-7.65(m, 1H), 7.25-7.21(m, 1H), 3.91-3.83(q, 2H), 3.73(t, 2H), 3.44(t, 2H), 2.75(s, 3H), 2.37(s, 3H) | D6-DMSO |
| 199 | 1.76 | 1.74 | 7.99-7.97(m, 1H), 7.35-7.32(m, 1H), 4.18-4.09(m, 1H), 3.98-3.92(m, 1H), 3.83-3.81(d, 1H), 3.76-3.74(d, 1H), 3.48(t, 2H), 2.77(s, 3H), 2.35(s, 3H) | D6-DMSO |
| 200 | 2.42 | 2.33 | 7.61(d, 1H), 7.39(d, 1H), 4.20(broad, 2H), 3.90(q, 2H), 2.93(s, 3H), 2.43(s, 3H) | D6-DMSO |
| 201 | 2.02 | 1.99 | 7.94(d, 1H), 7.51(d, 1H), 5.92-5.82(m, 1H), 5.37-5.31(m, 1H), 5.28-5.21(m, 1H), 4.35-4.22(m, 1H), 4.17(s, 2H), 4.00(d, 2H), 3.98-3.85(m, 1H), 2.42(s, 3H) | D6-DMSO |
| 202 | 3.39 | 3.35 | 7.62(d, 1H), 7.39(d, 1H), 4.21(broad, 2H), 3.90(q, 2H), 3.35(t, 2H), 2.44(s, 3H), 1.59-1.50(m, 2H), 1.38-1.28(m, 2H), 0.91(t, 3H) | D6-DMSO |
| 203 | 2.47 | 2.43 | 8.91(d, 1H), 7.50(d, 1H), 4.38-4.20(m, 1H), 4.22(s, 2H), 3.98-3.88(m, 1H), 3.36(t, 2H), 2.42(s, 3H), 1.60-1.50(m, 2H), 1.39-1.30(m, 2H), 0.92(t, 3H) | D6-DMSO |
| 204 | 3.49 | 3.48 | 7.69(d, 1H), 7.42-7.31(m, 6H), 4.48(s, 2H), 4.14(broad, 2H), 3.91(q, 2H), 2.45(s, 3H) | D6-DMSO |
| 205 | 2.60 | 2.52 | 7.99(d, 1H), 7.52(d, 1H), 7.42-7.31(m, 5H), 4.59(s, 2H), 4.38-4.21(m, 1H), 4.15(s, 2H), 3.99-3.85(m, 1H), 2.43(s, 3H) | D6-DMSO |
| 206 | 2.08 | | 7.99(dd, 1H), 7.21(d, 1H), 5.15-5.08(m, 1H), 3.52-3.41(m, 2H), 2.45(s, 3H), 1.76-1.73(m, 3H) | CDCl3 |
| 207 | 1.57 | −0.23 | 10.89(s, 1H), 7.99(d, 1H), 7.48(d, 1H), 4.25-4.16(m, 1H), 4.06-3.97(m, 1H), 2.73-2.66(m, 1H), 2.40(s, 3H), 0.91-0.87(m, 4H) | D6-DMSO |
| 208 | 1.68 | | 8.18(d, 1H), 7.11(d, 1H), 4.44(d, 1H), 4.27(d, 1H), 3.54-3.38(m, 2H), 3.14(s, 3H), 2.42(s, 3H) | CDCl3 |
| 209 | 1.92 | | 8.18(d, 1H), 7.10(d, 1H), 4.38(d, 1H), 4.18(d, 1H), 3.55-3.39(m, 2H), 2.73-2.67(m, 1H), 2.42(s, 3H), 1.05-1.04(m, 4H) | CDCl3 |

-continued

| Ex. No. | logP (HCOOH) | logP (neutral) | NMR data | Solvent |
|---|---|---|---|---|
| 210 | 2.91 | | 7.76(d, 1H), 7.05(d, 1H), 4.26(s, 2H), 3.35(q, 2H), 2.72-2.66(m, 1H), 2.48(s, 3H), 1.06-1.01(m, 4H) | CDCl3 |
| 211 | 2.66 | | 7.76(d, 1H), 7.06(d, 1H), 4.44(s, 2H), 3.34(q, 2H), 3.13(s, 3H), 2.48(s, 3H) | CDCl3 |
| 212 | 2.92 | | 7.60(d, 1H), 7.08(d, 1H), 4.51(q, 1H), 3.34(q, 2H), 3.12(s, 3H), 2.50(s, 3H), 1.37(d, 3H) | CDCl3 |
| 213 | 1.91 | | 8.12-7.97(m, 1H), 7.16-7.10(m, 1H), 4.62-4.49(m, 1H), 3.60-3.39(m, 2H), 3.13(s, 3H), 2.42(s, 3H), 1.40-1.37(m, 3H) -isomer mixture | CDCl3 |
| 214 | 3.12 | | 7.61(d, 1H), 7.07(d, 1H), 4.42(q, 1H), 3.32(q, 2H), 2.72-2.70(m, 1H), 2.49(s, 3H), 1.34(d, 3H), 1.06-0.97(m, 4H) | CDCl3 |
| 215 | 2.15 | | 8.13-7.95(m, 1H), 7.15-7.09(m, 1H), 4.55-4.40(m, 1H), 3.57-3.40(m, 2H), 2.72-2.69(m, 1H), 2.42(s, 3H), 1.37-1.26(m, 3H), 1.05-1.01(m, 4H) | CDCl3 |
| 216 | 2.05 | | 7.86(d, 1H), 7.17(d, 1H), 3.45(q, 2H), 3.14(s, 3H), 2.44(s, 3H), 1.47(s, 3H), 1.41(s, 3H) | CDCl3 |
| 217 | 3.11 | | 7.41(d, 1H), 7.14(d, 1H), 3.32(q, 2H), 3.12(s, 3H), 1.41(s, 3H), 1.40(s, 3H) | CDCl3 |

The optical rotations were determined on a Perkin Elmer 341, serial number 9123, at a wavelength of 589 nm and a temperature of 20° C., by the following formula:

$$(\text{Specific optical rotation } \alpha)_D^{*C} = \frac{\text{Rotation angle } \alpha * \text{ Solution volume(ml)}}{\text{cell length(dm)} * \text{weight(g)}}$$

The specific optical rotations below should be understood as an average from 5 different measurements:

| | |
|---|---|
| 151 | 88.7 in $CHCl_3$ (c = 0.009) |
| 197 | −89.1 in $CHCl_3$ (c = 0.009) |

Use Examples

*Amblyomma hebaraeum* Test (AMBYHE)

Solvent: dimethyl sulfoxide

To produce a suitable preparation of active compound, 10 mg of active compound are mixed with 0.5 ml of dimethyl sulfoxide, and the concentrate is diluted with water to the desired concentration.

Tick nymphs (*Amblyomma hebraeum*) are placed into perforated plastic beakers and immersed in the desired concentration for one minute. The ticks are transferred on filter paper into a Petri dish and stored in a climate-controlled cabinet.

After 42 days, the kill in % is determined. 100% means that all of the ticks have been killed; 0% means that none of the ticks have been killed.

In this test, for example, the following compounds of the preparation examples show an efficacy of 100% at an application rate of 100 ppm: 91

*Boophilus microplus*—Dip Test (BOOPMI Dip)

Test animals: cattle ticks (*Boophilus microplus*) Parkhurst strain, SP-resistant Solvent: dimethyl sulfoxide 10 mg of active compound are dissolved in 0.5 ml of dimethyl sulfoxide. To produce a suitable formulation, the active compound solution is diluted with water to the concentration desired in each case.

This active compound preparation is pipetted into tubes. 8-10 engorged adult female cattle ticks (*Boophilus microplus*) are transferred into a further tube with holes. The tube is immersed into the active compound preparation, and all the ticks are completely wetted. After the liquid has run out, the ticks are transferred on filter disks into plastic dishes and stored in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 100 ppm: 91

In this test, for example, the following compounds from the preparation examples show an efficacy of 90% at an application rate of 100 ppm: 141

*Boophilus microplus*—Injection Test (BOOPMI inj)

Solvent: dimethyl sulfoxide

To produce a suitable preparation of active compound, 10 mg of active compound are mixed with 0.5 ml of solvent and the concentrate is diluted with solvent to the desired concentration.

1 μl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 μg/animal: 13, 26, 34, 35, 37, 47, 54, 91, 104, 106, 115, 141, 208, 209, 210, 211 In this test, for example, the following compounds from the preparation examples show an efficacy of 80% at an application rate of 20 μg/animal: 16, 48

*Meloidogvne incognita* test (MELGIN)

Solvent: 125.0 parts by weight of acetone

To produce a suitable preparation of active compound, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples show an efficacy of 100% at an application rate of 20 ppm: 35, 36, 37, 38, 52, 83

In this test, for example, the following compounds from the preparation examples show an efficacy of 90% at an application rate of 20 ppm: 13, 20, 24, 27, 28, 29, 30, 33, 34, 41, 42, 44, 45, 54, 69, 70, 74, 80, 81, 127, 177, 179, 181, 182, 208, 209, 210

*Myzus persicae*—Spray Test (MYZUPE)

Solvent: 78 parts by weight of acetone 1.5 parts by weight of dimethylformamide

Emulsifier: alkylaryl polyglycol ether

To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Disks of Chinese cabbage leaves (*Brassica pekinensis*) infested by all stages of the green peach aphid (*Myzus persicae*) are sprayed with an active compound preparation of the desired concentration.

After 6 days, the efficacy in % is determined. 100% means that all the aphids have been killed; 0% means that none of the aphids have been killed.

In this test, for example, the following compounds from the preparation examples show an efficacy of 100% at an application rate of 500 g/ha: 141, 206

*Phaedon cochleariae*—Spray Test (PHAECO)

Solvent: 78.0 parts by weight of acetone 1.5 parts by weight of dimethylformamide Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

disks of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 500 g/ha: 52, 57, 84, 185, 186, 190, 200

In this test, for example, the following compounds from the preparation examples show an efficacy of 83% at an application rate of 500 g/ha: 60, 198, 211

*Spodoptera frugiperda*—Spray Test (SPODFR)

Solvent: 78.0 parts by weight of acetone 1.5 parts by weight of dimethylformamide Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Leaf disks of maize (*Zea mays*) are sprayed with an active compound preparation of the desired concentration and, after drying, populated with caterpillars of the armyworm (*Spodoptera frugiperda*).

After 7 days, the efficacy in % is determined. 100% means that all the caterpillars have been killed; 0% means that no caterpillars have been killed.

In this test, for example, the following compounds from the preparation examples show an efficacy of 100% at an application rate of 500 g/ha: 157, 200

In this test, for example, the following compounds from the preparation examples show an efficacy of 83% at an application rate of 500 g/ha: 207

*Tetranychus urticae*—Spray Test, OP-Resistant (TETRUR)

Solvent: 78.0 parts by weight of acetone 1.5 parts by weight of dimethylformamide Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

disks of bean leaves (*Phaseolus vulgaris*) infested with all stages of the greenhouse red spider mite (*Tetranychus urticae*) are sprayed with an active compound preparation of the desired concentration.

After 6 days, the efficacy in % is determined. 100% means that all the spider mites have been killed; 0% means that none of the spider mites have been killed.

In this test, for example, the following compounds from the preparation examples show an efficacy of 100% at an application rate of 500 g/ha: 2, 5, 8, 14, 15, 17, 18, 19, 20, 21, 23, 26, 27, 30, 32, 34, 35, 36, 37, 38, 39, 40, 42, 46, 48, 52, 53, 54, 58, 59, 65, 66, 67, 68, 76, 80, 83, 89, 90, 91, 92, 97, 101, 104, 106, 109, 113, 115, 116, 118, 121, 123, 124, 125, 127, 129, 130, 132, 133, 134, 139, 142, 143, 145, 147, 154, 159, 161, 171, 174, 175, 176, 178, 179, 180, 183, 184, 186, 191, 193, 198, 199, 201, 202, 204, 208, 209, 210, 211, 213, 214, 215

In this test, for example, the following compounds from the preparation examples show an efficacy of 90% at an application rate of 500 g/ha: 1, 3, 6, 9, 10, 11, 12, 13, 22, 24, 25, 29, 31, 33, 41, 43, 47, 49, 50, 51, 55, 56, 61, 62, 63, 64, 72, 82, 85, 87, 98, 99, 105, 108, 111, 114, 117, 120, 122, 126, 131, 135, 136, 137, 138, 140, 141, 150, 151, 155, 156, 163, 164, 165, 166, 167, 168, 170, 172, 173, 177, 181, 185, 187, 188, 189, 190, 192, 193, 194, 195, 196, 200, 203, 205, 207, 212, 217

In this test, for example, the following compounds from the preparation examples shows an efficacy of 100% at an application rate of 100 g/ha: 81, 110, 112, 160, 162

In this test, for example, the following compounds from the preparation examples shows an efficacy of 90% at an application rate of 100 g/ha: 74, 79, 94, 169

*Tetranychus urticae*—Spray Test, OP-Resistant (TETRUR)

Solvent: 7 parts by weight of dimethylformamide

Emulsifier: alkylaryl polyglycol ether

To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the preparation solution.

Bean plants (*Phaseolus vulgaris*) heavily infested by all stages of the greenhouse red spider mite (*Tetranychus urticae*) are treated by spraying with the active compound preparation of the desired concentration.

After 7 days, the efficacy in % is determined. 100% means that all the spider mites have been killed; 0% means that none of the spider mites have been killed.

In this test, for example, the following compound from the preparation examples shows an efficacy of 100% at an application rate of 20 ppm: 77

The invention claimed is:

1. A compound of formula (I)

(I)

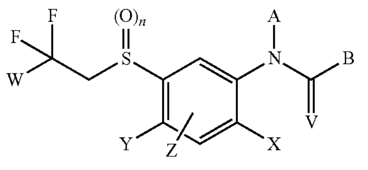

in which

A and B together with the atoms to which they are attached represent; a substructure selected from the group consisting of (I-A)

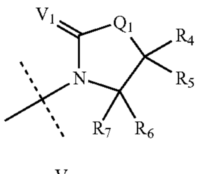

(I-B)

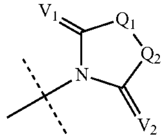

(I-C)

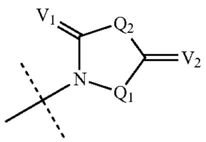

-continued (I-D)

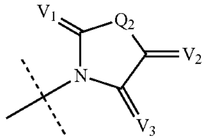

wherein when substructure of formula (I-A), (I-B) or (I-D) is present then $V^1$, $V^2$ and $V^3$ each independently of one another are oxygen; sulfur, an optionally substituted nitrogen or salts of an optionally substituted nitrogen; and wherein when substructure of formula (I-C) is present then $V^1$, $V^2$ and $V^3$ each independently of one another represent oxygen or sulfur, $Q^1$ and $Q^2$ each independently of one another represent oxygen, sulfur or an optionally substituted nitrogen; or represent an optionally substituted carbon atom; with the proviso, that $Q_1$ does not represent an alkylcarbonylamino radical;

$R^4$, $R^5$, $R^6$ and $R^7$ each independently of one another represent hydrogen, cyano, halogen or nitro; or represent alkyl, cycloalkylalkyl, haloalkyl, cyanoalkyl, hydroxyalkyl, alkoxyalkyl, aminoalkyl, alkoxycarbonylalkyl, alkylthioalkyl, haloalkylthioalkyl, alkoxyalkylthioalkyl, alkylsulfanylalkyl, alkylsulfinylalkyl, alkylsulfonylalkyl, haloalkylsulfanylalkyl, haloalkylsulfinylalkyl, haloalkylsulfonylalkyl, alkoxyalkylsulfanylalkyl, alkoxyalkylsulfinylalkyl, alkoxyalkylsulfonylalkyl, phenylalkyl, phenoxyalkyl, phenylsulfanylalkyl, phenylsulfinylalkyl, phenylsulfonylalkyl, hetarylalkyl, hetaryloxyalkyl or hetarylthioalkyl, where the aforementioned radicals may each be saturated or unsaturated and/or optionally substituted; or represent optionally substituted saturated or unsaturated cycloalkyl which may optionally be interrupted by one or more heteroatoms; or represent alkylcarbonyl, haloalkylcarbonyl, hydroxyalkylcarbonyl, alkoxyalkylcarbonyl, phenylcarbonyl, hetarylcarbonyl, alkoxycarbonyl, haloalkoxycarbonyl, aryloxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl (aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or represent carbonyl or carboxyl; or represent optionally substituted phenyl or optionally substituted hetaryl;

represent alkoxy, haloalkoxy, alkoxyalkoxy, aryloxy, arylalkyloxy, cycloalkyloxy, cycloalkylalkyloxy or carbonyloxy, where the aforementioned radicals may be saturated or unsaturated and/or optionally substituted, or represent hydroxyl; or represent alkylamino, dialkylamino, haloalkylamino, dihaloalkylamino, cycloalkylamino, dicycloalkylamino, cycloalkyl(alkyl)amino, arylamino, diarylamino, hetarylamino, dihetarylamino, alkyl(aryl) amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulfonylamino, or arylsulfonylamino, where the aforementioned radicals may each be saturated or unsaturated and/or optionally substituted, or represent amino; or represent alkylsulfanyl, alkylsulfinyl, alkylsulfonyl, haloalkylsulfanyl, haloalkylsulfinyl, haloalkylsulfonyl, cycloalkylsulfanyl, cycloalkylsulfinyl, cycloalkylsulfonyl, cycloalkylalkylsulfanyl, cycloalkylalkylsulfinyl, cycloalkylalkylsulfonyl, arylsulfanyl, arylsulfinyl, arylsulfonyl, arylalkylsulfanyl, arylalkylsulfinyl, arylalkylsulfonyl, aminosulfonyl, alkylaminosulfonyl, dialkylaminosulfonyl or arylaminosulfonyl, where the aforementioned radicals may each be saturated or unsaturated and/or optionally substituted, or represent sulfanyl; or $R^4$ and $R^5$ together with the atom to which they are attached may form an optionally substituted, saturated or unsaturated three- to eight-membered ring optionally interrupted by one or more heteroatoms which are selected independently from the group consisting of O, S and N; or $R^6$ and $R^7$ together with the atom to which they are attached may form an optionally substituted, saturated or unsaturated three- to eight-membered ring optionally interrupted by one or more heteroatoms which are selected independently from the group consisting of O, S and N;

W represents hydrogen or halogen;

V represents oxygen; sulfur, an optionally substituted nitrogen or salts of an optionally substituted nitrogen;

X, Y and Z each independently of one another represent hydrogen, halogen, hydroxyl, amino, cyano, nitro, OCN, SCN, $SF_5$; or represent trialkylsilyl, alkyl, haloalkyl, cyanoalkyl, hydroxyalkyl, alkoxycarbonylalkyl, alkoxyalkyl, alkenyl, haloalkenyl, cyanoalkenyl, alkynyl, haloalkynyl, cyanoalkynyl, alkoxy, haloalkoxy, cyanoalkoxy, hydroxycarbonylalkoxy, alkoxycarbonylalkoxy, alkoxyalkoxy, alkylhydroxyimino, alkoxyimino, alkylalkoxyimino, haloalkylalkoxyimino, alkylthio, haloalkylthio, alkoxyalkylthio, alkylthioalkyl, alkylsulfinyl, haloalkylsulfinyl, alkoxyalkylsulfinyl, alkylsulfinylalkyl, alkylsulfonyl, haloalkylsulfonyl, alkoxyalkylsulfonyl, alkylsulfonylalkyl, alkylsulfonyloxy, alkylcarbonyl, haloalkylcarbonyl, carboxyl, alkylcarbonyloxy, alkoxycarbonyl, haloalkoxycarbonyl, aminocarbonyl, alkylaminocarbonyl, dialkylaminocarbonyl, alkenylaminocarbonyl, dialkenylaminocarbonyl, cycloalkylaminocarbonyl, alkylsulfonylamino, aminosulfonyl, alkylaminosulfonyl, dialkylaminosulfonyl, alkylsulfoximino, aminothiocarbonyl, alkylaminothiocarbonyl or dialkylaminothiocarbonyl, where all the aforementioned radicals may optionally be substituted; or represent phenylalkyl, phenoxy, phenylalkyloxy, phenoxyalkyl, phenylthio, phenylthioalkyl, phenylsulfinyl, phenylsulfonyl, hetarylalkyl, hetaryloxy, hetarylalkyloxy, hetarylthio, hetarylsulfinyl or hetarylsulfonyl, where all the aforementioned radicals may optionally be substituted; or represent cycloalkylalkyl, cycloalkyloxy, cycloalkylalkoxy, cycloalkylthio, cycloalkylalkylthio, cycloalkylsulfinyl, cycloalkylalkylsulfinyl, cycloalkylsulfonyl, cycloalkylalkylsulfonyl or cycloalkenyl, where all the aforementioned radicals may each optionally be substituted; or represent NR'R", where R' and R" each independently of one another represent hydrogen, cyano, alkyl, haloalkyl, cyanoalkyl, hydroxyalkyl, alkoxyalkyl, alkylthioalkyl, alkenyl, haloalkenyl, cyanoalkenyl, alkynyl, haloalkynyl, cyanoalkynyl, acyl or alkoxycarbonyl; or R' and R" together with the nitrogen atom to which they are attached may form an optionally substituted, saturated or unsaturated five- to eight-membered ring optionally interrupted by one or more heteroatoms which are selected independently from the group consisting of O, S and N; or represent a 3- to 6-membered saturated, partly saturated or aromatic ring which may optionally contain one to three heteroatoms which are selected independently from the group consisting of O, S and N, and which may optionally be substituted;

or X and Z, or Y and Z, together with the carbon atoms to which they are attached, form a 5- or 6-membered ring which is optionally substituted and optionally interrupted by one or more heteroatoms which are selected independently from the group consisting of O, S, N and CO; and n represents the number 0, 1 or 2.

2. The compound as claimed in claim 1 in which

A and B together with the atoms to which they are attached represent a substructure selected from the group consisting of (I-A) to (I-D), wherein when substructure of formula (I-A), (I-B) or (I-D) is present then $V^1$, $V^2$ and $V^3$ each independently of one another, represent oxygen; sulfur, $NR^{11}$ or a salt of $NR^{11}$, and wherein substructure of formula (I-C) is present then $V^1$, $V^2$ and $V^3$ each independently of one another represent oxygen or sulfur;

$Q^1$ represents oxygen, sulfur, $NR^1$ or $CR^2R$;

$Q^2$ represents $NR^{10}$ or $CR^8R^9$;

$R^1$ represents hydrogen, cyano or nitro; or represents alkyl, cycloalkylalkyl, haloalkyl, cyanoalkyl, hydroxyalkyl, alkoxyalkyl, aminoalkyl, alkoxycarbonylalkyl, alkylsulfanylalkyl, alkylsulfinylalkyl, alkylsulfonylalkyl, haloalkylsulfanylalkyl, haloalkylsulfinylalkyl, haloalkylsulfonylalkyl, alkoxyalkylsulfanylalkyl, alkoxyalkylsulfinylalkyl, alkoxyalkylsulfonylalkyl, phenylalkyl, phenoxyalkyl, phenylsulfanylalkyl, phenylsulfinylalkyl, phenylsulfonylalkyl, hetarylalkyl, hetaryloxyalkyl, hetarylthioalkyl, alkoxycarbonyl, aryloxycarbonyl, arylcarbamoyl, where the aforementioned radicals may each be saturated or unsaturated and/or optionally substituted; or represents optionally substituted saturated or unsaturated cycloalkyl which may optionally be interrupted by one or more heteroatoms; or represents haloalkylcarbonyl, hydroxyalkylcarbonyl, alkoxyalkylcarbonyl, phenylcarbonyl, hetarylcarbonyl, haloalkoxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl(aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or represents carbonyl or carboxyl; or represents optionally substituted phenyl or optionally substituted hetaryl; or represents alkoxy, haloalkoxy, cycloalkyloxy, aryloxy, arylalkyloxy or carbonyloxy, where the aforementioned radicals may optionally be substituted, or represents hydroxyl; or represents alkylamino, haloalkylamino, dihaloalkylamino, dialkylamino, cycloalkylamino, dicycloalkylamino, cycloalkyl(alkyl)amino, arylamino, diarylamino, hetarylamino, dihetarylamino, alkyl(aryl)amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulfonylamino, or arylsulfonylamino, where the aforementioned radicals may each be saturated or unsaturated and/or optionally substituted, or represents amino; or represents alkylsulfanyl, alkylsulfinyl, alkylsulfonyl, haloalkylsulfanyl, haloalkylsulfinyl, haloalkylsulfanyl, cycloalkylsulfanyl, cycloalkylsulfinyl, cycloalkylsulfonyl, cycloalkylalkylsulfanyl, cycloalkylalkylsulfinyl, cycloalkylalkylsulfonyl, arylsulfanyl, arylsulfinyl, arylsulfonyl, arylalkylsulfanyl, arylalkylsulfinyl, arylalkylsulfonyl, aminosulfonyl, alkylaminosulfonyl, dialkylaminosulfonyl or arylaminosulfonyl, where the aforementioned radicals may each be saturated or unsaturated and/or optionally substituted, or represents sulfanyl; and $R^{10}$ and $R^{11}$ each independently of one another represent hydrogen, cyano or nitro; or represent alkyl, cycloalkylalkyl, haloalkyl, cyanoalkyl, hydroxyalkyl, alkoxyalkyl, aminoalkyl, alkoxycarbonylalkyl, alkylsulfanylalkyl, alkylsulfinylalkyl, alkylsulfonylalkyl, haloalkylsulfanylalkyl, haloalkylsulfinylalkyl, haloalkylsulfonylalkyl, alkoxyalkylsulfanylalkyl, alkoxyalkylsulfinylalkyl, alkoxyalkylsulfonylalkyl, phenylalkyl, phenoxyalkyl, phenylsulfanylalkyl, phenylsulfinylalkyl, phenylsulfonylalkyl, hetarylalkyl, hetaryloxyalkyl, hetarylthioalkyl, alkoxycarbonyl, aryloxycarbonyl, arylcarbamoyl, where the aforementioned radicals may each be saturated or unsaturated and/or optionally substituted; or represent optionally substituted saturated or unsaturated cycloalkyl which may optionally be interrupted by one or more heteroatoms; or represent alkylcarbonyl, haloalkylcarbonyl, hydroxyalkylcarbonyl, alkoxyalkylcarbonyl, phenylcarbonyl, hetarylcarbonyl, haloalkoxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl(aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or represents carbonyl or carboxyl; or represent optionally substituted phenyl or optionally substituted hetaryl; or represent alkoxy, haloalkoxy, cycloalkyloxy, aryloxy, arylalkyloxy or carbonyloxy, where the aforementioned radicals may optionally be substituted, or represents hydroxyl; or represent alkylamino, haloalkylamino, dihaloalkylamino, dialkylamino, cycloalkylamino, dicycloalkylamino, cycloalkyl(alkyl)amino, arylamino, diarylamino, hetarylamino, dihetarylamino, alkyl(aryl)amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulfonylamino, or arylsulfonylamino, where the aforementioned radicals may each be saturated or unsaturated and/or optionally substituted, or represents amino; or represent alkylsulfanyl, alkylsulfinyl, alkylsulfonyl, haloalkylsulfanyl, haloalkylsulfinyl, haloalkylsulfanyl, cycloalkylsulfanyl, cycloalkylsulfinyl, cycloalkylsulfonyl, cycloalkylalkylsulfanyl, cycloalkylalkylsulfinyl, cycloalkylalkylsulfonyl, arylsulfanyl, arylsulfinyl, arylsulfonyl, arylalkylsulfanyl, arylalkylsulfinyl, arylalkylsulfonyl, aminosulfonyl, alkylaminosulfonyl, dialkylaminosulfonyl or arylaminosulfonyl, where the aforementioned radicals may each be saturated or unsaturated and/or optionally substituted, or represents sulfanyl; and $R^2$, $R^3$, $R^4$, $R^5$, $R^6$, $R^7$, $R^8$, and $R^9$ each independently of one another represent hydrogen, cyano, halogen or nitro; or represent alkyl, cycloalkylalkyl, haloalkyl, cyanoalkyl, hydroxyalkyl, alkoxyalkyl, aminoalkyl, alkoxycarbonylalkyl, alkylthioalkyl, haloalkylthioalkyl, alkoxyalkylthioalkyl, alkylsulfanylalkyl, alkylsulfinylalkyl, alkylsulfonylalkyl, haloalkylsulfanylalkyl, haloalkylsulfinylalkyl, haloalkylsulfonylalkyl, alkoxyalkylsulfanylalkyl, alkoxyalkylsulfinylalkyl, alkoxyalkylsulfonylalkyl, phenylalkyl, phenoxyalkyl, phenylsulfanylalkyl, phenylsulfinylalkyl, phenylsulfonylalkyl, hetarylalkyl, hetaryloxyalkyl or hetarylthioalkyl, where the aforementioned radicals may each be saturated or unsaturated and/or optionally substituted; or represent optionally substituted saturated or unsaturated cycloalkyl which may optionally be interrupted by one or more heteroatoms; or represent alkylcarbonyl, haloalkylcarbonyl, hydroxyalkylcarbonyl, alkoxyalkylcarbonyl, phenylcarbonyl, hetarylcarbonyl, alkoxycarbonyl, haloalkoxycarbonyl, aryloxycarbonyl, aminocarbonyl, alkylaminocarbonyl, dialkylaminocarbonyl, cycloalkylaminocarbonyl, dicycloalkylaminocarbonyl, cycloalkyl(alkyl)aminocarbonyl, arylaminocarbonyl, diarylaminocarbonyl, alkyl(aryl)aminocarbonyl, cycloalkyl(aryl)aminocarbonyl, alkylaminothiocarbonyl, dialkylaminothiocarbonyl or aminothiocarbonyl, where the aforementioned radicals may each be saturated or unsaturated and/or optionally substituted, or represent carbonyl or carboxyl; or represent optionally substituted phenyl or optionally substituted hetaryl;

represent alkoxy, haloalkoxy, alkoxyalkoxy, aryloxy, arylalkyloxy, cycloalkyloxy, cycloalkylalkyloxy or carbonyloxy, where the aforementioned radicals may be saturated or unsaturated and/or optionally substituted, or represent hydroxyl; or represent alkylamino, dialkylamino, haloalkylamino, dihaloalkylamino, cycloalkylamino, dicycloalkylamino, cycloalkyl(alkyl)amino, arylamino, diarylamino, hetarylamino, dihetarylamino, alkyl(aryl)

amino, cycloalkyl(aryl)amino, alkylcarbonylamino, arylcarbonylamino, alkoxycarbonylamino, aryloxycarbonylamino, alkylcarbamoylamino, arylcarbamoylamino, alkylsulfonylamino, or arylsulfonylamino, where the aforementioned radicals may each be saturated or unsaturated and/or optionally substituted, or represent amino; or represent alkylsulfanyl, alkylsulfinyl, alkylsulfonyl, haloalkylsulfanyl, haloalkylsulfinyl, haloalkylsulfonyl, cycloalkylsulfanyl, cycloalkylsulfinyl, cycloalkylsulfonyl, cycloalkylalkylsulfanyl, cycloalkylalkylsulfinyl, cycloalkylalkylsulfonyl, arylsulfanyl, arylsulfinyl, arylsulfonyl, arylalkylsulfanyl, arylalkylsulfinyl, arylalkylsulfonyl, aminosulfonyl, alkylaminosulfonyl, dialkylaminosulfonyl or arylaminosulfonyl, where the aforementioned radicals may each be saturated or unsaturated and/or optionally substituted, or represent sulfanyl; or $R^2$ and $R^3$ together with the atom to which they are attached may form an optionally substituted, saturated or unsaturated three- to eight-membered ring optionally interrupted by one or more heteroatoms which are selected independently from the group consisting of O, S and N; or $R^4$ and $R^5$ together with the atom to which they are attached may form an optionally substituted, saturated or unsaturated three- to eight-membered ring optionally interrupted by one or more heteroatoms which are selected independently from the group consisting of O, S and N; or $R^6$ and $R^7$ together with the atom to which they are attached may form an optionally substituted, saturated or unsaturated three- to eight-membered ring optionally interrupted by one or more heteroatoms which are selected independently from the group consisting of O, S and N; or $R^8$ and $R^9$ together with the atom to which they are attached may form an optionally substituted, saturated or unsaturated three- to eight-membered ring optionally interrupted by one or more heteroatoms which are selected independently from the group consisting of O, S and N;

W represents hydrogen or halogen;

X, Y and Z each and independently of one another have the meanings mentioned above; and n represents the number 0 or 1.

3. The compound as claimed in claim 1 in which

A and B together with the atoms to which they are attached represent a substructure selected from the group consisting of (I-A) to (I-D), where wherein when substructure of formula (I-A), (I-B) or (I-D) is present then $V^1$, $V^2$ and $V^3$ each independently of one another, represent oxygen; sulfur, $NR^{11}$ or a salt of $NR^{11}$, and wherein substructure of formula (I-C) is present then $V^1$, $V^2$ and $V^3$ each independently of one another represent oxygen or sulphur;

$Q^1$ represents oxygen, sulfur, $NR^1$ or $CR^2R^3$;

$Q^2$ represents $NR^{10}$ or $CR^8R^9$;

$R^1$ represents hydrogen, cyano or nitro; or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl, hetarylsulfanyl$(C_1-C_6)$alkyl, hetarylsulfinyl$(C_1-C_6)$alkyl, hetarylsulfonyl$(C_1-C_6)$alkyl, $(C_1-C_6)$alkoxycarbonyl, aryloxycarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated $(C_3-C_6)$cycloalkyl which may optionally be interrupted by one or more heteroatoms; or represents halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl($(C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$(C_1-C_6)$alkylamino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl ($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, arylsulfanyl, arylsulfinyl, arylsulfonyl, aryl($C_1$-$C_6$)alkylsulfanyl, aryl($C_1$-$C_6$)alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^{10}$ and $R^{11}$ each independently of one another represent hydrogen, cyano or nitro; or represent ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylsulfanyl($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, halo($C_1$-$C_6$)alkylsulfanyl($C_1$-$C_6$)alkyl, halo($C_1$-$C_6$)alkylsulfinyl($C_1$-$C_6$)alkyl, halo($C_1$-$C_6$)alkylsulfonyl($C_1$-$C_6$)alkyl, ($C_1$-$C_6$)alkoxy($C_1$-$C_6$)alkylsulfanyl($C_1$-$C_6$)alkyl, ($C_1$-$C_6$)alkoxy($C_1$-$C_6$)alkylsulfinyl($C_1$-$C_6$)alkyl, ($C_1$-$C_6$)alkoxy($C_1$-$C_6$)alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$)alkyl, hetaryl($C_1$-$C_6$)alkyl, hetaryloxy($C_1$-$C_6$)alkyl, hetarylsulfanyl($C_1$-$C_6$)alkyl, hetarylsulfinyl($C_1$-$C_6$)alkyl, hetarylsulfonyl($C_1$-$C_6$)alkyl, ($C_1$-$C_6$)alkoxycarbonyl, aryloxycarbonyl, ($C_1$-$C_6$)alkylcarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represent optionally substituted saturated or unsaturated ($C_3$-$C_6$)cycloalkyl which may optionally be interrupted by one or more heteroatoms; or represent halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represent optionally substituted phenyl or optionally substituted hetaryl; or represent ($C_1$-$C_6$)alkoxy, halo($C_1$-$C_6$)alkoxy, ($C_3$-$C_6$)cycloalkyloxy, aryloxy, aryl($C_1$-$C_6$)alkyloxy or carbonyloxy, where the aforementioned radicals may each optionally be substituted, or represents hydroxyl; or represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_3$-$C_6$)cycloalkyl($C_1$-$C_6$)alkylamino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, arylsulfanyl, arylsulfinyl, arylsulfonyl, aryl($C_1$-$C_6$)alkylsulfanyl, aryl($C_1$-$C_6$)alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^2$, $R^3$, $R^4$, $R^5$, $R^6$, $R^7$, $R^8$ and $R^9$,in each case independently of one another, represent hydrogen, cyano, halogen or nitro; or represent ($C_1$-$C_6$)alkyl, ($C_3$-$C_6$)cycloalkyl($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylthio($C_1$-$C_6$)alkyl, halo($C_1$-$C_6$)alkylthio($C_1$-$C_6$)alkyl, ($C_1$-$C_6$)alkoxy($C_1$-$C_6$)alkylthioalkyl, ($C_1$-$C_6$)alkylsulfanyl($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, halo($C_1$-$C_6$)alkylsulfanyl($C_1$-$C_6$)alkyl, halo($C_1$-$C_6$)alkylsulfinyl($C_1$-$C_6$)alkyl, halo($C_1$-$C_6$)alkylsulfonyl($C_1$-$C_6$)alkyl, ($C_1$-$C_6$)alkoxy($C_1$-$C_6$)alkylsulfanyl($C_1$-$C_6$)alkyl, ($C_1$-$C_6$)alkoxy($C_1$-$C_6$)alkylsulfinyl($C_1$-$C_6$)alkyl, ($C_1$-$C_6$)alkoxy($C_1$-$C_6$)alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$)alkyl, hetaryl($C_1$-$C_6$)alkyl, hetaryloxy($C_1$-$C_6$)alkyl or hetarylthio($C_1$-$C_6$)alkyl, where the aforementioned radicals may each be saturated or unsaturated and/or optionally be substituted; or represent optionally substituted saturated or unsaturated ($C_3$-$C_6$)cycloalkyl which may optionally be interrupted by one or more heteroatoms; or represent ($C_1$-$C_6$)alkylcarbonyl, halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, ($C_1$-$C_6$)alkoxycarbonyl, halo($C_1$-$C_6$)alkoxycarbonyl, aryloxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represent carbonyl or carboxyl; or represent optionally substituted phenyl or optionally substituted hetaryl;

represent $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or represent hydroxyl; or represent $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl($(C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or are sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^4$ and $R^5$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^6$ and $R^7$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N;

W represents hydrogen or halogen;

X, Y and Z each and independently of one another have the meanings mentioned above; and n represents the number 0 or 1.

4. The compound as claimed in claim 1, in which

A and B together with the atoms to which they are bonded are a substructure of formula (I-A)

(I-A)

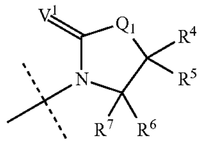

where $V^1$ represents oxygen, sulfur, $NR_I$ or a salt of NR";

$Q^1$ represents oxygen, sulfur, $NR^1$ or $CR^2R^3$;

$R^1$ represents hydrogen, cyano or nitro; or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl($C_1$-$C_6$)alkyl, phenylsulfonyl($C_1$-$C_6$)alkyl, hetaryl($C_1$-$C_6$)alkyl, hetaryloxy($C_1$-$C_6$)alkyl, hetarylsulfanyl($C_1$-$C_6$)alkyl, hetarylsulfinyl($C_1$-$C_6$)alkyl, hetarylsulfonyl($C_1$-$C_6$)alkyl, ($C_1$-$C_6$)alkoxycarbonyl, aryloxycarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated ($C_3$-$C_6$)cycloalkyl which may optionally be interrupted by one or more heteroatoms; or represents halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represents optionally substituted phenyl or optionally substituted hetaryl; or represents ($C_1$-$C_6$)alkoxy, halo($C_1$-$C_6$)alkoxy, ($C_3$-$C_6$)cycloalkyloxy, aryloxy, aryl($C_1$-$C_6$)alkyloxy or carbonyloxy, where the aforementioned radicals may each optionally be substituted, or represents hydroxyl; or represents ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_3$-$C_6$)cycloalkyl($C_1$-$C_6$)alkylamino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represents ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, arylsulfanyl, arylsulfinyl, arylsulfonyl, aryl($C_1$-$C_6$)alkylsulfanyl, aryl($C_1$-$C_6$)alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^{11}$ represents hydrogen, cyano or nitro; or represents ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylsulfanyl($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, halo($C_1$-$C_6$)alkylsulfanyl($C_1$-$C_6$)alkyl, halo($C_1$-$C_6$)alkylsulfinyl($C_1$-$C_6$)alkyl, halo($C_1$-$C_6$)alkylsulfonyl($C_1$-$C_6$)alkyl, ($C_1$-$C_6$)alkoxy($C_1$-$C_6$)alkylsulfanyl($C_1$-$C_6$)alkyl, ($C_1$-$C_6$)alkoxy($C_1$-$C_6$)alkylsulfinyl($C_1$-$C_6$)alkyl, ($C_1$-$C_6$)alkoxy($C_1$-$C_6$)alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$)alkyl, hetaryl($C_1$-$C_6$)alkyl, hetaryloxy($C_1$-$C_6$)alkyl, hetarylsulfanyl($C_1$-$C_6$)alkyl, hetarylsulfinyl($C_1$-$C_6$)alkyl, hetarylsulfonyl($C_1$-$C_6$)alkyl, ($C_1$-$C_6$)alkoxycarbonyl, aryloxycarbonyl, ($C_1$-$C_6$)alkylcarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated ($C_3$-$C_6$)cycloalkyl which may optionally be interrupted by one or more heteroatoms; or represents halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, halo($C_1$-$C_6$)alkoxycarbonyl, aryloxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl (($C_1$-$C_6$)alkyl) aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represents optionally substituted phenyl or optionally substituted hetaryl; or represents ($C_1$-$C_6$)alkoxy, halo($C_1$-$C_6$)alkoxy, ($C_3$-$C_6$)cycloalkyloxy, aryloxy, aryl($C_1$-$C_6$)alkyloxy or carbonyloxy, where the aforementioned radicals may each optionally be substituted, or represents hydroxyl; or represents ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_3$-$C_6$)cycloalkyl($C_1$-$C_6$)alkylamino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represents ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl ($C_1$-$C_6$)alkylsulfanyl, ($C_3$-$C_6$)cycloalkyl($C_1$-$C_6$) alkylsulfinyl, ($C_3$-$C_6$)cycloalkyl($C_1$-$C_6$) alkylsulfonyl, arylsulfanyl, arylsulfinyl, arylsulfonyl, aryl($C_1$-$C_6$)alkylsulfanyl, aryl($C_1$-$C_6$) alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^2$, $R^3$, $R^4$, $R^5$, $R^6$ and $R^7$ each independently of one another represent hydrogen, cyano, halogen or nitro; or represent ($C_1$-$C_6$)alkyl, ($C_3$-$C_6$)cycloalkyl($C_1$-$C_6$) alkyl, halo($C_1$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$) alkyl, ($C_1$-$C_6$)alkylthio($C_1$-$C_6$)alkyl, halo($C_1$-$C_6$) alkylthio($C_1$-$C_6$)alkyl, ($C_1$-$C_6$)alkoxy($C_1$-$C_6$)alkylthioalkyl, ($C_1$-$C_6$)alkylsulfanyl($C_1$-$C_6$)alkyl, ($C_1$-$C_6$)alkylsulfinyl($C_1$-$C_6$)alkyl, ($C_1$-$C_6$)alkylsulfonyl ($C_1$-$C_6$)alkyl, halo($C_1$-$C_6$)alkylsulfanyl($C_1$-$C_6$)alkyl, halo($C_1$-$C_6$)alkylsulfinyl($C_1$-$C_6$)alkyl, halo($C_1$-$C_6$) alkylsulfonyl($C_1$-$C_6$)alkyl, ($C_1$-$C_6$)alkoxy($C_1$-$C_6$) alkylsulfanyl($C_1$-$C_6$)alkyl, ($C_1$-$C_6$)alkoxy($C_1$-$C_6$) alkylsulfinyl($C_1$-$C_6$)alkyl, ($C_1$-$C_6$)alkoxy($C_1$-$C_6$) alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$) alkyl, hetaryl($C_1$-$C_6$)alkyl, hetaryloxy($C_1$-$C_6$)alkyl or hetarylthio($C_1$-$C_6$)alkyl, where the aforementioned radicals may each be saturated or unsaturated and/or optionally be substituted; or represent optionally substituted saturated or unsaturated ($C_3$-$C_6$)cycloalkyl which may optionally be interrupted by one or more heteroatoms; or represent ($C_1$-$C_6$)alkylcarbonyl, halo($C_1$-$C_6$)alkylcarbonyl, hydroxy($C_1$-$C_6$)alkylcarbonyl, ($C_1$-$C_6$)alkoxy ($C_1$-$C_6$)alkylcarbonyl, phenylcarbonyl, hetarylcarbonyl, ($C_1$-$C_6$)alkoxycarbonyl, halo($C_1$-$C_6$) alkoxycarbonyl, aryloxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl (($C_1$-$C_6$)alkyl) aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represent carbonyl or carboxyl; or represent optionally substituted phenyl or optionally substituted hetaryl;

represent ($C_1$-$C_6$)alkoxy, halo($C_1$-$C_6$)alkoxy, ($C_1$-$C_6$) alkoxy($C_1$-$C_6$)alkoxy, aryloxy, aryl($C_1$-$C_6$)alkyloxy, ($C_3$-$C_6$)cycloalkyloxy, ($C_3$-$C_6$)cycloalkyl($C_1$-$C_6$) alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or represent hydroxyl; or represent ($C_1$-$C_6$)alkylamino, di($C_1$-$C_6$)alkylamino, halo($C_1$-$C_6$)alkylamino, dihalo($C_1$-$C_6$)alkylamino, ($C_3$-$C_6$)cycloalkylamino, di($C_3$-$C_6$)cycloalkylamino, ($C_3$-$C_6$)cycloalkyl(($C_1$-$C_6$)alkyl)amino, arylamino, diarylamino, hetarylamino, dihetarylamino, ($C_1$-$C_6$)alkyl(aryl)amino, ($C_3$-$C_6$)cycloalkyl(aryl) amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl ($C_1$-$C_6$)alkylsulfanyl, ($C_3$-$C_6$)cycloalkyl($C_1$-$C_6$) alkylsulfinyl, ($C_3$-$C_6$)cycloalkyl($C_1$-$C_6$) alkylsulfonyl, arylsulfanyl, arylsulfinyl, arylsulfonyl, aryl($C_1$-$C_6$)alkylsulfanyl, aryl($C_1$-$C_6$) alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or are sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N; or $R^4$ and $R^5$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N; or $R^6$ and $R^7$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N; or W represents hydrogen, fluorine or chlorine;

X, Y and Z each independently of one another represent hydrogen, fluorine, chlorine, bromine, cyano, nitro, amino, hydroxyl, ($C_1$-$C_4$)alkyl, ($C_1$-$C_4$)haloalkyl, ($C_2$-$C_4$)alkenyl, ($C_2$-$C_4$)alkynyl, ($C_1$-$C_4$)alkoxy, ($C_1$-$C_4$)haloalkoxy or aminothiocarbonyl;

or represent a benzyl, phenoxy, phenylthio, cyclopropylmethyl, cyclopropyloxy or cyclopropylthio, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or represent cyclopropyl, cyclobutyl, cyclopentyl, cyclohexyl or phenyl, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl; and n represents the number 0 or 1.

5. The compound as claimed in claim 4, in which the substructure of formula (I-A) represents a substructure which is selected from the group consisting of (I-A-1)

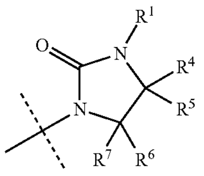

(I-A-2)

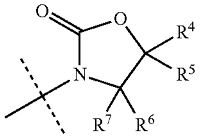

(I-A-3)

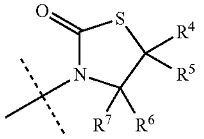

-continued (I-A-4)

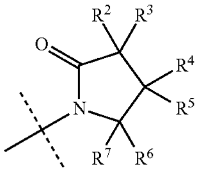

(I-A-5)

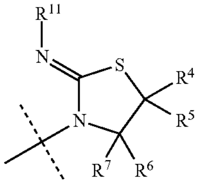

(I-A-6)

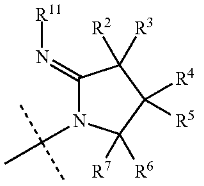

where represents hydrogen; or represents ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, ($C_1$-$C_6$)alkoxy($C_1$-$C_6$)alkyl, ($C_1$-$C_6$)alkoxycarbonyl($C_1$-$C_6$)alkyl, phenyl($C_1$-$C_6$)alkyl, hetaryl($C_1$-$C_6$)alkyl, ($C_2$-$C_6$)alkenyl, halo($C_2$-$C_6$)alkenyl, ($C_3$-$C_6$)cycloalkenyl($C_1$-$C_6$)alkyl, ($C_2$-$C_6$)alkynyl, where the aforementioned radicals may optionally be substituted; or represents optionally substituted ($C_3$-$C_6$)cycloalkyl, ($C_3$-$C_6$)cycloalkenyl, which may optionally be interrupted by one or more heteroatoms from the group of 0, S and N; or represents halo($C_1$-$C_6$)alkylcarbonyl, ($C_1$-$C_6$)alkoxy($C_1$-$C_6$)alkylcarbonyl, ($C_1$-$C_6$)alkoxycarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, ($C_1$-$C_6$)alkylaminothiocarbonyl, di($C_1$-$C_6$)alkylaminothiocarbonyl, ($C_2$-$C_6$)alkenylcarbonyl, ($C_3$-$C_6$)cycloalkenyl($C_1$-$C_6$)alkylcarbonyl, ($C_2$-$C_6$)alkynylcarbonyl or aminothiocarbonyl, where the aforementioned radicals may each optionally be substituted, or are carbonyl or carboxyl; or represents optionally substituted phenyl or optionally substituted hetaryl; or represents ($C_1$-$C_6$)alkoxy, halo($C_1$-$C_6$)alkoxy, ($C_3$-$C_6$)cycloalkyloxy, or carbonyloxy, where the aforementioned radicals may each optionally be substituted, or represents hydroxyl; or represents ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_1$-$C_6$)alkylcarbonylamino, ($C_1$-$C_6$)alkoxycarbonylamino, ($C_1$-$C_6$)alkylcarbamoylamino, ($C_1$-$C_6$)alkylsulfonylamino, ($C_2$-$C_6$)alkenylamino, ($C_3$-$C_6$)cycloalkenyl($C_1$-$C_6$)alkylamino, ($C_2$-$C_6$)alkynylamino, where the aforementioned radicals may each optionally be substituted, or represents amino; or represents $(C_1-C_6)$alkylsulfanyl, $(C_1-C_6)$alkylsulfinyl, $(C1-C_6)$alkylsulfonyl, halo$(C_1-C_6)$alkylsulfanyl, halo$(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted, or represents sulfanyl; and $R^{11}$ represents hydrogen or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may optionally be substituted; or represents optionally substituted $(C_3-C_6)$cycloalkyl, $(C_3-C_6)$cycloalkenyl, which may optionally be interrupted by one or more heteroatoms from the group of 0, S and N; or represents $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or represent carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C1-C_6)$alkylcarbamoylamino, $(C_1-C_6)$alkylsulfonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or represents amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted, or represents sulfanyl; and $R^2$, $R^3$, $R^4$, $R^5$, $R^6$ and $R^7$ each independently of one another represent hydrogen, cyano, halogen or nitro; or represent $(C_1-C_6)$alkyl, $(C_3-C_6)$cycloalkyl$(C_1-C_6)$alkyl, halo$(C_1-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$ alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may each optionally be substituted, or represent optionally substituted $(C_3-C_6)$cycloalkyl, $(C_3-C_6)$cycloalkenyl, which may optionally be interrupted by one or more heteroatoms from the group consisting of O, S and N; or represent $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or represent carbonyl or carboxyl; or represent optionally substituted phenyl or optionally substituted hetaryl;

represent $(C_1-C_6)$alkoxy, halo$(C_1-C_6)$alkoxy, $(C_1-C_6)$alkoxy$(C_1-C_6)$alkoxy, $(C_3-C_6)$cycloalkyloxy, $(C_3-C_6)$cycloalkyl$(C_1-C_6)$alkyloxy, $(C_2-C_6)$alkenyloxy, $(C_3-C_6)$cycloalkenyl$(C_1-C_6)$alkoxy, $(C_2-C_6)$alkynyloxy or carbonyloxy, where the aforementioned radicals may each optionally be substituted, or represent hydroxyl; or represent $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulfonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or represents amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted, or represent sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^4$ and $R^5$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or $R^6$ and $R^7$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N; or W represents hydrogen or fluorine;

X and Y independently of one another represent hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z represents hydrogen; and n represents the number 0 or 1.

6. The compound as claimed in claim 4, in which the substructure of formula (I-A) represents a substructure which is selected from the group consisting of (I-A-1)

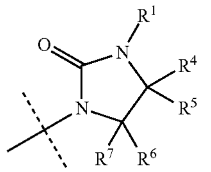

(I-A-2)

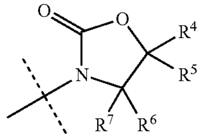

(I-A-6)

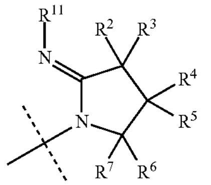

where $R^1$ and $R^{11}$ each independently of one another represent hydrogen, methyl, ethyl, propyl, isopropyl, cyclopropyl, cyclopropylmethyl, $CH_2CF_3$, $CH_2CHF_2$, $CH(CH_3)CF_3$, $CH_2CH_2CF_3$, $CH_2CH_2CHF_2$; or $R^2$, $R^3$, $R^4$, $R^5$, $R^6$ and $R^7$ each independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl or fluorine;

where X and Y represent in particular the following combinations (Y,X): (Me, F), (Me,H), (Me,Cl), (Me, Me), (Cl,Cl), (Cl,F), (CN,F), (Cl,H), (Br,H), (Br,F), (CN,H), (F,F), $(CF_3,H)$;

Z represents hydrogen; and n represents the number 0 or 1.

7. The compound as claimed in claim 1, in which

A and B together with the atoms to which they are attached are a substructure of formula (I-B)

(I-B)

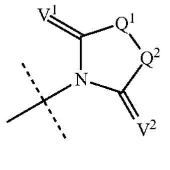

where $V^1$ and $V^2$ each independently of one another represent oxygen; sulfur, $NR^{11}$ or a salt of NR";

$Q^1$ represents oxygen, sulfur, $NR^1$ or $CR^2R^3$;

$Q^2$ represents $NR^{10}$ or $CR^8R^9$;

$R^1$ represents hydrogen, cyano or nitro; or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl, hetarylsulfanyl$(C_1-C_6)$alkyl, hetarylsulfinyl$(C_1-C_6)$alkyl, hetarylsulfonyl$(C_1-C_6)$alkyl, $(C_1-C_6)$alkoxycarbonyl, aryloxycarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated $(C_3-C_6)$cycloalkyl which may optionally be interrupted by one or more heteroatoms; or represents halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represents optionally substituted phenyl or optionally substituted hetaryl; or represents ($C_1$-$C_6$)alkoxy, halo($C_1$-$C_6$)alkoxy, ($C_3$-$C_6$)cycloalkyloxy, aryloxy, aryl($C_1$-$C_6$)alkyloxy or carbonyloxy, where the aforementioned radicals may each optionally be substituted, or represents hydroxyl; or represents ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_3$-$C_6$)cycloalkyl($C_1$-$C_6$)alkylamino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represents ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, arylsulfanyl, arylsulfinyl, arylsulfonyl, aryl($C_1$-$C_6$)alkylsulfanyl, aryl($C_1$-$C_6$)alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^{10}$ and $R^{11}$ each independently of one another represent hydrogen, cyano or nitro; or represent ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylsulfanyl($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, halo($C_1$-$C_6$)alkylsulfanyl($C_1$-$C_6$)alkyl, halo($C_1$-$C_6$)alkylsulfinyl($C_1$-$C_6$)alkyl, halo($C_1$-$C_6$)alkylsulfonyl($C_1$-$C_6$)alkyl, ($C_1$-$C_6$)alkoxy($C_1$-$C_6$)alkylsulfanyl($C_1$-$C_6$)alkyl, ($C_1$-$C_6$)alkoxy($C_1$-$C_6$)alkylsulfinyl($C_1$-$C_6$)alkyl, ($C_1$-$C_6$)alkoxy($C_1$-$C_6$)alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$)alkyl, hetaryl($C_1$-$C_6$)alkyl, hetaryloxy($C_1$-$C_6$)alkyl, hetarylsulfanyl($C_1$-$C_6$)alkyl, hetarylsulfinyl($C_1$-$C_6$)alkyl, hetarylsulfonyl($C_1$-$C_6$)alkyl, ($C_1$-$C_6$)alkoxycarbonyl, aryloxycarbonyl, ($C_1$-$C_6$)alkylcarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represent optionally substituted saturated or unsaturated ($C_3$-$C_6$)cycloalkyl which may optionally be interrupted by one or more heteroatoms; or represent halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, halo($C_1$-$C_6$)alkoxycarbonyl, aryloxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl) aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or is carbonyl or carboxyl; or represent optionally substituted phenyl or optionally substituted hetaryl; or represent ($C_1$-$C_6$)alkoxy, halo($C_1$-$C_6$)alkoxy, ($C_3$-$C_6$)cycloalkyloxy, aryloxy, aryl($C_1$-$C_6$)alkyloxy or carbonyloxy, where the aforementioned radicals may each optionally be substituted, or represents hydroxyl; or represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_3$-$C_6$)cycloalkyl($C_1$-$C_6$)alkylamino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, arylsulfanyl, arylsulfinyl, arylsulfonyl, aryl($C_1$-$C_6$)alkylsulfanyl, aryl($C_1$-$C_6$)alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^2$, $R^3$, $R^8$ and $R^9$ each independently of one another represent hydrogen, cyano, halogen or nitro; or represent ($C_1$-$C_6$)alkyl, ($C_3$-$C_6$)cycloalkyl($C_1$-$C_6$)alkyl, halo($C_1$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$) alkyl, ($C_1$-$C_6$)alkylthio($C_1$-$C_6$)alkyl, halo($C_1$-$C_6$) alkylthio($C_1$-$C_6$)alkyl, ($C_1$-$C_6$)alkoxy($C_1$-$C_6$)alkyl-thioalkyl, ($C_1$-$C_6$)alkylsulfanyl($C_1$-$C_6$)alkyl, ($C_1$-$C_6$)alkylsulfinyl($C_1$-$C_6$)alkyl, ($C_1$-$C_6$)alkylsulfonyl ($C_1$-$C_6$)alkyl, halo($C_1$-$C_6$)alkylsulfanyl($C_1$-$C_6$)alkyl, halo($C_1$-$C_6$)alkylsulfinyl($C_1$-$C_6$)alkyl, halo($C_1$-$C_6$) alkylsulfonyl($C_1$-$C_6$)alkyl, ($C_1$-$C_6$)alkoxy($C_1$-$C_6$) alkylsulfanyl($C_1$-$C_6$)alkyl, ($C_1$-$C_6$)alkoxy($C_1$-$C_6$) alkylsulfinyl($C_1$-$C_6$)alkyl, ($C_1$-$C_6$)alkoxy($C_1$-$C_6$) alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$) alkyl, hetaryl($C_1$-$C_6$)alkyl, hetaryloxy($C_1$-$C_6$)alkyl or hetarylthio($C_1$-$C_6$)alkyl, where the aforementioned radicals may each be saturated or unsaturated and/or optionally be substituted; or represent optionally substituted saturated or unsaturated ($C_3$-$C_6$)cycloalkyl which may optionally be interrupted by one or more heteroatoms; or represent ($C_1$-$C_6$)alkylcarbonyl, halo($C_1$-$C_6$)alkylcarbonyl, hydroxy($C_1$-$C_6$)alkylcarbonyl, ($C_1$-$C_6$)alkoxy ($C_1$-$C_6$)alkylcarbonyl, phenylcarbonyl, hetarylcarbonyl, ($C_1$-$C_6$)alkoxycarbonyl, halo($C_1$-$C_6$) alkoxycarbonyl, aryloxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl (($C_1$-$C_6$)alkyl) aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represent carbonyl or carboxyl; or represent optionally substituted phenyl or optionally substituted hetaryl;

represent ($C_1$-$C_6$)alkoxy, halo($C_1$-$C_6$)alkoxy, ($C_1$-$C_6$) alkoxy($C_1$-$C_6$)alkoxy, aryloxy, aryl($C_1$-$C_6$)alkyloxy, ($C_3$-$C_6$)cycloalkyloxy, ($C_3$-$C_6$)cycloalkyl($C_1$-$C_6$) alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or represent hydroxyl; or represent ($C_1$-$C_6$)alkylamino, di($C_1$-$C_6$)alkylamino, halo($C_1$-$C_6$)alkylamino, dihalo($C_1$-$C_6$)alkylamino, ($C_3$-$C_6$)cycloalkylamino, di($C_3$-$C_6$)cycloalkylamino, ($C_3$-$C_6$)cycloalkyl(($C_1$-$C_6$)alkyl)amino, arylamino, diarylamino, hetarylamino, dihetarylamino, ($C_1$-$C_6$)alkyl(aryl)amino, ($C_3$-$C_6$)cycloalkyl(aryl) amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl ($C_1$-$C_6$)alkylsulfanyl, ($C_3$-$C_6$)cycloalkyl($C_1$-$C_6$) alkylsulfinyl, ($C_3$-$C_6$)cycloalkyl($C_1$-$C_6$) alkylsulfonyl, arylsulfanyl, arylsulfinyl, arylsulfonyl, aryl($C_1$-$C_6$)alkylsulfanyl, aryl($C_1$-$C_6$) alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or are sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N;

W represents hydrogen, fluorine or chlorine;

X, Y and Z independently of one another represent hydrogen, fluorine, chlorine, bromine, cyano, nitro, amino, hydroxyl, ($C_1$-$C_4$)alkyl, ($C_1$-$C_4$)haloalkyl, ($C_2$-$C_4$)alkenyl, ($C_2$-$C_4$)alkynyl, ($C_1$-$C_4$)alkoxy, ($C_1$-$C_4$)haloalkoxy or aminothiocarbonyl;

or represent a benzyl, phenoxy, phenylthio, cyclopropylmethyl, cyclopropyloxy or cyclopropylthio, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or represent cyclopropyl, cyclobutyl, cyclopentyl, cyclohexyl or phenyl, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl; and n represents the number 0 or 1.

8. The compound as claimed in claim 7, in which the substructure of formula (I-B) represents substructure which is selected from the group consisting of (I-B-1)

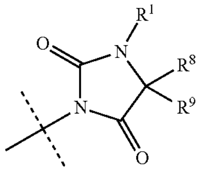

(I-B-2)

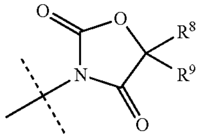

(I-B-3)

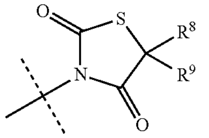

(I-B-4)

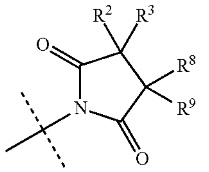

(I-B-5)

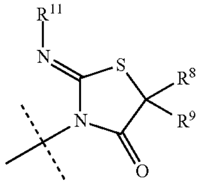

(I-B-6)

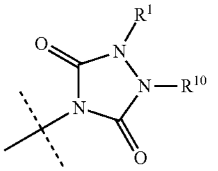

(I-B-7)

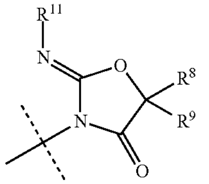

where $R^1$ represents hydrogen or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may optionally be substituted; or represents optionally substituted $(C_3-C_6)$cycloalkyl, $(C_3-C_6)$cycloalkenyl, which may optionally be interrupted by one or more heteroatoms from the group of O, S and N; or represents halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or are carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulfonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or represents amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted, or represents sulfanyl; and $R^{10}$ and $R^{11}$ each independently of one another represent hydrogen; or represent $(C_1-C_6)$alkyl, $(C_3-C_6)$cycloalkyl$(C_1-C_6)$alkyl, halo$(C_2-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may optionally be substituted; or represent optionally substituted $(C_3-C_6)$cycloalkyl, $(C_3-C_6)$cycloalkenyl, which may optionally be interrupted by one or more heteroatoms from the group of O, S and N; or represent $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or represent carbonyl or carboxyl; or represent optionally substituted phenyl or optionally substituted hetaryl; or represent ($C_1$-$C_6$)alkoxy, halo($C_1$-$C_6$)alkoxy, ($C_3$-$C_6$)cycloalkyloxy, or carbonyloxy, where the aforementioned radicals may each optionally be substituted, or represents hydroxyl; or represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_1$-$C_6$)alkylcarbonylamino, ($C_1$-$C_6$)alkoxycarbonylamino, ($C_1$-$C_6$)alkylcarbamoylamino, ($C_1$-$C_6$)alkylsulfonylamino, ($C_2$-$C_6$)alkenylamino, ($C_3$-$C_6$)cycloalkenyl($C_1$-$C_6$)alkylamino, ($C_2$-$C_6$)alkynylamino, where the aforementioned radicals may each optionally be substituted, or represents amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfanyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted, or represents sulfanyl; and $R^2$, $R^3$, $R^8$ and $R^9$ each independently of one another represent hydrogen, cyano, halogen or nitro; or represent ($C_1$-$C_6$)alkyl, ($C_3$-$C_6$)cycloalkyl($C_1$-$C_6$)alkyl, halo($C_1$-$C_6$)alkyl, cyano($C_1$-$C_6$)alkyl, ($C_1$-$C_6$)alkoxy($C_1$-$C_6$)alkyl, ($C_1$-$C_6$)alkoxycarbonyl($C_1$-$C_6$)alkyl, ($C_1$-$C_6$)alkylsulfanyl($C_1$-$C_6$)alkyl, ($C_1$-$C_6$)alkylsulfinyl($C_1$-$C_6$)alkyl, phenyl($C_1$-$C_6$)alkyl, hetaryl($C_1$-$C_6$)alkyl, ($C_2$-$C_6$)alkenyl, halo($C_2$-$C_6$)alkenyl, ($C_3$-$C_6$)cycloalkenyl($C_1$-$C_6$)alkyl, ($C_2$-$C_6$)alkynyl, where the aforementioned radicals may each optionally be substituted; or represent optionally substituted ($C_3$-$C_6$)cycloalkyl, ($C_3$-$C_6$)cycloalkenyl, which may optionally be interrupted by one or more heteroatoms from the group of O, S and N; or represent ($C_1$-$C_6$)alkylcarbonyl, halo($C_1$-$C_6$)alkylcarbonyl, ($C_1$-$C_6$)alkoxy($C_1$-$C_6$)alkylcarbonyl, ($C_1$-$C_6$)alkoxycarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, ($C_1$-$C_6$)alkylaminothiocarbonyl, di($C_1$-$C_6$)alkylaminothiocarbonyl, ($C_2$-$C_6$)alkenylcarbonyl, ($C_3$-$C_6$)cycloalkenyl($C_1$-$C_6$)alkylcarbonyl, ($C_2$-$C_6$)alkynylcarbonyl or aminothiocarbonyl, where the aforementioned radicals may each optionally be substituted, or represent carbonyl or carboxyl; or represent optionally substituted phenyl or optionally substituted hetaryl; or represent ($C_1$-$C_6$)alkoxy, halo($C_1$-$C_6$)alkoxy, ($C_1$-$C_6$)alkoxy($C_1$-$C_6$)alkoxy, ($C_3$-$C_6$)cycloalkyloxy, ($C_3$-$C_6$)cycloalkyl($C_1$-$C_6$)alkyloxy, ($C_2$-$C_6$)alkenyloxy, ($C_3$-$C_6$)cycloalkenyl($C_1$-$C_6$)alkoxy, ($C_2$-$C_6$)alkynyloxy or carbonyloxy, where the aforementioned radicals may each optionally be substituted, or represent hydroxyl; or represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_1$-$C_6$)alkylcarbonylamino, ($C_1$-$C_6$)alkoxycarbonylamino, ($C_1$-$C_6$)alkylcarbamoylamino, ($C_1$-$C_6$)alkylsulfonylamino, ($C_2$-$C_6$)alkenylamino, ($C_3$-$C_6$)cycloalkenyl($C_1$-$C_6$)alkylamino, ($C_2$-$C_6$)alkynylamino, where the aforementioned radicals may each optionally be substituted, or represent amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfanyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted, or represent sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N;

W represents hydrogen or fluorine;

X and Y independently of one another represent hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z represents hydrogen; and n represents the number 0 or 1.

9. The compound as claimed in claim 7, in which the substructure of formula (I-B) represents a substructure which is selected from the group consisting of (I-B-1)

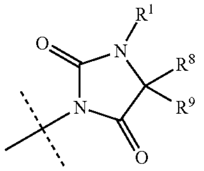

(I-B-4)

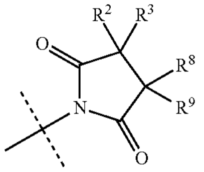

-continued (I-B-5)

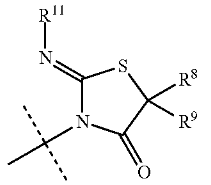

(I-B-2)

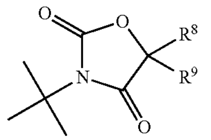

(I-B-6)

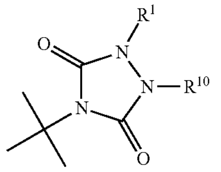

where $R^1$, $R^{10}$ and $R^{11}$ each independently of one another represent hydrogen, methyl, ethyl, propyl, isopropyl, n-butyl, cyclopropyl, cyclopropylmethyl, $CH_2CF_3$, $CH_2CHF_2$, $CH(CH_3)CF_3$, $CH_2CH_2CF_3$, $CH_2CH_2CHF_2$, $CH_2C(CH_3)_3$, $CH_2CH(CH_3)_2$, $CH_2CH{=}CH_2$ (=allyl), $CH_2CCH$ (=vinyl) or benzyl;

$R^2$, $R^3$, $R^8$ and $R^9$ each independently of one another represent hydrogen, methyl, trifluoromethyl or phenyl;

W represents hydrogen or fluorine;

X represents hydrogen, chlorine, fluorine or methyl;

Y represents chlorine, bromine, cyano, methyl, trifluoromethyl or fluorine;

X and Y represent in particular the following (Y,X) combinations: (Me, F), (Me,H), (Me, Cl), (Me,Me), (Cl,Cl), (Cl,F), (CN,F), (Cl,H), (Br,H), (Br,F), (CN,H), (F,F), ($CF_3$,H);

Z represents hydrogen; and n represents the number 0 or 1.

10. The compound as claimed in claim 1, in which

A and B together with the atoms to which they are attached represent a substructure of the formula (I-C)

(I-C)

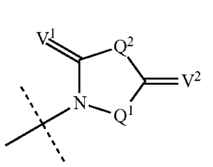

where $V^1$ and $V^2$ each independently of one another represent oxygen; or sulfur, $Q^1$ represents oxygen, sulfur, $NR_1$ or $CR_2R_3$;

$Q^2$ represents $NR_{10}$ or $CR_8R_9$;

represents hydrogen, cyano or nitro; or represents ($C_1$-$C_6$)alkyl, ($C_3$-$C_6$)cycloalkyl($C_1$-$C_6$)alkyl, halo($C_2$-$C_6$)alkyl, cyano($C_1$-$C_6$)alkyl, hydroxy($C_1$-$C_6$)alkyl, ($C_1$-$C_6$)alkoxy($C_1$-$C_6$)alkyl, amino($C_1$-$C_6$)alkyl, ($C_1$-$C_6$)alkoxycarbonyl($C_1$-$C_6$)alkyl, ($C_1$-$C_6$)alkylsulfanyl($C_1$-$C_6$)alkyl, ($C_1$-$C_6$)alkylsulfinyl($C_1$-$C_6$)alkyl, ($C_1$-$C_6$)alkylsulfonyl($C_1$-$C_6$)alkyl, halo($C_1$-$C_6$)alkylsulfanyl($C_1$-$C_6$)alkyl, halo($C_1$-$C_6$)alkylsulfinyl($C_1$-$C_6$)alkyl, halo($C_1$-$C_6$)alkylsulfonyl($C_1$-$C_6$)alkyl, ($C_1$-$C_6$)alkoxy($C_1$-$C_6$)alkylsulfanyl($C_1$-$C_6$)alkyl, ($C_1$-$C_6$)alkoxy($C_1$-$C_6$)alkylsulfinyl($C_1$-$C_6$)alkyl, ($C_1$-$C_6$)alkoxy($C_1$-$C_6$)alkylsulfonyl($C_1$-$C_6$)alkyl, phenyl($C_1$-$C_6$)alkyl, phenoxy($C_1$-$C_6$)alkyl, phenylsulfanyl($C_1$-$C_6$)alkyl, phenylsulfinyl($C_1$-$C_6$)alkyl, phenylsulfonyl($C_1$-$C_6$)alkyl, hetaryl($C_1$-$C_6$)alkyl, hetaryloxy($C_1$-$C_6$)alkyl, hetarylsulfanyl($C_1$-$C_6$)alkyl, hetarylsulfinyl($C_1$-$C_6$)alkyl, hetarylsulfonyl($C_1$-$C_6$)alkyl, ($C_1$-$C_6$)alkoxycarbonyl, aryloxycarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated ($C_3$-$C_6$)cycloalkyl which may optionally be interrupted by one or more heteroatoms; or represents halo($C_1$-$C_6$)alkylcarbonyl, hydroxy($C_1$-$C_6$)alkylcarbonyl, ($C_1$-$C_6$)alkoxy($C_1$-$C_6$)alkylcarbonyl, phenylcarbonyl, hetarylcarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, di($C_3$-$C_6$)cycloalkylaminocarbonyl, ($C_3$-$C_6$)cycloalkyl(($C_1$-$C_6$)alkyl)aminocarbonyl, arylaminocarbonyl, diarylaminocarbonyl, ($C_1$-$C_6$)alkyl(aryl)aminocarbonyl, ($C_3$-$C_6$)cycloalkyl(aryl)aminocarbonyl, ($C_1$-$C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represents carbonyl or carboxyl; or represents optionally substituted phenyl or optionally substituted hetaryl; or represents ($C_1$-$C_6$)alkoxy, halo($C_1$-$C_6$)alkoxy, ($C_3$-$C_6$)cycloalkyloxy, aryloxy, aryl($C_1$-$C_6$)alkyloxy or carbonyloxy, where the aforementioned radicals may each optionally be substituted, or represents hydroxyl; or represents ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_3$-$C_6$)cycloalkyl($C_1$-$C_6$)alkylamino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represents ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl $(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^{10}$ and $R^{11}$ each independently of one another represent hydrogen, cyano or nitro; or represent $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl, hetarylsulfanyl$(C_1-C_6)$alkyl, hetarylsulfinyl$(C_1-C_6)$alkyl, hetarylsulfonyl$(C_1-C_6)$alkyl, $(C_1-C_6)$alkoxycarbonyl, aryloxycarbonyl, $(C_1-C_6)$alkylcarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated $(C_3-C_6)$cycloalkyl which may optionally be interrupted by one or more heteroatoms; or represent halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl($(C_1-C_6)$alkyl)aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represents carbonyl or carboxyl; or represent optionally substituted phenyl or optionally substituted hetaryl; or represent $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or represents hydroxyl; or represent $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$(C_1-C_6)$alkylamino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; and $R^2$, $R^3$, $R^8$ and $R^9$ each independently of one another represent hydrogen, cyano, halogen or nitro; or represent $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylthio$(C_1-C_6)$alkyl, halo$(C_1-C_6)$alkylthio$(C_1-C_6)$alkyl, $(C_1-C_6)$alkoxy$(C_1-C_6)$alkylthioalkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl or hetarylthio$(C_1-C_6)$alkyl, where the aforementioned radicals may each be saturated or unsaturated and/or optionally be substituted; or represent optionally substituted saturated or unsaturated $(C_3-C_6)$cycloalkyl which may optionally be interrupted by one or more heteroatoms; or represent $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl($(C_1-C_6)$alkyl) aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-$ $C_6$)alkylaminothiocarbonyl, di($C_1$-$C_6$)alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represent carbonyl or carboxyl; or represent optionally substituted phenyl or optionally substituted hetaryl;

represent ($C_1$-$C_6$)alkoxy, halo($C_1$-$C_6$)alkoxy, ($C_1$-$C_6$)alkoxy($C_1$-$C_6$)alkoxy, aryloxy, aryl($C_1$-$C_6$)alkyloxy, ($C_3$-$C_6$)cycloalkyloxy, ($C_3$-$C_6$)cycloalkyl($C_1$-$C_6$)alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or represent hydroxyl; or represent ($C_1$-$C_6$)alkylamino, di($C_1$-$C_6$)alkylamino, halo($C_1$-$C_6$)alkylamino, dihalo($C_1$-$C_6$)alkylamino, ($C_3$-$C_6$)cycloalkylamino, di($C_3$-$C_6$)cycloalkylamino, ($C_3$-$C_6$)cycloalkyl(($C_1$-$C_6$)alkyl)amino, arylamino, diarylamino, hetarylamino, dihetarylamino, ($C_1$-$C_6$)alkyl(aryl)amino, ($C_3$-$C_6$)cycloalkyl(aryl)amino, ($C_1$-$C_6$)alkylcarbonylamino, arylcarbonylamino, ($C_1$-$C_6$)alkoxycarbonylamino, aryloxycarbonylamino, ($C_1$-$C_6$)alkylcarbamoylamino, arylcarbamoylamino, ($C_1$-$C_6$)alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfonyl, ($C_3$-$C_6$)cycloalkylsulfanyl, ($C_3$-$C_6$)cycloalkylsulfinyl, ($C_3$-$C_6$)cycloalkylsulfonyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, arylsulfanyl, arylsulfinyl, arylsulfonyl, aryl($C_1$-$C_6$)alkylsulfanyl, aryl($C_1$-$C_6$)alkylsulfinyl, aryl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N;

W represents hydrogen, fluorine or chlorine;

X, Y and Z each independently of one another represent hydrogen, fluorine, chlorine, bromine, cyano, nitro, amino, hydroxyl, ($C_1$-$C_4$)alkyl, ($C_1$-$C_4$)haloalkyl, ($C_2$-$C_4$)alkenyl, ($C_2$-$C_4$)alkynyl, ($C_1$-$C_4$)alkoxy, ($C_1$-$C_4$)haloalkoxy or aminothiocarbonyl;

or represent a benzyl, phenoxy, phenylthio, cyclopropylmethyl, cyclopropyloxy or cyclopropylthio, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or represent cyclopropyl, cyclobutyl, cyclopentyl, cyclohexyl or phenyl, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl; and n represents the number 0 or 1.

11. The compound as claimed in claim 10, in which the substructure of the formula (I-C) represents a substructure which is selected from the group consisting of (I-C-1)

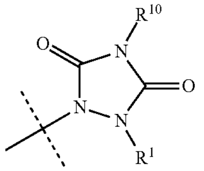

(I-C-2)

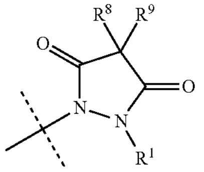

(I-C-3)

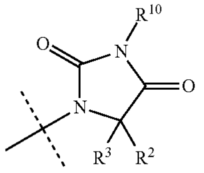

-continued (I-C-4)

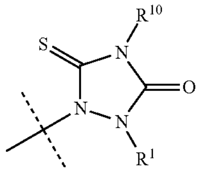

(I-C-5)

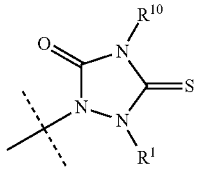

(I-C-6)

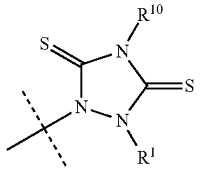

where $R^1$ represents hydrogen or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may optionally be substituted; or represents optionally substituted $(C_3-C_6)$cycloalkyl, $(C_3-C_6)$cycloalkenyl, which may optionally be interrupted by one or more heteroatoms from the group of O, S and N; or represents halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or are carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulfonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or represents amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted, or represents sulfanyl; and $R^{10}$ represents hydrogen; or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may optionally be substituted; or represents optionally substituted $(C_3-C_6)$cycloalkyl, $(C_3-C_6)$cycloalkenyl, which may optionally be interrupted by one or more heteroatoms from the group of O, S and N; or represents $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or represent carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulfonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or represents amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted, or represents sulfanyl; and $R^2$, $R^3$, $R^8$ and $R^9$ each independently of one another represent hydrogen, cyano, halogen or nitro; or represent $(C_1-C_6)$alkyl, $(C_3-C_6)$cycloalkyl$(C_1-C_6)$alkyl, halo$(C_1-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$ alkylsulfinyl($C_1$-$C_6$)alkyl, phenyl($C_1$-$C_6$)alkyl, hetaryl($C_1$-$C_6$)alkyl, ($C_2$-$C_6$)alkenyl, halo($C_2$-$C_6$)alkenyl, ($C_3$-$C_6$)cycloalkenyl($C_1$-$C_6$)alkyl, ($C_2$-$C_6$)alkynyl, where the aforementioned radicals may each optionally be substituted; or represent optionally substituted ($C_3$-$C_6$)cycloalkyl, ($C_3$-$C_6$)cycloalkenyl, which may optionally be interrupted by one or more heteroatoms from the group of O, S and N; or represent ($C_1$-$C_6$)alkylcarbonyl, halo($C_1$-$C_6$)alkylcarbonyl, ($C_1$-$C_6$)alkoxy($C_1$-$C_6$)alkylcarbonyl, ($C_1$-$C_6$)alkoxycarbonyl, halo($C_1$-$C_6$)alkoxycarbonyl, aminocarbonyl, ($C_1$-$C_6$)alkylaminocarbonyl, di($C_1$-$C_6$)alkylaminocarbonyl, ($C_3$-$C_6$)cycloalkylaminocarbonyl, ($C_1$-$C_6$)alkylaminothiocarbonyl, di($C_1$-$C_6$)alkylaminothiocarbonyl, ($C_2$-$C_6$)alkenylcarbonyl, ($C_3$-$C_6$)cycloalkenyl($C_1$-$C_6$)alkylcarbonyl, ($C_2$-$C_6$)alkynylcarbonyl or aminothiocarbonyl, where the aforementioned radicals may each optionally be substituted, or represent carbonyl or carboxyl; or represent optionally substituted phenyl or optionally substituted hetaryl; or represent ($C_1$-$C_6$)alkoxy, halo($C_1$-$C_6$)alkoxy, ($C_1$-$C_6$)alkoxy($C_1$-$C_6$)alkoxy, ($C_3$-$C_6$)cycloalkyloxy, ($C_3$-$C_6$)cycloalkyl($C_1$-$C_6$)alkyloxy, ($C_2$-$C_6$)alkenyloxy, ($C_3$-$C_6$)cycloalkenyl($C_1$-$C_6$)alkoxy, ($C_2$-$C_6$)alkynyloxy or carbonyloxy, where the aforementioned radicals may each optionally be substituted, or represent hydroxyl; or represent ($C_1$-$C_6$)alkylamino, halo($C_1$-$C_6$)alkylamino, dihalo($C_1$-$C_6$)alkylamino, di($C_1$-$C_6$)alkylamino, ($C_3$-$C_6$)cycloalkylamino, di($C_3$-$C_6$)cycloalkylamino, ($C_1$-$C_6$)alkylcarbonylamino, ($C_1$-$C_6$)alkoxycarbonylamino, ($C_1$-$C_6$)alkylcarbamoylamino, ($C_1$-$C_6$)alkylsulfonylamino, ($C_2$-$C_6$)alkenylamino, ($C_3$-$C_6$)cycloalkenyl($C_1$-$C_6$)alkylamino, ($C_2$-$C_6$)alkynylamino, where the aforementioned radicals may each optionally be substituted, or represents amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfanyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted, or represent sulfanyl; or $R^2$ and $R^3$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N;

W represents hydrogen or fluorine;

X and Y each independently of one another represent hydrogen, fluorine, chlorine, bromine, methyl, ethyl, trifluoromethyl, (2,2)-difluoromethyl, difluoromethoxy, trifluoromethoxy, cyclopropyl, cyano, amino, hydroxyl or nitro;

Z represents hydrogen; and n represents the number 0 or 1.

12. The compound as claimed in claim 10, in which the substructure of formula (I-C) represents a substructure which is selected from the group consisting of (I-C-1)

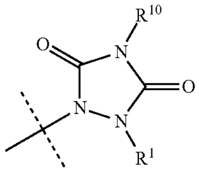

(I-C-2)

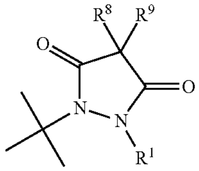

(I-C-3)

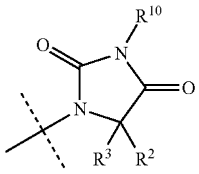

(I-C-5)

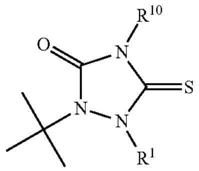

(I-C-6)

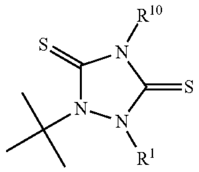

where $R^1$ and $R^{10}$ each independently of one another represent hydrogen, ($C_1$-$C_4$)alkyl, ($C_2$-$C_4$)haloalkyl, ($C_1$-$C_3$)alkoxy($C_1$-$C_4$)alkyl or ($C_2$-$C_4$)alkenyl; or represent saturated or unsaturated ($C_3$-$C_6$)cycloalkyl, ($C_3$-$C_6$)cycloalkyl($C_1$-$C_2$)alkyl, phenyl or phenyl($C_1$-$C_2$)alkyl, where the aforementioned radicals may each be mono- or polysubstituted by halogen, cyano, nitro, amino, hydroxy, methyl, ethyl, trifluoromethyl, difluoromethyl, trifluoroethyl, difluoroethyl, methoxy, ethoxy, trifluoromethoxy, trifluoroethoxy, trifluoroethylsulfanyl or optionally methyl-, fluorine-, chlorine-, cyano-substituted cyclopropyl;

$R^2$, $R^3$, $R^8$ and $R^9$ each independently of one another represent hydrogen; or represent $(C_1-C_6)$alkyl, $(C_2-C_6)$alkenyl, $(C_2-C_6)$alkynyl, halo$(C_1-C_6)$alkyl or phenyl$(C_1-C_3)$alkyl, where the aforementioned radicals may each be mono- or polysubstituted by halogen, cyano, nitro, amino, hydroxy, methyl, ethyl, trifluoromethyl, difluoromethyl, trifluoroethyl, difluoroethyl, methoxy, ethoxy, trifluoromethoxy, trifluoroethoxy, trifluoroethylsulfanyl or optionally methyl-, fluorine-, chlorine-, cyano-substituted cyclopropyl;

represent $(C_3-C_6)$cycloalkyl, or phenyl, where the aforementioned radicals may each be mono- or polysubstituted by halogen, cyano, nitro, amino, hydroxy, methyl, ethyl, trifluoromethyl, difluoromethyl, trifluoroethyl, difluoroethyl, methoxy, ethoxy, trifluoromethoxy, trifluoroethoxy, trifluoroethylsulfanyl or optionally methyl-, fluorine-, chlorine-, cyano-substituted cyclopropyl;

$R^2$ and $R^3$ together with the atom to which they are attached may form a cyclopropyl, cyclobutyl, cyclopentyl or cyclohexyl ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl; or $R^8$ and $R^9$ together with the atom to which they are attached may form a cyclopropyl, cyclobutyl, cyclopentyl or cyclohexyl ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl;

W represents hydrogen or fluorine;

X represents hydrogen, chlorine, fluorine or methyl;

Y represents chlorine, bromine, cyano, methyl, trifluoromethyl or fluorine;

where X and Y represent in particular the following combinations (Y,X): (Me, F), (Me,H), (Me,Cl), (Me, Me), (Cl,Cl), (Cl,F), (CN,F), (Cl,H), (Me,H), (Br,H), (Br,F), (CN,H), (F,F), $(CF_3,H)$;

Z represents hydrogen; and n represents the number 0 or 1.

13. The compound as claimed in claim 1, in which

A and B together with the atoms to which they are bonded are a substructure of formula (I-D)

(I-D)

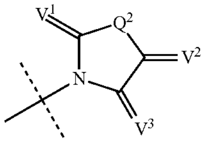

where $V^1$, $V^2$ and $V^3$ each independently of one another represent oxygen; sulfur, $NR_{11}$ or a salt of $NR_{11}$;

$Q^2$ represents $NR^{10}$ or $CR^8R^9$;

$R^{10}$ and $R_{11}$ independently represents hydrogen, cyano or nitro; or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl, hetarylsulfanyl$(C_1-C_6)$alkyl, hetarylsulfinyl$(C_1-C_6)$alkyl, hetarylsulfonyl$(C_1-C_6)$alkyl, $(C_1-C_6)$alkoxycarbonyl, aryloxycarbonyl, $(C_1-C_6)$alkylcarbonyl, arylcarbamoyl, where the aforementioned radicals may each optionally be substituted and/or, under the condition that, in the case of an unsaturated radical, the defined minimum number of carbon atoms is 2, the radicals may be saturated or unsaturated; or represents optionally substituted saturated or unsaturated $(C_3-C_6)$cycloalkyl which may optionally be interrupted by one or more heteroatoms; or represents halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl) aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represents carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, aryloxy, aryl$(C_1-C_6)$alkyloxy or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_3-C_6)$cycloalkyl$(C_1-C_6)$alkylamino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represents amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represents sulfanyl; and $R^8$ and $R^9$ each independently of one another represent hydrogen, cyano, halogen or nitro; or represent $(C_1-C_6)$alkyl, $(C_3-C_6)$cycloalkyl$(C_1-C_6)$alkyl, halo$(C_1-C_6)$alkyl, cyano$(C_1-C_6)$alkyl, hydroxy$(C_1-C_6)$alkyl, $(C_1-C_6)$alkoxy$(C_1-C_6)$alkyl, amino$(C_1-C_6)$alkyl, $(C_1-C_6)$alkoxycarbonyl$(C_1-C_6)$alkyl, $(C_1-C_6)$alkylthio$(C_1-C_6)$alkyl, halo$(C_1-C_6)$alkylthio$(C_1-C_6)$alkyl, $(C_1-C_6)$alkoxy$(C_1-C_6)$alkylthioalkyl, $(C_1-C_6)$alkylsulfanyl$(C_1-C_6)$alkyl, $(C_1-C_6)$alkylsulfinyl$(C_1-C_6)$alkyl, $(C_1-C_6)$alkylsulfonyl$(C_1-C_6)$alkyl, halo$(C_1-C_6)$alkylsulfanyl$(C_1-C_6)$alkyl, halo$(C_1-C_6)$alkylsulfinyl$(C_1-C_6)$alkyl, halo$(C_1-C_6)$alkylsulfonyl$(C_1-C_6)$alkyl, $(C_1-C_6)$alkoxy$(C_1-C_6)$alkylsulfanyl$(C_1-C_6)$alkyl, $(C_1-C_6)$alkoxy$(C_1-C_6)$alkylsulfinyl$(C_1-C_6)$alkyl, $(C_1-C_6)$alkoxy$(C_1-C_6)$alkylsulfonyl$(C_1-C_6)$alkyl, phenyl$(C_1-C_6)$alkyl, phenoxy$(C_1-C_6)$alkyl, phenylsulfanyl$(C_1-C_6)$alkyl, phenylsulfinyl$(C_1-C_6)$alkyl, phenylsulfonyl$(C_1-C_6)$alkyl, hetaryl$(C_1-C_6)$alkyl, hetaryloxy$(C_1-C_6)$alkyl or hetarylthio$(C_1-C_6)$alkyl, where the aforementioned radicals may each be saturated or unsaturated and/or optionally be substituted; or represent optionally substituted saturated or unsaturated $(C_3-C_6)$cycloalkyl which may optionally be interrupted by one or more heteroatoms; or represent $(C_1-C_6)$alkylcarbonyl, halo$(C_1-C_6)$alkylcarbonyl, hydroxy$(C_1-C_6)$alkylcarbonyl, $(C_1-C_6)$alkoxy$(C_1-C_6)$alkylcarbonyl, phenylcarbonyl, hetarylcarbonyl, $(C_1-C_6)$alkoxycarbonyl, halo$(C_1-C_6)$alkoxycarbonyl, aryloxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, di$(C_3-C_6)$cycloalkylaminocarbonyl, $(C_3-C_6)$cycloalkyl$((C_1-C_6)$alkyl) aminocarbonyl, arylaminocarbonyl, diarylaminocarbonyl, $(C_1-C_6)$alkyl(aryl)aminocarbonyl, $(C_3-C_6)$cycloalkyl(aryl)aminocarbonyl, $(C_1-C_6)$alkylaminothiocarbonyl, di$(C_1-C_6)$alkylaminothiocarbonyl or aminothiocarbonyl, where the aforementioned radicals may each optionally be substituted and/or, under the condition that, in the case of an unsaturated radical, the defined minimum number of carbon atoms is 2, the radicals may be saturated or unsaturated, or represent carbonyl or carboxyl; or represent optionally substituted phenyl or optionally substituted hetaryl;

represent $(C_1-C_6)$alkoxy, halo$(C_1-C_6)$alkoxy, $(C_1-C_6)$alkoxy$(C_1-C_6)$alkoxy, aryloxy, aryl$(C_1-C_6)$alkyloxy, $(C_3-C_6)$cycloalkyloxy, $(C_3-C_6)$cycloalkyl$(C_1-C_6)$alkyloxy or carbonyloxy, where the aforementioned radicals may each optionally be substituted and/or, under the condition that, in the case of an unsaturated radical, the defined minimum number of carbon atoms is 2, the radicals may be saturated or unsaturated, or represent hydroxyl; or represent $(C_1-C_6)$alkylamino, di$(C_1-C_6)$alkylamino, halo$(C_1-C_6)$alkylamino, dihalo$(C_1-C_6)$alkylamino, $(C_3-C_6)$cycloalkylamino, di$(C_3-C_6)$cycloalkylamino, $(C_3-C_6)$cycloalkyl$((C_1-C_6)$alkyl)amino, arylamino, diarylamino, hetarylamino, dihetarylamino, $(C_1-C_6)$alkyl(aryl)amino, $(C_3-C_6)$cycloalkyl(aryl)amino, $(C_1-C_6)$alkylcarbonylamino, arylcarbonylamino, $(C_1-C_6)$alkoxycarbonylamino, aryloxycarbonylamino, $(C_1-C_6)$alkylcarbamoylamino, arylcarbamoylamino, $(C_1-C_6)$alkylsulfonylamino, or arylsulfonylamino, where the aforementioned radicals may each optionally be substituted and/or, under the condition that, in the case of an unsaturated radical, the defined minimum number of carbon atoms is 2, the radicals may be saturated or unsaturated, or represent amino; or represent $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfonyl, $(C_3-C_6)$cycloalkylsulfanyl, $(C_3-C_6)$cycloalkylsulfinyl, $(C_3-C_6)$cycloalkylsulfonyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, arylsulfanyl, arylsulfinyl, arylsulfonyl, aryl$(C_1-C_6)$alkylsulfanyl, aryl$(C_1-C_6)$alkylsulfinyl, aryl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted and/or, under the condition that, in the case of an unsaturated radical, the defined minimum number of carbon atoms is 2, the radicals may be saturated or unsaturated, or represent sulfanyl; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted $(C_3-C_6)$cycloalkyl and which is optionally interrupted by heteroatoms from the group consisting of O, S and N;

W represents hydrogen, fluorine or chlorine;

X, Y and Z each independently of one another represent hydrogen, fluorine, chlorine, bromine, cyano, nitro, amino, hydroxyl, $(C_1-C_4)$alkyl, $(C_1-C_4)$haloalkyl, $(C_2-C_4)$alkenyl, $(C_2-C_4)$alkynyl, $(C_1-C_4)$alkoxy, $(C_1-C_4)$haloalkoxy or aminothiocarbonyl;

or represent a benzyl, phenoxy, phenylthio, cyclopropylmethyl, cyclopropyloxy or cyclopropylthio, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl;

or represent cyclopropyl, cyclobutyl, cyclopentyl, cyclohexyl or phenyl, which is optionally mono- or polysubstituted by identical or different substituents from the group consisting of fluorine, chlorine, bromine, cyano, nitro, hydroxyl, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted cyclopropyl; and n represents the number 0 or 1.

14. The compound as claimed in claim 13, in which the substructure of formula (I-D) represents a substructure which is selected from the group consisting of (I-D-1)

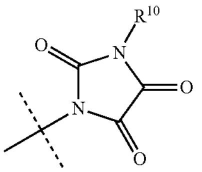

(I-D-2)

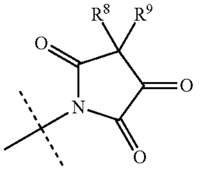

(I-D-3)

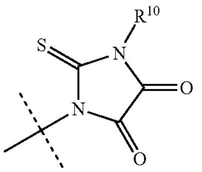

where $R^{10}$ represents hydrogen or represents $(C_1-C_6)$alkyl, $(C_3-C_6)$cycloalkyl$(C_1-C_6)$alkyl, halo$(C_2-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may optionally be substituted; or represents optionally substituted $(C_3-C_6)$cycloalkyl, $(C_3-C_6)$cycloalkenyl, which may optionally be interrupted by one or more heteroatoms from the group of O, S and N; or represents $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or represents carbonyl or carboxyl; or represents optionally substituted phenyl or optionally substituted hetaryl; or represents $(C_1-C_6)$alkoxy, halo$(C_1-C_6)$alkoxy, $(C_3-C_6)$cycloalkyloxy, or carbonyloxy, where the aforementioned radicals may each optionally be substituted, or represents hydroxyl; or represents $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-C_6)$alkylsulfonylamino, $(C_2-C_6)$alkenylamino, $(C_3-C_6)$cycloalkenyl$(C_1-C_6)$alkylamino, $(C_2-C_6)$alkynylamino, where the aforementioned radicals may each optionally be substituted, or represents amino; or represents $(C_1-C_6)$alkylsulfanyl, $(C_1-C_6)$alkylsulfinyl, $(C_1-C_6)$alkylsulfonyl, halo$(C_1-C_6)$alkylsulfanyl, halo$(C_1-C_6)$alkylsulfinyl, halo$(C_1-C_6)$alkylsulfanyl, $(C_3-C_6)$cycloalkyl$(C_1-C_6)$alkylsulfanyl, $(C_3-C_6)$cycloalkyl$(C_1-C_6)$alkylsulfinyl, $(C_3-C_6)$cycloalkyl$(C_1-C_6)$alkylsulfonyl, aminosulfonyl, $(C_1-C_6)$alkylaminosulfonyl, di$(C_1-C_6)$alkylaminosulfonyl or arylaminosulfonyl, where the aforementioned radicals may each optionally be substituted, or represents sulfanyl; and $R^8$ and $R^9$ each independently of one another represent hydrogen, cyano, halogen or nitro; or represent $(C_1-C_6)$alkyl, $(C_3-C_6)$cycloalkyl$(C_1-C_6)$alkyl, halo$(C_1-C_6)$alkyl, cyano$(C_1-C_6)$alkyl, $(C_1-C_6)$alkoxy$(C_1-C_6)$alkyl, $(C_1-C_6)$alkoxycarbonyl$(C_1-C_6)$alkyl, $(C_1-C_6)$alkylsulfanyl$(C_1-C_6)$alkyl, $(C_1-C_6)$alkylsulfinyl$(C_1-C_6)$alkyl, phenyl$(C_1-C_6)$alkyl, hetaryl$(C_1-C_6)$alkyl, $(C_2-C_6)$alkenyl, halo$(C_2-C_6)$alkenyl, $(C_3-C_6)$cycloalkenyl$(C_1-C_6)$alkyl, $(C_2-C_6)$alkynyl, where the aforementioned radicals may each optionally be substituted; or represent optionally substituted $(C_3-C_6)$cycloalkyl, $(C_3-C_6)$cycloalkenyl, which may optionally be interrupted by one or more heteroatoms from the group of O, S and N; or represent $(C_1-C_6)$alkylcarbonyl, halo$(C_1-C_6)$alkylcarbonyl, $(C_1-C_6)$alkoxy$(C_1-C_6)$alkylcarbonyl, $(C_1-C_6)$alkoxycarbonyl, halo$(C_1-C_6)$alkoxycarbonyl, aminocarbonyl, $(C_1-C_6)$alkylaminocarbonyl, di$(C_1-C_6)$alkylaminocarbonyl, $(C_3-C_6)$cycloalkylaminocarbonyl, $(C_1-C_6)$alkylaminothiocarbonyl, di$(C_1-C_6)$alkylaminothiocarbonyl, $(C_2-C_6)$alkenylcarbonyl, $(C_3-C_6)$cycloalkenyl$(C_1-C_6)$alkylcarbonyl, $(C_2-C_6)$alkynylcarbonyl or aminothiocarbonyl, where the aforementioned radicals may each optionally be substituted, or represent carbonyl or carboxyl; or represent optionally substituted phenyl or optionally substituted hetaryl; or represent $(C_1-C_6)$alkoxy, halo$(C_1-C_6)$alkoxy, $(C_1-C_6)$alkoxy$(C_1-C_6)$alkoxy, $(C_3-C_6)$cycloalkyloxy, $(C_3-C_6)$cycloalkyl$(C_1-C_6)$alkyloxy, $(C_2-C_6)$alkenyloxy, $(C_3-C_6)$cycloalkenyl$(C_1-C_6)$alkoxy, $(C_2-C_6)$alkynyloxy or carbonyloxy, where the aforementioned radicals may each optionally be substituted, or represent hydroxyl; or represent $(C_1-C_6)$alkylamino, halo$(C_1-C_6)$alkylamino, dihalo$(C_1-C_6)$alkylamino, di$(C_1-C_6)$alkylamino, $(C_3-C_6)$cycloalkylamino, di$(C_3-C_6)$cycloalkylamino, $(C_1-C_6)$alkylcarbonylamino, $(C_1-C_6)$alkoxycarbonylamino, $(C_1-C_6)$alkylcarbamoylamino, $(C_1-$ $C_6$)alkylsulfonylamino, ($C_2$-$C_6$)alkenylamino, ($C_3$-$C_6$)cycloalkenyl($C_1$-$C_6$)alkylamino, ($C_2$-$C_6$) alkynylamino, where the aforementioned radicals may each optionally be substituted, or represent amino; or represent ($C_1$-$C_6$)alkylsulfanyl, ($C_1$-$C_6$)alkylsulfinyl, ($C_1$-$C_6$)alkylsulfonyl, halo($C_1$-$C_6$)alkylsulfanyl, halo($C_1$-$C_6$)alkylsulfinyl, halo($C_1$-$C_6$)alkylsulfanyl, ($C_3$-$C_6$)cycloalkyl($C_1$-$C_6$)alkylsulfanyl, ($C_3$-$C_6$)cycloalkyl($C_1$-$C_6$)alkylsulfinyl, ($C_3$-$C_6$)cycloalkyl($C_1$-$C_6$)alkylsulfonyl, aminosulfonyl, ($C_1$-$C_6$)alkylaminosulfonyl, di($C_1$-$C_6$)alkylaminosulfonyl or arylaminosulfonyl, where the aforementioned radicals may each optionally be substituted, or represent sulfanyl; or $R^8$ and $R^9$ together with the atom to which they are attached may form a saturated or unsaturated three- to six-membered ring which is optionally substituted by identical or different substituents from the group consisting of halogen, cyano, nitro, hydroxy, amino, methyl, ethyl, trifluoromethyl, difluoromethyl, trifluoroethyl, difluoroethyl, methoxy, ethoxy, trifluoromethoxy, trifluoroethoxy and optionally methyl-, fluorine-, chlorine-, cyano-substituted ($C_3$-$C_6$)cycloalkyl and which is optionally interrupted by heteroatoms from the group consisting of O, S and N;

W represents hydrogen or fluorine;

X and Y each independently of one another represent hydrogen, fluorine, chlorine, bromine, methyl, ethyl, trifluoromethyl, 2,2-difluoromethyl, difluoromethoxy, trifluoromethoxy, cyclopropyl, cyano, amino, hydroxyl or nitro;

Z represents hydrogen; and n represents the number 0 or 1.

15. The compound as claimed in claim 13, in which the substructure of formula (I-D) represents a substructure which is selected from the group consisting of (I-D-1)

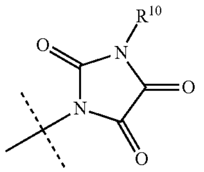

-continued (I-D-3)

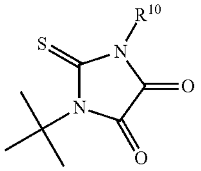

where $R^{10}$ represents hydrogen, methyl, ethyl, propyl, isopropyl, tert-butyl, cyclopropylmethyl, $CH_2CH(CH_3)_2$, $CH_2C(CH_3)_3$, $CH_2CF_3$, $CH_2CHF_2$, $CH(CH_3)CF_3$, $CH_2CH_2CF_3$, $CH_2CH_2CHF_2$ or optionally methyl-, fluorine-, chlorine-, cyano-substituted cyclopropyl or optionally methyl-, fluorine-, chlorine-, cyano-substituted cyclohexyl or optionally methyl-, fluorine-, chlorine-, cyano-substituted cyclopropylmethyl;

W represents hydrogen or fluorine;

X represents hydrogen, chlorine, fluorine or methyl;

Y represents chlorine, bromine, cyano, methyl, trifluoromethyl or fluorine;

where X and Y represent in particular the following combinations (Y,X): (Me, F), (Me,H), (Me, Cl), (Me,Me), (Cl,Cl), (Cl,F), (CN,F), (Cl,H), (Me,H), (Br,H), (Br,F), (CN,H), (F,F), ($CF_3$,H);

Z represents hydrogen; and n represents the number 0 or 1.

16. The compound of formula (I) as claimed in claim 1 capable of being used for controlling one or more animal pests in crop protection, and/or in the protection of one or more materials and/or in the veterinary sector.

17. An active compound composition comprising at least one compound of formula (I) as claimed in claim 1 and at least one further insecticidally, acaricidally or nematicidally active compound.

18. An agrochemical composition, comprising at least one compound of formula (I) as claimed in claim 1, and one or more extenders and/or surfactants.

19. A process for producing an agrochemical composition, comprising mixing a compound of formula (I) as claimed in claim 1 with one or more extenders and/or surfactants.

20. A method for controlling one or more animal pests, comprising allowing a compound of formula (I) as claimed in claim 1 to act on said one or more animal pests and/or a habitat thereof.

* * * * *